US011685863B2

(12) United States Patent
Haensel et al.

(10) Patent No.: US 11,685,863 B2
(45) Date of Patent: Jun. 27, 2023

(54) POLYMERISABLE COMPOUNDS AND THE USE THEREOF IN LIQUID-CRYSTAL DISPLAYS

(71) Applicant: MERCK PATENT GMBH, Darmstadt (DE)

(72) Inventors: Helmut Haensel, Muehltal (DE); Qiong Tong, Darmstadt (DE); Rocco Fortte, Frankfurt am Main (DE); Edward Plummer, Frankfurt am Main (DE); Thomas Eichhorn, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 17/431,045

(22) PCT Filed: Feb. 14, 2020

(86) PCT No.: PCT/EP2020/053855
§ 371 (c)(1),
(2) Date: Aug. 13, 2021

(87) PCT Pub. No.: WO2020/165394
PCT Pub. Date: Aug. 20, 2020

(65) Prior Publication Data
US 2022/0127532 A1    Apr. 28, 2022

(30) Foreign Application Priority Data
Feb. 15, 2019  (EP) .................... 19157543.0

(51) Int. Cl.
| C09K 19/54 | (2006.01) |
| C07C 69/533 | (2006.01) |
| C07D 211/46 | (2006.01) |
| C07D 211/94 | (2006.01) |
| C07D 319/06 | (2006.01) |
| C08F 222/26 | (2006.01) |
| C09K 19/30 | (2006.01) |

(52) U.S. Cl.
CPC .......... *C09K 19/542* (2013.01); *C07C 69/533* (2013.01); *C07D 211/46* (2013.01); *C07D 211/94* (2013.01); *C07D 319/06* (2013.01); *C08F 222/26* (2013.01); *C09K 19/3003* (2013.01); *C09K 2019/301* (2013.01); *C09K 2019/3004* (2013.01); *C09K 2019/3009* (2013.01); *C09K 2019/3016* (2013.01); *C09K 2019/548* (2013.01)

(58) Field of Classification Search
CPC .............. C09K 19/542; C09K 19/3003; C09K 19/3066; C09K 19/062; C09K 19/32; C09K 2019/3004; C09K 2019/3009; C09K 2019/301; C09K 2019/3016; C09K 2019/548; C09K 2019/0448; C08F 222/26; C07D 319/06; C07D 211/94; C07C 69/533
See application file for complete search history.

(56) References Cited

U.S. PATENT DOCUMENTS

| 3,821,227 | A | 6/1974 | Hall et al. |
| 7,323,538 | B2 * | 1/2008 | Nakano .................... C08K 5/00 528/425 |
| 9,096,795 | B2 * | 8/2015 | Taugerbeck ......... C07D 307/91 |
| 2012/0069289 | A1 | 3/2012 | Taugerbeck et al. |
| 2022/0127532 | A1 * | 4/2022 | Haensel ............. C09K 19/3066 |

FOREIGN PATENT DOCUMENTS

| DE | 102009022309 A1 | 11/2010 | |
| JP | 2008-31223 A * | 2/2008 | ............. C08F 12/32 |

OTHER PUBLICATIONS

International Search Report for PCT/EP2020/053855 dated May 25, 2020.
Bachman, G. B. et al., "Condensation of Aldehydes with Fluorene and Nitrofluorences," Contribution from the Purdue Research Foundation and the Department of Chemistry, Purdue University 1951, 1690-1696.
Rusanov et al. "Reactions using nitro-containing monomers for the synthesis of aromatic polymers," Russian Chemical Reviews, 1991, vol. 60, No. 7, pp. 1449-1472.

* cited by examiner

*Primary Examiner* — Geraldina Visconti
(74) *Attorney, Agent, or Firm* — Millen, White, Zelano and Branigan, P.C.; Harry B. Shubin

(57) ABSTRACT

The present invention relates to polymerisable compounds, to processes and intermediates for the preparation thereof, to liquid-crystal (LC) media comprising them, and to the use of the polymerisable compounds and LC media for optical, electro-optical and electronic purposes, in particular in LC displays, especially in LC displays of the polymer sustained alignment (PS, PSA) and self-aligning (SA) type.

23 Claims, No Drawings

POLYMERISABLE COMPOUNDS AND THE USE THEREOF IN LIQUID-CRYSTAL DISPLAYS

The present invention relates to polymerisable compounds, to processes and intermediates for the preparation thereof, to liquid-crystal (LC) media comprising them, and to the use of the polymerisable compounds and LC media for optical, electro-optical and electronic purposes, in particular in LC displays, especially in LC displays of the polymer sustained alignment (PS, PSA) and self-aligning (SA) type.

BACKGROUND OF THE INVENTION

One of the liquid-crystal display (LCD) modes used at present is the TN ("twisted nematic") mode. However, TN LCDs have the disadvantage of a strong viewing-angle dependence of the contrast.

In addition, so-called VA ("vertically aligned") displays are known which have a broader viewing angle. The LC cell of a VA display contains a layer of an LC medium between two transparent electrodes, where the LC medium usually has a negative dielectric anisotropy. In the switched-off state, the molecules of the LC layer are aligned perpendicular to the electrode surfaces (homeotropically) or have a tilted homeotropic alignment. On application of an electrical voltage to the two electrodes, a realignment of the LC molecules parallel to the electrode surfaces takes place.

Furthermore, OCB ("optically compensated bend") displays are known which are based on a birefringence effect and have an LC layer with a so-called "bend" alignment and usually positive dielectric anisotropy. On application of an electrical voltage, a realignment of the LC molecules perpendicular to the electrode surfaces takes place. In addition, OCB displays normally contain one or more birefringent optical retardation films in order to prevent undesired transparency to light of the bend cell in the dark state. OCB displays have a broader viewing angle and shorter response times compared with TN displays.

Also known are so-called IPS ("in-plane switching") displays, which contain an LC layer between two substrates, where the two electrodes are arranged on only one of the two substrates and preferably have intermeshed, comb-shaped structures. On application of a voltage to the electrodes, an electric field which has a significant component parallel to the LC layer is thereby generated between them. This causes realignment of the LC molecules in the layer plane.

Furthermore, so-called FFS ("fringe-field switching") displays have been reported (see, inter alia, S. H. Jung et al., Jpn. J. Appl. Phys., Volume 43, No. 3, 2004, 1028), which contain two electrodes on the same substrate, one of which structured in a comb-shaped manner and the other is unstructured. A strong, so-called "fringe field" is thereby generated, i.e. a strong electric field close to the edge of the electrodes, and, throughout the cell, an electric field which has both a strong vertical component and also a strong horizontal component. FFS displays have a low viewing-angle dependence of the contrast. FFS displays usually contain an LC medium with positive dielectric anisotropy, and an alignment layer, usually of polyimide, which provides planar alignment to the molecules of the LC medium.

FFS displays can be operated as active-matrix or passive-matrix displays. In the case of active-matrix displays, individual pixels are usually addressed by integrated, non-linear active elements, such as, for example, transistors (for example thin-film transistors ("TFTs")), while in the case of passive-matrix displays, individual pixels are usually addressed by the multiplex method, as known from the prior art.

Furthermore, FFS displays have been disclosed (see S. H. Lee et al., Appl. Phys. Lett. 73(20), 1998, 2882-2883 and S. H. Lee et al., Liquid Crystals 39(9), 2012, 1141-1148), which have similar electrode design and layer thickness as FFS displays, but comprise a layer of an LC medium with negative dielectric anisotropy instead of an LC medium with positive dielectric anisotropy. The LC medium with negative dielectric anisotropy shows a more favourable director orientation that has less tilt and more twist orientation compared to the LC medium with positive dielectric anisotropy, as a result of which these displays have a higher transmission. The displays further comprise an alignment layer, preferably of polyimide provided on at least one of the substrates that is in contact with the LC medium and induces planar alignment of the LC molecules of the LC medium. These displays are also known as "Ultra Brightness FFS (UB-FFS)" mode displays. These displays require an LC medium with high reliability.

The term "reliability" as used hereinafter means the quality of the performance of the display during time and with different stress loads, such as light load, temperature, humidity, voltage, and comprises display effects such as image sticking (area and line image sticking), mura, yogore etc. which are known to the skilled person in the field of LC displays. As a standard parameter for categorising the reliability usually the voltage holding ration (VHR) value is used, which is a measure for maintaining a constant electrical voltage in a test display. Among other factors, a high VHR is a prerequisite for a high reliability of the LC medium.

In VA displays of the more recent type, uniform alignment of the LC molecules is restricted to a plurality of relatively small domains within the LC cell. Disclinations may exist between these domains, also known as tilt domains. VA displays having tilt domains have, compared with conventional VA displays, a greater viewing-angle independence of the contrast and the grey shades. In addition, displays of this type are simpler to produce since additional treatment of the electrode surface for uniform alignment of the molecules in the switched-on state, such as, for example, by rubbing, is no longer necessary. Instead, the preferential direction of the tilt or pretilt angle is controlled by a special design of the electrodes.

In so-called MVA ("multidomain vertical alignment") displays, this is usually achieved by the electrodes having protrusions which cause a local pretilt. As a consequence, the LC molecules are aligned parallel to the electrode surfaces in different directions in different, defined regions of the cell on application of a voltage. "Controlled" switching is thereby achieved, and the formation of interfering disclination lines is prevented. Although this arrangement improves the viewing angle of the display, it results, however, in a reduction in its transparency to light. A further development of MVA uses protrusions on only one electrode side, while the opposite electrode has slits, which improves the transparency to light. The slitted electrodes generate an inhomogeneous electric field in the LC cell on application of a voltage, meaning that controlled switching is still achieved. For further improvement of the transparency to light, the separations between the slits and protrusions can be increased, but this in turn results in a lengthening of the response times. In so-called PVA ("patterned VA") displays, protrusions are rendered completely superfluous in that both electrodes are structured by means of slits on the opposite sides, which results in increased contrast and improved transparency to light, but is technologically difficult and makes the display more sensitive to mechanical influences ("tapping", etc.). For many applications, such as, for example, monitors and especially TV screens, however, a shortening of the response times and an improvement in the contrast and luminance (transmission) of the display are demanded.

A further development are displays of the so-called PS ("polymer sustained") or PSA ("polymer sustained alignment") type, for which the term "polymer stabilised" is also occasionally used. In these, a small amount (for example 0.3% by weight, typically <1% by weight) of one or more polymerisable, compound(s), preferably polymerisable monomeric compound(s), is added to the LC medium and, after filling the LC medium into the display, is polymerised or crosslinked in situ, usually by UV photopolymerisation, optionally while a voltage is applied to the electrodes of the display. The polymerisation is carried out at a temperature where the LC medium exhibits a liquid crystal phase, usually at room temperature. The addition of polymerisable mesogenic or liquid-crystalline compounds, also known as reactive mesogens or "RMs", to the LC mixture has proven particularly suitable.

Unless indicated otherwise, the term "PSA" is used hereinafter when referring to displays of the polymer sustained alignment type in general, and the term "PS" is used when referring to specific display modes, like PS-VA, PS-TN and the like.

Also, unless indicated otherwise, the term "RM" is used hereinafter when referring to a polymerisable mesogenic or liquid-crystalline compound.

In the meantime, the PS(A) principle is being used in various conventional LC display modes. Thus, for example, PS-VA, PS-OCB, PS-IPS, PS-FFS, PS-UB-FFS and PS-TN displays are known. The polymerisation of the RMs preferably takes place with an applied voltage in the case of PS-VA and PS-OCB displays, and with or without, preferably without, an applied voltage in the case of PS-IPS displays. As can be demonstrated in test cells, the PS(A) method results in a pretilt in the cell. In the case of PS-OCB displays, for example, it is possible for the bend structure to be stabilised so that an offset voltage is unnecessary or can be reduced. In the case of PS-VA displays, the pretilt has a positive effect on response times. For PS-VA displays, a standard MVA or PVA pixel and electrode layout can be used. In addition, however, it is also possible, for example, to manage with only one structured electrode side and no protrusions, which significantly simplifies production and at the same time results in very good contrast and in very good transparency to light.

Furthermore, the so-called posi-VA displays ("positive VA") have proven to be a particularly suitable mode. Like in classical VA displays, the initial orientation of the LC molecules in posi-VA displays is homeotropic, i.e. substantially perpendicular to the substrates, in the initial state when no voltage is applied. However, in contrast to classical VA displays, in posi-VA displays LC media with positive dielectric anisotropy are used. Like in the usually used IPS displays, the two electrodes in posi-VA displays are arranged on only one of the two substrates, and preferably exhibit intermeshed and comb-shaped (interdigital) structures. By application of a voltage to the interdigital electrodes, which create an electrical field that is substantially parallel to the layer of the LC medium, the LC molecules are transferred into an orientation that is substantially parallel to the substrates. In posi-VA displays polymer stabilisation, by addition of RMs to the LC medium which are polymerised in the display, has also proven to be advantageous, as a significant reduction of the switching times could thereby be realised.

PS-VA displays are described, for example, in EP 1 170 626 A2, U.S. Pat. Nos. 6,861,107, 7,169,449, US 2004/0191428 A1, US 2006/0066793 A1 and US 2006/0103804 A1. PS-OCB displays are described, for example, in T.-J-Chen et al., Jpn. J. Appl. Phys. 45, 2006, 2702-2704 and S. H. Kim, L.-C-Chien, Jpn. J. Appl. Phys. 43, 2004, 7643-7647. PS-IPS displays are described, for example, in U.S. Pat. No. 6,177,972 and Appl. Phys. Lett. 1999, 75(21), 3264. PS-TN displays are described, for example, in Optics Express 2004, 12(7), 1221.

Below the layer formed by the phase-separated and polymerised RMs which induce the above mentioned pretilt angle, the PSA display typically contains an alignment layer, for example of polyimide, that provides the initial alignment of the LC molecules before the polymer stabilisation step.

Rubbed polyimide layers have been used for a long time as alignment layers. However, the rubbing process causes a number of problems, like mura, contamination, problems with static discharge, debris, etc. Therefore instead of rubbed polyimide layers it was proposed to use polyimide layers prepared by photoalignment, utilizing a light-induced orientational ordering of the alignment surface. This can be achieved through photodecomposition, photodimerisation or photoisomerisation by means of polarised light.

However, still a suitably derivatised polyimide layer is required that comprises the photoreactive group. Generally the effort and costs for production of such a polyimide layer, treatment of the poylimide and improvement with bumps or polymer layers are relatively great.

In addition, it was observed that unfavourable interaction of the polyimide alignment layer with certain compounds of the LC medium often leads to a reduction of the electrical resistance of the display. The number of suitable and available LC compounds is thus significantly reduced, at the expense of display parameters like viewing-angle dependence, contrast, and response times which are aimed to be improved by the use of such LC compounds. It was therefore desired to omit the polyimide alignment layers.

For some display modes this was achieved by adding a self alignment agent or additive to the LC medium that induces the desired alignment, for example homeotropic or planar alignment, in situ by a self assembling mechanism. Thereby the alignment layer can be omitted on one or both of the substrates. These display modes are also known as "self-aligned" or "self-aligning" (SA) modes.

In SA displays a small amount, typically 0.1 to 2.5%, of a self-aligning additive is added to the LC medium. Suitable self-aligning additives are for example compounds having an organic core group and attached thereto one or more polar anchor groups, which are capable of interacting with the substrate surface, causing the additives on the substrate surface to align and induce the desired alignment also in the LC molecules. Preferred self-aligning additives comprise for example a mesogenic group and a straight-chain or branched alkyl side chain that is terminated with one or more polar anchor groups, for example selected from hydroxy, carboxy, amino or thiol groups. The self-aligning additives may also contain one or more polymerisable groups that can be polymerised under similar conditions as the RMs used in the PSA process.

Hitherto SA-VA displays and SA-FFS displays haven been disclosed. Suitable self-aligning additives to induce homeotropic alignment, especially for use in SA-VA mode displays, are disclosed for example in US 2013/0182202 A1, US 2014/0138581 A1, US 2015/0166890 A1 and US 2015/0252265 A1.

The SA mode can also be used in combination with the PSA mode. An LC medium for use in a display of such a combined mode thus contains both one or more RMs and one or more self-aligning additives.

Like the conventional LC displays described above, PSA displays can be operated as active-matrix or passive-matrix displays. In the case of active-matrix displays, individual pixels are usually addressed by integrated, non-linear active elements, such as, for example, transistors (for example thin-film transistors ("TFTs")), while in the case of passive-matrix displays, individual pixels are usually addressed by the multiplex method, as known from the prior art.

The PSA display may also comprise an alignment layer on one or both of the substrates forming the display cell. The alignment layer is usually applied on the electrodes (where such electrodes are present) such that it is in contact with the LC medium and induces initial alignment of the LC molecules. The alignment layer may comprise or consist of, for example, a polyimide, which may also be rubbed, or may be prepared by a photoalignment method.

In particular for monitor and especially TV applications, optimisation of the response times, but also of the contrast and luminance (thus also transmission) of the LC display continues to be demanded. The PSA method can provide significant advantages here. In particular in the case of PS-VA, PS-IPS, PS-FFS and PS-posi-VA displays, a shortening of the response times, which correlate with a measurable pretilt in test cells, can be achieved without significant adverse effects on other parameters.

Prior art has suggested biphenyl diacrylates or dimethacrylates, which are optionally fluorinated as RMs for use in PSA displays However, the problem arises that not all combinations consisting of an LC mixture and one or more RMs are suitable for use in PSA displays because, for example, an inadequate tilt or none at all becomes established or since, for example, the VHR is inadequate for TFT display applications. In addition, it has been found that, on use in PSA displays, the LC mixtures and RMs known from the prior art do still have some disadvantages. Thus, not every known RM which is soluble in LC mixtures is suitable for use in PSA displays. In addition, it is often difficult to find a suitable selection criterion for the RM besides direct measurement of the pretilt in the PSA display. The choice of suitable RMs becomes even smaller if polymerisation by means of UV light without the addition of photoinitiators is desired, which may be advantageous for certain applications.

In addition, the selected combination of LC host mixture/RM should have the lowest possible rotational viscosity and the best possible electrical properties. In particular, it should have the highest possible VHR. In PSA displays, a high VHR after irradiation with UV light is particularly necessary since UV exposure is a requisite part of the display production process, but also occurs as normal exposure during operation of the finished display.

In particular, it would be desirable to have available novel materials for PSA displays which produce a particularly small tilt angle. Preferred materials here are those which produce a lower tilt angle during polymerisation for the same exposure time than the materials known to date, and/or through the use of which the (higher) tilt angle that can be achieved with known materials can already be achieved after a shorter exposure time. The production time ("tact time") of the display could thus be shortened and the costs of the production process reduced.

A further problem in the production of PSA displays is the presence or removal of residual amounts of unpolymerised RMs, in particular after the polymerisation step for production of the tilt angle in the display. For example, unreacted RMs of this type may adversely affect the properties of the display by, for example, polymerising in an uncontrolled manner during operation after finishing of the display.

Thus, the PSA displays known from the prior art often exhibit the undesired effect of so-called "image sticking" or "image burn", i.e. the image produced in the LC display by temporary addressing of individual pixels still remains visible even after the electric field in these pixels has been switched off or after other pixels have been addressed.

This "image sticking" can occur on the one hand if LC host mixtures having a low VHR are used. The UV component of daylight or the backlighting can cause undesired decomposition reactions of the LC molecules therein and thus initiate the production of ionic or free-radical impurities. These may accumulate, in particular, at the electrodes or the alignment layers, where they may reduce the effective applied voltage. This effect can also be observed in conventional LC displays without a polymer component.

In addition, an additional "image sticking" effect caused by the presence of unpolymerised RMs is often observed in PSA displays. Uncontrolled polymerisation of the residual RMs is initiated here by UV light from the environment or by the backlighting. In the switched display areas, this changes the tilt angle after a number of addressing cycles. As a result, a change in transmission in the switched areas may occur, while it remains unchanged in the unswitched areas.

It is therefore desirable for the polymerisation of the RMs to proceed as completely as possible during production of the PSA display and for the presence of unpolymerised RMs in the display to be excluded as far as possible or reduced to a minimum. Thus, RMs and LC mixtures are required which enable or support highly effective and complete polymerisation of the RMs. In addition, controlled reaction of the residual RM amounts would be desirable. This would be simpler if the RM polymerised more rapidly and effectively than the compounds known to date.

A further problem that has been observed in the operation of PSA displays is the stability of the tilt angle. Thus, it was observed that the tilt angle, which was generated during display manufacture by polymerising the RM as described above, does not remain constant but can deteriorate after the display was subjected to voltage stress during its operation. This can negatively affect the display performance, e.g. by increasing the black state transmission and hence lowering the contrast.

Another problem to be solved is that the RMs of prior art do often have high melting points, and do only show limited solubility in many currently common LC mixtures, and therefore frequently tend to spontaneously crystallise out of the mixture. In addition, the risk of spontaneous polymerisation prevents the LC host mixture being warmed in order to dissolve the polymerisable component, meaning that the best possible solubility even at room temperature is necessary. In addition, there is a risk of separation, for example on introduction of the LC medium into the LC display (chromatography effect), which may greatly impair the homogeneity of the display. This is further increased by the fact that the LC media are usually introduced at low temperatures in order to reduce the risk of spontaneous polymerisation (see above), which in turn has an adverse effect on the solubility.

Another problem observed in prior art is that the use of conventional LC media in LC displays, including but not limited to displays of the PSA type, often leads to the occurrence of mura in the display, especially when the LC medium is filled in the display cell manufactured using the one drop filling (ODF) method. This phenomenon is also known as "ODF mura". It is therefore desirable to provide LC media which lead to reduced ODF mura.

Another problem observed in prior art is that LC media for use in PSA displays, including but not limited to displays of the PSA type, do often exhibit high viscosities and, as a consequence, high switching times. In order to reduce the viscosity and switching time of the LC medium, it has been suggested in prior art to add LC compounds with an alkenyl group. However, it was observed that LC media containing alkenyl compounds often show a decrease of the reliability and stability, and a decrease of the VHR especially after exposure to UV radiation. Especially for use in PSA displays this is a considerable disadvantage, because the photopolymerisation of the RMs in the PSA display is usually carried out by exposure to UV radiation, which may cause a VHR drop in the LC medium.

There is thus still a great demand for PSA displays and LC media and polymerisable compounds for use in such displays, which do not show the drawbacks as described above, or only do so to a small extent, and have improved properties.

In particular, there is a great demand for PSA displays, and LC media and polymerisable compounds for use in such PSA displays, which enable a high specific resistance at the same time as a large working-temperature range, short response times, even at low temperatures, and a low threshold voltage, a low tilt angle, a multiplicity of grey shades, high contrast and a broad viewing angle, have high reliability and high values for the VHR after UV exposure, and, in case of the polymerisable compounds, have low melting points and a high solubility in the LC host mixtures. In PSA displays for mobile applications, it is especially desired to have available LC media that show low threshold voltage and high birefringence.

In prior art several types of RMs have been reported for use in PSA displays, for example RMs having a biphenyl or terphenyl mesogenic core and attached thereto two or three polymerisable acrylate or methacrylate groups. Biphenyl RMs were shown to exhibit limited polymerisation speed but good reliability parameters, like high VHR or tilt stability, while terphenyl RMs were shown to exhibit fast polymerisation speed but limited reliability parameters. It is therefore desirable to have available RMs that exhibit both fast polymerisation speed and good reliability parameters.

The invention is based on the object of providing novel suitable materials, in particular RMs and LC media comprising the same, for use in PSA displays, which do not have the disadvantages indicated above or do so to a reduced extent.

In particular, the invention is based on the object of providing RMs, and LC media comprising them, for use in PSA displays, which enable very high specific resistance values, high VHR values, high reliability, low threshold voltages, short response times, high birefringence, show good UV absorption especially at longer wavelengths, enable quick and complete polymerisation of the RMs, allow the generation of a low tilt angle, preferably as quickly as possible, enable a high stability of the tilt angle even after longer time and/or after UV exposure, reduce or prevent the occurrence of "image sticking" and "ODF mura" in the display, and in case of the RMs polymerise as rapidly and completely as possible and show a high solubility in the LC media which are typically used as host mixtures in PSA displays.

A further object of the invention is to provide RMs for use in PSA displays which exhibit both fast polymerisation speed and good reliability parameters, like high VHR or tilt stability.

A further object of the invention is the provision of novel RMs, in particular for optical, electro-optical and electronic applications, and of suitable processes and intermediates for the preparation thereof.

These objects have been achieved in accordance with the present invention by materials and processes as described in the present application. In particular, it has been found, surprisingly, that the use of RMs of formula I as described hereinafter allows achieving the advantageous effects as mentioned above. These compounds are characterized in that they contain an aromatic mesogenic core, which comprises an alkylidene-fluorene group and one or more polymerisable reactive groups attached thereto.

It was surprisingly found that the use of these RMs, and of LC media comprising them, in PSA displays facilitates a quick and complete UV-photopolymerisation reaction in particular at longer UV wavelengths in the range from 300-380 nm and especially above 320 nm, even without the addition of photoinitiator, leads to a fast generation of a low and stable tilt angle, reduces image sticking and ODF mura in the display, leads to a high reliability and a high VHR value after UV photopolymerisation, especially in case of LC host mixtures containing LC compounds with an alkenyl group, and enables to achieve fast response times, a low threshold voltage and a high birefringence.

In addition, the RMs according to the invention have low melting points, good solubility in a wide range of LC media, especially in commercially available LC host mixtures for PSA use, and a low tendency to crystallisation. Besides, they show good absorption at longer UV wavelengths, in particular in the range from 300-380 nm, and enable a quick and complete polymerisation with small amounts of residual, unreacted RMs in the cell.

Also, it was surprisingly found that the RMs according to the present invention combine a fast polymerisation speed like that of terphenyl RMs with good reliability parameters like those of biphenyl RMs. This results in a superior overall performance compared to RMs of the state of the art.

SUMMARY OF THE INVENTION

The invention relates to a compound of formula I

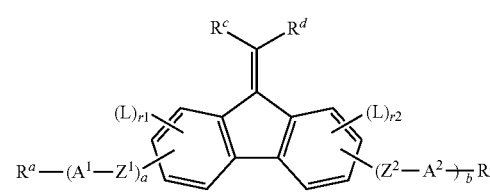

wherein the individual radicals, independently of each other and on each occurrence identically or differently, have the following meanings $A^1$, $A^2$ an aromatic or heteroaromatic group with 4 to 30 ring atoms, which may also contain fused rings, and is optionally substituted by one or more groups L, R or P-Sp-, $Z^1$, $Z^2$ —O—, —S—, —CO—, —CO—O—, —O—CO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CH$_2$)$_{n1}$—, —CF$_2$CH$_2$—, —CH$_2$CF$_2$—, —(CF$_2$)$_{n1}$—, —CH=CH—, —CF=CF—, —CH=CF—, —CF=CH—, —C≡C—, —CH=CH—CO—O—, —O—CO—CH=CH—, —CH$_2$—CH$_2$—CO—O—, —O—CO—CH$_2$—CH$_2$—, —CR$^0$R$^{00}$—, or a single bond, R$^0$, R$^{00}$ H or alkyl having 1 to 12 C atoms, R$^a$, R$^b$ P-Sp-, R or H, wherein at least one of R$^a$ and R$^b$ denotes P-Sp-, R$^c$, R$^d$ H, straight-chain or branched alkyl with 1 to 12, preferably 1 to 6 C atoms, or straight-chain or branched alkenyl with 2 to 12, preferably 2 to 7 C atoms, wherein one or more H atoms are optionally replaced by F or Cl, R H, F, Cl, —CN, or straight chain, branched or cyclic alkyl having 1 to 25 C atoms, wherein one or more non-adjacent CH$_2$-groups are optionally replaced by —O—, —S—, —CO—, —CO—O—, —O—CO—, —O—CO—O—, —N(R$^0$)—, —Si(R$^0$R$^{00}$)—, —CH=CH— or —C≡C— in such a manner that O- and/or S-atoms are not directly connected with each other, and wherein one or more H atoms are each optionally replaced by F or Cl, P a polymerisable group, Sp a spacer group that is optionally substituted by one or more groups P, or a single bond, L F, Cl, —CN, P, P-Sp-, or straight chain, branched or cyclic alkyl having 1 to 25 C atoms, wherein one or more non-adjacent CH$_2$-groups are optionally replaced by —O—, —S—, —CO—, —CO—O—, —O—CO—, —O—CO—O—, —N(R$^0$)—, —Si(R$^0$R$^{00}$)—, —CH=CH— or —C≡C— in such a manner that O- and/or S-atoms are not directly connected with each other, and wherein one or more H atoms are each optionally replaced by P, P-Sp-, F or Cl, a, b 0, 1 or 2, r1, r2 0, 1, 2 or 3, n1 1, 2, 3 or 4.

The invention further relates to the use of compounds of formula I as polymerisable compounds in LC media and LC displays, especially in the LC medium, active layer or alignment layer of an LC display, wherein the LC displays are preferably PSA displays.

The invention further relates to methods for preparing compounds of formula I, and to novel intermediates used or obtained in these methods.

The invention furthermore relates to an LC medium comprising one or more compounds of formula I.

The invention furthermore relates to an LC medium comprising one or more polymerisable compounds, at least one of which is a compound of formula I.

The invention furthermore relates to an LC medium comprising
a polymerisable component A) comprising, preferably consisting of, one or more polymerisable compounds, at least one of which is a compound of formula I, and
a liquid-crystalline component B), hereinafter also referred to as "LC host mixture", comprising, preferably consisting of, one or more mesogenic or liquid-crystalline compounds.

The liquid-crystalline component B) of an LC medium according to the present invention is hereinafter also referred to as "LC host mixture", and preferably comprises one or more, preferably at least two mesogenic or LC compounds selected from low-molecular-weight compounds which are unpolymerisable.

The invention furthermore relates to an LC medium as described above and below, wherein the LC host mixture or component B) comprises at least one mesogenic or LC compound comprising an alkenyl group.

The invention furthermore relates to an LC medium or LC display as described above, wherein the compounds of formula I, or the polymerisable compounds of component A), are polymerised.

The invention furthermore relates to a process for preparing an LC medium as described above and below, comprising the steps of mixing one or more mesogenic or LC compounds, or an LC host mixture or LC component B) as described above and below, with one or more compounds of formula I, and optionally with further LC compounds and/or additives.

The invention furthermore relates to the use of compounds of formula I and LC media according to the invention in PSA displays, in particular the use in PSA displays containing an LC medium, for the production of a tilt angle in the LC medium by in-situ polymerisation of the compound(s) of the formula I in the display, preferably in an electric or magnetic field.

The invention furthermore relates to an LC display comprising one or more compounds of formula I or an LC medium according to the invention, in particular a PSA display, particularly preferably a PS-VA, PS-OCB, PS-IPS, PS-FFS, PS-UB-FFS, PS-posi-VA or PS-TN display.

The invention furthermore relates to the use of compounds of formula I and LC media according to the invention in polymer stabilised SA displays, especially in polymer stabilised SA-VA and SA-FFS displays, and to a polymer stabilised SA, SA-VA or SA-HB-FFS display comprising one or more compounds of formula I or an LC medium according to the invention.

The invention furthermore relates to an LC display comprising a polymer obtainable by polymerisation of one or more compounds of formula I or of a polymerisable component A) as described above, or comprising an LC medium according to the invention, which is preferably a PSA or a polymer stabilised SA display, very preferably a PS-VA, PS-OCB, PS-IPS, PS-FFS, PS-UB-FFS, PS-posi-VA, PS-TN, or polymer stabilised SA-VA or SA-HB-FFS display.

The invention furthermore relates to an LC display of the PSA type comprising two substrates, at least one which is transparent to light, an electrode provided on each substrate or two electrodes provided on only one of the substrates, and located between the substrates a layer of an LC medium that comprises one or more polymerisable compounds and an LC component as described above and below, wherein the polymerisable compounds are polymerised between the substrates of the display.

The invention furthermore relates to a process for manufacturing an LC display as described above and below, comprising the steps of filling or otherwise providing an LC medium, which comprises one or more polymerisable compounds as described above and below, between the substrates of the display, and polymerising the polymerisable compounds.

The PSA displays according to the invention have two electrodes, preferably in the form of transparent layers, which are applied to one or both of the substrates. In some displays, for example in PS-VA, PS-OCB, PS-TN or polymer stabilised SA-VA displays, one electrode is applied to each of the two substrates. In other displays, for example in PS-posi-VA, PS-IPS or PS-FFS, PS-UB-FFS or polymer stabilised SA-FFS displays, both electrodes are applied to only one of the two substrates.

In a preferred embodiment the polymerisable component is polymerised in the LC display while a voltage is applied to the electrodes of the display.

The polymerisable compounds of the polymerisable component are preferably polymerised by photopolymerisation, very preferably by UV photopolymerisation.

The alkenyl group in the compounds of formula I as disclosed and claimed in this application is not considered to be within the meaning of the term "polymerisable group" as used herein. Preferably the LC media disclosed and claimed in the present application do not contain an additive that initiates or enhances participation of the alkenyl group in a polymerisation reaction.

The invention furthermore relates to a compound of formula IN

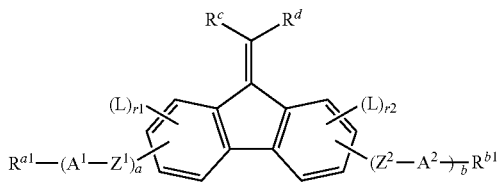

IN wherein one of $R^{a1}$ and $R^{b1}$ is Pg-Sp- and the other is R or Pg-Sp-, Pg is OH or a protected or masked OH group, and $R^c$, $R^d$, R, Sp, $A^1$, $A^2$, $Z^1$, $Z^2$, L, a, b, r1 and r2 have the meanings of formula I or one of the preferred meanings above and below.

The invention furthermore relates to the use of compounds of formula IN as intermediates in the synthesis of polymerisable compounds, especially those of formula I.

The invention furthermore relates to a process for synthesizing compounds of formula I by esterification or etherification of the compounds of formula IN, wherein Pg denotes OH, using corresponding acids, acid derivatives, or halogenated compounds containing a polymerisable group P.

DETAILED DESCRIPTION OF THE INVENTION

The compounds of formula I show the following advantageous properties when used in PSA displays:
- a suitable tilt generation which is inside a certain process window,
- fast polymerization leading to minimal residues of RM after the UV-process,
- a high voltage-holding-ratio after the UV-process,
- good tilt stability,
- sufficient stability against heat,
- sufficient solubility in organic solvents typically used in display manufacture.

In addition the compounds of formula I allow to solve one or more of the following problems:
- to generate a stable tilt angle to a desired degree after exposure to UV-light,
- to control enable of the time range of the first UV-step in which the pre-tile angle is generated during UV-processing,
- to keep the time range of the second UV-step as short as possible to minimize production cost,
- after the first and second UV-exposure step, to reduce or avoid any negative effects of the residual RM on the LC mixture performance parameters, such as VHR, tilt stability, etc.
- to provide good solubility and stability in the LC host mixture in a broad temperature range, preferably from −40° C. to ca. 140° C.,
- for use in SA-VA displays, to provide RMs which can, together with SA-VA additives, form a polymer layer with low reflectivity after UV processing.

In particular the compounds of formula I combine a fast polymerisation speed which is similar to terphenyl RMs with good reliability parameters similar to biphenyl RMs. This results in a superior overall performance of the compounds compared to RMs of the state of the art when used in PSA displays.

The alkenyl group in the compounds of formula as disclosed and claimed in this application is not considered to be within the meaning of the term "polymerisable group" as used herein. The conditions for the polymerisation of compounds of formula I are preferably selected such that the alkenyl substituents do not participate in the polymerisation reaction. Preferably the LC media disclosed and claimed in the present application do not contain an additive that initiates or enhances the participation of the alkenyl group in a polymerisation reaction.

Unless stated otherwise, the compounds of formula I are preferably selected from achiral compounds.

As used herein, the terms "active layer" and "switchable layer" mean a layer in an electrooptical display, for example an LC display, that comprises one or more molecules having structural and optical anisotropy, like for example LC molecules, which change their orientation upon an external stimulus like an electric or magnetic field, resulting in a change of the transmission of the layer for polarized or unpolarized light.

As used herein, the terms "tilt" and "tilt angle" will be understood to mean a tilted alignment of the LC molecules of an LC medium relative to the surfaces of the cell in an LC display (here preferably a PSA display), and will be understood to be inclusive of "pretilt" and "pretilt angle". The tilt angle here denotes the average angle (<90°) between the longitudinal molecular axes of the LC molecules (LC director) and the surface of the plane-parallel outer plates which form the LC cell. A low absolute value for the tilt angle (i.e. a large deviation from the 90° angle) corresponds to a large tilt here. A suitable method for measurement of the tilt angle is given in the examples. Unless indicated otherwise, tilt angle values disclosed above and below relate to this measurement method.

As used herein, the terms "reactive mesogen" and "RM" will be understood to mean a compound containing a mesogenic or liquid crystalline skeleton, and one or more functional groups attached thereto which are suitable for polymerisation and are also referred to as "polymerisable group" or "P".

Unless stated otherwise, the term "polymerisable compound" as used herein will be understood to mean a polymerisable monomeric compound.

An SA-VA or SA-FFS according to the present invention will be of the polymer stabilised mode as it contains, or is manufactured by use of, an LC medium containing an RM of formula I. Consequently as used herein, the terms "SA-VA display" and "SA-FFS display", when referring to a display according to the present invention, will be understood to refer to a polymer stabilised SA-VA or SA-FFS display even if not explicitly mentioned.

As used herein, the term "low-molecular-weight compound" will be understood to mean to a compound that is monomeric and/or is not prepared by a polymerisation reaction, as opposed to a "polymeric compound" or a "polymer".

As used herein, the term "unpolymerisable compound" will be understood to mean a compound that does not contain a functional group that is suitable for polymerisation under the conditions usually applied for the polymerisation of the RMs.

The term "mesogenic group" as used herein is known to the person skilled in the art and described in the literature, and means a group which, due to the anisotropy of its attracting and repelling interactions, essentially contributes to causing a liquid-crystal (LC) phase in low-molecular-weight or polymeric substances. Compounds containing mesogenic groups (mesogenic compounds) do not necessarily have to have an LC phase themselves. It is also possible for mesogenic compounds to exhibit LC phase behaviour only after mixing with other compounds and/or after polymerisation. Typical mesogenic groups are, for example, rigid rod- or disc-shaped units. An overview of the terms and definitions used in connection with mesogenic or LC compounds is given in *Pure Appl. Chem.* 2001, 73(5), 888 and C. Tschierske, G. Pelzl, S. Diele, *Angew. Chem.* 2004, 116, 6340-6368.

The term "spacer group", hereinafter also referred to as "Sp", as used herein is known to the person skilled in the art and is described in the literature, see, for example, *Pure Appl. Chem.* 2001, 73(5), 888 and C. Tschierske, G. Pelzl, S. Diele, *Angew. Chem.* 2004, 116, 6340-6368. As used herein, the terms "spacer group" or "spacer" mean a flexible group, for example an alkylene group, which connects the mesogenic group and the polymerisable group(s) in a polymerisable mesogenic compound.

Above and below, d

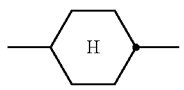

denotes a trans-1,4-cyclohexylene ring, and

denotes a 1,4-phenylene ring.

In a group

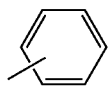

the single bond shown between the two ring atoms can be attached to any free position of the benzene ring.

"Halogen" denotes F, Cl, Br or I, preferably F or Cl.

—CO—, —C(=O)— and —C(O)— denote a carbonyl group, i.e.

The terms "alkyl", "aryl", "heteroaryl", etc., also encompass polyvalent groups, for example alkylene, arylene, heteroarylene, etc.

Preferred alkyl groups are, for example, methyl, ethyl, n-propyl, isopropyl, n-butyl, isobutyl, s-butyl, t-butyl, 2-methylbutyl, n-pentyl, s-pentyl, cyclopentyl, n-hexyl, cyclohexyl, 2-ethylhexyl, n-heptyl, cycloheptyl, n-octyl, cyclooctyl, n-nonyl, n-decyl, n-undecyl, n-dodecyl, dodecanyl, trifluoromethyl, perfluoro-n-butyl, 2,2,2-trifluoroethyl, perfluorooctyl, perfluorohexyl, etc.

Preferred alkenyl groups are, for example, ethenyl, propenyl, butenyl, pentenyl, cyclopentenyl, hexenyl, cyclohexenyl, heptenyl, cycloheptenyl, octenyl, cyclooctenyl, etc.

Preferred alkynyl groups are, for example, ethynyl, propynyl, butynyl, pentynyl, hexynyl, octynyl, etc.

Preferred alkoxy groups are, for example, methoxy, ethoxy, 2-methoxy-ethoxy, n-propoxy, i-propoxy, n-butoxy, i-butoxy, s-butoxy, t-butoxy, 2-methylbutoxy, n-pentoxy, n-hexoxy, n-heptoxy, n-octoxy, n-nonoxy, n-decoxy, n-undecoxy, n-dodecoxy, etc.

Aromatic and heteroaromtaic groups can be monocyclic or polycyclic, i.e. they can contain one ring (such as, for example, phenyl) or two or more rings, which may also be fused (such as, for example, naphthyl) or covalently bonded (such as, for example, biphenyl), or contain a combination of fused and linked rings. Heteroaromatic groups contain one or more heteroatoms, preferably selected from O, N, S and Se.

Particular preference is given to mono-, bi- or tricyclic aromaticl groups having 6 to 25 C atoms and mono-, bi- or tricyclic heteroaryl groups having 5 to 25 ring atoms, which optionally contain fused rings and are optionally substituted. Preference is furthermore given to 5-, 6- or 7-membered aromatic and heteroaromatic groups, in which, in addition, one or more CH groups may be replaced by N, S or O in such a way that O atoms and/or S atoms are not linked directly to one another.

Preferred aromatic groups are, for example, phenyl, biphenyl, terphenyl, [1,1':3',1"]terphenyl-2'-yl, naphthyl, anthracene, binaphthyl, phenanthrene, 9,10-dihydrophenanthrene, pyrene, dihydropyrene, chrysene, perylene, tetracene, pentacene, benzopyrene, fluorene, indene, indenofluorene, spirobifluorene, etc.

Preferred heteroaromatic groups are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]thiophene, thieno[3,2b]thiophene, dithienothiophene, isobenzothiophene, dibenzothiophene, benzothiophene, benzothiadiazothiophene, or combinations of these groups.

The aromatic and heteroaromatic groups mentioned above and below may also be substituted by alkyl, alkoxy, thioalkyl, fluoro or fluoroalkyl groups or by alicyclic, heterocyclic, aromatic or heteroaromatic groups.

Preferred (non-aromatic) alicyclic and heterocyclic groups encompass both saturated rings, i.e. those containing exclusively single bonds, and also partially unsaturated rings, i.e. those which may also contain multiple bonds. Heterocyclic rings contain one or more heteroatoms, preferably selected from Si, O, N, S and Se.

Preferred (non-aromatic) alicyclic and heterocyclic groups can be monocyclic, i.e. contain only one ring (such as, for example, cyclohexane), or polycyclic, i.e. contain a plurality of rings (such as, for example, decahydronaphthalene or bicyclooctane). Particular preference is given to saturated groups. Preference is furthermore given to mono-, bi- or tricyclic groups having 5 to 25 ring atoms, which optionally contain fused rings and are optionally substituted. Preference is furthermore given to 5-, 6-, 7- or 8-membered carbocyclic groups, in which, in addition, one or more C atoms may be replaced by Si and/or one or more CH groups may be replaced by N and/or one or more non-adjacent $CH_2$ groups may be replaced by —O— and/or —S—.

Preferred alicyclic and heterocyclic groups are, for example, 5-membered groups, such as cyclopentane, tetrahydrofuran, tetrahydrothiofuran, pyrrolidine, 6-membered groups, such as cyclohexane, silinane, cyclohexene, tetrahydropyran, tetrahydrothiopyran, 1,3-dioxane, 1,3-dithiane, piperidine, 7-membered groups, such as cycloheptane, and fused groups, such as tetrahydronaphthalene, decahydronaphthalene, indane, bicyclo[1.1.1]-pentane-1,3-diyl, bicyclo[2.2.2]octane-1,4-diyl, spiro[3.3]heptane-2,6-diyl, octahydro-4,7-methanoindane-2,5-diyl.

Preferred substituents on the aromatic and heteroaromatic groups, hereinafter also referred to as "$L^S$", are, for example, F, Cl, Br, I, —CN, —$NO_2$, —NCO, —NCS, —OCN, —SCN, —C(=O)N($R^x$)$_2$, —C(=O)$Y^1$, —C(=O)$R^x$, —N($R^x$)$_2$, straight-chain or branched alkyl, alkoxy, alkyl-carbonyl, alkoxycarbonyl, alkylcarbonyloxy or alkoxycarbonyloxy each having 1 to 25 C atoms, in which one or more H atoms may optionally be replaced by F or Cl, optionally substituted silyl having 1 to 20 Si atoms, or optionally substituted aryl having 6 to 25, preferably 6 to 15, C atoms, wherein $R^x$ denotes H, F, Cl, CN, or straight chain, branched or cyclic alkyl having 1 to 25 C atoms, wherein one or more non-adjacent $CH_2$-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F, Cl, P- or P-Sp-, and $Y^1$ denotes halogen.

"Substituted silyl or aryl" preferably means substituted by halogen, —CN, $R^0$, —$OR^0$, —CO—$R^0$, —C—O—$R^0$, —O—CO—$R^0$ or —O—CO—O—$R^0$, wherein $R^0$ denotes H or alkyl with 1 to 20 C atoms.

Particularly preferred substituents $L^S$ are, for example, F, Cl, CN, $NO_2$, $CH_3$, $C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$, furthermore phenyl.

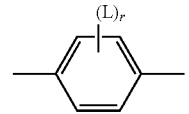

is preferably

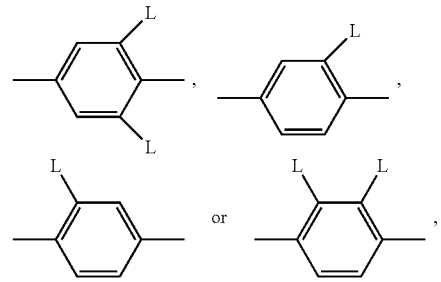

in which L has one of the meanings indicated above.

The polymerisable group P is a group which is suitable for a polymerisation reaction, such as, for example, free-radical or ionic chain polymerisation, polyaddition or polycondensation, or for a polymer-analogous reaction, for example addition or condensation onto a main polymer chain. Particular preference is given to groups for chain polymerisation, in particular those containing a C=C double bond or —C≡C— triple bond, and groups which are suitable for polymerisation with ring opening, such as, for example, oxetane or epoxide groups.

Preferred groups P are selected from the group consisting of $CH_2$=$CW^1$—CO—O—, $CH_2$=$CW^1$—CO—,

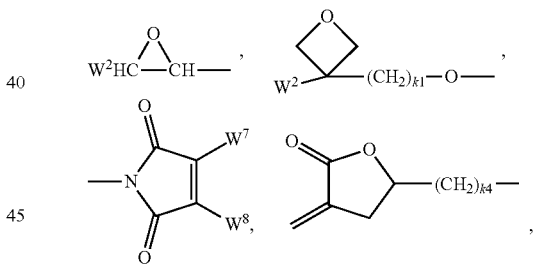

$CH_2$=$CW^2$—(O)$_{k3}$—, $CW^1$=CH—CO—(O)$_{k3}$—, $CW^1$=CH—CO—NH—, $CH_2$=$CW^1$—CO—NH—, $CH_3$—CH=CH—O—, ($CH_2$=CH)$_2$CH—OCO—, ($CH_2$=CH—$CH_2$)$_2$CH—OCO—, ($CH_2$=CH)$_2$CH—O—, ($CH_2$=CH—$CH_2$)$_2$N—, ($CH_2$=CH—$CH_2$)$_2$N—CO—, HO—$CW^2W^3$—, HS—$CW^2W^3$—, $HW^2$N—, HO—$CW^2W^3$—NH—, $CH_2$=$CW^1$—CO—NH—, $CH_2$=CH—(COO)$_{k1}$-Phe-(O)$_{k2}$—, $CH_2$=CH—(CO)$_{k1}$-Phe-(O)$_{k2}$—, Phe-CH=CH—, HOOC—, OCN— and $W^4W^5W^6$Si—, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonyl-alkyl having 1 to 5 C atoms, $W^7$ and $W^8$ each, independently of one another, denote H, Cl or alkyl having 1 to 5 C atoms, Phe denotes 1,4-phenylene, which is optionally substituted by one or more radicals L as defined above which are other than P-Sp-, $k_1$, $k_2$ and $k_3$ each, independently of one another, denote 0 or 1, $k_3$ preferably denotes 1, and $k_4$ denotes an integer from 1 to 10.

Very preferred groups P are selected from the group consisting of $CH_2$=$CW^1$—CO—O—, $CH_2$=$CW^1$—CO—,

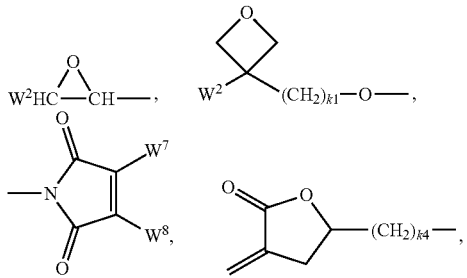

$CH_2$=$CW^2$—O—, $CH_2$=$CW^2$—, $CW^1$=CH—CO—(O)$_{k3}$—, $CW^1$=CH—CO—NH—, $CH_2$=$CW^1$—CO—NH—, $(CH_2$=$CH)_2CH$—OCO—, $(CH_2$=CH—$CH_2)_2$CH—OCO—, $(CH_2$=$CH)_2CH$—O—, $(CH_2$=CH—$CH_2)_2$N—, $(CH_2$=CH—$CH_2)_2$N—CO—, $CH_2$=$CW^1$—CO—NH—, $CH_2$=CH—$(COO)_{k1}$-Phe-$(O)_{k2}$—, $CH_2$=CH—$(CO)_{k1}$-Phe-$(O)_{k2}$—, Phe-CH=CH— and $W^4W^5W^6$Si—, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, $k_1$, $k_2$ and $k_3$ each, independently of one another, denote 0 or 1, $k_3$ preferably denotes 1, and $k_4$ denotes an integer from 1 to 10.

Very particularly preferred groups P are selected from the group consisting of $CH_2$=$CW^1$—CO—O—, in particular $CH_2$=CH—CO—O—, $CH_2$=C($CH_3$)—CO—O- and $CH_2$=CF—CO—O—, furthermore $CH_2$=CH—O—, $(CH$=$CH)_2CH$—O—CO—, $(CH$=$CH)_2CH$—O—,

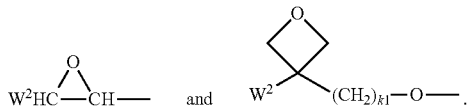

Further preferred polymerisable groups P are selected from the group consisting of vinyloxy, acrylate, methacrylate, fluoroacrylate, chloroacrylate, oxetane and epoxide, most preferably from acrylate and methacrylate.

If the spacer group Sp is different from a single bond, it is preferably of the formula Sp"-X", so that the respective radical P-Sp- conforms to the formula P-Sp"-X"—, wherein
Sp" denotes linear or branched alkylene having 1 to 20, preferably 1 to 12, C atoms, which is optionally mono- or polysubstituted by F, Cl, Br, I or CN and in which, in addition, one or more non-adjacent $CH_2$ groups may each be replaced, independently of one another, by —O—, —S—, —NH—, —N($R^0$)—, —Si($R^0R^{00}$)—, —CO—, —CO—O—, —O—CO—, —O—CO—O—, —S—CO—, —CO—S—, —N($R^{00}$)—CO—O—, —O—CO—N($R^0$)—, —N($R^0$)—CO—N($R^{00}$)—, —CH=CH— or —C≡C— in such a way that O and/or S atoms are not linked directly to one another,
X" denotes —O—, —S—, —CO—, —CO—O—, —O—CO—, —O—CO—O—, —CO—N($R^0$)—, —N($R^0$)—CO—, —N($R^0$)—CO—N($R^{00}$)—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=$CR^0$—, —$CY^2$=$CY^3$—, —C≡C—, —CH=CH—CO—O—, —O—CO—CH=CH— or a single bond,
$R^0$ and $R^{00}$ each, independently of one another, denote H or alkyl having 1 to 20 C atoms, and
$Y^2$ and $Y^3$ each, independently of one another, denote H, F, Cl or CN.
X" is preferably —O—, —S—, —CO—, —COO—, —OCO—, —O—COO—, —CO—$NR^0$—, —$NR^0$—CO—, —$NR^0$—CO—$NR^{00}$— or a single bond.

Typical spacer groups Sp and —Sp"—X"— are, for example, —$(CH_2)_{p1}$—, —$(CH_2)_{p1}$—O—, —$(CH_2)_{p1}$—O—CO—, —$(CH_2)_{p1}$—CO—O—, —$(CH_2)_{p1}$—O—CO—O—, —$(CH_2CH_2O)_{q1}$—$CH_2CH_2$—, —$CH_2CH_2$—S—$CH_2CH_2$—, —$CH_2CH_2$—NH—$CH_2CH_2$— or —$(SiR^0R^{00}$—O$)_{p1}$—, in which p1 is an integer from 1 to 12, q1 is an integer from 1 to 3, and $R^0$ and $R^{00}$ have the meanings indicated above.

Particularly preferred groups Sp and —Sp"—X"— are —$(CH_2)_{p1}$—, —$(CH_2)_{p1}$—O—, —$(CH_2)_{p1}$—O—CO—, —$(CH_2)_{p1}$—CO—O—, —$(CH_2)_{p1}$—O—CO—O—, in which p1 and q1 have the meanings indicated above.

Particularly preferred groups Sp" are, in each case straight-chain, ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene and butenylene.

In a preferred embodiment of the invention the compounds of formula I and its subformulae contain a spacer group Sp that is substituted by one or more polymerisable groups P, so that the group Sp-P corresponds to Sp(P)$_s$, with s being ≥2 (branched polymerisable groups).

Preferred compounds of formula I according to this preferred embodiment are those wherein s is 2, i.e. compounds which contain a group Sp(P)$_2$. Very preferred compounds of formula I according to this preferred embodiment contain a group selected from the following formulae:

| | |
|---|---|
| —X-alkyl-CHPP | S1 |
| —X-alkyl-CH$((CH_2)_{aa}$P$)((CH_2)_{bb}$P$)$ | 2 |
| —X—N$((CH_2)_{aa}$P$)((CH_2)_{bb}$P$)$ | 3 |
| —X-alkyl-CHP—$CH_2$—$CH_2$P | 4 |
| —X-alkyl-C$(CH_2$P$)(CH_2$P$)$—$C_{aa}H_{2aa+1}$ | 5 |
| —X-alkyl-CHP—$CH_2$P | 6 |
| —X-alkyl-CPP—$C_{aa}H_{2aa+1}$ | 7 |
| —X-alkyl-CHPCHP—$C_{aa}H_{2aa+1}$ | 8 | in which P is as defined in formula I,
alkyl denotes a single bond or straight-chain or branched alkylene having 1 to 12 C atoms which is unsubstituted or mono- or polysubstituted by F, Cl or CN and in which one or more non-adjacent $CH_2$ groups may each, independently of one another, be replaced by —C(R⁰)
═C(R⁰)—, —C≡C—, —N(R⁰)—, —O—, —S—,
—CO—, —CO—O—, —O—CO—, —O—CO—O—
in such a way that O and/or S atoms are not linked
directly to one another, where R⁰ has the meaning
indicated above, aa and bb each, independently of one another, denote 0, 1, 2, 3, 4, 5 or 6, X has one of the meanings indicated for X″, and is preferably O, CO, SO₂, O—CO—, CO—O or a single bond.

Preferred spacer groups Sp(P)₂ are selected from formulae S1, S2 and S3.

Very preferred spacer groups Sp(P)₂ are selected from the following subformulae:

| | |
|---|---|
| —CHPP | S1a |
| —O—CHPP | S1b |
| —CH₂—CHPP | S1c |
| —OCH₂—CHPP | S1d |
| —CH(CH₂—P)(CH₂—P) | S2a |
| —OCH(CH₂—P)(CH₂—P) | S2b |
| —CH₂—CH(CH₂—P)(CH₂—P) | S2c |
| —OCH₂—CH(CH₂—P)(CH₂—P) | S2d |
| —CO—N H((CH₂)₂P)((CH₂)₂P) | S3a |

In the compounds of formula I and its subformulae as described above and below, P is preferably selected from the group consisting of vinyloxy, acrylate, methacrylate, fluoroacrylate, chloroacrylate, oxetane and epoxide, most preferably from acrylate and methacrylate.

Further preferred are compounds of formula I and its subformulae as described above and below, wherein all polymerisable groups P that are present in the compound have the same meaning, and very preferably denote acrylate or methacrylate, most preferably methacrylate.

Further preferred are compounds of formula I and its subformulae as described above and below, wherein R^b is P-Sp-.

Further preferred are compounds of formula I and its subformulae as described above and below, wherein Sp denotes a single bond or —(CH₂)ₚ₁—, —(CH₂)ₚ₂—CH═CH—(CH₂)ₚ₃—, —O—(CH₂)ₚ₁—, —O—CO—(CH₂)ₚ₁, or —CO—O—(CH₂)ₚ₁, wherein p1 is 2, 3, 4, 5 or 6, p2 and p3 are independently of each other 0, 1, 2 or 3 and, if Sp is —O—(CH₂)ₚ₁—, —O—CO—(CH₂)ₚ₁ or —CO—O—(CH₂)ₚ₁ the O-atom or CO-group, respectively, is linked to the benzene ring.

Further preferred are compounds of formula I and its subformulae as described above and below, wherein at least one group Sp is a single bond.

Further preferred are compounds of formula I and its subformulae as described above and below, wherein at least one group Sp is different from a single bond, and is preferably selected from —(CH₂)ₚ₁—, —(CH₂)ₚ₂—CH═CH—(CH₂)ₚ₃—, —O—(CH₂)ₚ₁—, —O—CO—(CH₂)ₚ₁, or —CO—O—(CH₂)ₚ₁, wherein p1 is 2, 3, 4, 5 or 6, p2 and p3 are independently of each other 0, 1, 2 or 3 and, if Sp is —O—(CH₂)ₚ₁—, —O—CO—(CH₂)ₚ₁ or —CO—O—(CH₂)ₚ₁ the O-atom or CO-group, respectively, is linked to the benzene ring.

Further preferred are compounds of formula I and its subformulae as described above and below, wherein A¹ and A² are selected from the group consisting of benzene, naphthalene, phenanthrene, anthracene, dibenzofuran, dibenzothiophene or carbazole, all of which are optionally substituted by one or more groups L or P-Sp-.

Further preferred are compounds of formula I and its subformulae as described above and below, wherein (A¹-Z¹)ₐ and (Z²-A²)ᵦ are selected from the group consisting of benzene, biphenylene, p-terphenylene (1,4-diphenylbenzene), m-terphenylene (1,3-diphenylbenzene), naphthylene, 2-phenyl-naphthylene, phenanthrene or anthracene, dibenzofuran or dibenzothiophene, all of which are optionally substituted by one or more groups L or P-Sp-.

Further preferred are compounds of formula I and its subformulae as described above and below, wherein a is 0 or 1 and b is 0 or 1, very preferably wherein a=b=0, or a=b=1, or a=0 and b=1.

Further preferred compounds of formula I are selected of formula IA

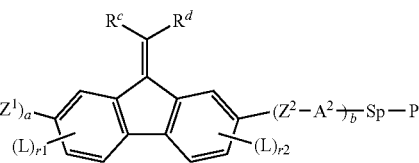

wherein P, Sp, R^c, R^d, A¹, A², Z¹, Z², L, a, b, r1 and r2 have the meanings given in formula I or one of the preferred meanings as described above and below.

Very preferred compounds of formula I and IA are selected from the following subformulae

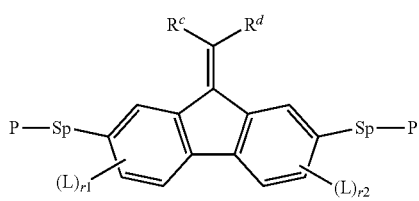

I1

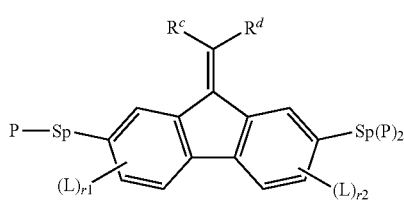

I2

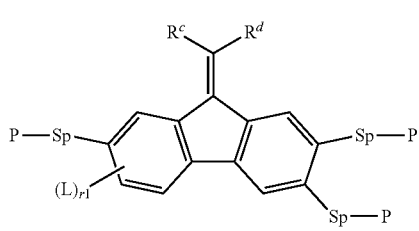

I3

-continued

I4
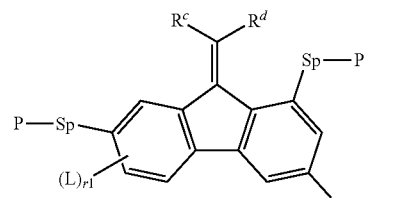

I5
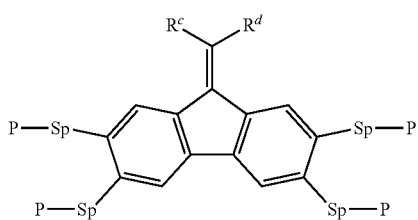

I6
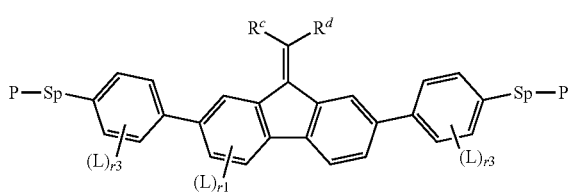

I7
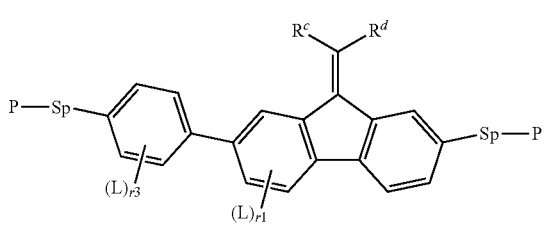

I8
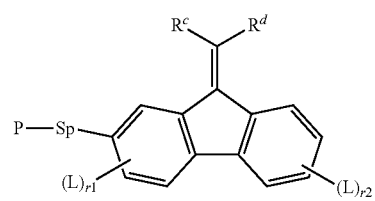

wherein P, Sp, $R^c$, $R^d$, L, r1 and r2 have the meanings given in formula I or one of the preferred meanings as described above and below, and r3 and r4 are independently of each other 0, 1, 2, 3 or 4, and L preferably does not denote P or P-Sp-.

Further preferred compounds of formula I, IA and I1-I8 are those wherein $R^c$ and $R^d$ are selected from the group consisting of H, CH$_3$, C$_2$H$_5$, C$_3$H$_7$, —CH═CH$_2$ and —CH$_2$—CH═CH$_2$, very preferably from the group consisting of H, CH$_3$ and —CH═CH$_2$.

Further preferred compounds of formula I, IA and I1-I8 are those wherein

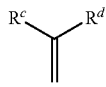

denotes

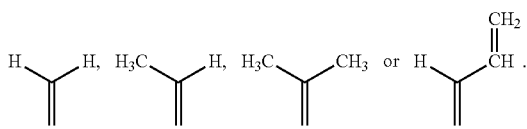

Further preferred compounds of formula I, IA and I1-I8 are those wherein the groups P denote independently of each other acrylate or methacrylate, very preferably methacrylate.

Further preferred compounds of formula I, IA and I1-I8 are those wherein Sp is a single bond.

Further preferred compounds of formula I, IA and I1-I8 are those wherein at least one, preferably exactly one of the groups Sp is a single bond and the other groups Sp are different from a single bond.

Further preferred compounds of formula I, IA and I1-I8 are those wherein Sp, when being different from a single bond, denotes alkylene with 2 to 6 C atoms or alkenylene with 2 to 6 C atoms.

Further preferred compounds of formula I, IA and I1-I8 are those wherein Sp(P)$_2$ is selected from formulae S1 to S8 or S1a to S3a as defined above.

Further preferred compounds of formula I, IA and I1-I8 are those wherein r1 and r2 are 0.

Further preferred compounds of formula I, IA and I1-I8 are those wherein r1 and/or r2 is 1 or 2, preferably 1, very preferably both r1 and r2 are 1, and L is selected from F, Cl, CN, alkyl, alkoxy, alkylcarbonyl, alkoxycarbonyl, alkylcarbonyloxy or alkoxycarbonyloxy each having 1 to 6 C atoms, in which one or more H atoms may optionally be replaced by F or Cl, preferably F, Cl, CN or OCH$_3$, very preferably F.

Preferred compounds of formula I, IA, I1-I8, IN and their subformulae are selected from the following preferred embodiments, including any combination thereof:

a and b are 0, 1 or 2, preferably 0 or 1,
a=b=0,
a=b=1,
a=0 and b=1,
the compounds contain exactly two polymerizable groups (represented by the groups P),
the compounds contain exactly three polymerizable groups (represented by the groups P),
P is selected from the group consisting of acrylate, methacrylate and oxetane, very preferably acrylate or methacrylate,
P is methacrylate,
Pg is a hydroxyl group,
all groups Sp are a single bond,
at least one of the groups Sp is a single bond and at least one of the groups Sp is different from a single bond,
Sp, when being different from a single bond, is —(CH$_2$)$_{p1}$—, —(CH$_2$)$_{p2}$—CH═CH—(CH$_2$)$_{p3}$—, —O—(CH$_2$)$_{p1}$—, —O—CO—(CH$_2$)$_{p1}$—, or —CO—O—(CH$_2$)$_{p1}$—, wherein p1 is 2, 3, 4, 5 or 6, p2 and p3 are independently of each other 0, 1, 2 or 3 and the O-atom or CO-group, respectively, is linked to the benzene ring,
Sp is a single bond or denotes is —(CH$_2$)$_{p1}$—, —(CH$_2$)$_{p2}$—CH═CH—(CH$_2$)$_{p3}$—, —O—(CH$_2$)$_{p1}$—, —O—CO—(CH$_2$)$_{p1}$—, or —CO—O—(CH$_2$)$_{p1}$—, wherein p1 is 2, 3, 4, 5 or 6, p2 and p3 are independently of each other 0, 1, 2 or 3 and the O-atom or CO-group, respectively, is linked to the benzene ring, Sp(P)₂ is selected from formulae S1 to S8 and S1a to S3a, $R^b$ denotes P-Sp-, $R^b$ does not denote or contain a polymerizable group, $R^b$ does not denote or contain a polymerizable group and denotes H, F, Cl, CN or straight chain, branched or cyclic alkyl having 1 to 25 C atoms, wherein one or more non-adjacent CH₂-groups are optionally replaced by —O—, —S—, —CO—, —CO—O—, —O—CO—, —O—CO—O— in such a manner that O- and/or S-atoms are not directly connected with each other, and wherein one or more H atoms are each optionally replaced by F or Cl, $R^c$ and $R^d$ are selected from the group consisting of H, CH₃, C₂H₅, C₃H₇, —CH=CH₂, —CH₂—CH=CH₂, very preferably from the group consisting of H, CH₃ and —CH=CH₂, r1, r2, r3 and r4 are 0, r1 and r2 are 1 or 2, preferably 1, one of r1 and r2 is 0, 1 or 2, preferably 0, and the other is 1 or 2, L is selected from the group consisting of F, Cl, CN, alkyl, alkoxy, alkylcarbonyl, alkoxycarbonyl, alkylcarbonyloxy or alkoxycarbonyloxy each having 1 to 6 C atoms, in which one or more H atoms may optionally be replaced by F or Cl, preferably F, Cl, CN or OCH₃, very preferably F, L does not denote P or P-Sp-.

Very preferred compounds of formula I and its subformulae are selected from the following subformulae:

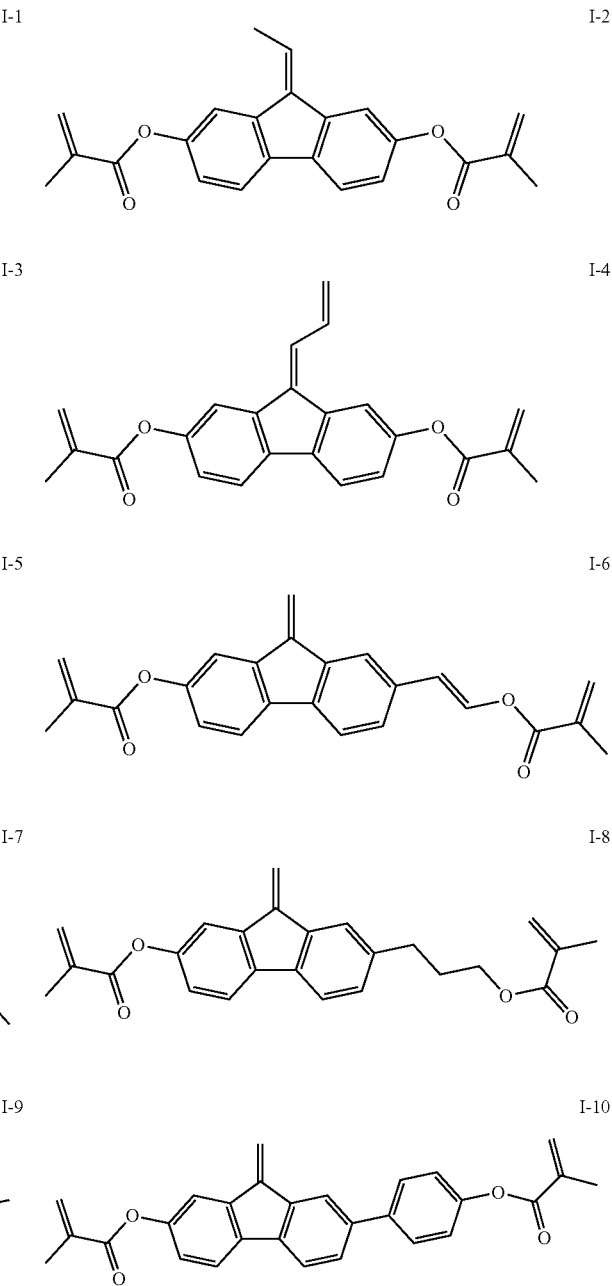

-continued
I-11
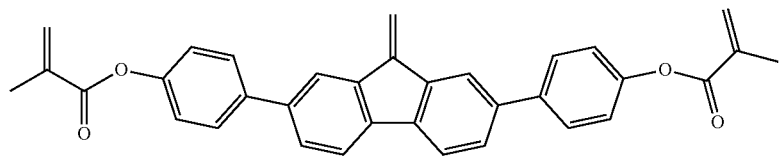
I-12
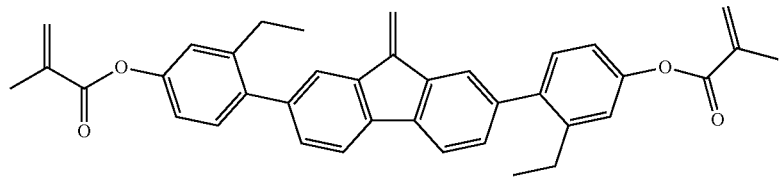
I-13
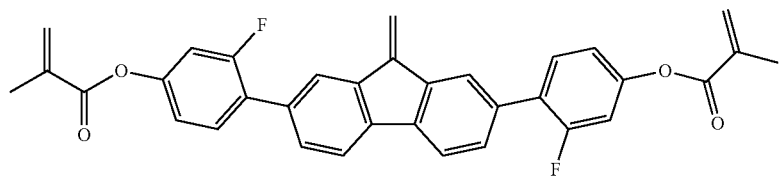
I-14
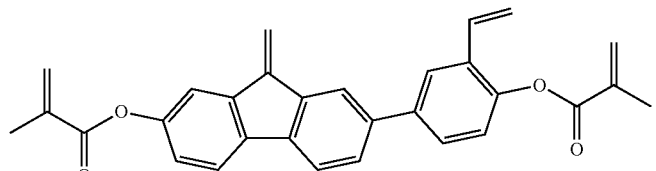
I-15
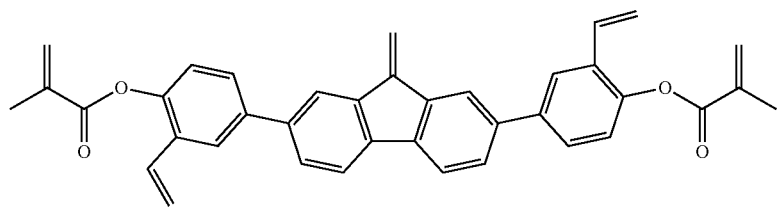
I-16
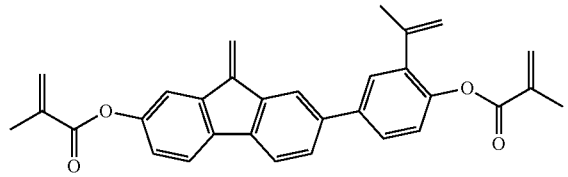
I-17
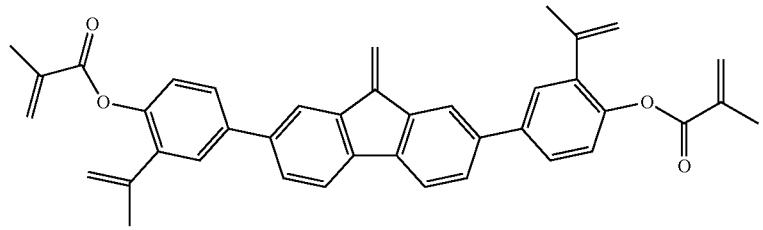
I-18
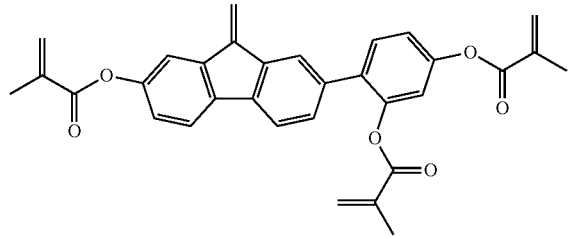

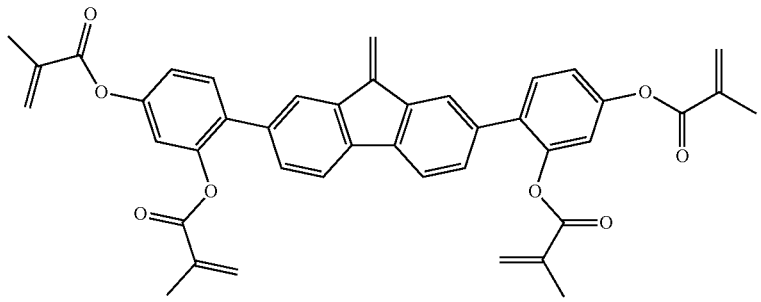

I-19

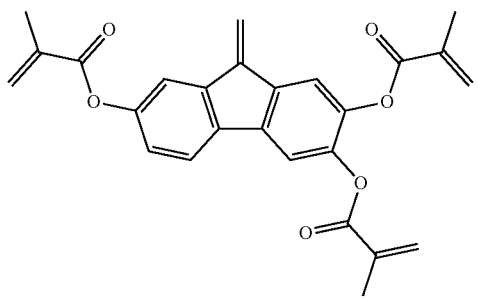

I-20

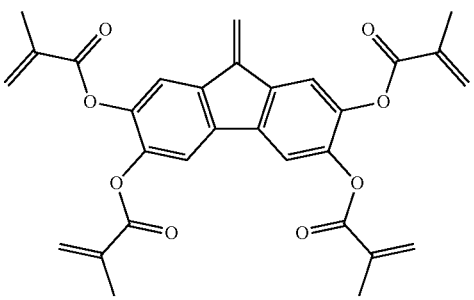

I-21

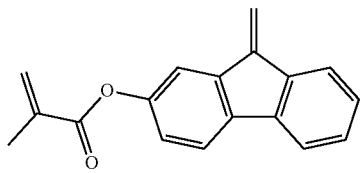

I-22

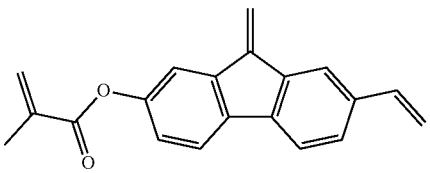

I-23

Further preferred are compounds of formula I-1 to I-23 wherein one, two or all of the methacrylate groups are replaced by acrylate groups.

Preferred compounds of formula IN are those selected from subformulae IA, I1-I8 and I-1 to I-23 wherein each group P and each methacrylate group is replaced by Pg as defined in formula IN, preferably by OH.

Suitable protected hydroxyl groups Pg for use in compounds of formula IN and its subformulae are known to the person skilled in the art. Preferred protecting groups for hydroxyl groups are alkyl, alkoxyalkyl, acyl, alkylsilyl, arylsilyl and arylmethyl groups, especially 2-tetrahydropyranyl, methoxymethyl, methoxyethoxymethyl, acetyl, triisopropylsilyl, tert-butyl-dimethylsilyl or benzyl.

The term "masked hydroxyl group" is understood to mean any functional group that can be chemically converted into a hydroxyl group. Suitable masked hydroxyl groups Pg are known to the person skilled in the art.

The compounds of formula IN are suitable as intermediates for the preparation of compounds of the formula I and its subformulae.

The invention further relates to the use of the compounds of formula IN as intermediates for the preparation of compounds of the formula I and its subformulae.

The compounds and intermediates of the formulae I and IN and sub-formulae thereof can be prepared analogously to processes known to the person skilled in the art and described in standard works of organic chemistry, such as, for example, in Houben-Weyl, Methoden der organischen Chemie [Methods of Organic Chemistry], Thieme-Verlag, Stuttgart.

For example, compounds of formula I can be synthesised by esterification or etherification of the intermediates of formula IN, wherein Pg denotes OH, using corresponding acids, acid derivatives, or halogenated compounds containing a polymerisable group P.

For example, acrylic or methacrylic esters can be prepared by esterification of the corresponding alcohols with acid derivatives like, for example, (meth)acryloyl chloride or (meth)acrylic anhydride in the presence of a base like pyridine or triethyl amine, and 4-(N,N-dimethylamino)pyridine (DMAP). Alternatively the esters can be prepared by esterification of the alcohols with (meth)acrylic acid in the presence of a dehydrating reagent, for example according to Steglich with dicyclohexylcarbodiimide (DCC), N-(3-dimethylaminopropyl)-N'-ethylcarbodiimide (EDC) or N-(3-dimethylaminopropyl)-N'-ethylcarbodiimide hydrochloride and DMAP.

Suitable and preferred synthesis methods for the compounds of formula I and IN are exemplarily illustrated in Scheme 1 below. Further compounds of formula I and IN can be prepared in analogy thereto.

Scheme 1

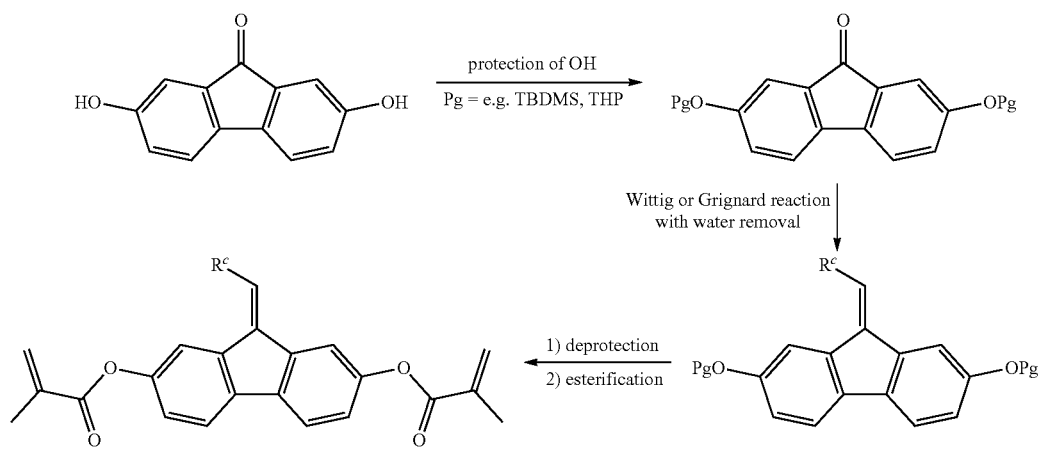

Further suitable synthesis methods are shown in the examples below.

The invention furthermore relates to an LC medium comprising one or more compounds of formula I. Preferably the LC medium comprises one or more polymerisable compounds, at least one of which is a compound of formula I.

Further preferably the LC medium comprises
a polymerisable component A) comprising, preferably consisting of, one or more polymerisable compounds, at least one of which is a compound of formula I, and
a liquid-crystalline component B), hereinafter also referred to as "LC host mixture", comprising, preferably consisting of, one or more mesogenic or liquid-crystalline compounds.

The invention furthermore relates to an LC medium or LC display as described above, wherein the compounds of formula I, or the polymerisable compounds of component A), are polymerised.

The invention furthermore relates to the use of compounds of formula I and LC media as described above and below in PSA displays or polymer stabilised SA-VA or HB-SA-FFS displays, and to an LC display comprising one or more compounds of formula I or an LC medium according to the invention, in particular a PSA display, particularly preferably a PS-VA, PS-OCB, PS-IPS, PS-FFS, PS-UB-FFS, PS-posi-VA, PS-TN display, polymer stabilised SA-VA or polymer stabilised SA-HB-FFS display.

For the production of PSA or polymer stabilised SA displays, the polymerisable compounds contained in the LC medium are polymerised or crosslinked (if one compound contains two or more polymerisable groups) by in-situ polymerisation in the LC medium between the substrates of the LC display, optionally while a voltage is applied to the electrodes.

The structure of the displays according to the invention corresponds to the usual geometry for PSA displays, as described in the prior art cited at the outset. Geometries without protrusions are preferred, in particular those in which, in addition, the electrode on the colour filter side is unstructured and only the electrode on the TFT side has slots. Particularly suitable and preferred electrode structures for PS-VA displays are described, for example, in US 2006/0066793 A1.

A preferred PSA type LC display of the present invention comprises:
a first substrate including a pixel electrode defining pixel areas, the pixel electrode being connected to a switching element disposed in each pixel area and optionally including a micro-slit pattern, and optionally a first alignment layer disposed on the pixel electrode,
a second substrate including a common electrode layer, which may be disposed on the entire portion of the second substrate facing the first substrate, and optionally a second alignment layer,
an LC layer disposed between the first and second substrates and including an LC medium comprising a polymerisable component A and a liquid crystal component B as described above and below, wherein the polymerisable component A may also be polymerised.

The first and/or second alignment layer controls the alignment direction of the LC molecules of the LC layer. For example, in PS-VA displays the alignment layer is selected such that it imparts to the LC molecules homeotropic (or vertical) alignment (i.e. perpendicular to the surface) or tilted alignment. Such an alignment layer may for example comprise a polyimide, which may also be rubbed, or may be prepared by a photoalignment method.

The LC layer with the LC medium can be deposited between the substrates of the display by methods that are conventionally used by display manufacturers, for example the so-called one-drop-filling (ODF) method. The polymerisable component of the LC medium is then polymerised for example by UV photopolymerisation. The polymerisation can be carried out in one step or in two or more steps.

The PSA display may comprise further elements, like a colour filter, a black matrix, a passivation layer, optical retardation layers, transistor elements for addressing the individual pixels, etc., all of which are well known to the person skilled in the art and can be employed without inventive skill.

The electrode structure can be designed by the skilled person depending on the individual display type. For example for PS-VA displays a multi-domain orientation of the LC molecules can be induced by providing electrodes having slits and/or bumps or protrusions in order to create two, four or more different tilt alignment directions.

Upon polymerisation the polymerisable compounds form a crosslinked polymer, which causes a certain tilt angle of the LC molecules in the LC medium. Without wishing to be bound to a specific theory, it is believed that at least a part of the crosslinked polymer, which is formed by the polymerisable compounds, will phase-separate or precipitate from the LC medium and form a polymer layer on the substrates or electrodes, or the alignment layer provided thereon. Microscopic measurement data (like SEM and AFM) have confirmed that at least a part of the formed polymer accumulates at the LC/substrate interface.

The polymerisation can be carried out in one step. It is also possible firstly to carry out the polymerisation, optionally while applying a voltage, in a first step in order to produce a tilt angle, and subsequently, in a second polymerisation step without an applied voltage, to polymerise or crosslink the compounds which have not reacted in the first step ("end curing").

Suitable and preferred polymerisation methods are, for example, thermal or photopolymerisation, preferably photopolymerisation, in particular UV induced photopolymerisation, which can be achieved by exposure of the polymerisable compounds to UV radiation.

Optionally one or more polymerisation initiators are added to the LC medium. Suitable conditions for the polymerisation and suitable types and amounts of initiators are known to the person skilled in the art and are described in the literature. Suitable for free-radical polymerisation are, for example, the commercially available photoinitiators Irgacure651®, Irgacure184®, Irgacure907®, Irgacure369® or Darocure1173® (Ciba AG). If a polymerisation initiator is employed, its proportion is preferably 0.001 to 5% by weight, particularly preferably 0.001 to 1% by weight.

The polymerisable compounds according to the invention are also suitable for polymerisation without an initiator, which is accompanied by considerable advantages, such, for example, lower material costs and in particular less contamination of the LC medium by possible residual amounts of the initiator or degradation products thereof. The polymerisation can thus also be carried out without the addition of an initiator. In a preferred embodiment, the LC medium thus does not contain a polymerisation initiator.

The the LC medium may also comprise one or more stabilisers in order to prevent undesired spontaneous polymerisation of the RMs, for example during storage or transport. Suitable types and amounts of stabilisers are known to the person skilled in the art and are described in the literature. Particularly suitable are, for example, the commercially available stabilisers from the Irganox® series (Ciba AG), such as, for example, Irganox® 1076. If stabilisers are employed, their proportion, based on the total amount of RMs or the polymerisable component (component A), is preferably 10-50,000 ppm, particularly preferably 50-5,000 ppm.

In a preferred embodiment the liquid-crystalline media contain one or more chiral dopants, preferably in a concentration from 0.01 to 1% by weight, very preferably from 0.05 to 0.5% by weight. The chiral dopants are preferably selected from the group consisting of compounds from Table B below, very preferably from the group consisting of R- or S-1011, R- or S-2011, R- or S-3011, R- or S-4011, and R- or S-5011.

In another preferred embodiment the liquid-crystalline media contain a racemate of one or more chiral dopants, which are preferably selected from the chiral dopants mentioned in the previous paragraph.

In another preferred embodiment of the present invention the liquid-crystalline media contain one or more further stabilisers, preferably selected from the the group consisting of the following formulae

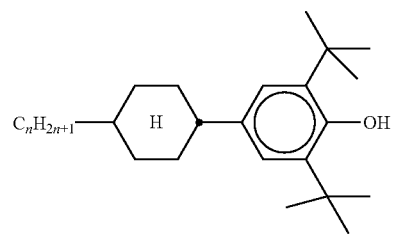

S1

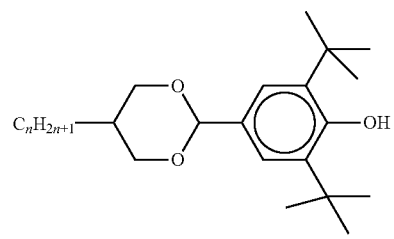

S2

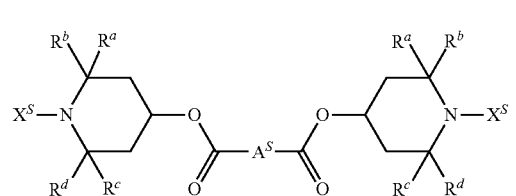

S3 wherein the individual radicals, independently of each other and on each occurrence identically or differently, have the following meanings $R^{a-d}$ straight-chain or branched alkyl with 1 to 10, preferably 1 to 6, very preferably 1 to 4 C atoms, most preferably methyl, $X^S$ H, $CH_3$, OH or O—, $A^S$ straight-chain, branched or cyclic alkylene with 1 to 20 C atoms which is optionally substituted, n an integer from 1 to 6, preferably 3.

Preferred stabilisers of formula S3 are selected from formula S3A

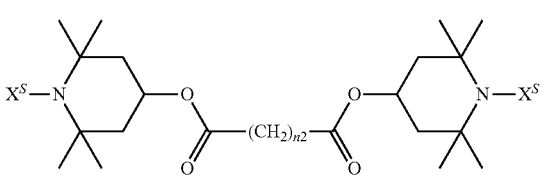

S3A wherein n2 is an integer from 1 to 12, and wherein one or more H atoms in the group $(CH_2)_{n2}$ are optionally replaced by methyl, ethyl, propyl, butyl, pentyl or hexyl.

Very preferred stabilisers are selected from the group consisting of the following formulae
S1-1
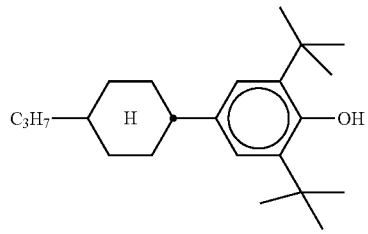
S2-1
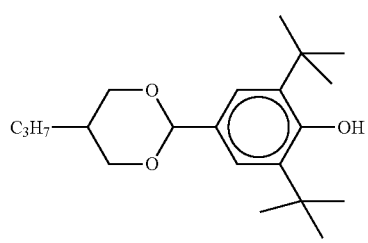
S3-1
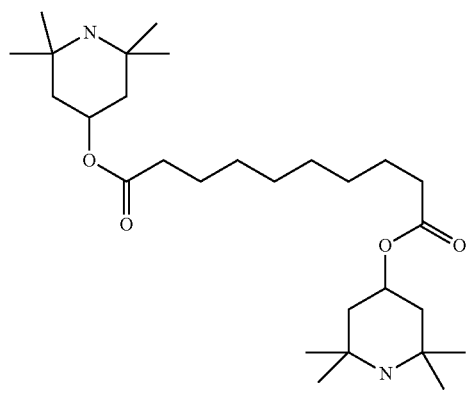
S3-2
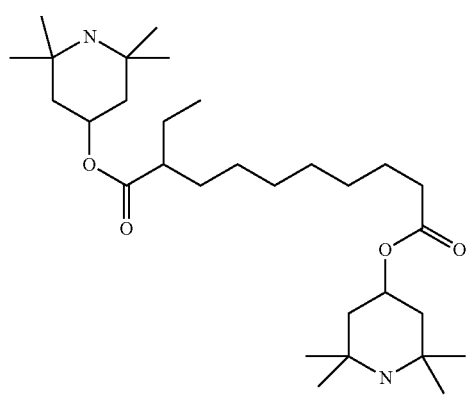
S3-3
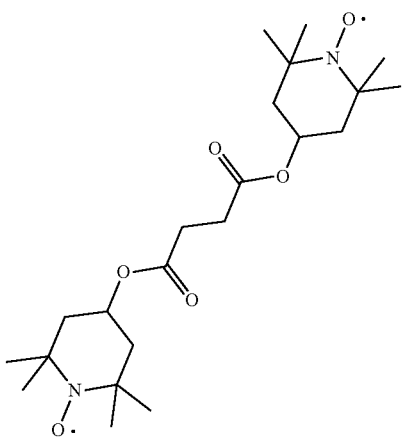
S3-4
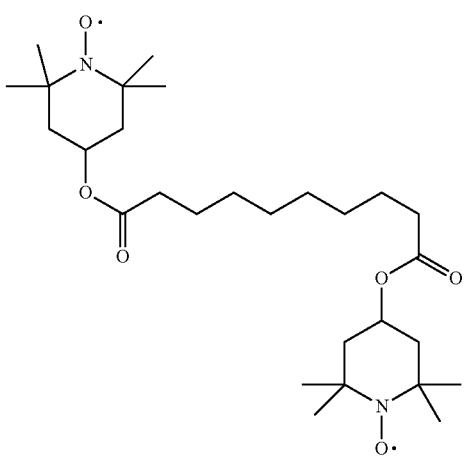
S3-5
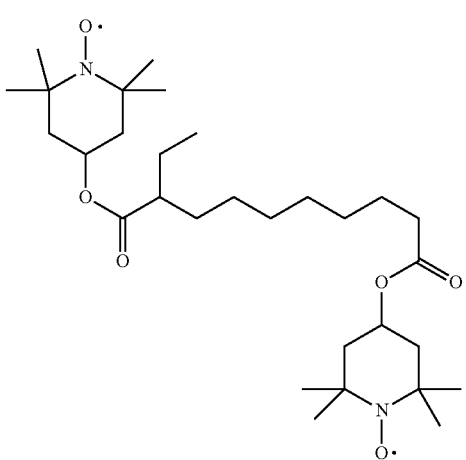

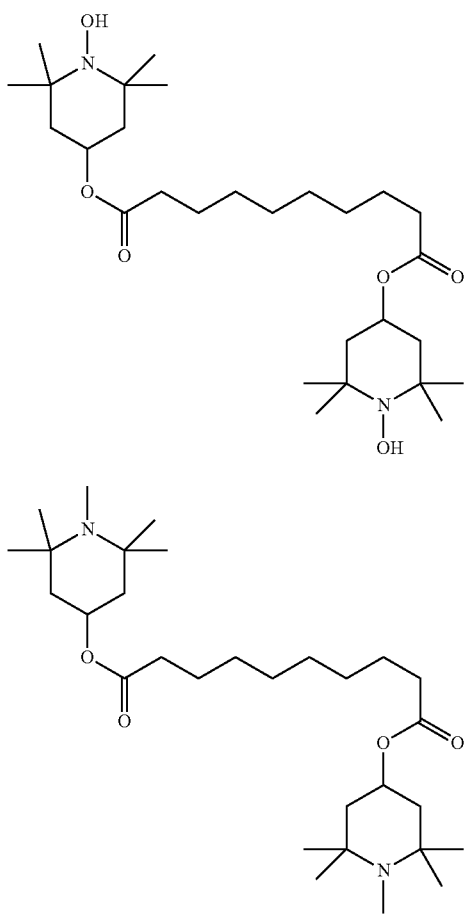

S3-6

S3-7

In a preferred embodiment the liquid-crystalline medium comprises one or more stabilisers selected from the group consisting of formulae S1-1, S2-1, S3-1, S3-1 and S3-3.

In a preferred embodiment the liquid-crystalline medium comprises one or more stabilisers selected from Table C below.

Preferably the proportion of stabilisers, like those of formula $S_1$-$S_3$, in the liquid-crystalline medium is from 10 to 500 ppm, very preferably from 20 to 100 ppm.

In another preferred embodiment the LC medium according to the present invention contains a self-aligning (SA) additive, preferably in a concentration of 0.1 to 2.5%.

In another preferred embodiment the LC medium according to the present invention contains a self-aligning (SA) additive, preferably in a concentration of 0.1 to 2.5%. An LC medium according to this preferred embodiment is especially suitable for use in SA-VA and SA-HB-FFS displays.

In a preferred embodiment the SA-VA or SA-HB-FFS display according to the present invention does not contain a polyimide alignment layer. In another preferred embodiment the SA-VA or SA-HB-FFS display according to preferred embodiment contains a polyimide alignment layer.

Preferred SA additives for use in this preferred embodiment are selected from compounds comprising a mesogenic group and a straight-chain or branched alkyl side chain that is terminated with one or more polar anchor groups selected from hydroxy, carboxy, amino or thiol groups.

Further preferred SA additives contain one or more polymerisable groups which are attached, optionally via spacer groups, to the mesogenic group. These polymerisable SA additives can be polymerised in the LC medium under similar conditions as applied for the RMs in the PSA process.

Suitable SA additives to induce homeotropic alignment, especially for use in SA-VA mode displays, are disclosed for example in US 2013/0182202 A1, US 2014/0838581 A1, US 2015/0166890 A1 and US 2015/0252265 A1.

In another preferred embodiment the LC medium according to the present invention comprises one or more SA additives selected from formula A $$\text{MES-R}^a \qquad \qquad \text{II}$$

wherein the individual radicals, independently of each other and on each occurrence identically or differently, have the following meanings MES a calamitic mesogenic group comprising two or more rings, which are connected directly or indirectly to each other or which are condensed to each other, which are optionally substituted and which mesogenic group is optionally substituted additionally by one or more polymerizable groups, which are connected to MES directly or via a spacer, and $R^a$ a polar anchor group, residing in a terminal position of the calamitic mesogenic group MES which comprises at least one carbon atom and at least one group selected from —OH, —SH, —COOH, —CHO or primary or secondary amine function, preferably one or two OH groups, and which optionally contains one or two polymerizable groups P, P one of the meanings given in formula I or one of the preferred meanings given above and below.

Self-alignment additives containing a polymerisable group can be polymerised in the LC medium under similar conditions as applied for the RMs in the PSA process.

Preferably in the self-alignment additives of formula II the group MES contains two or more rings which are selected from aromatic, alicyclic and heterocyclic groups as defined above, including their preferred meanings. Most preferred rings are 1,4-phenylene, which may be substituted by $L^{12}$ and P-Sp- as defined below, or 1,4-cyclohexylene.

In formula II the group MES preferably is a group selected from the following structures, which may be mono- or polysubstituted by any of the substituents $L^{12}$ and P-Sp-:

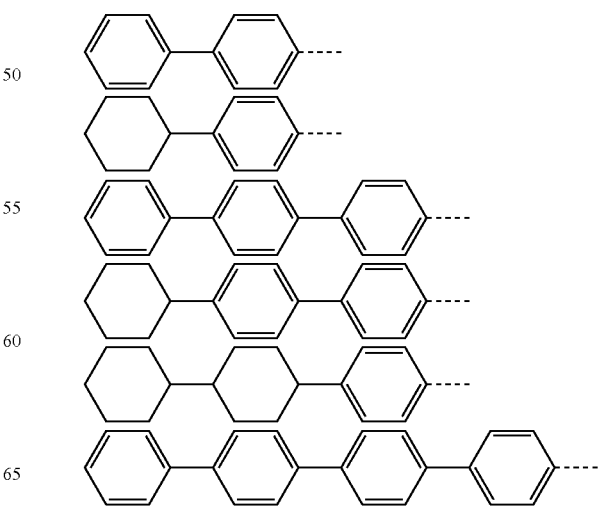

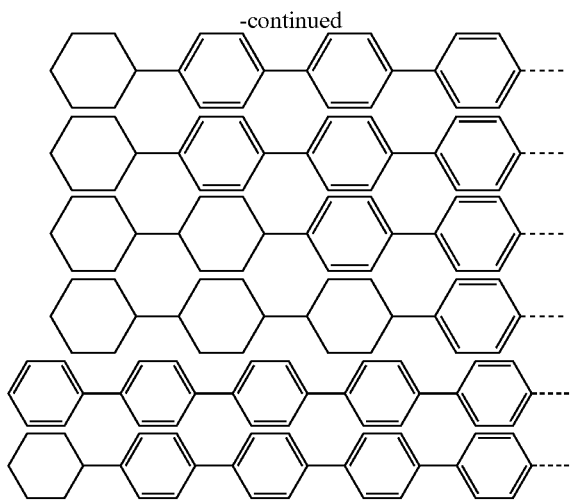

wherein $L^{12}$ in each case, independently of one another, denotes F, Cl, Br, I, —CN, —NO$_2$, —NCO, —NCS, —OCN, —SCN, —C(=O)N(R$^0$)$_2$, —C(=O)R$^0$, optionally substituted silyl, optionally substituted aryl or cycloalkyl having 3 to 20 C atoms, or straight-chain or branched alkyl, alkoxy, alkylcarbonyl, alkoxycarbonyl, alkylcarbonyloxy or alkoxycarbonyloxy having up to 25 C atoms, in which, in addition, one or more H atoms may each be replaced by F or Cl, P denotes a polymerizable group, and Sp denotes a spacer group or a single bond, and the dotted line indicates the attachment point of the polar anchor group R$^a$.

Preferably the self-alignment additive for vertical alignment is selected of formula IIa $$R^{21}—[A^{22}—Z^{22}]_{m2}—A^{22}—R^a \quad \text{IIa}$$

in which $A^{21}$, $A^{22}$ each, independently of one another, denote an aromatic, heteroaromatic, alicyclic or heterocyclic group, which may also contain fused rings, and which may also be mono- or polysubstituted by a group $L^{12}$ or -Sp-P, $L^{12}$ in each case, independently of one another, denotes F, Cl, Br, I, —CN, —NO$_2$, —NCO, —NCS, —OCN, —SCN, —C(=O)N(R$^0$)$_2$, —C(=O)R$^0$, optionally substituted silyl, optionally substituted aryl or cycloalkyl having 3 to 20 C atoms, or straight-chain or branched alkyl, alkoxy, alkylcarbonyl, alkoxycarbonyl, alkyl-carbonyloxy or alkoxycarbonyloxy having up to 25 C atoms, in which, in addition, one or more H atoms may each be replaced by F or Cl, P denotes a polymerizable group, Sp denotes a spacer group or a single bond, $Z^{22}$ in each case, independently of one another, denotes a single bond, —O—, —S—, —CO—, —CO—O—, —OCO—, —O—CO—O—, —OCH$_2$—, —CH$_2$O—, —SCH$_2$—, —CH$_2$S—, —CF$_2$O—, —COF$_2$—, —CF$_2$S—, —SCF$_2$—, —(CH$_2$)$_{n1}$—, —CF$_2$CH$_2$—, —CH$_2$CF$_2$—, —(CF$_2$)$_{n1}$—, —CH=CH—, —CF=CF—, —C≡C—, —CH=CH—COO—, —OCO—CH=CH—, —(CR$^0$R$^{00}$)$_{n1}$—, —CH(—Sp-P)—, —CH$_2$CH(—Sp-P)—, or —CH(—Sp-P)CH(-Sp-P)-, n1 denotes 1, 2, 3 or 4, m2 denotes 1, 2, 3, 4, 5 or 6, $R^0$ in each case, independently of one another, denotes alkyl having 1 to 12 C atoms, $R^{00}$ in each case, independently of one another, denotes H or alkyl having 1 to 12 C atoms, $R^{21}$ independently of one another, denotes H, halogen, straight-chain, branched or cyclic alkyl having 1 to 25 C atoms, in which, in addition, one or more non-adjacent CH$_2$ groups may each be replaced by —O—, —S—, —CO—, —CO—O—, —O—CO—, or —O—CO—O— in such a way that O and/or S atoms are not linked directly to one another and in which, in addition, one or more H atoms may each be replaced by F or Cl, or a group P-Sp-, and $R^a$ is defined as above, preferably denotes a polar anchor group further defined by having at least one group selected from —OH, —NH$_2$, NHR$^{22}$, C(O)OH and —CHO, where R$^{22}$ denotes alkyl having 1 to 12 C atoms.

In another preferred embodiment an LC medium or a polymer stabilised SA-VA display according to the present invention contains one or more self-alignment additives selected from Table E below.

The anchor group $R^a$ of the self-alignment additive is more preferably defined as $R^a$ an anchor group of the formula

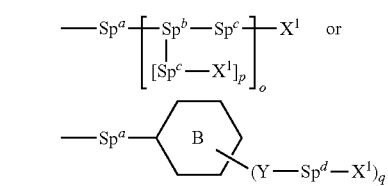

wherein p denotes 1 or 2, q denotes 2 or 3,

B denotes a substituted or unsubstituted ring system or condensed ring system, preferably a ring system selected from benzene, pyridine, cyclohexane, dioxane or tetrahydropyran, Y on each occurrence identically or differently denotes —O—, —S—, —C(O)—, —C(O)O—, —OC(O)—, —NR$^{11}$— or a single bond, o denotes 0 or 1, $X^1$ on each occurrence identically or differently denotes H, alkyl, fluoroalkyl, OH, NH$_2$, NHR$^{22}$, NR$^{22}$$_2$, OR$^{22}$, C(O)OH, or —CHO, where at least one group $X^1$ denotes a radical selected from —OH, —NH$_2$, NHR$^{22}$, C(O)OH and —CHO, $R^{22}$ denotes alkyl having 1 to 12 C atoms, Sp$^a$, Sp$^c$, Sp$^d$ each, independently of one another, denote a spacer group or a single bond, and Sp$^b$ denotes a tri- or tetravalent group, preferably CH, N or C.

Formulae II and IIa optionally include polymerizable compounds. Within this disclosure the "medium comprising a compound of formula II/IIa" refers to both, the medium comprising the compound of formula II/IIa and, alternatively, to the medium comprising the compound in its polymerized form.

For the case the one or more compounds of formula II are substituted with one or more polymerizable groups (-Sp-P), the LC medium according to the invention comprises a polymerisable component A) comprising, preferably consisting of, polymerisable compounds, at least one of which is a compound of formula I and at least one of which is of formula II, a liquid-crystalline component B), hereinafter also referred to as "LC host mixture", comprising, preferably consisting of, one or more mesogenic or liquid-crystalline compounds.

In the compounds of the formulae IIa, and subformulae thereof, $Z^{22}$ preferably denotes a single bond, —$C_2H_4$—, —$CF_2O$— or —$CH_2O$—. In a specifically preferred embodiment $Z^{22}$ denotes a single bond.

In the compounds of the formula IIa, the group $L^{12}$, in each case independently, preferably denotes F or alkyl, preferably $CH_3$, $C_2H_5$ or $C_3H_7$.

Preferred compounds of the formula IIa are illustrated by the following sub-formulae II-A to II-D

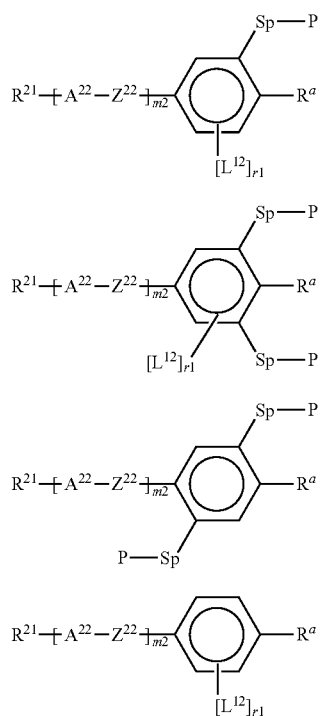

in which $R^{21}$, $R^a$, $A^{22}$, $Z^{22}$, Sp, P and $L^{12}$ have the meanings as defined for formula IIa above,
m2 independently is 1, 2 or 3, and
r1 independently is 0, 1, 2, 3, or 4, preferably 0, 1 or 2.

In the compounds of the formulae II-A to II-D, $L^{12}$ preferably denotes F or alkyl, preferably $CH_3$, $C_2H_5$ or $C_3H_7$.

In a preferred embodiment r1 denotes 0.

The polymerizable group P of formulae II, IIa, II-A to II-D preferably is methacrylate, acrylate or another substituted acrylate, most preferably methacrylate.

In the above and below formulae IIa or II-A to II-D and their subformulae $Z^{22}$ preferably independently denotes a single bond or —$CH_2CH_2$—, and very particularly a single bond.

$R^a$ denotes preferably

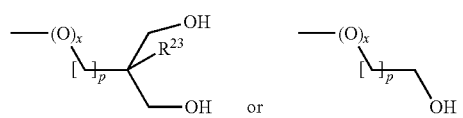

wherein
p is 1, 2, 3, 4, 5 or 6,
x is 1 or 0, preferably 1, and
$R^{23}$ is H, methyl, ethyl, n-propyl, i-propyl, n-butyl, tert-butyl, n-pentyl, or —$CH_2CH_2$-tert-butyl
$R^a$ denotes very preferably —$O(CH_2)_2$—OH, —$O(CH_2)_3$—OH,

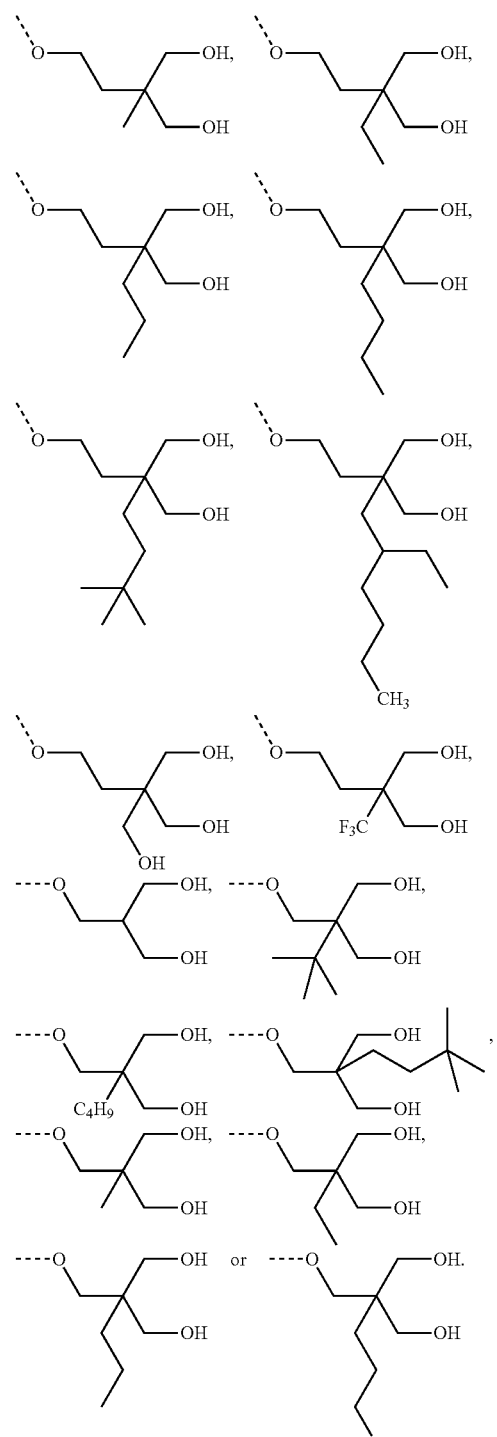

In the formula IIa and in the sub-formulae of the formula IIa $R^{21}$ preferably denotes a straight-chain alkyl or branched alkyl radical having 1-8 C atoms, preferably a straight-chain alkyl radical. In the compounds of the formulae IIa or II-A to II-D $R^1$ more preferably denotes $CH_3$, $C_2H_5$, n-$C_3H_7$, n-$C_4H_9$, n-$C_5H_{11}$, n-$C_6H_{13}$ or $CH_2CH(C_2H_5)C_4H_9$. $R^{21}$ furthermore may denote alkenyloxy, in particular $OCH_2CH=CH_2$, $OCH_2CH=CHCH_3$, $OCH_2CH=CHC_2H_5$, or alkoxy, in particular $OC_2H_5$, $OC_3H_7$, $OC_4H_9$, $OC_5H_{11}$ and $OC_6H_{13}$. Particularly preferable $R^{21}$ denotes a straight chain alkyl residue, preferably $C_5H_{11}$.

In a preferred embodiment of the invention the LC medium comprises a compound of formula II, which is polymerizable.

In another preferred embodiment an LC medium or a polymer stabilised SA-VA or SA-FFS display according to the present invention contains one or more self-aligning additives selected from Table E below.

In another preferred embodiment the LC medium according to the present invention contains one or more SA additives, preferably selected from formula II or its subformulae or selected from Table E, in a concentration from 0.1 to 5%, very preferably from 0.2 to 3%, most preferably from 0.2 to 1.5%.

The polymerisable compounds of formula I do in particular show good UV absorption in, and are therefore especially suitable for, a process of preparing a PSA display including one or more of the following features:
  the polymerisable medium is exposed to UV light in the display in a 2-step process, including a first UV exposure step ("UV-1 step") to generate the tilt angle, and a second UV exposure step ("UV-2 step") to finish polymerization,
  the polymerisable medium is exposed to UV light in the display generated by an energy-saving UV lamp (also known as "green UV lamps"). These lamps are characterized by a relative low intensity (1/100-1/10 of a conventional UV1 lamp) in their absorption spectra from 300-380 nm, and are preferably used in the UV2 step, but are optionally also used in the UV1 step when avoiding high intensity is necessary for the process.
  the polymerisable medium is exposed to UV light in the display generated by a UV lamp with a radiation spectrum that is shifted to longer wavelengths, preferably 340 nm or more, to avoid short UV light exposure in the PS-VA process.

Both using lower intensity and a UV shift to longer wavelengths protect the organic layer against damage that may be caused by the UV light.

A preferred embodiment of the present invention relates to a process for preparing a PSA display as described above and below, comprising one or more of the following features:
  the polymerisable LC medium is exposed to UV light in a 2-step process, including a first UV exposure step ("UV-1 step") to generate the tilt angle, and a second UV exposure step ("UV-2 step") to finish polymerization,
  the polymerisable LC medium is exposed to UV light generated by a UV lamp having an intensity of from 0.5 mW/cm² to 10 mW/cm² in the wavelength range from 300-380 nm, preferably used in the UV2 step, and optionally also in the UV1 step,
  the polymerisable LC medium is exposed to UV light having a wavelength of 340 nm or more, and preferably 400 nm or less.

This preferred process can be carried out for example by using the desired UV lamps or by using a band pass filter and/or a cut-off filter, which are substantially transmissive for UV light with the respective desired wavelength(s) and are substantially blocking light with the respective undesired wavelengths. For example, when irradiation with UV light of wavelengths λ of 300-400 nm is desired, UV exposure can be carried out using a wide band pass filter being substantially transmissive for wavelengths 300 nm<λ<400 nm. When irradiation with UV light of wavelength λ of more than 340 nm is desired, UV exposure can be carried out using a cut-off filter being substantially transmissive for wavelengths λ>340 nm.

"Substantially transmissive" means that the filter transmits a substantial part, preferably at least 50% of the intensity, of incident light of the desired wavelength(s). "Substantially blocking" means that the filter does not transmit a substantial part, preferably at least 50% of the intensity, of incident light of the undesired wavelengths. "Desired (undesired) wavelength" e.g. in case of a band pass filter means the wavelengths inside (outside) the given range of λ, and in case of a cut-off filter means the wavelengths above (below) the given value of λ.

This preferred process enables the manufacture of displays by using longer UV wavelengths, thereby reducing or even avoiding the hazardous and damaging effects of short UV light components.

UV radiation energy is in general from 6 to 100 J, depending on the production process conditions.

Preferably the LC medium according to the present invention does essentially consist of a polymerisable component A), or one or more polymerisable compounds of formula I, and an LC component B), or LC host mixture, as described above and below. However, the LC medium may additionally comprise one or more further components or additives, preferably selected from the list including but not limited to co-monomers, chiral dopants, polymerisation initiators, inhibitors, stabilizers, surfactants, wetting agents, lubricating agents, dispersing agents, hydrophobing agents, adhesive agents, flow improvers, defoaming agents, deaerators, diluents, reactive diluents, auxiliaries, colourants, dyes, pigments and nanoparticles.

Particular preference is given to LC media comprising one, two or three polymerisable compounds of formula I.

Preference is furthermore given to LC media in which the polymerisable component A) comprises exclusively polymerisable compounds of formula I.

Preference is furthermore given to LC media in which the liquid-crystalline component B) or the LC host mixture has a nematic LC phase, and preferably has no chiral liquid crystal phase.

The LC component B), or LC host mixture, is preferably a nematic LC mixture.

Preference is furthermore given to achiral compounds of formula I, and to LC media in which the compounds of component A and/or B are selected exclusively from the group consisting of achiral compounds.

Preferably the proportion of the polymerisable component A) in the LC medium is from >0 to <5%, very preferably from >0 to <3%, more preferably from 0.01 to 2.0, especially for use in SA-VA displays. In another preferred embodiment the proportion of the polymerisable component A) in the LC medium is from 0.01 to 1.0%, most preferably from 0.01 to 0.5%, especially for use in PSA displays.

Preferably the proportion of compounds of formula I in the LC medium is from >0 to <5%, very preferably from >0 to <3%, more preferably from 0.01 to 2.0, especially for use in SA-VA displays. In another preferred embodiment the proportion of the compounds of formula I in the LC medium is from 0.01 to 1.0%, most preferably from 0.01 to 0.5%, especially for use in PSA displays.

Preferably the proportion of the LC component B) in the LC medium is from 95 to <100%, very preferably from 96.5 to <100%, most preferably from 98 to <100%. In another preferred embodiment the proportion of the LC component B) in the LC medium is from 99 to <100%.

In a preferred embodiment the polymerisable compounds of the polymerisable component B) are exclusively selected from formula I.

In another preferred embodiment the polymerisable component B) comprises, in addition to the compounds of formula I, one or more further polymerisable compounds ("co-monomers"), preferably selected from RMs.

Suitable and preferred mesogenic comonomers are selected from the following formulae:

M1
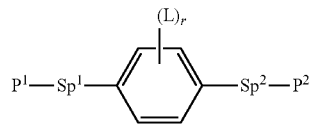

M2
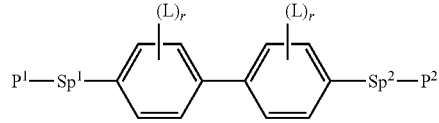

M3
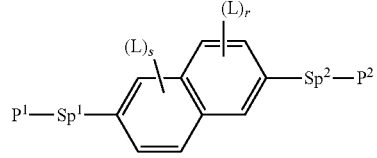

M4
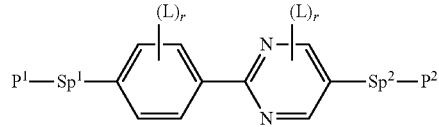

M5
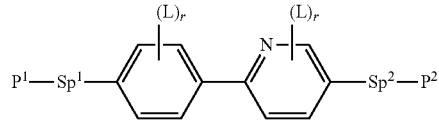

M6
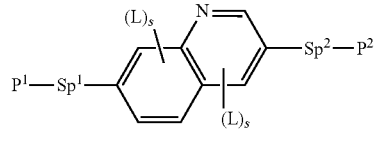

M7
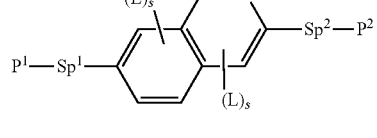

M8
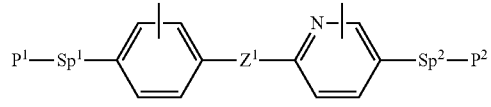

M9
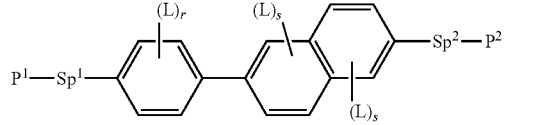

M10
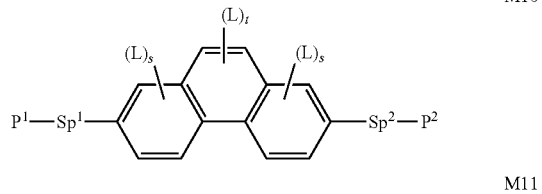

M11
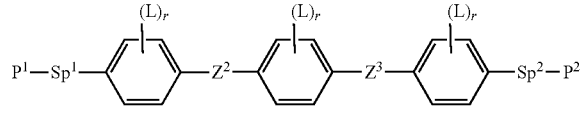

M12
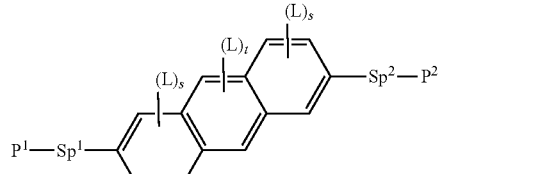

M13
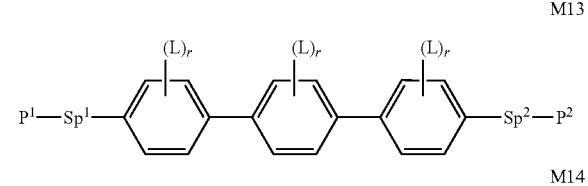

M14
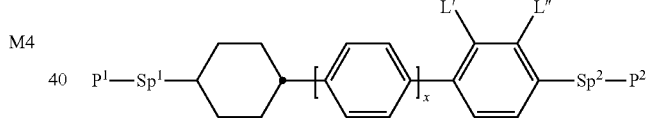

M15
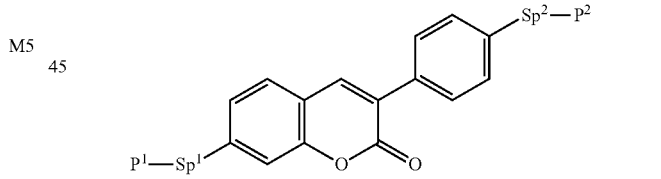

M16
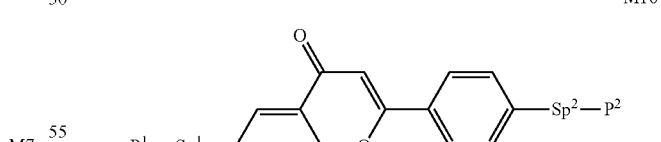

M17
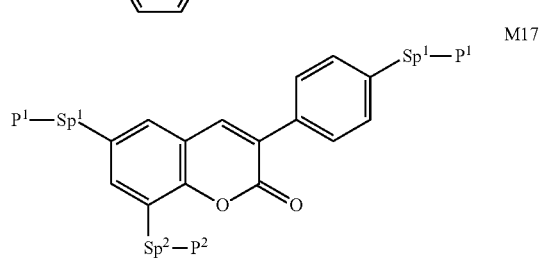

M18
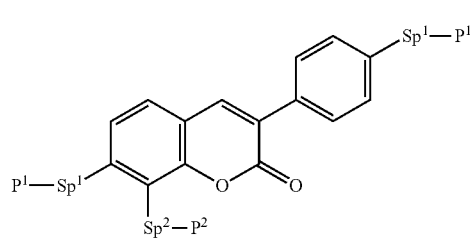
M19
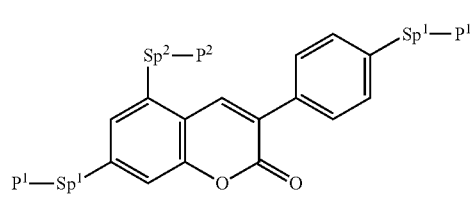
M20
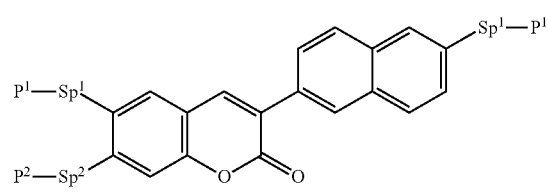
M21
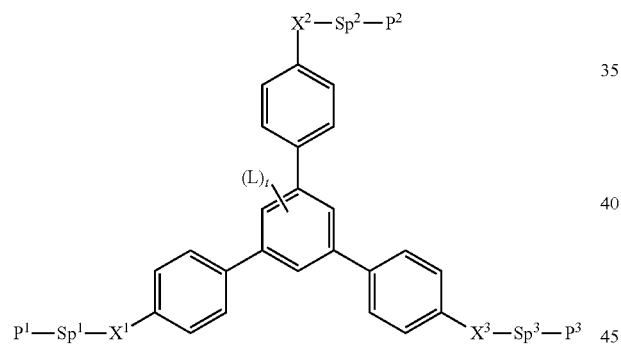
M22
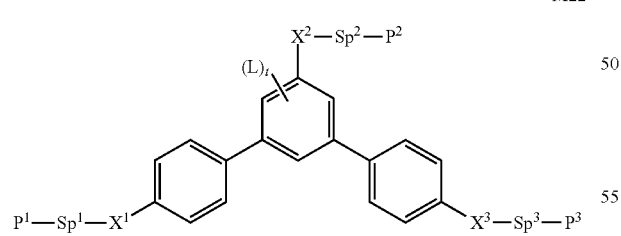
M23
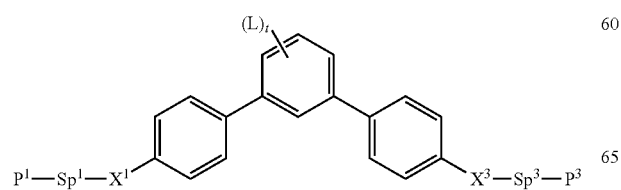
M24
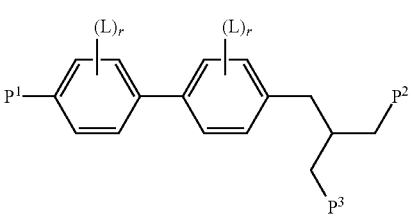
M25
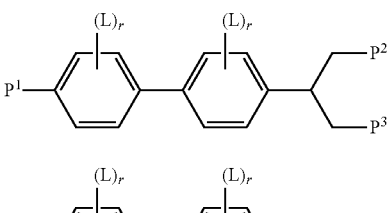
M26
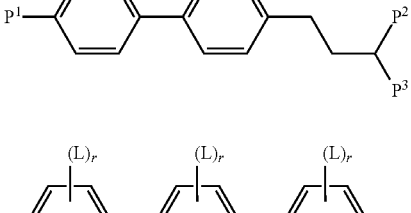
M27
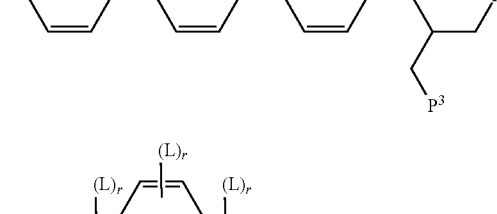
M28
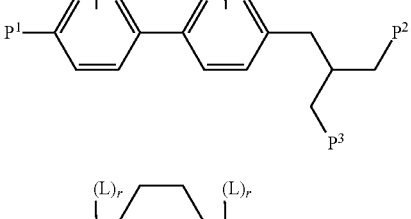
M29
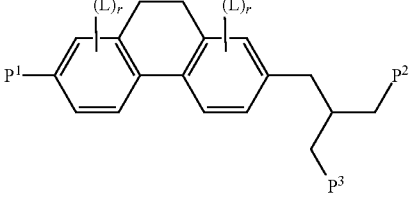
M30
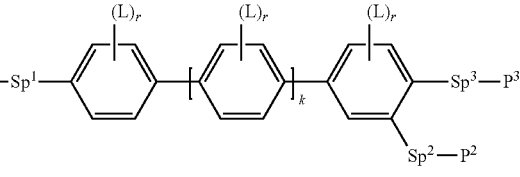
M31
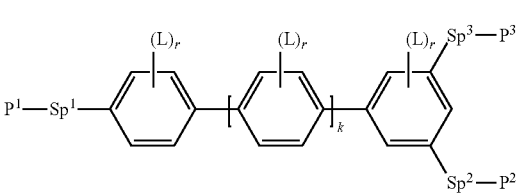

M32

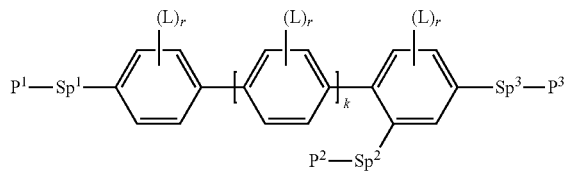

in which the individual radicals have the following meanings:

$P^1$, $P^2$ and $P^3$ each, independently of one another, denote an acrylate or methacrylate group, $Sp^1$, $Sp^2$ and $Sp^3$ each, independently of one another, denote a single bond or a spacer group having one of the meanings indicated above and below for Sp, and particularly preferably denote $-(CH_2)_{p1}-$, $-(CH_2)_{p1}-O-$, $-(CH_2)_{p1}-CO-O-$, $-(CH_2)_{p1}-O-CO-$ or $-(CH_2)_{p1}-O-CO-O-$, in which p1 is an integer from 1 to 12, where, in addition, one or more of the radicals $P^1$-$Sp^1$-, $P^2$-$Sp^2$- and $P^3$-$Sp^3$- may denote $R^{aa}$, with the proviso that at least one of the radicals $P^2$-$Sp^2$-, $P^1$-$Sp^1$-, and $P^3$-$Sp^3$- present is different from $R^{aa}$, $R^{aa}$ denotes H, F, Cl, CN or straight-chain or branched alkyl having 1 to 25 C atoms, in which, in addition, one or more non-adjacent $CH_2$ groups may each be replaced, independently of one another, by $C(R^0)=C(R^{00})-$, $-C\equiv C-$, $-N(R^0)-$, $-O-$, $-S-$, $-CO-$, $-CO-O-$, $-O-CO-$, $-O-CO-O-$ in such a way that O and/or S atoms are not linked directly to one another, and in which, in addition, one or more H atoms may be replaced by F, Cl, CN or $P^1$-$Sp^1$-, particularly preferably straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms (where the alkenyl and alkynyl radicals have at least two C atoms and the branched radicals have at least three C atoms), $R^0$, $R^{00}$ each, independently of one another and identically or differently on each occurrence, denote H or alkyl having 1 to 12 C atoms, $R^y$ and $R^z$ each, independently of one another, denote H, F, $CH_3$ or $CF_3$, $X^1$, $X^2$ and $X^3$ each, independently of one another, denote $-CO-O-$, $-O-CO-$ or a single bond, $Z^1$ denotes $-O-$, $-CO-$, $-C(R^yR^z)-$ or $-CF_2CF_2-$, $Z^2$ and $Z^3$ each, independently of one another, denote $-CO-O-$, $-O-CO-$, $-CH_2O-$, $-OCH_2-$, $-CF_2O-$, $-OCF_2-$ or $-(CH_2)_n-$, where n is 2, 3 or 4, L on each occurrence, identically or differently, denotes F, Cl, CN or straight-chain or branched, optionally mono- or poly-fluorinated alkyl, alkoxy, alkenyl, alkynyl, alkylcarbonyl, alkoxycarbonyl, alkylcarbonyloxy or alkoxycarbonyloxy having 1 to 12 C atoms, preferably F, L' and L" each, independently of one another, denote H, F or Cl, k denotes 0 or 1, r denotes 0, 1, 2, 3 or 4, s denotes 0, 1 or 2, t denotes 0, 1 or 2, x denotes 0 or 1.

Especially preferred are compounds of formulae M2, M13, M17, M22, M23, M24, M30, M31 and M32.

Further preferred are trireactive compounds M15 to M30, in particular M17, M18, M19, M22, M23, M24, M25, M26, M30, M31 and M32.

In another preferred embodiment the polymerisable component B) comprises, in addition to the compounds of formula I, one or more comonomers selected from formula M2 and M13 wherein at least one r is 1 and L is an alkenyl group with 2 to 7 C atoms.

In another preferred embodiment the the polymerisable component B) comprises, in addition to the compounds of formula I, one or more co-monomers selected from Table D below.

In the compounds of formulae M1 to M32 the group

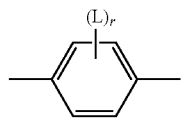

is preferably

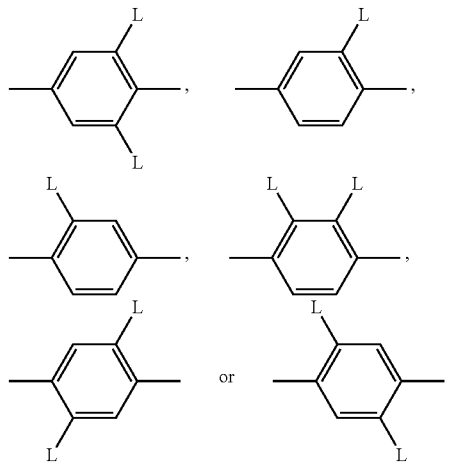

wherein L on each occurrence, identically or differently, has one of the meanings given above or below, and is preferably F, Cl, CN, $NO_2$, $CH_3$, $C_2H_5$, $C(CH_3)_3$, $CH(CH_3)_2$, $CH_2CH(CH_3)C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$ or P-Sp-, very preferably F, Cl, CN, $CH_3$, $C_2H_5$, $OCH_3$, $COCH_3$, $OCF_3$ or P-Sp-, more preferably F, Cl, $CH_3$, $OCH_3$, $COCH_3$ oder $OCF_3$, especially F or $CH_3$.

Besides the polymerisable compounds described above, the LC media for use in the LC displays according to the invention comprise an LC mixture ("host mixture") comprising one or more, preferably two or more LC compounds which are selected from low-molecular-weight compounds that are unpolymerisable. These LC compounds are selected such that they stable and/or unreactive to a polymerisation reaction under the conditions applied to the polymerisation of the polymerisable compounds.

In principle, any LC mixture which is suitable for use in conventional displays is suitable as host mixture. Suitable LC mixtures are known to the person skilled in the art and are described in the literature, for example mixtures in VA displays in EP 1 378 557 A1 and mixtures for OCB displays in EP 1 306 418 A1 and DE 102 24 046 A1.

The polymerisable compounds of formula I are especially suitable for use in an LC host mixture that comprises one or more mesogenic or LC compounds comprising an alkenyl group (hereinafter also referred to as "alkenyl compounds"), wherein said alkenyl group is stable to a polymerisation reaction under the conditions used for polymerisation of the compounds of formula I and of the other polymerisable compounds contained in the LC medium. Compared to RMs known from prior art the compounds of formula I do in such an LC host mixture exhibit improved properties, like solubility, reactivity or capability of generating a tilt angle.

Thus, in addition to the polymerisable compounds of formula I, the LC medium according to the present invention comprises one or more mesogenic or liquid crystalline compounds comprising an alkenyl group, ("alkenyl compound"), where this alkenyl group is preferably stable to a polymerisation reaction under the conditions used for the polymerisation of the polymerisable compounds of formula I or of the other polymerisable compounds contained in the LC medium.

The alkenyl groups in the alkenyl compounds are preferably selected from straight-chain, branched or cyclic alkenyl, in particular having 2 to 25 C atoms, particularly preferably having 2 to 12 C atoms, in which, in addition, one or more non-adjacent CH$_2$ groups may be replaced by —O—, —S—, —CO—, —CO—O—, —O—CO—, —O—CO—O— in such a way that O and/or S atoms are not linked directly to one another, and in which, in addition, one or more H atoms may be replaced by F and/or Cl.

Preferred alkenyl groups are straight-chain alkenyl having 2 to 7 C atoms and cyclohexenyl, in particular ethenyl, propenyl, butenyl, pentenyl, hexenyl, heptenyl, 1,4-cyclohexen-1-yl and 1,4-cyclohexen-3-yl.

The concentration of compounds containing an alkenyl group in the LC host mixture (i.e. without any polymerisable compounds) is preferably from 5% to 100%, very preferably from 20% to 60%.

Especially preferred are LC mixtures containing 1 to 5, preferably 1, 2 or 3 compounds having an alkenyl group.

The mesogenic and LC compounds containing an alkenyl group are preferably selected from formulae AN and AY as defined below.

Besides the polymerisable component A) as described above, the LC media according to the present invention comprise an LC component B), or LC host mixture, comprising one or more, preferably two or more LC compounds which are selected from low-molecular-weight compounds that are unpolymerisable. These LC compounds are selected such that they stable and/or unreactive to a polymerisation reaction under the conditions applied to the polymerisation of the polymerisable compounds.

In a first preferred embodiment the LC medium contains an LC component B), or LC host mixture, based on compounds with negative dielectric anisotropy. Such LC media are especially suitable for use in PS-VA, SA-VA and PS-UB-FFS displays. Particularly preferred embodiments of such an LC medium are those of sections a)-z3) below:

a) LC medium wherein the component B) or LC host mixture comprises one or more compounds selected from formulae CY and PY:

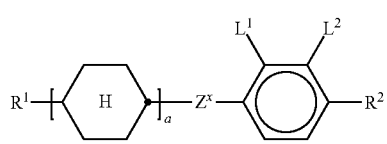
CY

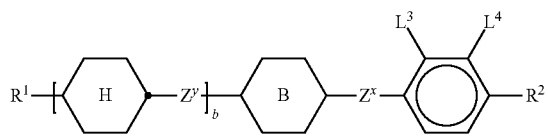
PY wherein
a denotes 1 or 2,
b denotes 0 or 1,

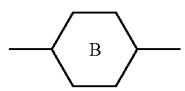

denotes

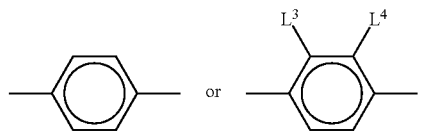

R$^1$ and R$^2$ each, independently of one another, denote alkyl having 1 to 12 C atoms, where, in addition, one or two non-adjacent CH$_2$ groups may be replaced by —O—, —CH═CH—, —CO—, —OCO— or —COO— in such a way that O atoms are not linked directly to one another, preferably alkyl or alkoxy having 1 to 6 C atoms, Z$^x$ and Z$^y$ each, independently of one another, denote —CH$_2$CH$_2$—, —CH═CH—, —CF$_2$O—, —OCF$_2$—, —CH$_2$O—, —OCH$_2$—, —CO—O—, —O—CO—, —C$_2$F$_4$—, —CF═CF—, —CH═CH—CH$_2$O— or a single bond, preferably a single bond, L$^{1-4}$ each, independently of one another, denote F, Cl, OCF$_3$, CF$_3$, CH$_3$, CH$_2$F, CHF$_2$.

Preferably, both L$^1$ and L$^2$ denote F or one of L$^1$ and L$^2$ denotes F and the other denotes Cl, or both L$^3$ and L$^4$ denote F or one of L$^3$ and L$^4$ denotes F and the other denotes Cl.

The compounds of the formula CY are preferably selected from the group consisting of the following sub-formulae:

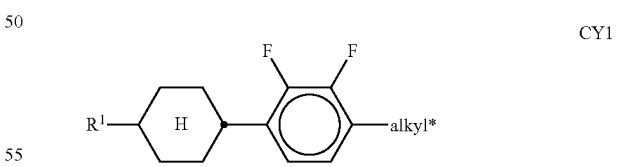
CY1

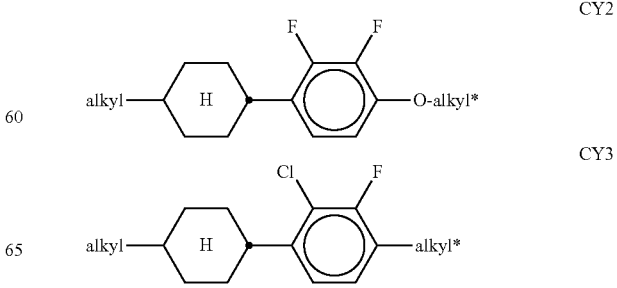
CY2

CY3

-continued
CY4
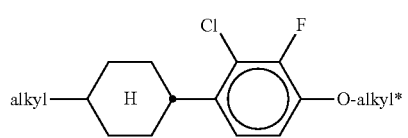
CY5
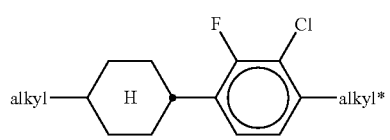
CY6
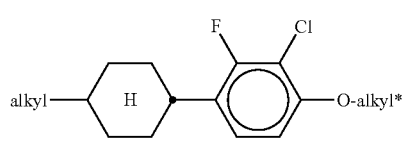
CY7
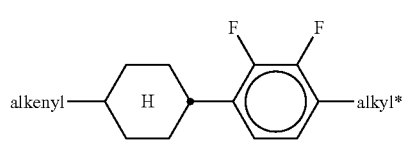
CY8
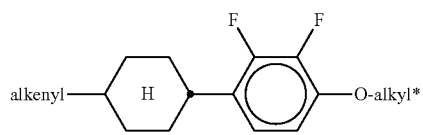
CY9
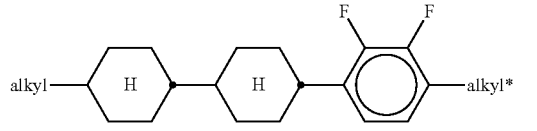
CY10
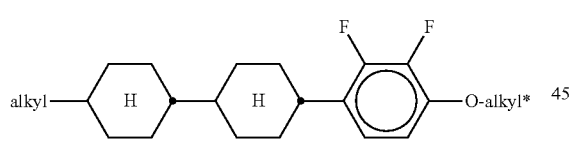
CY11
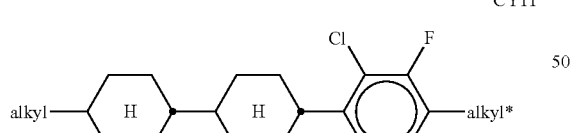
CY12
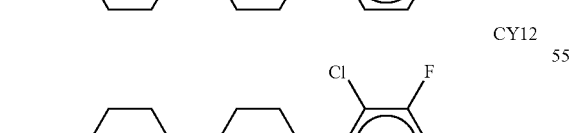
CY13
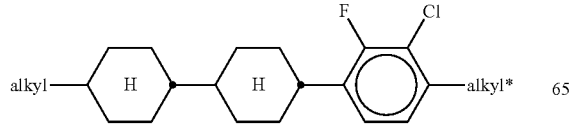
-continued
CY14
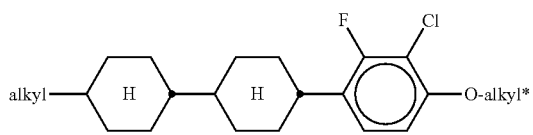
CY15
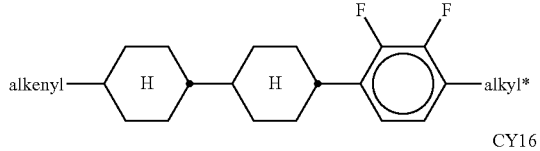
CY16
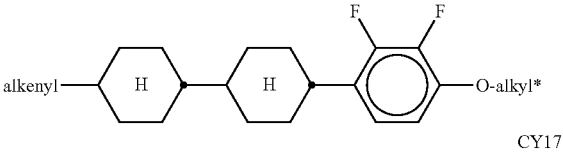
CY17
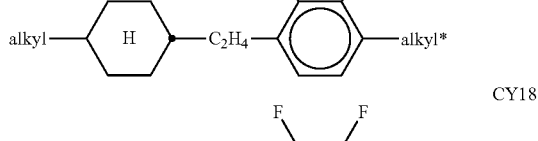
CY18
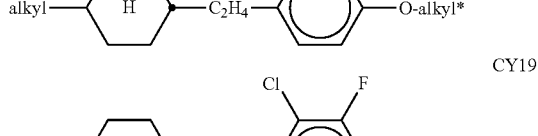
CY19
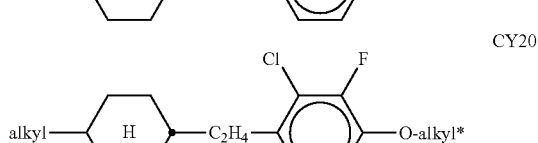
CY20
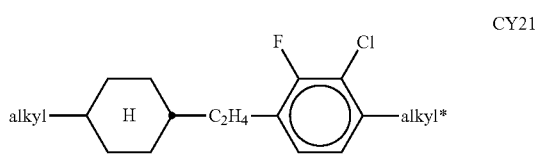
CY21
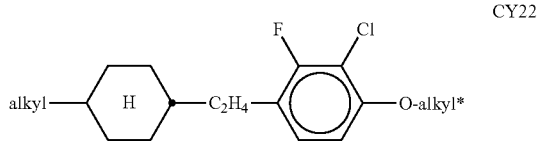
CY22
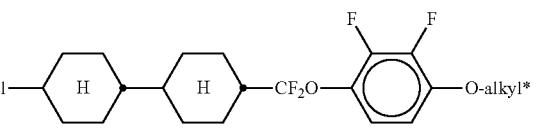
CY23
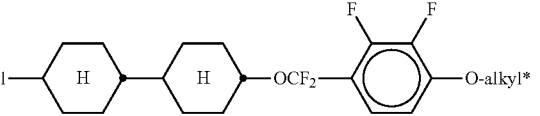
CY24


in which a denotes 1 or 2, alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2$=CH—, $CH_2$=$CHCH_2CH_2$—, $CH_3$—CH=CH—, $CH_3$—$CH_2$—CH=CH—, $CH_3$—$(CH_2)_2$—CH=CH—, $CH_3$—$(CH_2)_3$—CH=CH— or $CH_3$—CH=CH—$(CH_2)_2$—.

The compounds of the formula PY are preferably selected from the group consisting of the following sub-formulae:

-continued

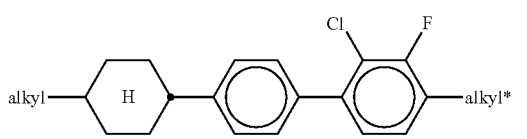
PY11

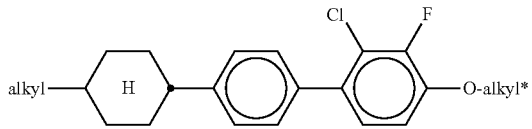
PY12

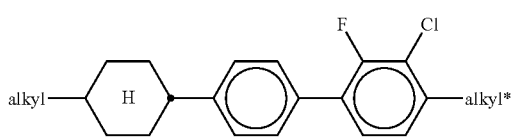
PY13

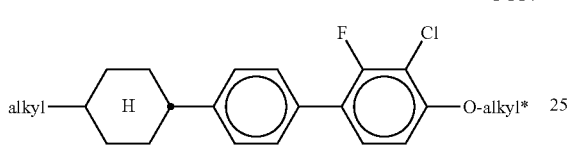
PY14

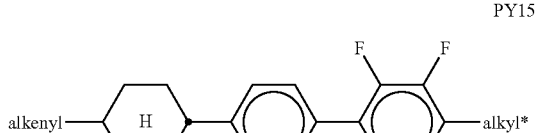
PY15

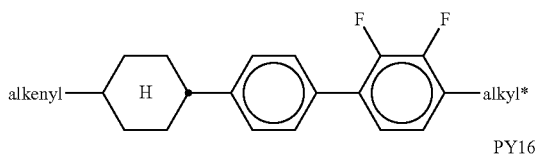
PY16

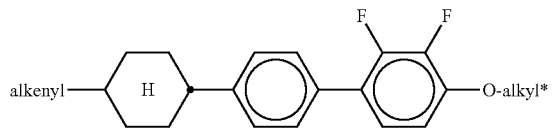
PY17

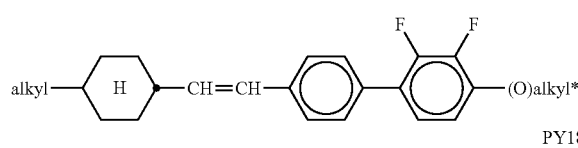
PY18

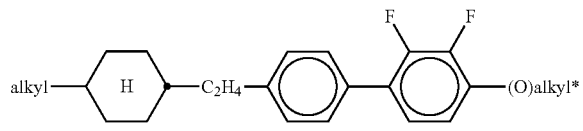
PY19

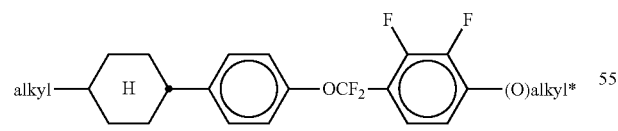
PY20

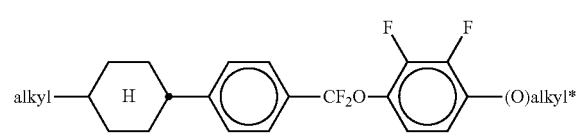

in which alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

b) LC medium wherein the component B) or LC host mixture comprises one or more mesogenic or LC compounds comprising an alkenyl group (hereinafter also referred to as "alkenyl compounds"), wherein said alkenyl group is stable to a polymerisation reaction under the conditions used for polymerisation of the polymerisable compounds contained in the LC medium.

Preferably the component B) or LC host mixture comprises one or more alkenyl compounds selected from formulae AN and AY

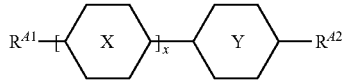
AN

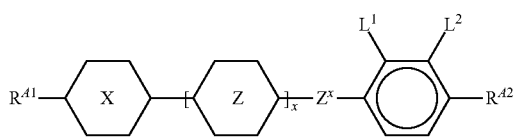
AY in which the individual radicals, on each occurrence identically or differently, and each, independently of one another, have the following meaning:

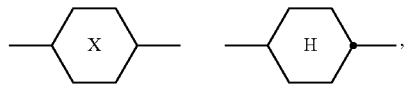

 or

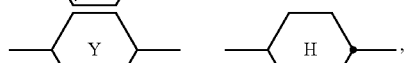

 or

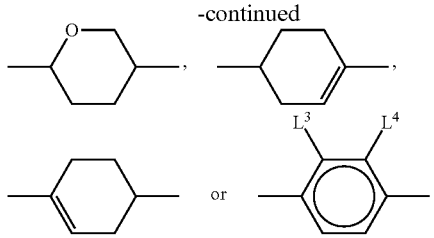

$R^{41}$ alkenyl having 2 to 9 C atoms or, if at least one of the rings X, Y and Z denotes cyclohexenyl, also one of the meanings of $R^{42}$, $R^{42}$ alkyl having 1 to 12 C atoms, in which, in addition, one or two non-adjacent CH$_2$ groups may be replaced by —O—, —CH=CH—, —CO—, —OCO— or —COO— in such a way that O atoms are not linked directly to one another, $Z^x$ —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O—, or a single bond, preferably a single bond, $L^{1,2}$ H, F, Cl, OCF$_3$, CF$_3$, CH$_3$, CH$_2$F or CHF$_2$H, preferably H, F or Cl, x 1 or 2, z 0 or 1.

Preferred compounds of formula AN and AY are those wherein $R^{42}$ is selected from ethenyl, propenyl, butenyl, pentenyl, hexenyl and heptenyl.

In a preferred embodiment the component B) or LC host mixture comprises one or more compounds of formula AN selected from the following sub-formulae:

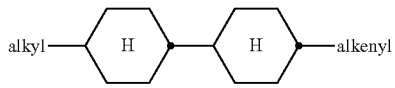
AN1

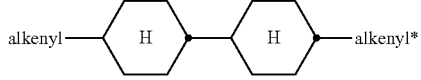
AN2

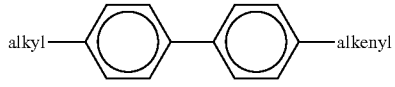
AN3

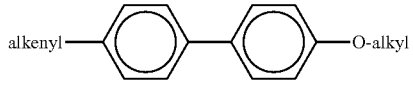
AN4

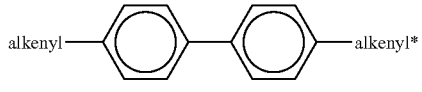
AN5

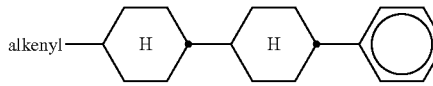
AN6

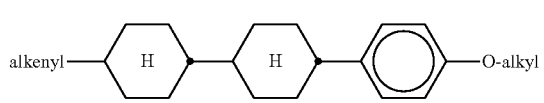
AN7

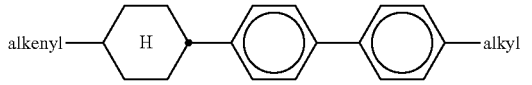
AN8

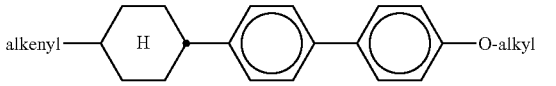
AN9

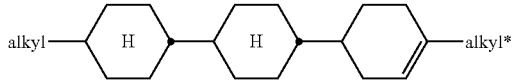
AN10

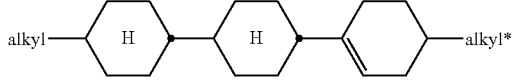
AN11

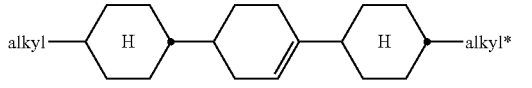
AN12 in which alkyl and alkyl* each, independently of one another, denote a straight-chain alkyl radical having 1-6 C atoms, and alkenyl and alkenyl* each, independently of one another, denote a straight-chain alkenyl radical having 2-7 C atoms. Alkenyl and alkenyl* preferably denote CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

Preferably the the component B) or LC host mixture comprises one or more compounds selected from formulae AN1, AN2, AN3 and AN6, very preferably one or more compounds of formula AN1.

In another preferred embodiment the component B) or LC host mixture comprises one or more compounds of formula AN selected from the following sub-formulae:

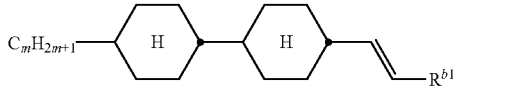
AN1a

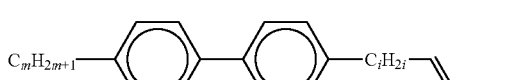
AN3a

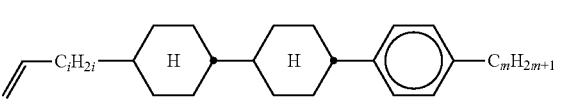
AN6a in which m denotes 1, 2, 3, 4, 5 or 6, i denotes 0, 1, 2 or 3, and $R^{b1}$ denotes H, CH$_3$ or C$_2$H$_5$.

In another preferred embodiment the component B) or LC host mixture comprises one or more compounds selected from the following sub-formulae:

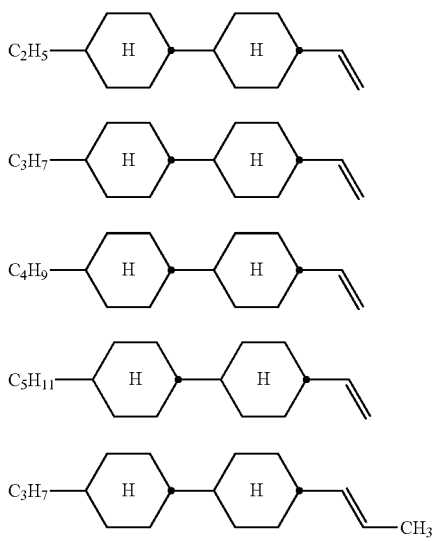
AN1a1
AN1a2
AN1a3
AN1a4
AN1a5
Most preferred are compounds of formula AN1a2 and AN1a5.
In another preferred embodiment the component B) or LC host mixture comprises one or more compounds of formula AY selected from the following sub-formulae:
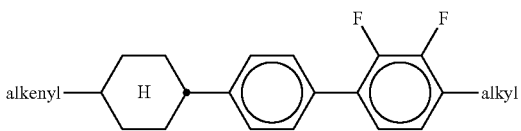
AY1
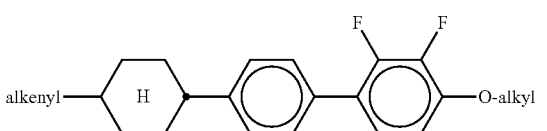
AY2
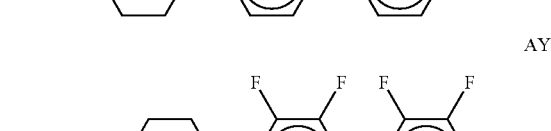
AY3
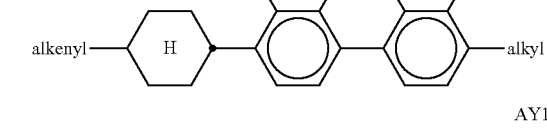
AY4
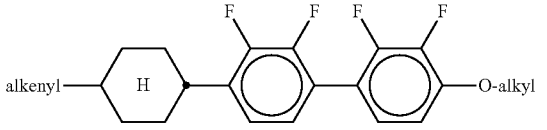
AY5
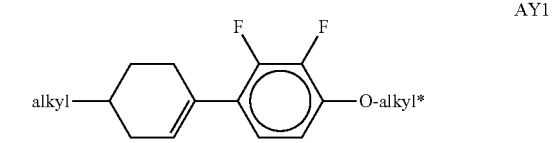
AY6
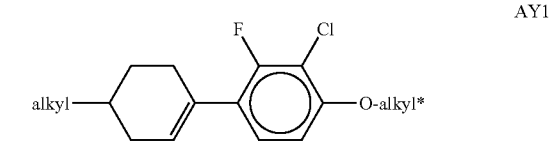
AY7
AY8
AY9
AY10
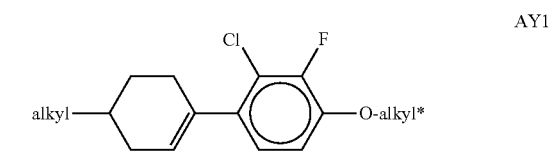
AY11
AY12
AY13
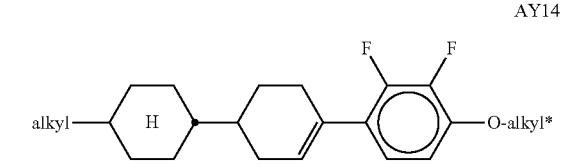
AY14
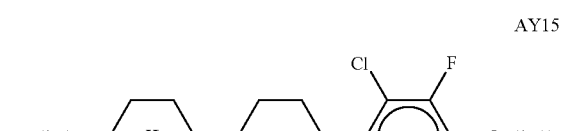
AY15
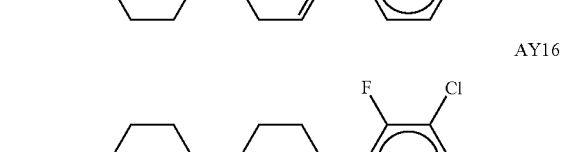
AY16

-continued

AY17
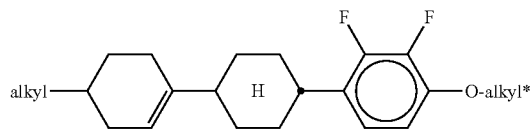

AY18
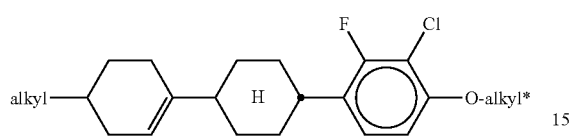

AY19
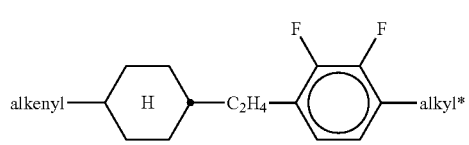

AY20
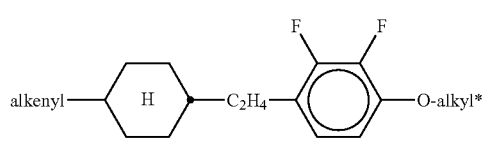

AY21
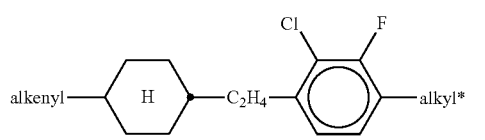

AY22
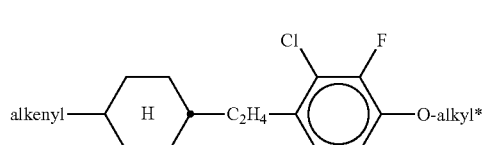

AY23
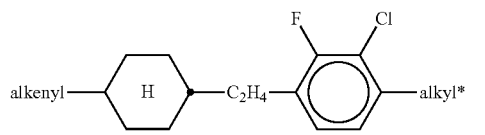

AY24
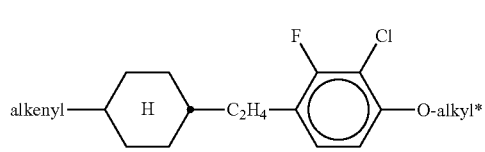

AY25
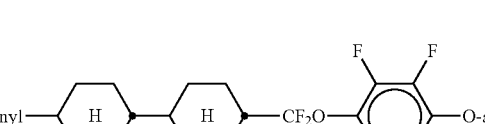

AY26
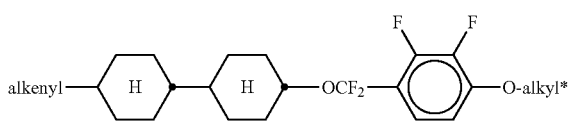

-continued

AY27
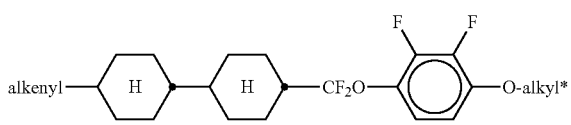

AY28

AY29

AY30

AY31
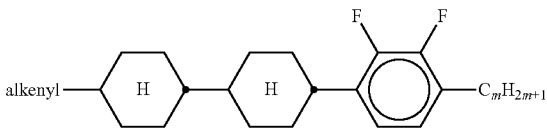

in which alkyl and alkyl* each, independently of one another, denote a straight-chain alkyl radical having 1-6 C atoms, "(O)" denotes an O— atom or a single bond, and alkenyl and alkenyl* each, independently of one another, denote a straight-chain alkenyl radical having 2-7 C atoms. Alkenyl and alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

In another preferred embodiment the component B) or LC host mixture comprises one or more compounds of formula AY selected from the following sub-formulae:

AY5a

AY6a
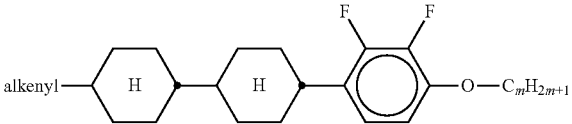

-continued

AY9a alkenyl—[H]—[2,3-F,F / 2',3'-F,F biphenyl]—$C_mH_{2m+1}$

AY10a alkenyl—[H]—[2,3-F,F / 2',3'-F,F biphenyl]—O—$C_mH_{2m+1}$

AY11a $C_nH_{2n+1}$—[cyclohexyl]—[2,3-F phenyl]—O—$C_mH_{2m+1}$

AY14a $C_nH_{2n+1}$—[H]—[cyclohexenyl]—[2,3-F phenyl]—O—$C_mH_{2m+1}$ in which m and n each, independently of one another, denote 1, 2, 3, 4, 5 or 6, and alkenyl denotes —CH=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

Preferably the proportion of compounds of formula AN and AY in the LC medium is from 2 to 70% by weight, very preferably from 5 to 60% by weight, most preferably from 10 to 50% by weight.

Preferably the LC medium or LC host mixture contains 1 to 5, preferably 1, 2 or 3 compounds selected from formulae AN and AY.

In another preferred embodiment of the present invention the LC medium comprises one or more compounds of formula AY14, very preferably of AY14a. The proportion of compounds of formula AY14 or AY14a in the LC medium is preferably 3 to 20% by weight.

The addition of alkenyl compounds of formula AN and/or AY enables a reduction of the viscosity and response time of the LC medium.

c) LC medium wherein the component B) or LC host mixture comprises one or more compounds of the following formula:

ZK $R^3$—[C]—$Z^y$—[D]—$R^4$ in which the individual radicals have the following meanings:

[C] denotes

[cyclohexyl], [tetrahydropyran], [pyran], [cyclohexene], [cyclohexene]

or

[D] denotes

[H cyclohexyl]

denotes

[H cyclohexyl] or [phenyl], $R^3$ and $R^4$ each, independently of one another, denote alkyl having 1 to 12 C atoms, in which, in addition, one or two non-adjacent CH$_2$ groups may be replaced by —O—, —CH=CH—, —CO—, —O—CO— or —CO—O— in such a way that O atoms are not linked directly to one another, $Z^y$ denotes —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond.

The compounds of the formula ZK are preferably selected from the group consisting of the following sub-formulae:

ZK1 alkyl—[H]—[H]—alkyl*

ZK2 alkyl—[H]—[H]—O-alkyl*

ZK3 alkenyl—[H]—[H]—alkyl

ZK4 alkenyl—[H]—[H]—alkenyl*

ZK5 alkyl—[H]—[phenyl]—alkyl*

ZK6 alkyl—[H]—[phenyl]—O-alkyl*

-continued

ZK7
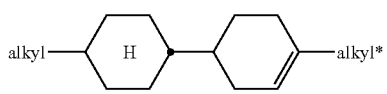

ZK8
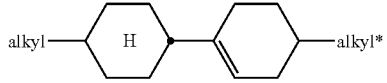

ZK9
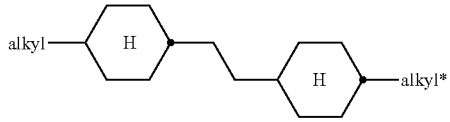

ZK10
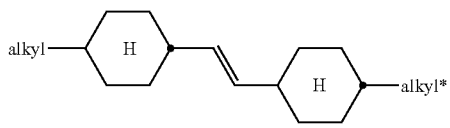

in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

Especially preferred are compounds of formula ZK1.

Particularly preferred compounds of formula ZK are selected from the following sub-formulae:

ZK1a
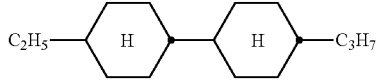

ZK1b
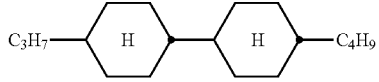

ZK1c
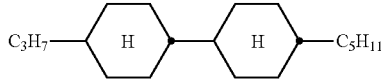

ZK1d
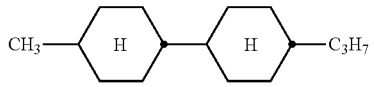

wherein the propyl, butyl and pentyl groups are straight-chain groups.

Most preferred are compounds of formula ZK1a.

d) LC medium wherein component B) or the LC host mixture additionally comprises one or more compounds of the following formula:

DK
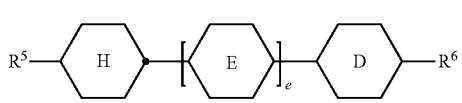

in which the individual radicals on each occurrence, identically or differently, have the following meanings:

R$^5$ and R$^6$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another, preferably alkyl or alkoxy having 1 to 6 C atoms,

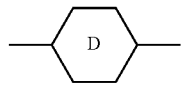

denotes

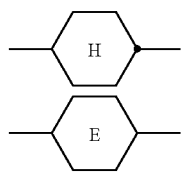

denotes

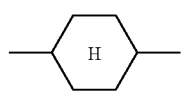

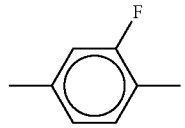

and e denotes 1 or 2.

The compounds of the formula DK are preferably selected from the group consisting of the following sub-formulae:

DK1

DK2
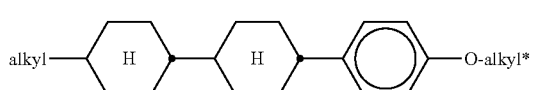

DK3
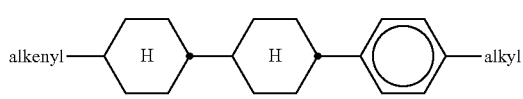

DK4

DK5
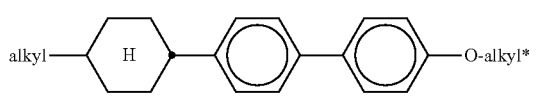

-continued

DK6

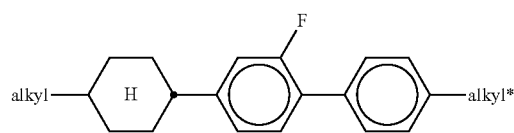
DK7

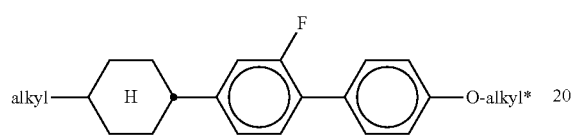
DK8

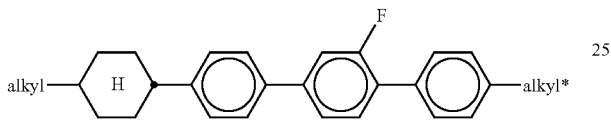
DK9

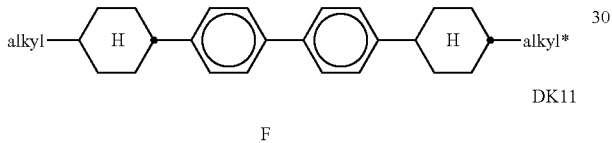
DK10

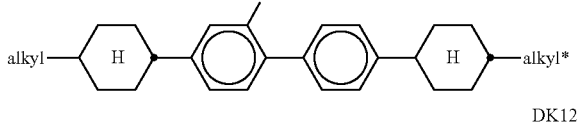
DK11

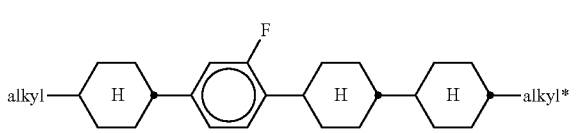
DK12 in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

e) LC medium wherein component B) or the LC host mixture additionally comprises one or more compounds of the following formula:

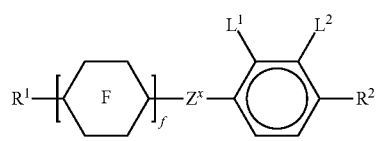
LY in which the individual radicals have the following meanings:

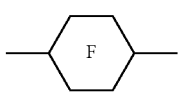

denotes

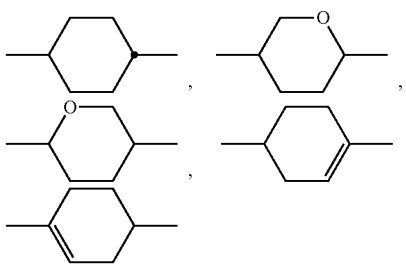

with at least one ring F being different from cyclohexylene,
f denotes 1 or 2,
R$^1$ and R$^2$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another,
Z$^x$ denotes —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond,
L$^1$ and L$^2$ each, independently of one another, denote F, Cl, OCF$_3$, CF$_3$, CH$_3$, CH$_2$F, CHF$_2$.
Preferably, both radicals L$^1$ and L$^2$ denote F or one of the radicals L$^1$ and L$^2$ denotes F and the other denotes Cl.

The compounds of the formula LY are preferably selected from the group consisting of the following sub-formulae:

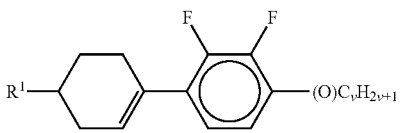
LY1

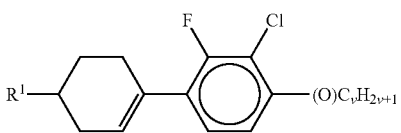
LY2

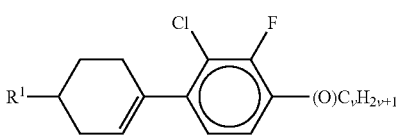
LY3

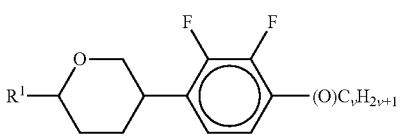
LY4

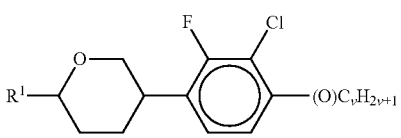
LY5

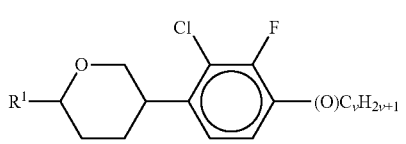
LY6

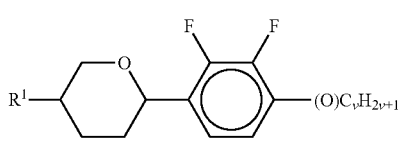
LY7

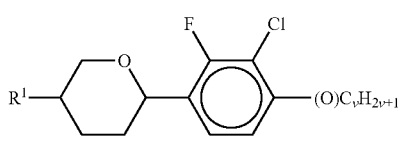
LY8

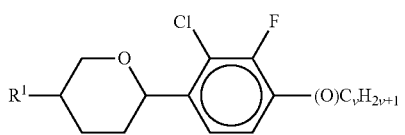
LY9

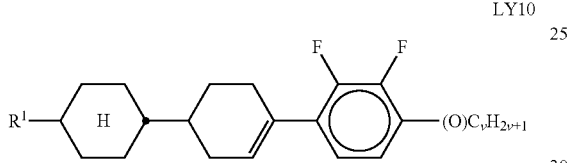
LY10

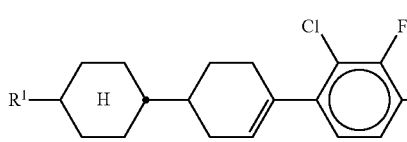
LY11

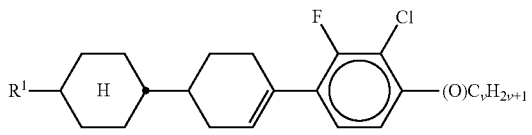
LY12

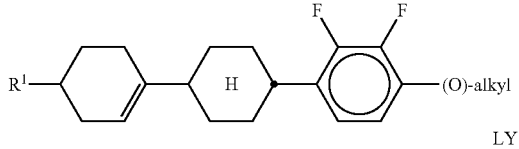
LY13

LY14

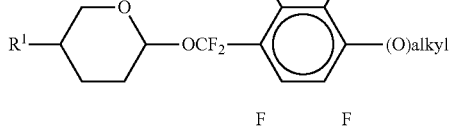
LY15

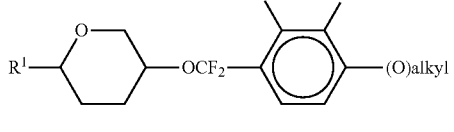
LY16

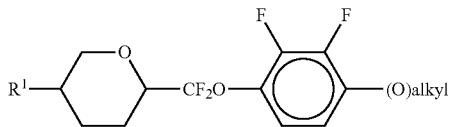
LY17

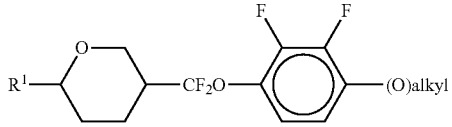
LY18

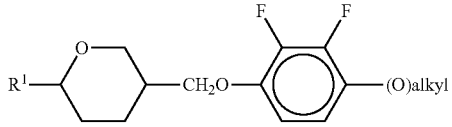
LY19

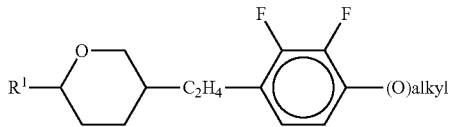
LY20

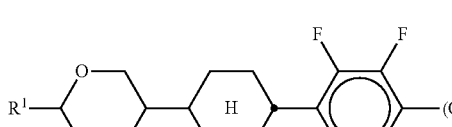
LY21

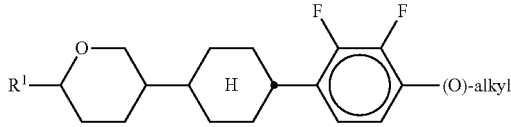
LY22

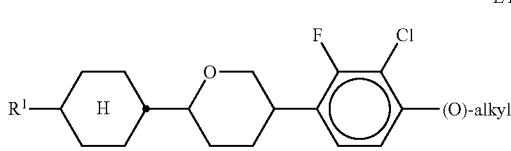
LY23

LY24

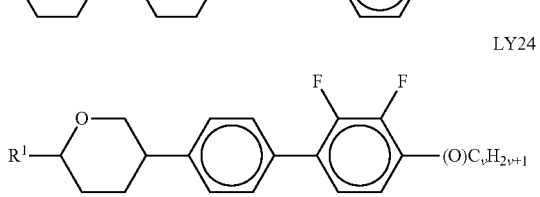

in which $R^1$ has the meaning indicated above, alkyl denotes a straight-chain alkyl radical having 1-6 C atoms, (O) denotes an oxygen atom or a single bond, and v denotes an integer from 1 to 6. $R^1$ preferably denotes straight-chain alkyl having 1 to 6 C atoms or straight-chain alkenyl having 2 to 6 C atoms, in particular $CH_3$, $C_2H_5$, n-$C_3H_7$, n-$C_4H_9$, n-$C_5H_{11}$, $CH_2$=CH—, $CH_2$=CHCH$_2$CH$_2$—, $CH_3$—CH=CH—, $CH_3$—CH$_2$—CH=CH—, $CH_3$—(CH$_2$)$_2$—CH=CH—, $CH_3$—(CH$_2$)$_3$—CH=CH— or $CH_3$—CH=CH—(CH$_2$)$_2$—.

f) LC medium wherein component B) or the LC host mixture additionally comprises one or more compounds selected from the group consisting of the following formulae:

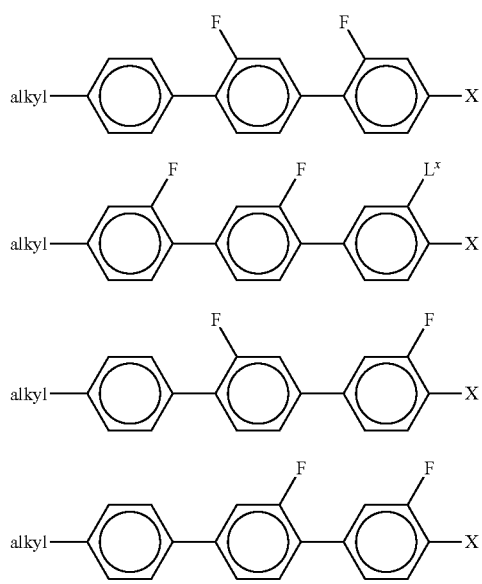
in which alkyl denotes $C_{1-6}$-alkyl, $L^X$ denotes H or F, and X denotes F, Cl, $OCF_3$, $OCHF_2$ or $OCH=CF_2$. Particular preference is given to compounds of the formula G1 in which X denotes F.
g) LC medium wherein component B) or the LC host mixture additionally comprises one or more compounds selected from the group consisting of the following formulae:
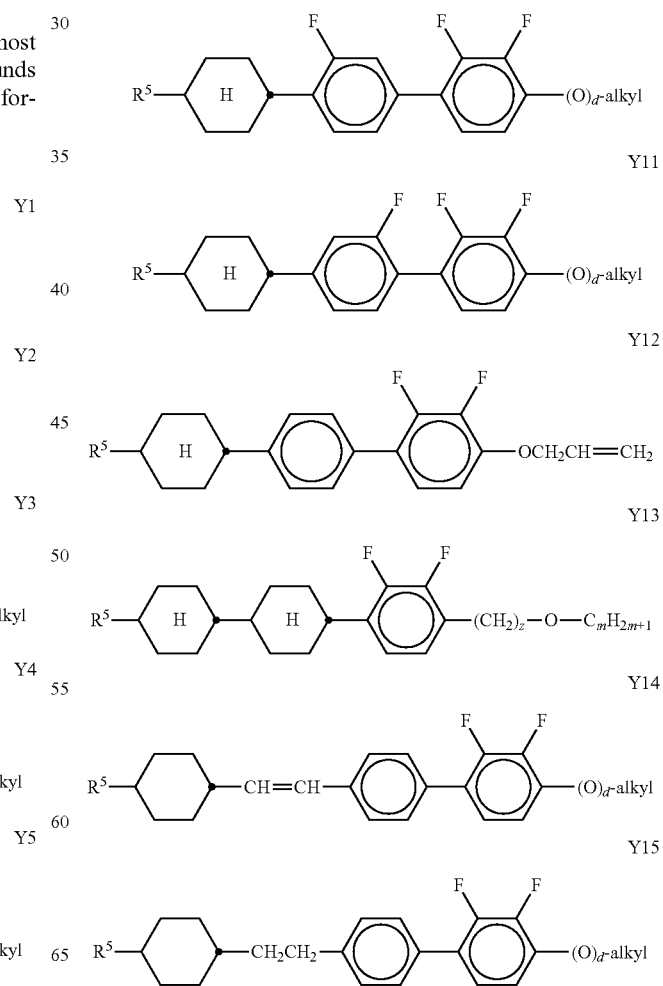

Y16

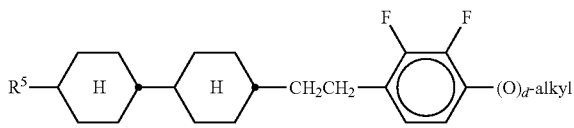

in which $R^5$ has one of the meanings indicated above for $R^1$, alkyl denotes $C_{1-6}$-alkyl, d denotes 0 or 1, and z and m each, independently of one another, denote an integer from 1 to 6. $R^5$ in these compounds is particularly preferably $C_{1-6}$-alkyl or -alkoxy or $C_{2-6}$-alkenyl, d is preferably 1. The LC medium according to the invention preferably comprises one or more compounds of the above-mentioned formulae in amounts of 5% by weight.

h) LC medium wherein component B) or the LC host mixture additionally comprises one or more biphenyl compounds selected from the group consisting of the following formulae:

B1

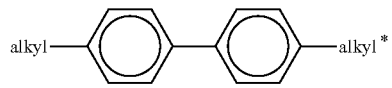

B2

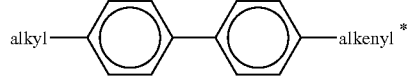

B3

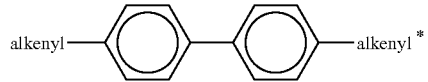

in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

The proportion of the biphenyls of the formulae B1 to B3 in the LC host mixture is preferably at least 3% by weight, in particular 5% by weight.

The compounds of the formula B2 are particularly preferred.

The compounds of the formulae B1 to B3 are preferably selected from the group consisting of the following sub-formulae:

B1a

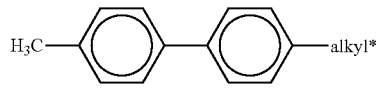

B2a

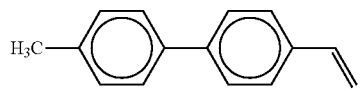

B2b

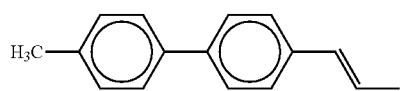

B2c

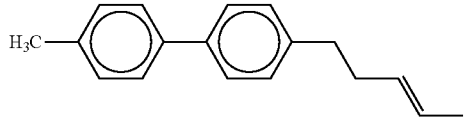

in which alkyl* denotes an alkyl radical having 1-6 C atoms. The medium according to the invention particularly preferably comprises one or more compounds of the formulae B1a and/or B2c.

i) LC medium wherein component B) or the LC host mixture additionally comprises one or more terphenyl compounds of the following formula:

T

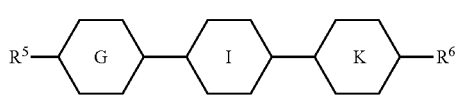

in which $R^5$ and $R^6$ each, independently of one another, have one of the meanings indicated above, and

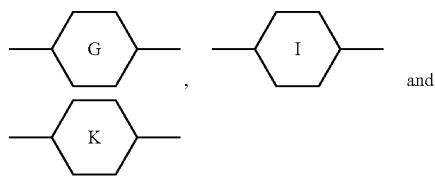

each, independently of one another, denote

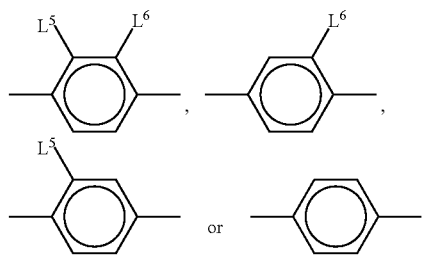

in which $L^5$ denotes F or Cl, preferably F, and $L^6$ denotes F, Cl, $OCF_3$, $CF_3$, $CH_3$, $CH_2F$ or $CHF_2$, preferably F.

The compounds of the formula T are preferably selected from the group consisting of the following sub-formulae:

T1

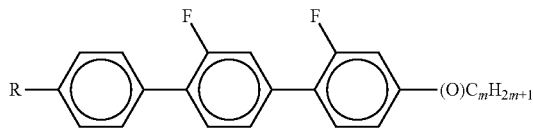

T2

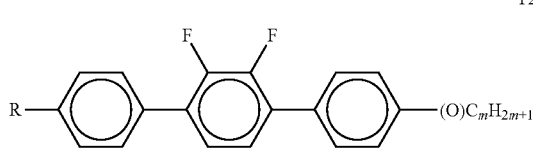

T3
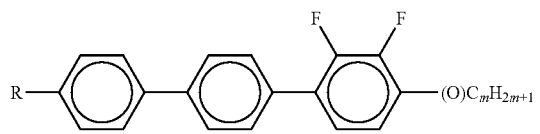
T4
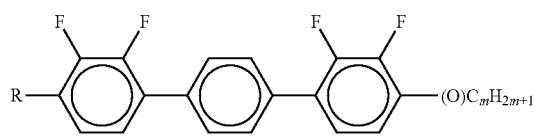
T5
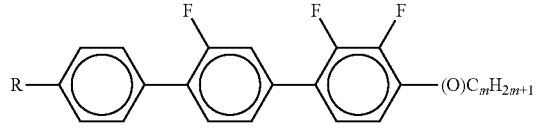
T6
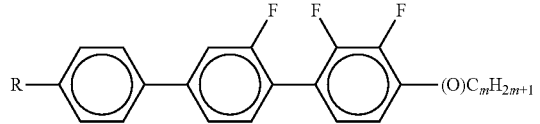
T7
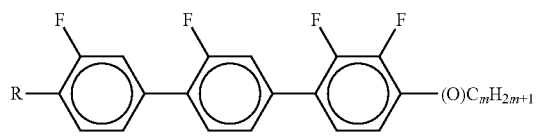
T8
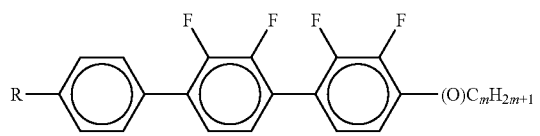
T9
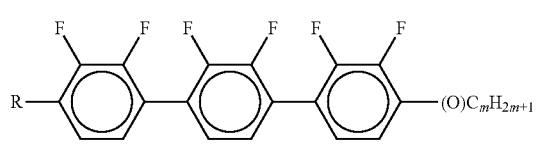
T10
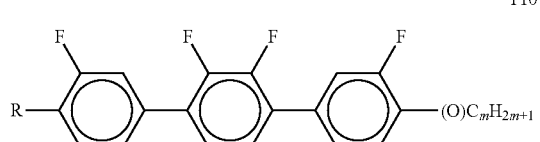
T11
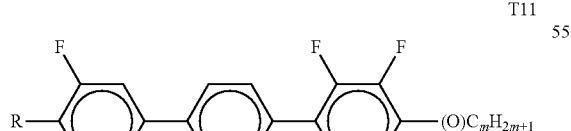
T12
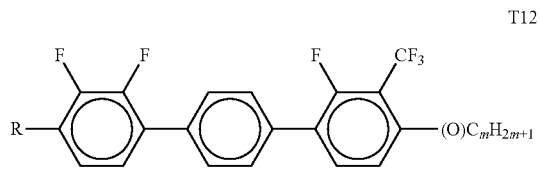
T13
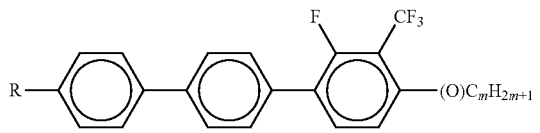
T14
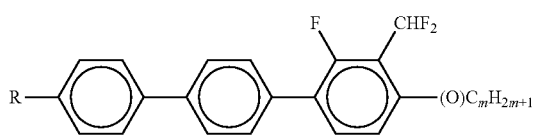
T15
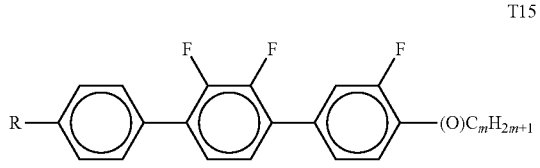
T16
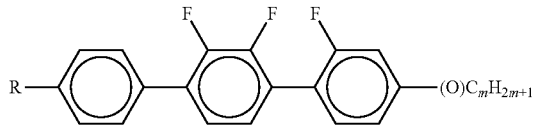
T17
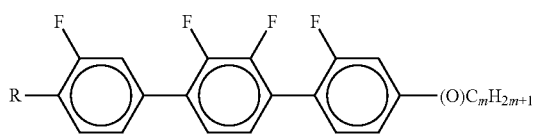
T18
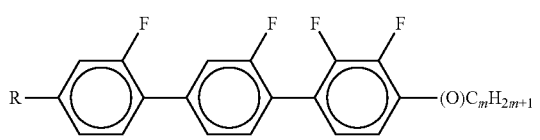
T19
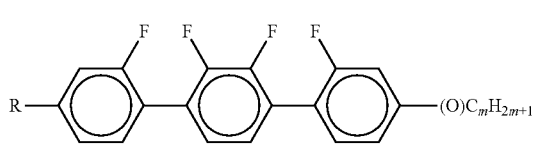
T20
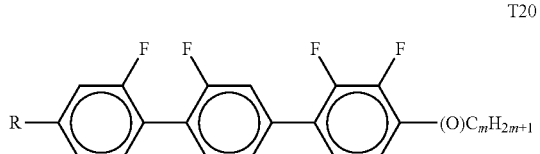
T21
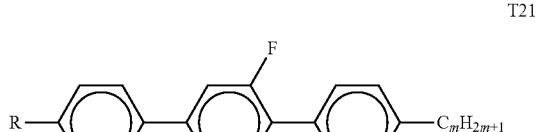
T22
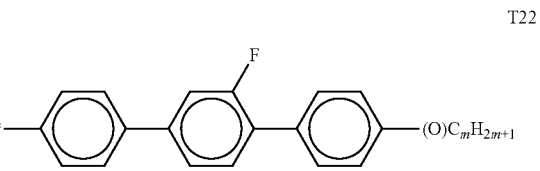

-continued

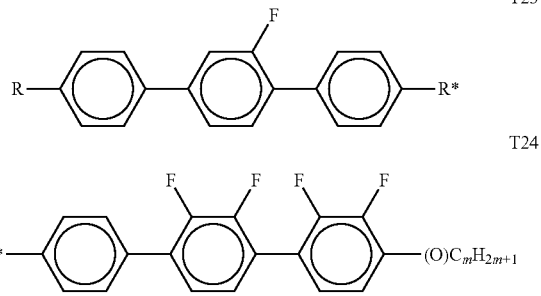

T23

T24 in which R denotes a straight-chain alkyl or alkoxy radical having 1-7 C atoms, R* denotes a straight-chain alkenyl radical having 2-7 C atoms, (O) denotes an oxygen atom or a single bond, and m denotes an integer from 1 to 6. R* preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

R preferably denotes methyl, ethyl, propyl, butyl, pentyl, hexyl, methoxy, ethoxy, propoxy, butoxy or pentoxy.

The LC host mixture according to the invention preferably comprises the terphenyls of the formula T and the preferred sub-formulae thereof in an amount of 0.5-30% by weight, in particular 1-20% by weight.

Particular preference is given to compounds of the formulae T1, T2, T3 and T21. In these compounds, R preferably denotes alkyl, furthermore alkoxy, each having 1-5 C atoms.

The terphenyls are preferably employed in LC media according to the invention if the Δn value of the mixture is to be ≥0.1. Preferred LC media comprise 2-20% by weight of one or more terphenyl compounds of the formula T, preferably selected from the group of compounds T1 to T22.

k) LC medium wherein component B) or the LC host mixture additionally comprises one or more quaterphenyl compounds selected from the group consisting of the following formulae:

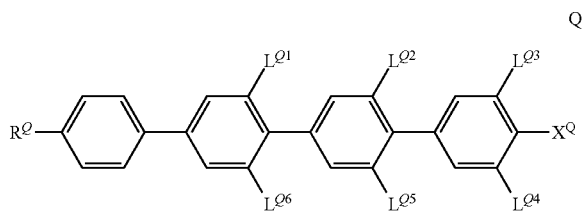

Q wherein
$R^Q$ is alkyl, alkoxy, oxaalkyl or alkoxyalkyl having 1 to 9 C atoms or alkenyl or alkenyloxy having 2 to 9 C atoms, all of which are optionally fluorinated,
$X^Q$ is F, Cl, halogenated alkyl or alkoxy having 1 to 6 C atoms or halogenated alkenyl or alkenyloxy having 2 to 6 C atoms,
$L^{Q1}$ to $L^{Q6}$ independently of each other are H or F, with at least one of $L^{Q1}$ to $L^{Q6}$ being F.

Preferred compounds of formula Q are those wherein $R^O$ denotes straight-chain alkyl with 2 to 6 C-atoms, very preferably ethyl, n-propyl or n-butyl.

Preferred compounds of formula Q are those wherein $L^{Q3}$ and $L^{Q4}$ are F. Further preferred compounds of formula Q are those wherein $L^{Q3}$, $L^{Q4}$ and one or two of $L^{Q1}$ and $L^{Q2}$ are F.

Preferred compounds of formula Q are those wherein $X^Q$ denotes F or $OCF_3$, very preferably F.

The compounds of formula Q are preferably selected from the following subformulae

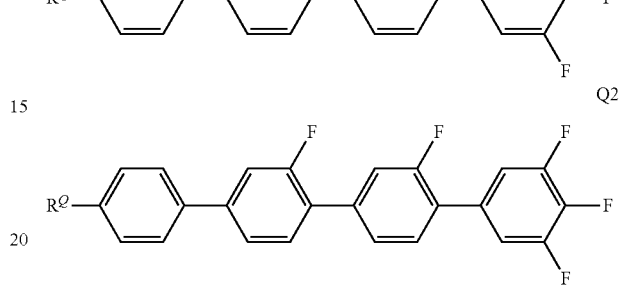

Q1

Q2 wherein $R^O$ has one of the meanings of formula Q or one of its preferred meanings given above and below, and is preferably ethyl, n-propyl or n-butyl.

Especially preferred are compounds of formula Q1, in particular those wherein $R^O$ is n-propyl.

Preferably the proportion of compounds of formula Q in the LC host mixture is from >0 to ≤5% by weight, very preferably from 0.1 to 2% by weight, most preferably from 0.2 to 1.5% by weight.

Preferably the LC host mixture contains 1 to 5, preferably 1 or 2 compounds of formula Q.

The addition of quaterphenyl compounds of formula Q to the LC host mixture enables to reduce ODF mura, whilst maintaining high UV absorption, enabling quick and complete polymerisation, enabling strong and quick tilt angle generation, and increasing the UV stability of the LC medium.

Besides, the addition of compounds of formula Q, which have positive dielectric anisotropy, to the LC medium with negative dielectric anisotropy allows a better control of the values of the dielectric constants $\varepsilon_\parallel$ and $\varepsilon_\perp$, and in particular enables to achieve a high value of the dielectric constant $\varepsilon_\parallel$ while keeping the dielectric anisotropy Δε constant, thereby reducing the kick-back voltage and reducing image sticking.

l) LC medium wherein component B) or the LC host mixture additionally comprises one or more compounds of formula C:

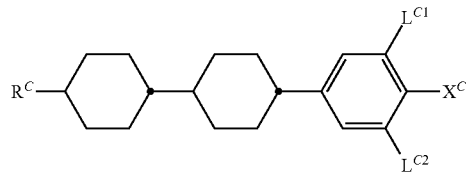

C wherein
$R^C$ denotes alkyl, alkoxy, oxaalkyl or alkoxyalkyl having 1 to 9 C atoms or alkenyl or alkenyloxy having 2 to 9 C atoms, all of which are optionally fluorinated,
$X^C$ denotes F, Cl, halogenated alkyl or alkoxy having 1 to 6 C atoms or halogenated alkenyl or alkenyloxy having 2 to 6 C atoms, $L^{C1}$, $L^{C2}$ independently of each other denote H or F, with at least one of $L^{C1}$ and $L^{C2}$ being F.

Preferred compounds of formula C are those wherein $R^C$ denotes straight-chain alkyl with 2 to 6 C-atoms, very preferably ethyl, n-propyl or n-butyl.

Preferred compounds of formula C are those wherein $L^{C1}$ and $L^{C2}$ are F.

Preferred compounds of formula C are those wherein $X^C$ denotes F or $OCF_3$, very preferably F.

Preferred compounds of formula C are selected from the following formula

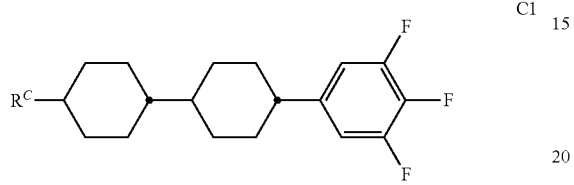

C1 wherein $R^C$ has one of the meanings of formula C or one of its preferred meanings given above and below, and is preferably ethyl, n-propyl or n-butyl, very preferably n-propyl.

Preferably the proportion of compounds of formula C in the LC host mixture is from >0 to ≤10% by weight, very preferably from 0.1 to 8% by weight, most preferably from 0.2 to 5% by weight.

Preferably the LC host mixture contains 1 to 5, preferably 1, 2 or 3 compounds of formula C.

The addition of compounds of formula C, which have positive dielectric anisotropy, to the LC medium with negative dielectric anisotropy allows a better control of the values of the dielectric constants $\varepsilon_\parallel$ and $\varepsilon_\perp$, and in particular enables to achieve a high value of the dielectric constant $\varepsilon_\parallel$ while keeping the dielectric anisotropy $\Delta\varepsilon$ constant, thereby reducing the kick-back voltage and reducing image sticking. Besides, the addition of compounds of formula C enables to reduce the viscosity and the response time of the LC medium.

m) LC medium wherein component B) or the LC host mixture additionally comprises one or more compounds selected from the group consisting of the following formulae:

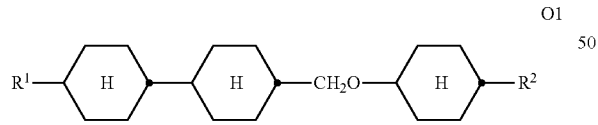

O1

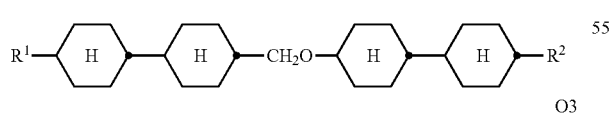

O2

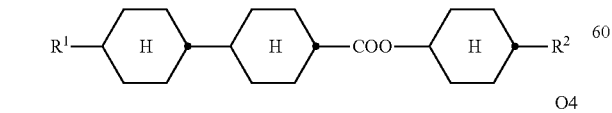

O3

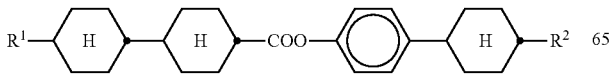

O4

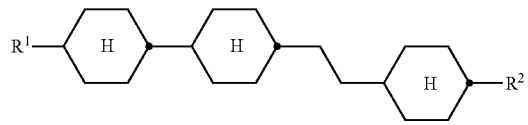

O5

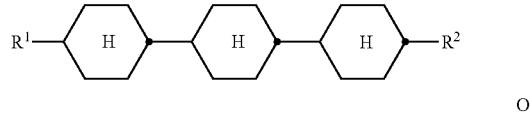

O6

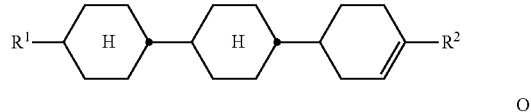

O7

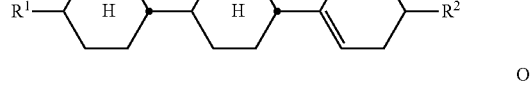

O8

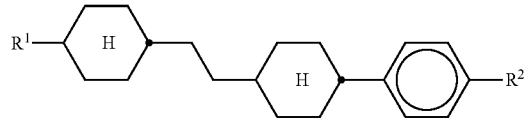

O9

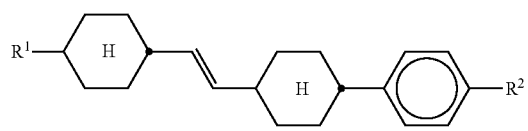

O10

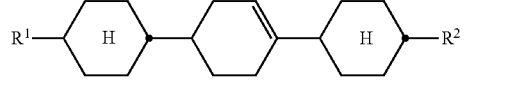

O11 in which $R^1$ and $R^2$ have the meanings indicated above and preferably each, independently of one another, denote straight-chain alkyl having 1 to 6 C atoms or straight-chain alkenyl having 2 to 6 C atoms.

Preferred media comprise one or more compounds selected from the formulae O1, O3 and O4.

n) LC medium wherein component B) or the LC host mixture additionally comprises one or more compounds of the following formula:

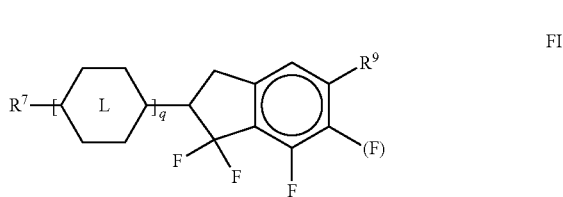

FI in which denotes

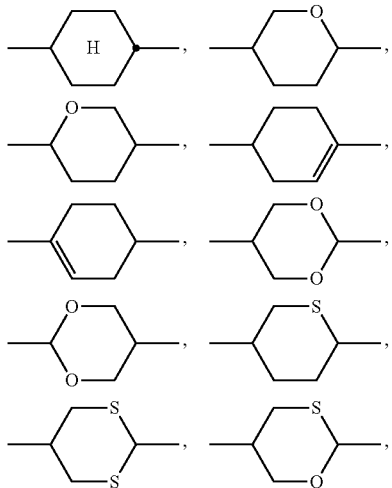

$R^9$ denotes H, $CH_3$, $C_2H_5$ or n-$C_3H_7$, (F) denotes an optional fluorine substituent, and q denotes 1, 2 or 3, and $R^7$ has one of the meanings indicated for $R^1$, preferably in amounts of >3% by weight, in particular 5% by weight and very particularly preferably 5-30% by weight.

Particularly preferred compounds of the formula FI are selected from the group consisting of the following sub-formulae:

FI1

FI2

FI3

FI4

FI5

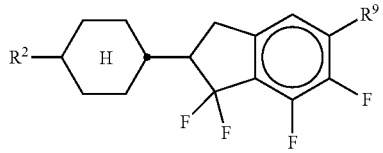

FI6

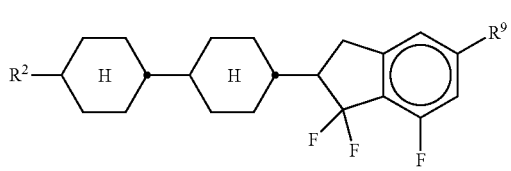

FI7

FI8

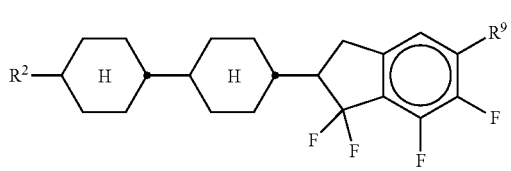

in which $R^7$ preferably denotes straight-chain alkyl, and $R^9$ denotes $CH_3$, $C_2H_5$ or n-$C_3H_7$. Particular preference is given to the compounds of the formulae FI1, FI2 and FI3.

o) LC medium wherein component B) or the LC host mixture additionally comprises one or more compounds selected from the group consisting of the following formulae:

VK1

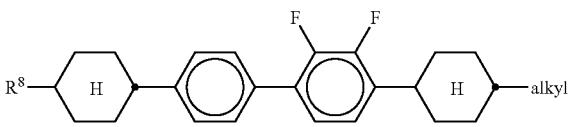

VK2

VK3

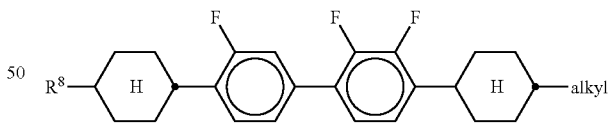

VK4

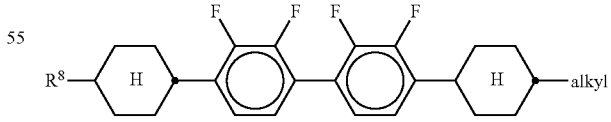

in which $R^8$ has the meaning indicated for $R^1$, and alkyl denotes a straight-chain alkyl radical having 1-6 C atoms.

p) LC medium wherein component B) or the LC host mixture additionally comprises one or more compounds which contain a tetrahydronaphthyl or naphthyl unit, such as, for example, the compounds selected from the group consisting of the following formulae:

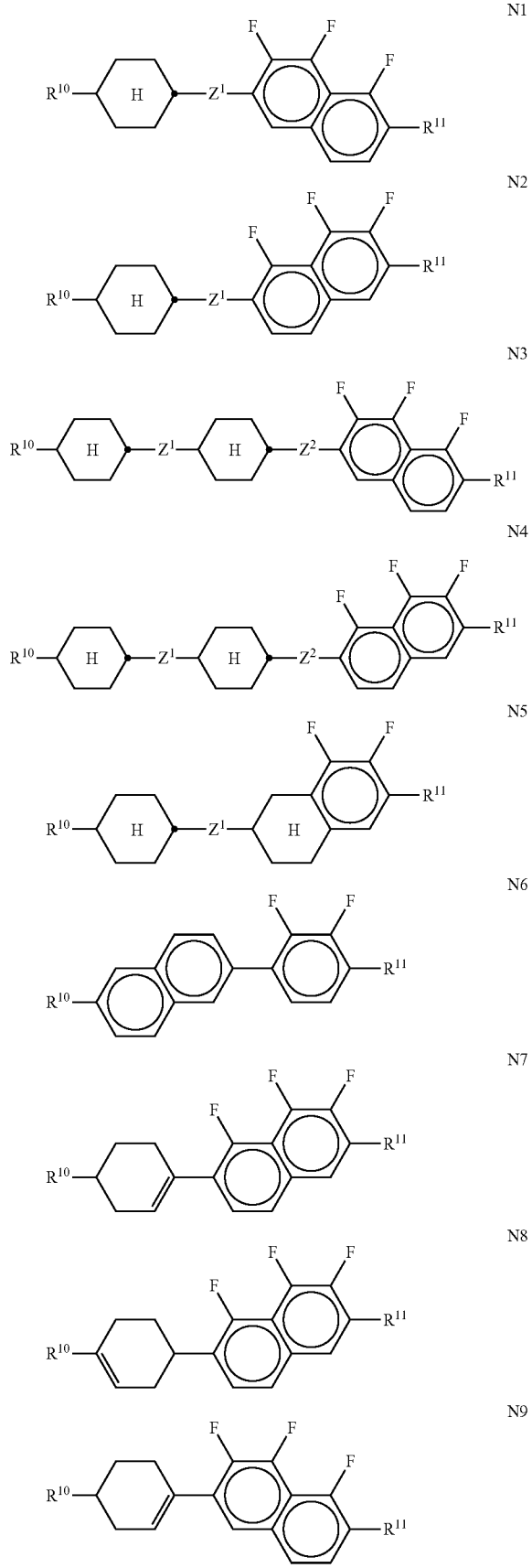

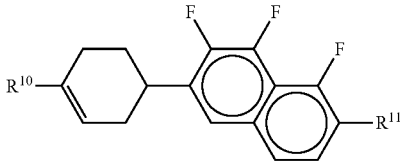

in which

R$^{10}$ and R$^{11}$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another, preferably alkyl or alkoxy having 1 to 6 C atoms, and R$^{10}$ and R$^{11}$ preferably denote straight-chain alkyl or alkoxy having 1 to 6 C atoms or straight-chain alkenyl having 2 to 6 C atoms, and Z$^1$ and Z$^2$ each, independently of one another, denote —C$_2$H$_4$—, —CH=CH—, —(CH$_2$)$_4$—, —(CH$_2$)$_3$O—, —O(CH$_2$)$_3$—, —CH=CH—CH$_2$CH$_2$—, —CH$_2$CH$_2$CH=CH—, —CH$_2$O—, —OCH$_2$—, —CO—O—, —O—CO—, —C$_2$F$_4$—, —CF=CF—, —CF=CH—, —CH=CF—, —CH$_2$— or a single bond.

q) LC medium wherein component B) or the LC host mixture additionally comprises one or more difluorodibenzochromans and/or chromans of the following formulae:

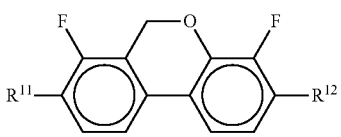

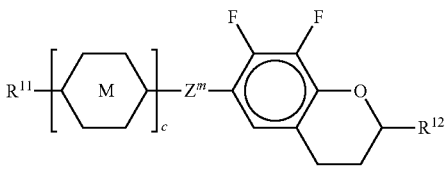

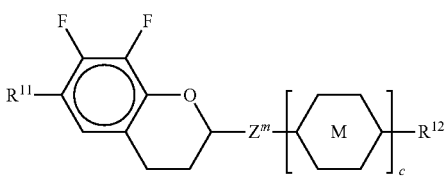

in which

R$^{11}$ and R$^{12}$ each, independently of one another, have one of the meanings indicated above for R$^{11}$, ring M is trans-1,4-cyclohexylene or 1,4-phenylene, Z$^m$ —C$_2$H$_4$—, —CH$_2$O—, —OCH$_2$—, —CO—O— or —O—CO—, c is 0, 1 or 2, preferably in amounts of 3 to 20% by weight, in particular in amounts of 3 to 15% by weight.

Particularly preferred compounds of the formulae BC, CR and RC are selected from the group consisting of the following sub-formulae:

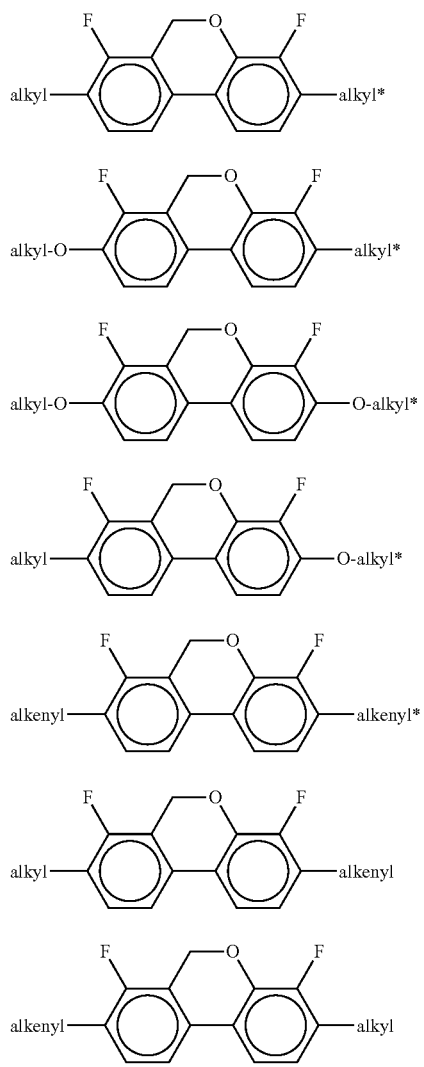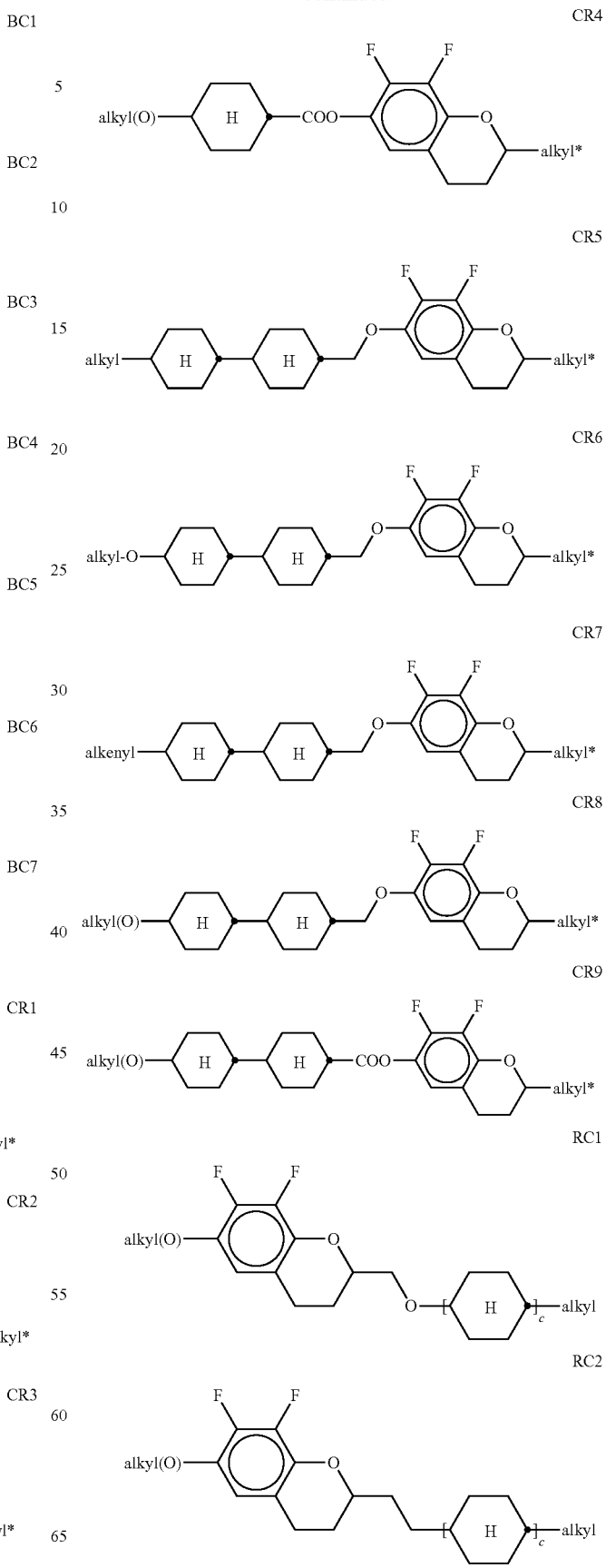

-continued

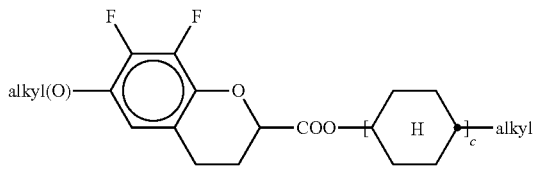
RC3 in which alkyl and alkyl* each, independently of one another, denote a straight-chain alkyl radical having 1-6 C atoms, (O) denotes an oxygen atom or a single bond, c is 1 or 2, and alkenyl and alkenyl* each, independently of one another, denote a straight-chain alkenyl radical having 2-6 C atoms. Alkenyl and alkenyl* preferably denote CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

Very particular preference is given to LC host mixtures comprising one, two or three compounds of the formula BC-2.

r) LC medium wherein component B) or the LC host mixture additionally comprises one or more fluorinated phenanthrenes and/or dibenzofurans of the following formulae:

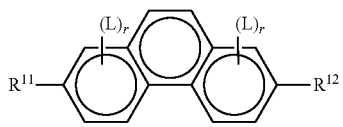
PH

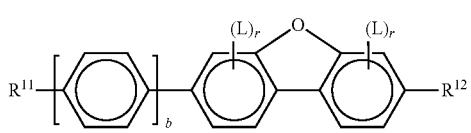
BF in which R$^{11}$ and R$^{12}$ each, independently of one another, have one of the meanings indicated above for R$^{11}$, b denotes 0 or 1, L denotes F, and r denotes 1, 2 or 3.

Particularly preferred compounds of the formulae PH and BF are selected from the group consisting of the following sub-formulae:

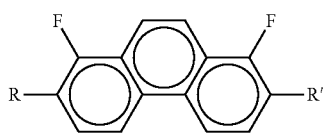
PH1

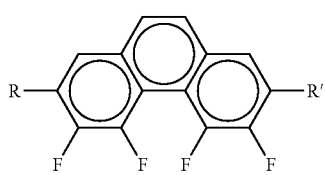
PH2

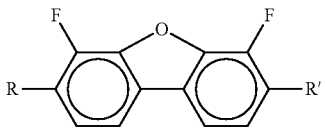
BF1

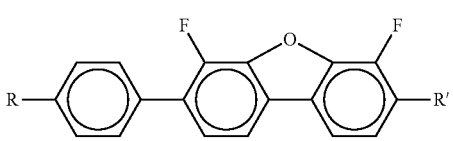
BF2 in which R and R' each, independently of one another, denote a straight-chain alkyl or alkoxy radical having 1-7 C atoms.

s) LC medium wherein component B) or the LC host mixture additionally comprises one or more monocyclic compounds of the following formula

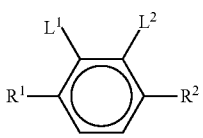
Y wherein
R$^1$ and R$^2$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another, preferably alkyl or alkoxy having 1 to 6 C atoms,
L$^1$ and L$^2$ each, independently of one another, denote F, Cl, OCF$_3$, CF$_3$, CH$_3$, CH$_2$F, CHF$_2$.
Preferably, both L$^1$ and L$^2$ denote F or one of L$^1$ and L$^2$ denotes F and the other denotes Cl,
The compounds of the formula Y are preferably selected from the group consisting of the following sub-formulae:

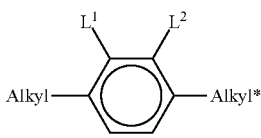
Y1

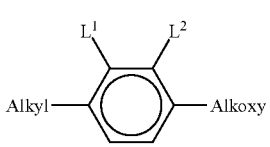
Y2

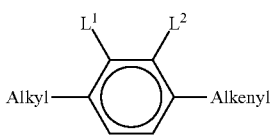
Y3

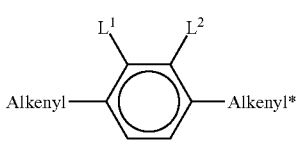
Y4

-continued

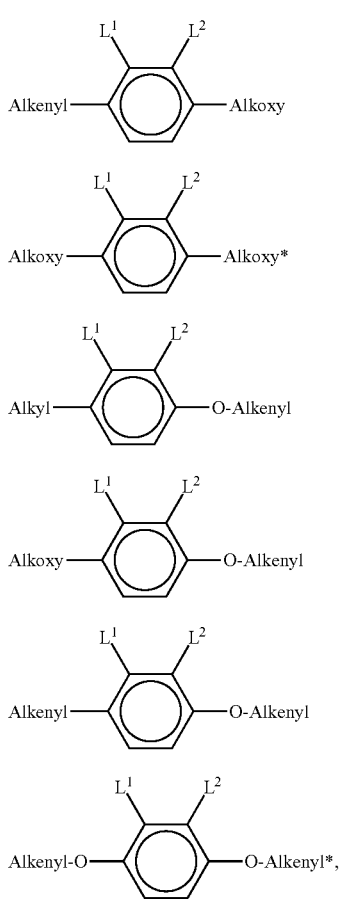

in which, Alkyl and Alkyl* each, independently of one another, denote a straight-chain alkyl radical having 1-6 C atoms, Alkoxy denotes a straight-chain alkoxy radical having 1-6 C atoms, Alkenyl and Alkenyl* each, independently of one another, denote a straight-chain alkenyl radical having 2-6 C atoms, and O denotes an oxygen atom or a single bond. Alkenyl and Alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

Particularly preferred compounds of the formula Y are selected from the group consisting of the following sub-formulae:

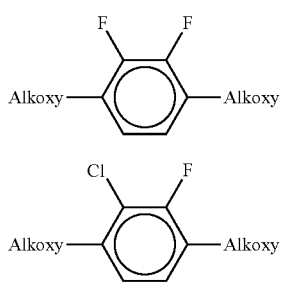

wherein Alkoxy preferably denotes straight-chain alkoxy with 3, 4, or 5 C atoms.

t) LC medium which, apart from the polymerisable compounds as described above and below, does not contain a compound which contains a terminal vinyloxy group ($-O-CH=CH_2$).

u) LC medium wherein component B) or the LC host mixture comprises 1 to 8, preferably 1 to 5, compounds of the formulae CY1, CY2, PY1 and/or PY2. The proportion of these compounds in the LC host mixture as a whole is preferably 5 to 60%, particularly preferably 10 to 35%. The content of these individual compounds is preferably in each case 2 to 20%.

v) LC medium wherein component B) or the LC host mixture comprises 1 to 8, preferably 1 to 5, compounds of the formulae CY9, CY10, PY9 and/or PY10. The proportion of these compounds in the LC host mixture as a whole is preferably 5 to 60%, particularly preferably 10 to 35%. The content of these individual compounds is preferably in each case 2 to 20%.

w) LC medium wherein component B) or the LC host mixture comprises 1 to 10, preferably 1 to 8, compounds of the formula ZK, in particular compounds of the formulae ZK1, ZK2 and/or ZK6. The proportion of these compounds in the LC host mixture as a whole is preferably 3 to 25%, particularly preferably 5 to 45%. The content of these individual compounds is preferably in each case 2 to 20%.

x) LC medium in which the proportion of compounds of the formulae CY, PY and ZK in the LC host mixture as a whole is greater than 70%, preferably greater than 80%.

y) LC medium in which the LC host mixture contains one or more compounds containing an alkenyl group, preferably selected from formulae AN and AY, very preferably selected from formulae AN1, AN3, AN6 and AY14, most preferably from formulae AN1a, AN3a, AN6a and AY14. The concentration of these compounds in the LC host mixture is preferably from 2 to 70%, very preferably from 3 to 55%.

z) LC medium wherein component B) or the LC host mixture contains one or more, preferably 1 to 5, compounds selected of formula PY1-PY8, very preferably of formula PY2. The proportion of these compounds in the LC host mixture as a whole is preferably 1 to 30%, particularly preferably 2 to 20%. The content of these individual compounds is preferably in each case 1 to 20%.

z1) LC medium wherein component B) or the LC host mixture contains one or more, preferably 1, 2 or 3, compounds selected from formulae T1, T2 and T5, very preferably from formula T2. The content of these compounds in the LC host mixture as a whole is preferably 1 to 20%.

z2) LC medium in which the LC host mixture contains one or more compounds selected from formulae CY and PY, one or more compounds selected from formulae AN and AY, and one or more compounds selected from formulae T and Q.

z3) LC medium in which the LC host mixture contains one or more, preferably 1, 2 or 3, compounds of formula BF1, and one or more, preferably 1, 2 or 3, compounds selected from formulae AY14, AY15 and AY16, very preferably of formula AY14. The proportion of the compounds of formula AY14-AY16 in the LC host mixture is preferably from 2 to 35%, very preferably from 3 to 30%. The proportion of the compounds of formula BF1 in the LC host mixture is preferably from 0.5 to 20%, very preferably from 1 to 15%. Further preferably the LC host mixture according to this preferred embodiment contains one or more, preferably 1, 2 or 3 compounds of formula T, preferably selected from formula T1, T2 and T5, very preferably from formula T2 or T5. The proportion of the compounds of formula T in the LC host mixture medium is preferably from 0.5 to 15%, very preferably from 1 to 10%.

In a second preferred embodiment the LC medium contains an LC host mixture based on compounds with positive dielectric anisotropy. Such LC media are especially suitable for use in PS-OCB, PS-TN, PS-Posi-VA, PS-IPS, PS-FFS or SA-HB-FFS displays.

A

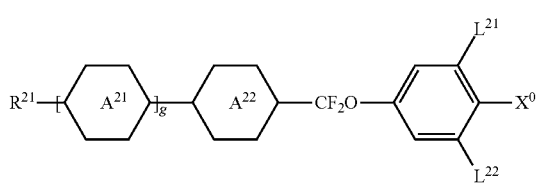

B

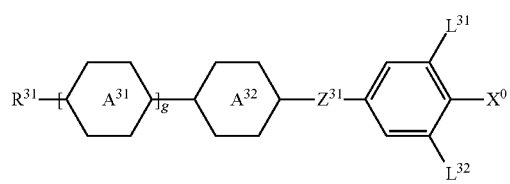

in which the individual radicals have, independently of each other and on each occurrence identically or differently, the following meanings:

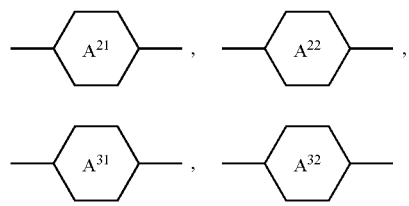

each, independently of one another, and on each occurrence, identically or differently

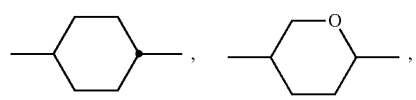

-continued

[additional ring structures]

$R^{21}$, $R^{31}$ each, independently of one another, alkyl, alkoxy, oxaalkyl or alkoxyalkyl having 1 to 9 C atoms or alkenyl or alkenyloxy having 2 to 9 C atoms, all of which are optionally fluorinated, $X^0$ F, Cl, halogenated alkyl or alkoxy having 1 to 6 C atoms or halogenated alkenyl or alkenyloxy having 2 to 6 C atoms, $Z^{31}$ —CH$_2$CH$_2$—, —CF$_2$CF$_2$—, —COO—, trans-CH=CH—, trans-CF=CF—, —CH$_2$O— or a single bond, preferably —CH$_2$CH$_2$—, —COO—, trans-CH=CH— or a single bond, particularly preferably —COO—, trans-CH=CH— or a single bond, $L^{21}$, $L^{22}$, $L^{31}$, $L^{32}$ each, independently of one another, H or F, g 0, 1, 2 or 3.

In the compounds of formula A and B, $X^0$ is preferably F, Cl, CF$_3$, CHF$_2$, OCF$_3$, OCHF$_2$, OCFHCF$_3$, OCFHCHF$_2$, OCFHCHF$_2$, OCF$_2$CH$_3$, OCF$_2$CHF$_2$, OCF$_2$CHF$_2$, OCF$_2$CF$_2$CHF$_2$, OCF$_2$CF$_2$CHF$_2$, OCFHCF$_2$CF$_3$, OCFHCF$_2$CHF$_2$, OCF$_2$CF$_2$CF$_3$, OCF$_2$CF$_2$CClF$_2$, OCClFCF$_2$CF$_3$ or CH=CF$_2$, very preferably F or OCF$_3$, most preferably F.

In the compounds of formula A and B, $R^{21}$ and $R^{31}$ are preferably selected from straight-chain alkyl or alkoxy with 1, 2, 3, 4, 5 or 6 C atoms, and straight-chain alkenyl with 2, 3, 4, 5, 6 or 7 C atoms.

In the compounds of formula A and B, g is preferably 1 or 2.

In the compounds of formula B, $Z^{31}$ is preferably COO, trans-CH=CH or a single bond, very preferably COO or a single bond.

Preferably component B) of the LC medium comprises one or more compounds of formula A selected from the group consisting of the following formulae:

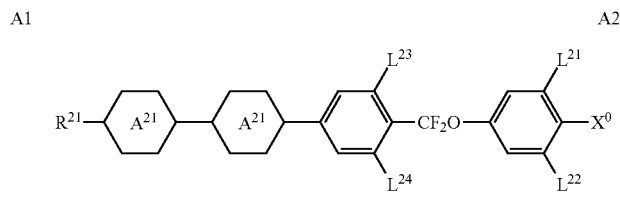

A3

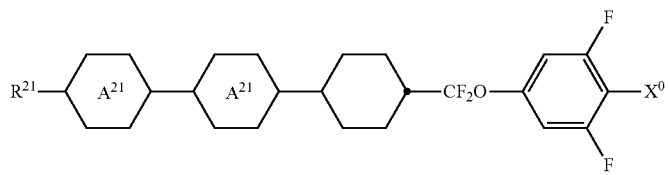

A4

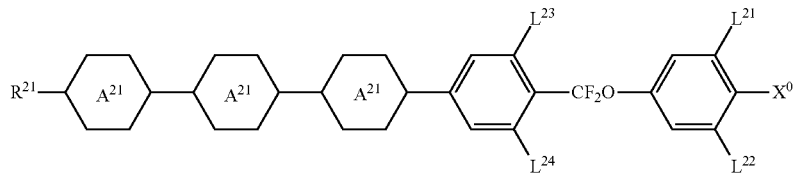

in which $A^{21}$, $A^{22}$, $R^{21}$, $X^0$, $L^{21}$ and $L^{22}$ have the meanings given in formula A, $L^{23}$ and $L^{24}$ each, independently of one another, are H or F, and $X^0$ is preferably F. Particularly preferred are compounds of formulae A1 and A2.

Particularly preferred compounds of formula A1 are selected from the group consisting of the following subformulae:

A1a

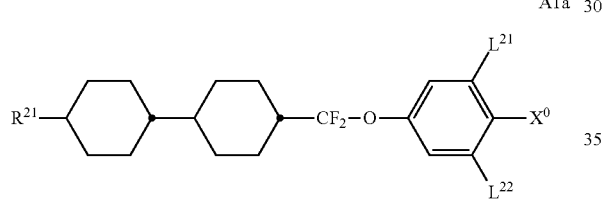

A1b

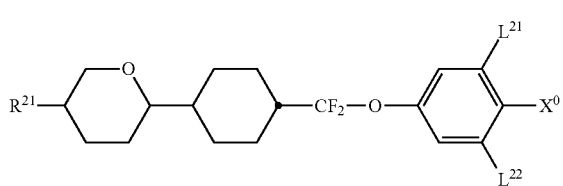

A1c

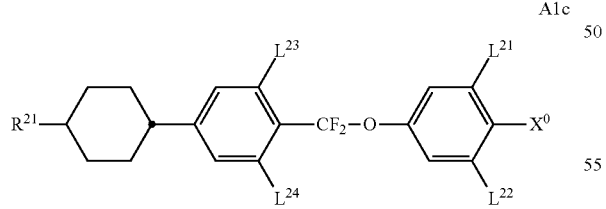

A1d

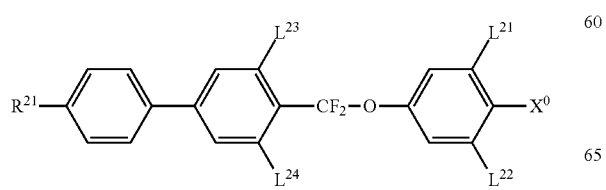

A1e

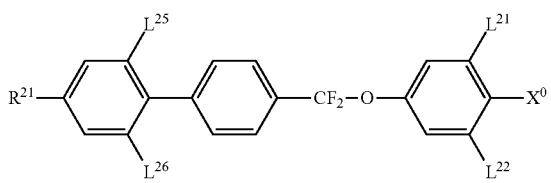

A1f

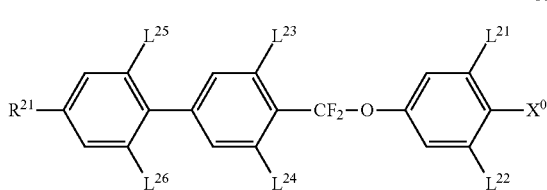

in which $R^{21}$, $X^0$, $L^{21}$ and $L^{22}$ have the meaning given in formula A1, $L^{23}$, $L^{24}$, $L^{25}$ and $L^{26}$ are each, independently of one another, H or F, and $X^0$ is preferably F.

Very particularly preferred compounds of formula A1 are selected from the group consisting of the following subformulae:

A1a1

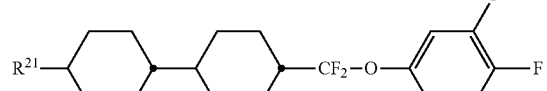

A1a2

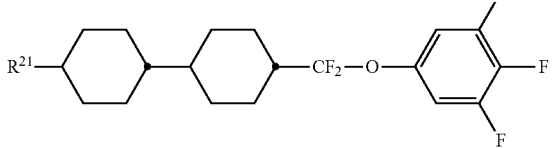

A1b1
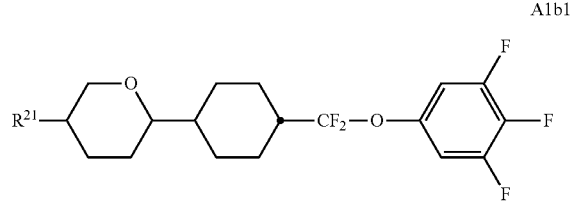

A1d1
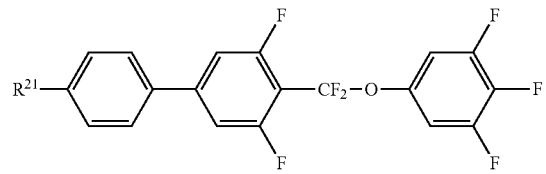

A1e1
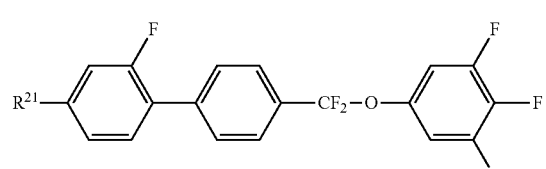

A1f1
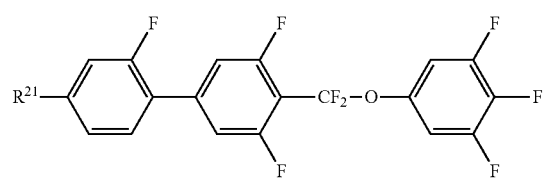

In which $R^{21}$ is as defined in formula A1.

Particularly preferred compounds of formula A2 are selected from the group consisting of the following subformulae:

A2a
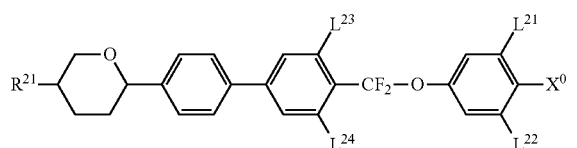

A2b
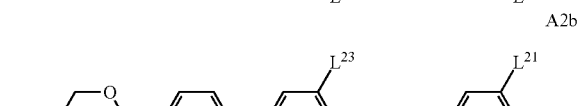

A2c
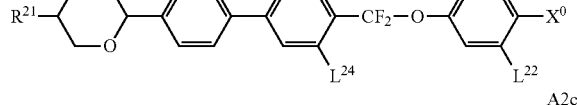

A2d
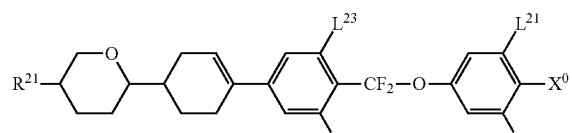

A2e

A2f
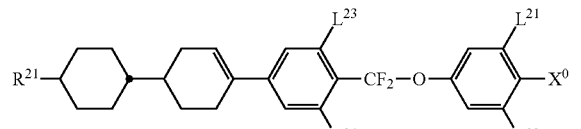

A2g
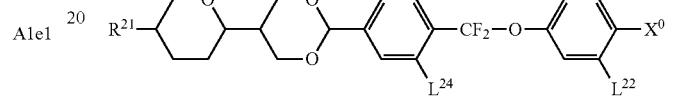

A2h
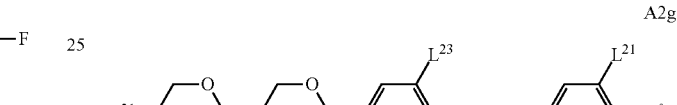

A2i
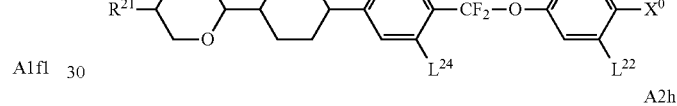

A2k
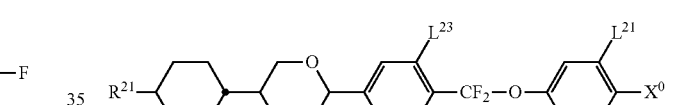

A2l
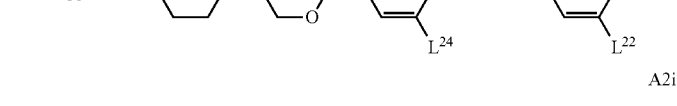

in which $R^{21}$, $X^0$, $L^{21}$ and $L^{22}$ have the meaning given in formula A2, $L^{23}$, $L^{24}$, $L^{25}$ and $L^{26}$ each, independently of one another, are H or F, and $X^0$ is preferably F.

Very particularly preferred compounds of formula A2 are selected from the group consisting of the following subformulae:

A2a1
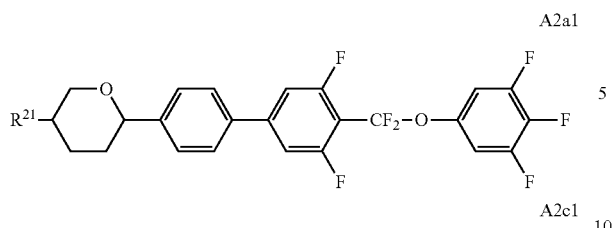
A2c1
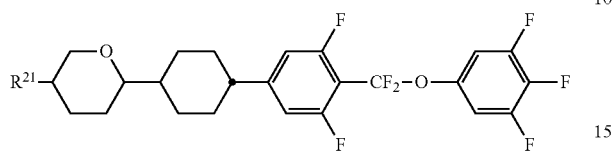
A2d1
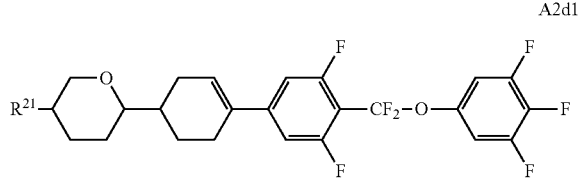
A2e1
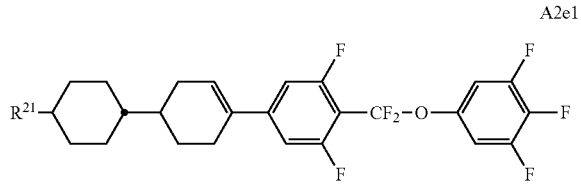
A2f1
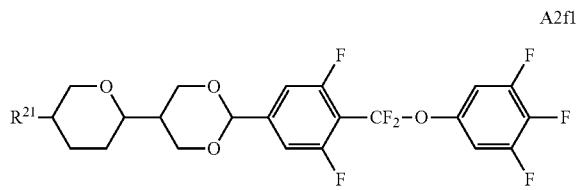
A2h1
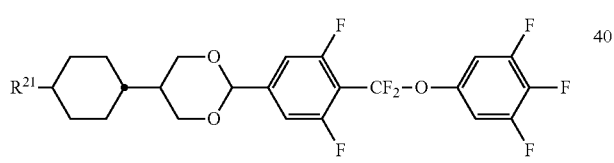
A2i1
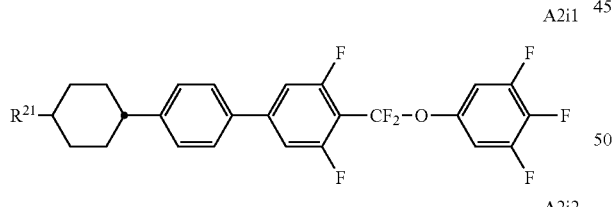
A2i2
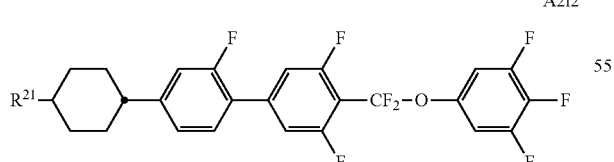
A2k1
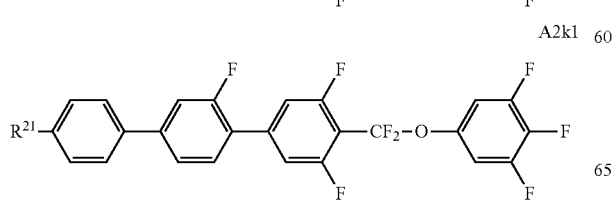
A2k2
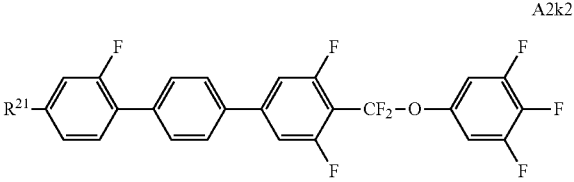
A2l2
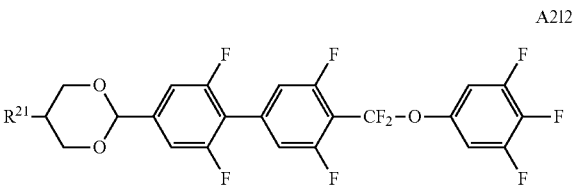
in which $R^{21}$ and $X^0$ are as defined in formula A2.
Particularly preferred compounds of formula A3 are selected from the group consisting of the following subformulae:
A3a
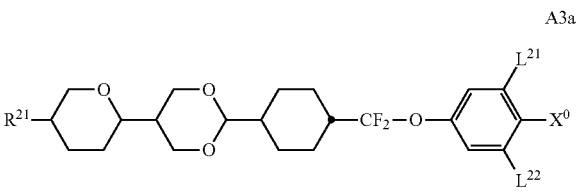
A3b
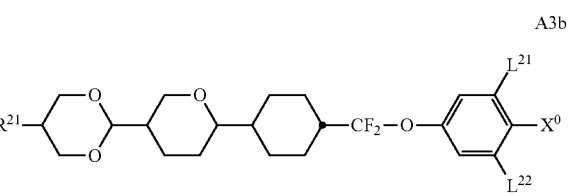
A3c
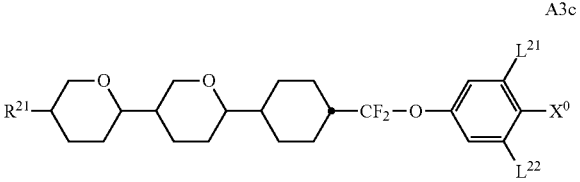
in which $R^{21}$, $X^0$, $L^{21}$ and $L^{22}$ have the meaning given in formula A3, and $X^0$ is preferably F.

Particularly preferred compounds of formula A4 are selected from the group consisting of the following subformulae:

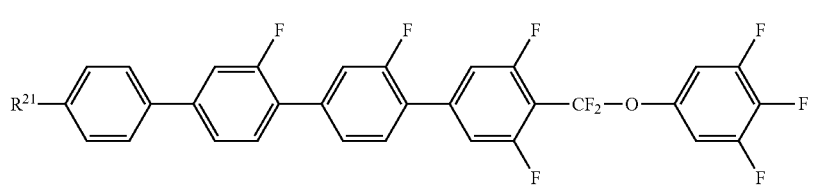

A4a in which $R^{21}$ is as defined in formula A4.

Preferably component B) of the LC medium comprises one or more compounds of formula B selected from the group consisting of the following formulae:

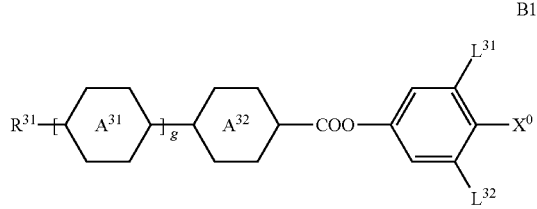

B1

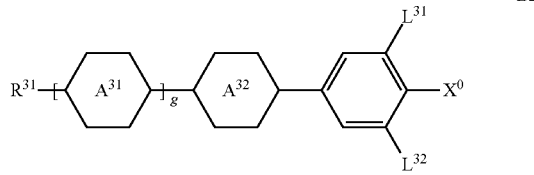

B2

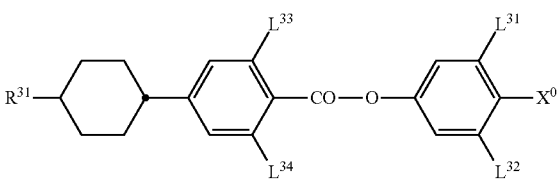

B3 in which g, $A^{31}$, $A^{32}$, $R^{31}$, $X^0$, $L^{31}$ and $L^{32}$ have the meanings given in formula B, and $X^0$ is preferably F. Particularly preferred are compounds of formulae B1 and B2.

Particularly preferred compounds of formula B1 are selected from the group consisting of the following subformulae:

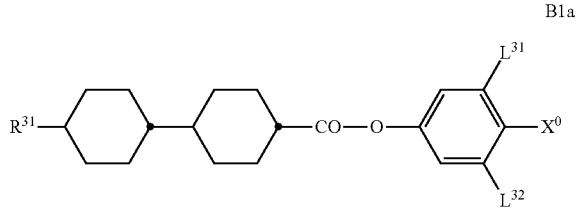

B1a

-continued

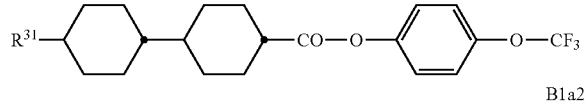

B1b in which $R^{31}$, $X^0$, $L^{31}$ and $L^{32}$ have the meaning given in formula B1, and $X^0$ is preferably F.

Very particularly preferred compounds of formula B1a are selected from the group consisting of the following subformulae:

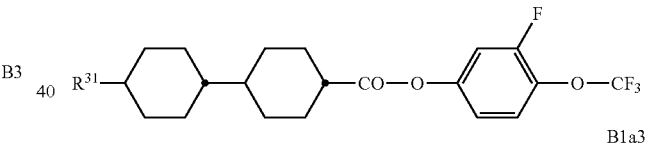

B1a1

B1a2

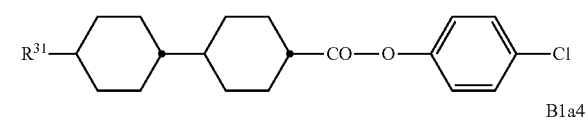

B1a3

B1a4

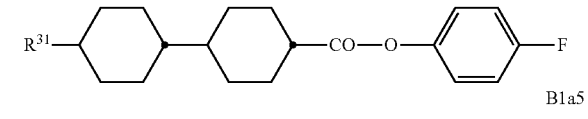

B1a5

B1a6

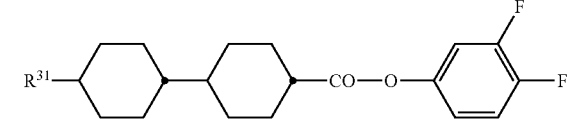

in which $R^{31}$ is as defined in formula B1.

Very particularly preferred compounds of formula B1 b are selected from the group consisting of the following subformulae:

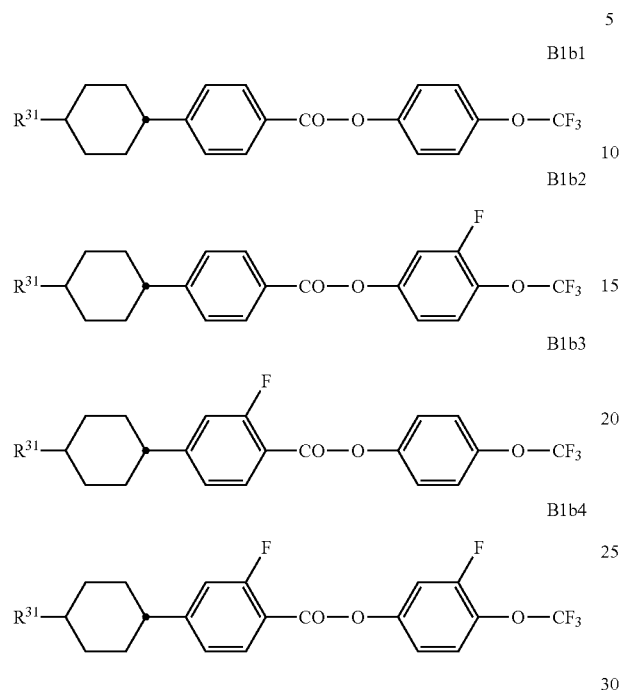

B1b1
B1b2
B1b3
B1b4 in which $R^{31}$ is as defined in formula B1.

Particularly preferred compounds of formula B2 are selected from the group consisting of the following subformulae:

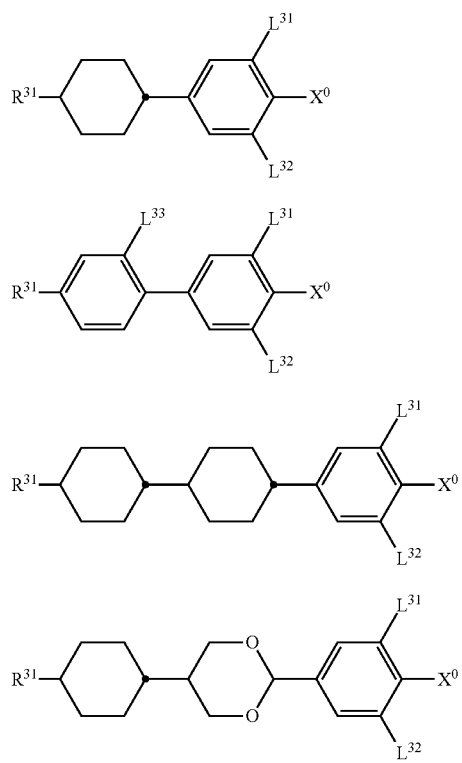

B2a
B2b
B2c
B2d

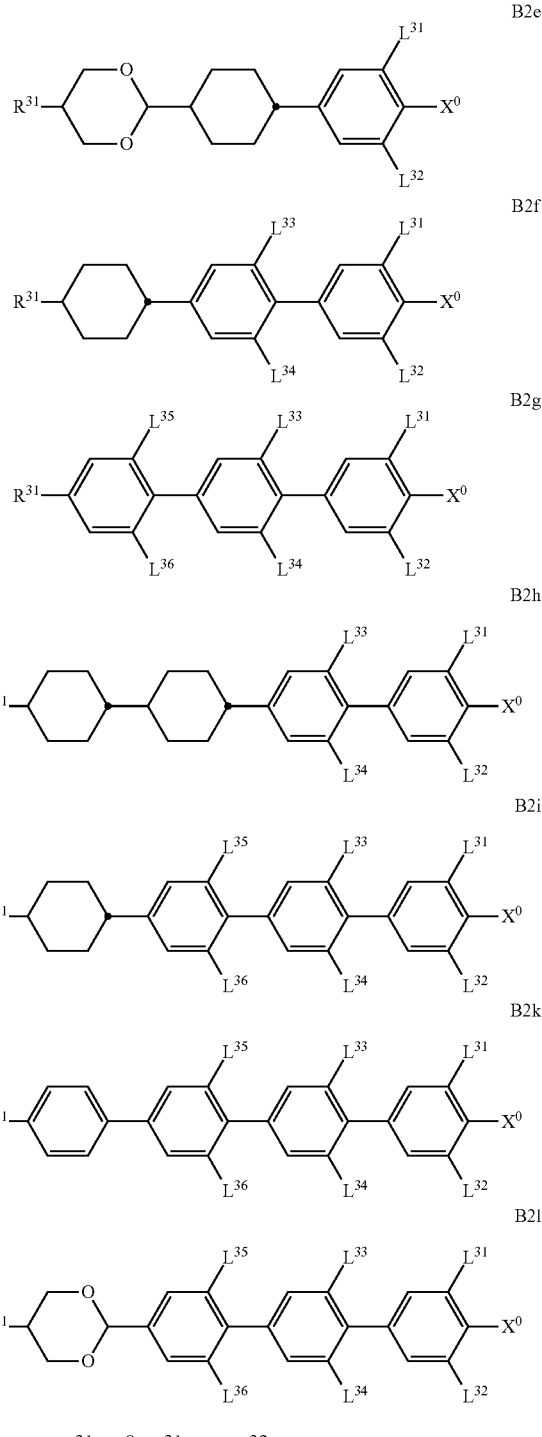

B2e
B2f
B2g
B2h
B2i
B2k
B2l in which $R^{31}$, $X^0$, $L^{31}$ and $L^{32}$ have the meaning given in formula B2, $L^{33}$, $L^{34}$, $L^{35}$ and $L^{36}$ are each, independently of one another, H or F, and $X^0$ is preferably F.

Very particularly preferred compounds of formula B2 are selected from the group consisting of the following subformulae:

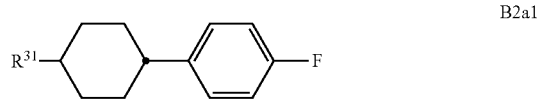

B2a1

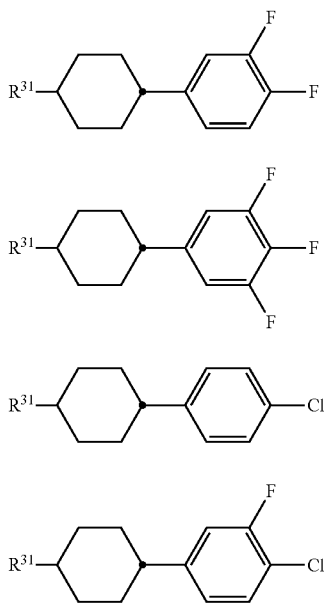

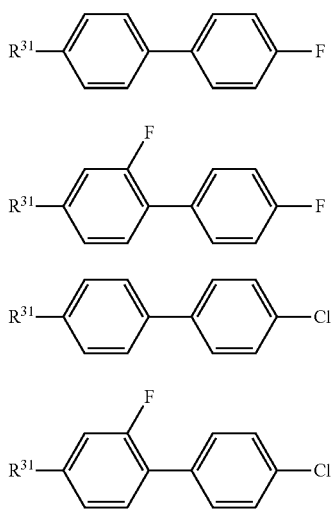

in which $R^{31}$ is as defined in formula B2.

Very particularly preferred compounds of formula B2b are selected from the group consisting of the following subformulae

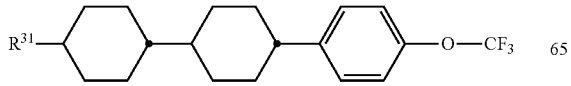

in which $R^{31}$ is as defined in formula B2.

Very particularly preferred compounds of formula B2c are selected from the group consisting of the following subformulae:

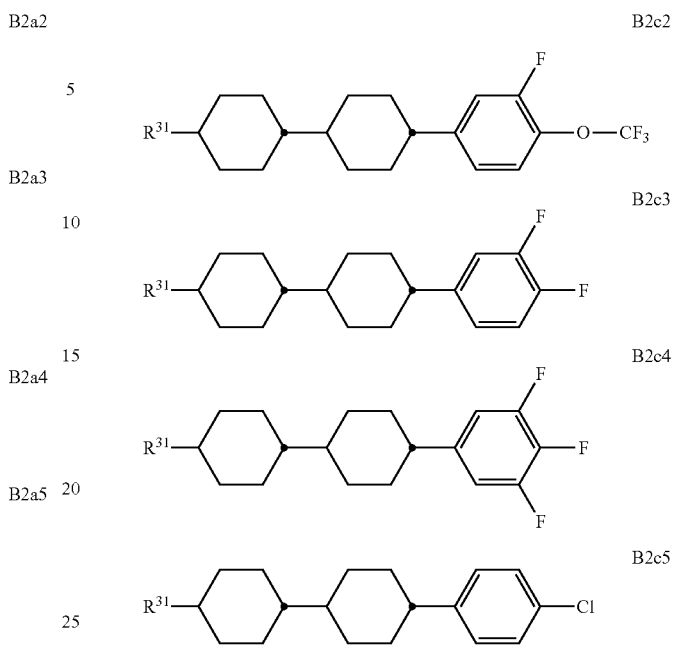

in which $R^{31}$ is as defined in formula B2.

Very particularly preferred compounds of formula B2d and B2e are selected from the group consisting of the following subformulae:

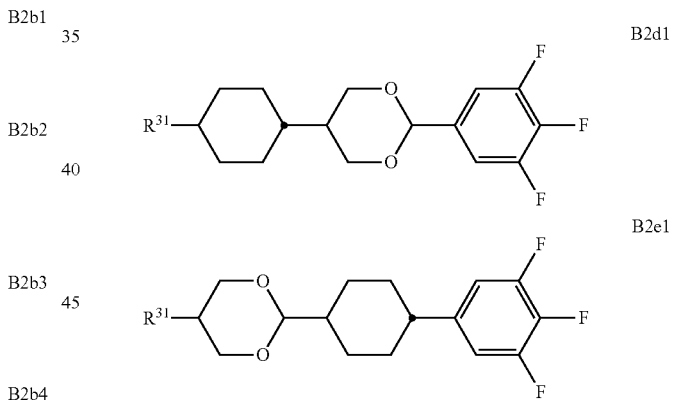

in which $R^{31}$ is as defined in formula B2.

Very particularly preferred compounds of formula B2f are selected from the group consisting of the following subformulae:

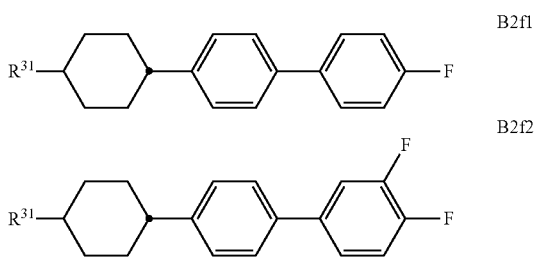

-continued

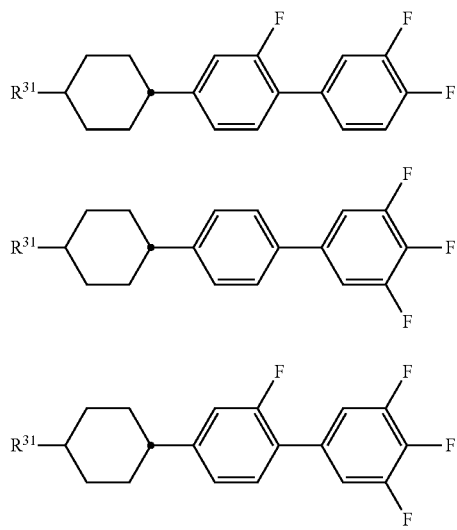

B2f3

B2f4

B2f5 in which $R^{31}$ is as defined in formula B2.

Very particularly preferred compounds of formula B2g are selected from the group consisting of the following subformulae:

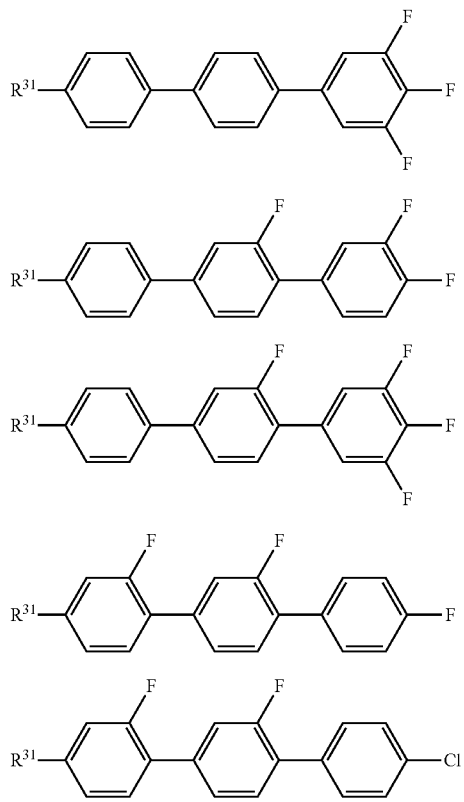

B2g1

B2g2

B2g3

B2g4

B2g5 in which $R^{31}$ is as defined in formula B2.

Very particularly preferred compounds of formula B2 h are selected from the group consisting of the following subformulae:

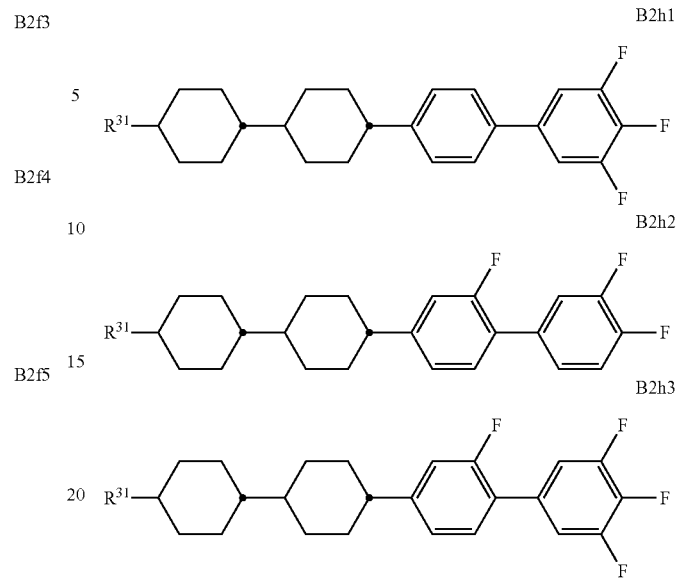

B2h1

B2h2

B2h3 in which $R^{31}$ is as defined in formula B2.

Very particularly preferred compounds of formula B2i are selected from the group consisting of the following subformulae:

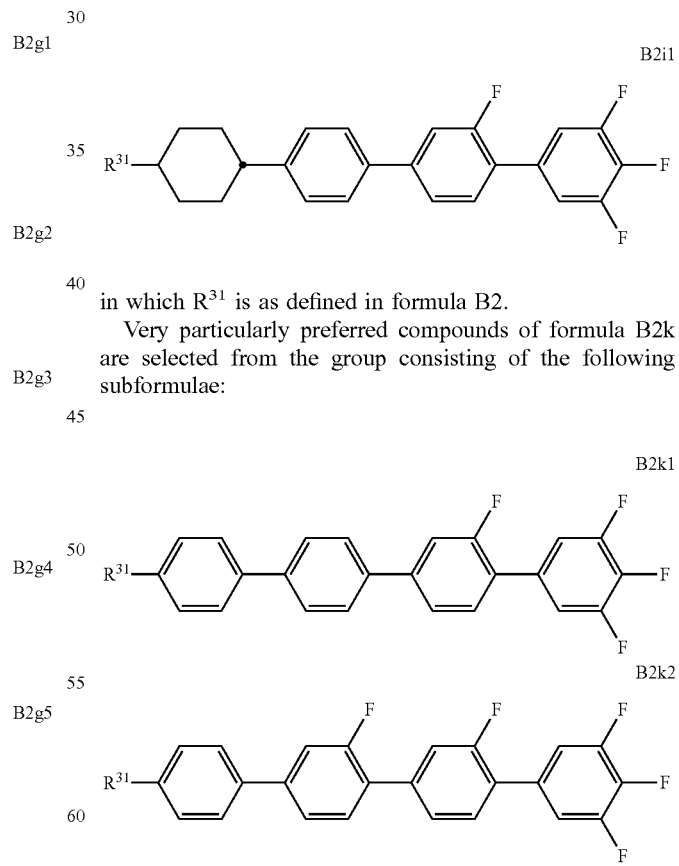

B2i1 in which $R^{31}$ is as defined in formula B2.

Very particularly preferred compounds of formula B2k are selected from the group consisting of the following subformulae:

B2k1

B2k2 in which $R^{31}$ is as defined in formula B2.

Very particularly preferred compounds of formula B2l are selected from the group consisting of the following subformulae:

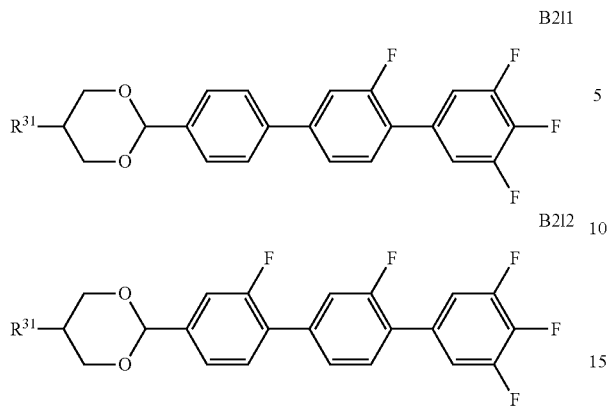

B2l1

B2l2 in which $R^{31}$ is as defined in formula B2.

Alternatively to, or in addition to, the compounds of formula B1 and/or B2 component B) of the LC medium may also comprise one or more compounds of formula B3 as defined above.

Particularly preferred compounds of formula B3 are selected from the group consisting of the following subformulae:

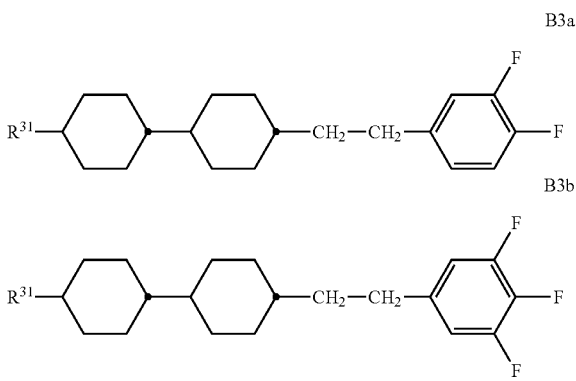

B3a

B3b in which $R^{31}$ is as defined in formula B3.

Preferably component B) of the LC medium comprises, in addition to the compounds of formula A and/or B, one or more compounds of formula C

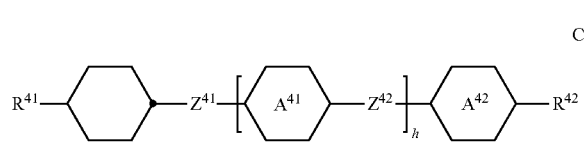

C in which the individual radicals have the following meanings:

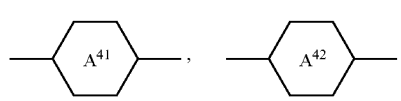

each, independently of one another, and on each occurrence, identically or differently

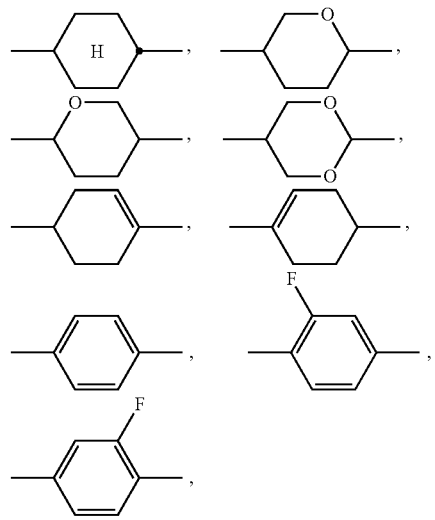

$R^{41}$, $R^{42}$ each, independently of one another, alkyl, alkoxy, oxaalkyl or alkoxyalkyl having 1 to 9 C atoms or alkenyl or alkenyloxy having 2 to 9 C atoms, all of which are optionally fluorinated, $Z^{41}$, $Z^{42}$ each, independently of one another, —CH$_2$CH$_2$—, —COO—, trans-CH=CH—, trans-CF=CF—, —CH$_2$O—, —CF$_2$O—, —C≡C— or a single bond, preferably a single bond, h 0, 1, 2 or 3.

In the compounds of formula C, $R^{41}$ and $R^{42}$ are preferably selected from straight-chain alkyl or alkoxy with 1, 2, 3, 4, 5 or 6 C atoms, and straight-chain alkenyl with 2, 3, 4, 5, 6 or 7 C atoms.

In the compounds of formula C, h is preferably 0, 1 or 2.

In the compounds of formula C, $Z^{41}$ and $Z^{42}$ are preferably selected from COO, trans-CH=CH and a single bond, very preferably from COO and a single bond.

Preferred compounds of formula C are selected from the group consisting of the following subformulae:

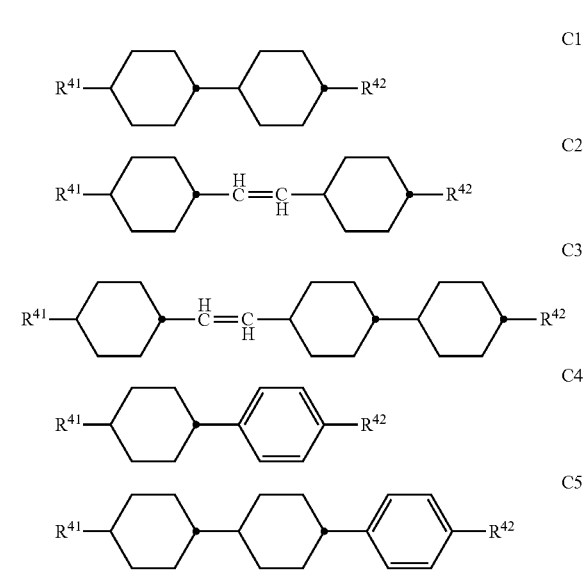

C1

C2

C3

C4

C5

C6
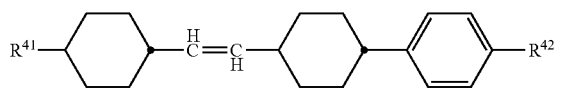

C7
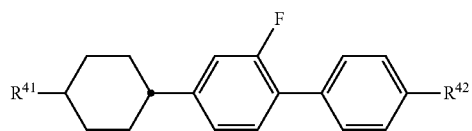

C8
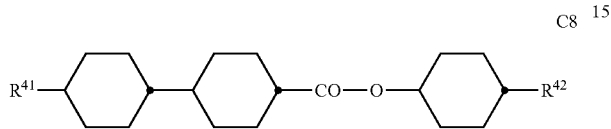

C9
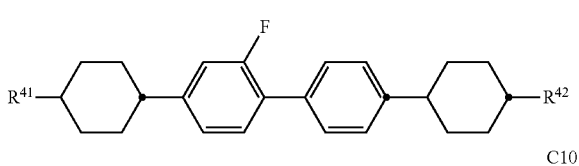

C10
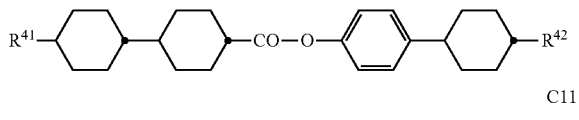

C11
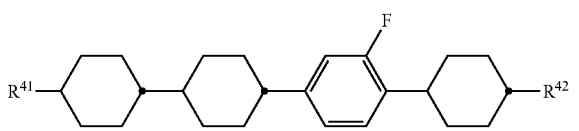

C12
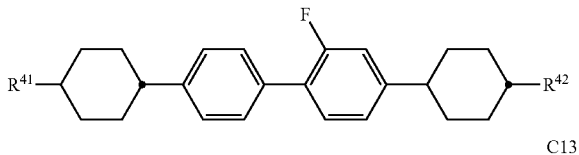

C13
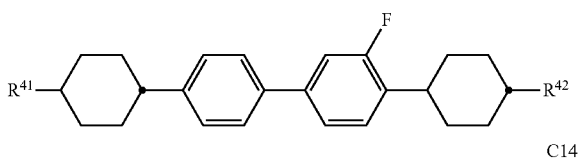

C14
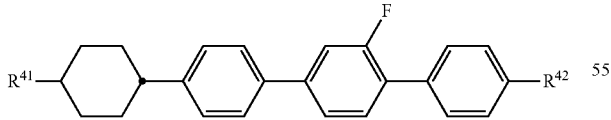

wherein $R^{41}$ and $R^{42}$ have the meanings given in formula C, and preferably denote each, independently of one another, alkyl, alkoxy, fluorinated alkyl or fluorinated alkoxy with 1 to 7 C atoms, or alkenyl, alkenyloxy, alkoxyalkyl or fluorinated alkenyl with 2 to 7 C atoms.

Further preferably component B) of the LC medium comprises, in addition to the compounds of formula A and/or B, one or more compounds of formula D D
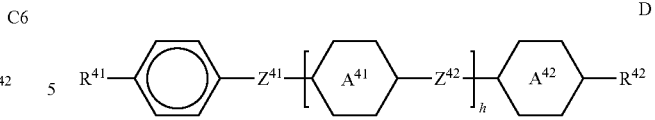

in which $A^{41}$, $A^{42}$, $Z^{41}$, $Z^{42}$, $R^{41}$, $R^{42}$ and h have the meanings given in formula C or one of the preferred meanings given above.

Preferred compounds of formula D are selected from the group consisting of the following subformulae:

D1
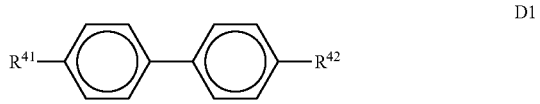

D2
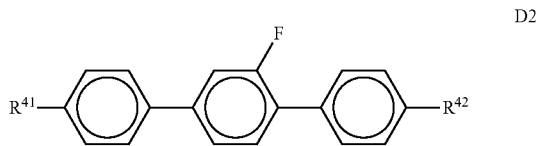

in which $R^{41}$ and $R^{42}$ have the meanings given in formula D and $R^{41}$ preferably denotes alkyl bedeutet, and in formula D1 $R^{42}$ preferably denotes alkenyl, particularly preferably —(CH$_2$)$_2$—CH=CH—CH$_3$, and in formula D2 $R^{42}$ preferably denotes alkyl, —(CH$_2$)$_2$—CH=CH$_2$ or —(CH$_2$)$_2$—CH=CH—CH$_3$.

Further preferably component B) of the LC medium comprises, in addition to the compounds of formula A and/or B, one or more compounds of formula E containing an alkenyl group E
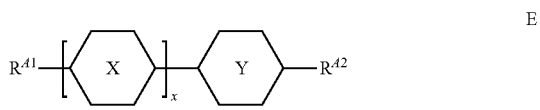

in which the individual radicals, on each occurrence identically or differently, each, independently of one another, have the following meaning:

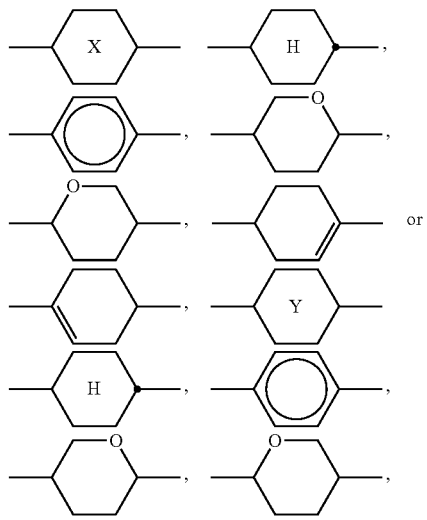

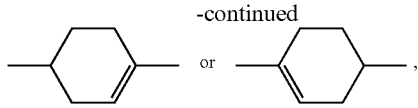 , $R^{A1}$ alkenyl having 2 to 9 C atoms or, if at least one of the rings X, Y and Z denotes cyclohexenyl, also one of the meanings of $R^{A2}$, $R^{A2}$ alkyl having 1 to 12 C atoms, in which, in addition, one or two non-adjacent CH$_2$ groups may be replaced by —O—, —CH=CH—, —CO—, —OCO— or —COO— in such a way that O atoms are not linked directly to one another, x 1 or 2.

$R^{A2}$ is preferably straight-chain alkyl or alkoxy having 1 to 8 C atoms or straight-chain alkenyl having 2 to 7 C atoms.

Preferred compounds of formula E are selected from the following sub-formulae:

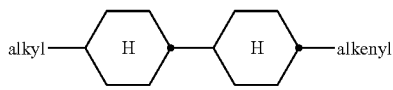 E1

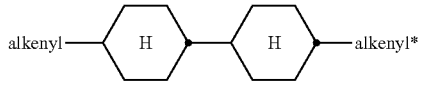 E2

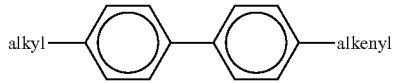 E3

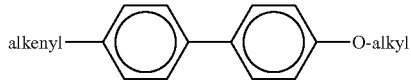 E4

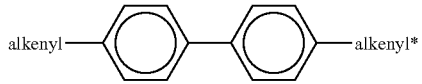 E5

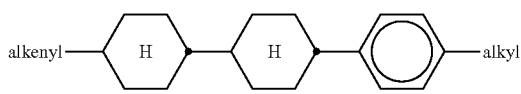 E6

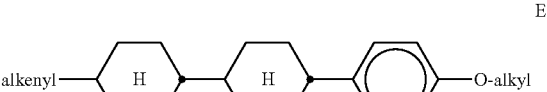 E7

 E8

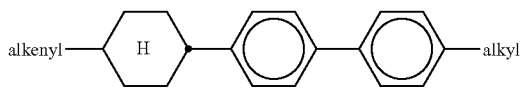 E9

 E10

 E11

 E12 in which alkyl and alkyl* each, independently of one another, denote a straight-chain alkyl radical having 1-6 C atoms, and alkenyl and alkenyl* each, independently of one another, denote a straight-chain alkenyl radical having 2-7 C atoms. Alkenyl and alkenyl* preferably denote CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

Very preferred compounds of the formula E are selected from the following sub-formulae:

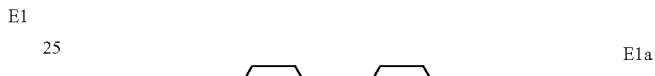 E1a

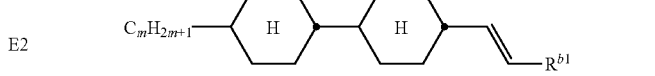 E3a

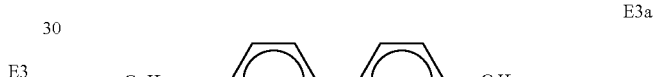 E6a in which m denotes 1, 2, 3, 4, 5 or 6, i denotes 0, 1, 2 or 3, and $R^{b1}$ denotes H, CH$_3$ or C$_2$H$_5$.

Very particularly preferred compounds of the formula E are selected from the following sub-formulae:

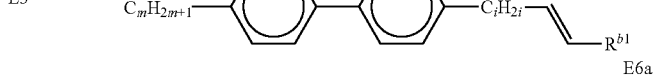 E1a1

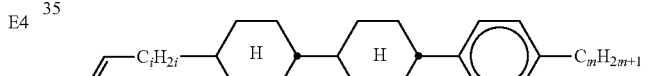 E1a2

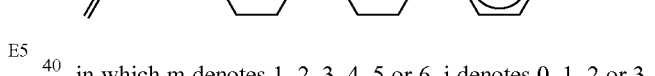 E1a3

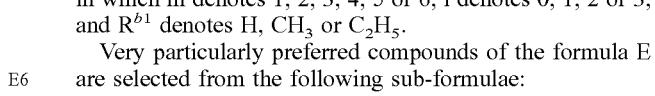 E1a4

 E1a5

-continued

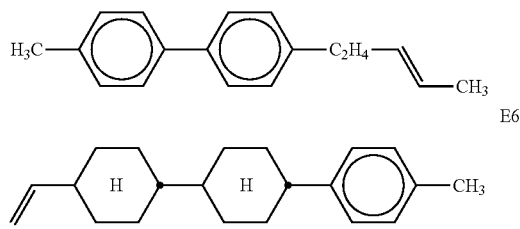

Most preferred are compounds of formula E1a2, E1a5, E3a1 and E6a1.

Further preferably component B) of the LC medium comprises, in addition to the compounds of formula A and/or B, one or more compounds of formula F

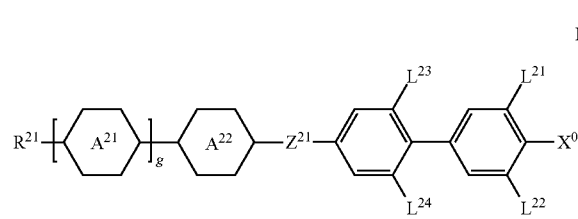

in which the individual radicals have, independently of each other and on each occurrence identically or differently, the following meanings:

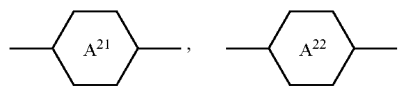

denote

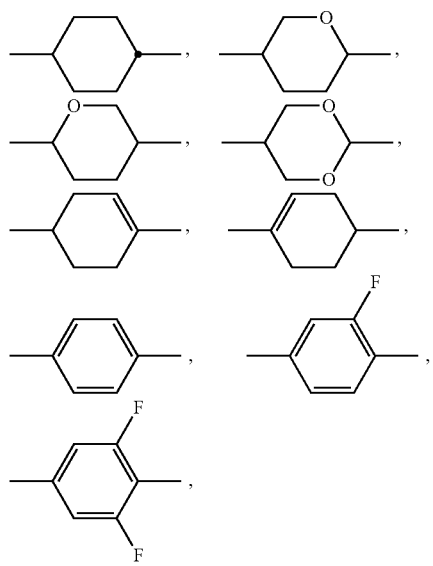

$R^{21}$, $R^{31}$ each, independently of one another, alkyl, alkoxy, oxaalkyl or alkoxyalkyl having 1 to 9 C atoms or alkenyl or alkenyloxy having 2 to 9 C atoms, all of which are optionally fluorinated, $X^0$ F, Cl, halogenated alkyl or alkoxy having 1 to 6 C atoms or halogenated alkenyl or alkenyloxy having 2 to 6 C atoms, $Z^{21}$ —CH$_2$CH$_2$—, —CF$_2$CF$_2$—, —COO—, trans-CH=CH—, trans-CF=CF—, —CH$_2$O— or a single bond, preferably —CH$_2$CH$_2$—, —COO—, trans-CH=CH— or a single bond, particularly preferably —COO—, trans-CH=CH— or a single bond, $L^{21}$, $L^{22}$, $L^{23}$, $L^{24}$ each, independently of one another, H or F, g 0, 1, 2 or 3.

Particularly preferred compounds of formula F are selected from the group consisting of the following formulae:

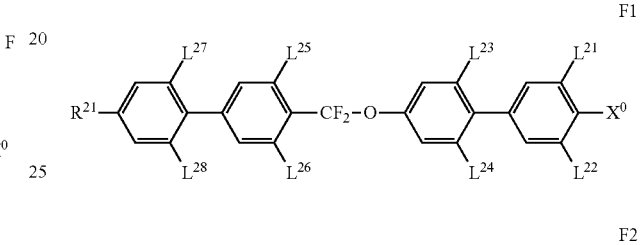

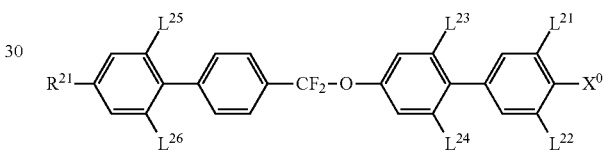

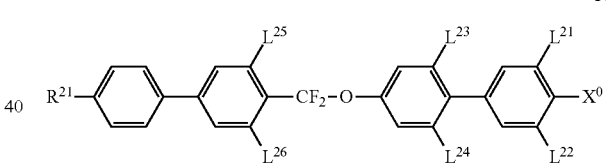

in which $R^{21}$, $X^0$, $L^{21}$ and $L^{22}$ have the meaning given in formula F, $L^{25}$ and $L^{26}$ are each, independently of one another, H or F, and $X^0$ is preferably F.

Very particularly preferred compounds of formula F1-F3 are selected from the group consisting of the following subformulae:

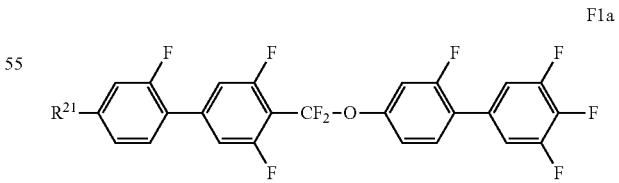

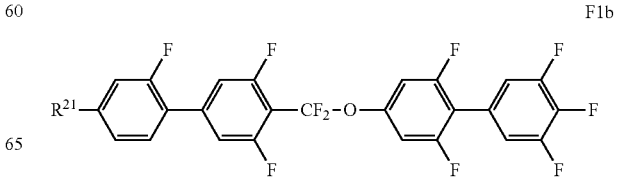

-continued

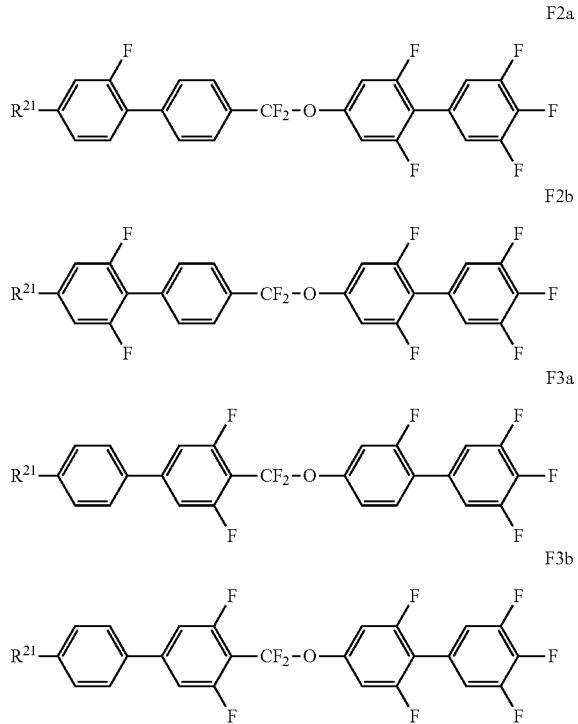

In which $R^{21}$ is as defined in formula F1.

The concentration of the compounds of formula A and B in the LC host mixture is preferably from 2 to 60%, very preferably from 3 to 45%, most preferably from 4 to 35%.

The concentration of the compounds of formula C and D in the LC host mixture is preferably from 2 to 70%, very preferably from 5 to 65%, most preferably from 10 to 60%.

The concentration of the compounds of formula E in the LC host mixture is preferably from 5 to 50%, very preferably from 5 to 35%.

The concentration of the compounds of formula F in the LC host mixture is preferably from 2 to 30%, very preferably from 5 to 20%.

Further preferred embodiments of this second preferred embodiment of the present invention are listed below, including any combination thereof.

2a) The LC host mixture comprises one or more compounds of formula A and/or B with high positive dielectric anisotropy, preferably with $\Delta\varepsilon>15$.
2b) The LC host mixture comprises one or more compounds selected from the group consisting of formulae A1a2, A1 b1, A1 d1, A1 f1, A2a1, A2h1, A2l2, A2k1, B2h3, B2l1, F1a. The proportion of these compounds in the LC host mixture is preferably from 4 to 40%, very preferably from 5 to 35%.
2c) The LC host mixture comprises one or more compounds selected from the group consisting of formulae B2c1, B2c4, B2f4, C14. The proportion of these compounds in the LC host mixture is preferably from 4 to 40%, very preferably from 5 to 35%.
2d) The LC host mixture comprises one or more compounds selected from the group consisting of formulae C3, C4, C5, C9 and D2. The proportion of these compounds in the LC host mixture is preferably from 8 to 70%, very preferably from 10 to 60%.
2e) The LC host mixture comprises one or more compounds selected from the group consisting of formulae E1, E3 and E6, preferably E1a, E3a and E6a, very preferably E1a2, E1a5, E3a1 and E6a1. The proportion of these compounds in the LC host mixture is preferably from 5 to 60%, very preferably from 10 to 50%.

The combination of compounds of the preferred embodiments mentioned above with the polymerised compounds described above causes low threshold voltages, low rotational viscosities and very good low-temperature stabilities in the LC media according to the invention at the same time as constantly high clearing points and high HR values, and allows the rapid establishment of a particularly low tilt angle (i.e. a large tilt) in PSA displays. In particular, the LC media exhibit significantly shortened response times, in particular also the grey-shade response times, in PSA displays compared with the media from the prior art.

The LC media and LC host mixtures of the present invention preferably have a nematic phase range of at least 80 K, particularly preferably at least 100 K, and a rotational viscosity ≤250 mPa·s, preferably ≤200 mPa·s, at 20° C.

In the VA-type displays according to the invention, the molecules in the layer of the LC medium in the switched-off state are aligned perpendicular to the electrode surfaces (homeotropically) or have a a tilted homeotropic alignment. On application of an electrical voltage to the electrodes, a re-alignment of the LC molecules takes place with the longitudinal molecular axes parallel to the electrode surfaces.

LC media according to the invention based on compounds with negative dielectric anisotropy according to the first preferred embodiment, in particular for use in displays of the PS-VA, PS-UB-FFS and SA-VA type, have a negative dielectric anisotropy $\Delta\varepsilon$, preferably from −0.5 to −10, in particular from −2.5 to −7.5, at 20° C. and 1 kHz.

The birefringence $\Delta n$ in LC media according to the invention for use in displays of the PS-VA, PS-UB-FFS and SA-VA type is preferably below 0.16, particularly preferably from 0.06 to 0.14, very particularly preferably from 0.07 to 0.12.

In the OCB-type displays according to the invention, the molecules in the layer of the LC medium have a "bend" alignment. On application of an electrical voltage, a realignment of the LC molecules takes place with the longitudinal molecular axes perpendicular to the electrode surfaces.

LC media according to the invention, based on compounds with positive dielectric anisotropy according to the second preferred embodiment, for use in displays of the PS-TN-, PS-posi-VA-, PS-IPS-, PS-FFS and SA-FFS type, preferably have a positive dielectric anisotropy $\Delta\varepsilon$ from +2 to +30, particularly preferably from +3 to +20, at 20° C. and 1 kHz.

The birefringence $\Delta n$ in LC media according to the invention for use in displays of the PS-OCB type is preferably from 0.14 to 0.22, particularly preferably from 0.16 to 0.22.

The birefringence $\Delta n$ in LC media according to the invention for use in displays of the PS-TN-, PS-posi-VA-, PS-IPS-, PS-FFS and SA-FFS type is preferably from 0.07 to 0.15, particularly preferably from 0.08 to 0.13.

The LC media according to the invention may also comprise further additives which are known to the person skilled in the art and are described in the literature, such as, for example, polymerisation initiators, inhibitors, stabilisers, surface-active substances or chiral dopants. These may be polymerisable or non-polymerisable. Polymerisable additives are accordingly ascribed to the polymerisable component or component A). Non-polymerisable additives are accordingly ascribed to the non-polymerisable component or component B).

Furthermore, it is possible to add to the LC media, for example, 0 to 15% by weight of pleochroic dyes, furthermore nanoparticles, conductive salts, preferably ethyldimethyldodecylammonium 4-hexoxybenzoate, tetrabutyl-ammonium tetraphenylborate or complex salts of crown ethers (cf., for example, Haller et al., Mol. Cryst. Liq. Cryst. 24, 249-258 (1973)), for improving the conductivity, or substances for modifying the dielectric anisotropy, the viscosity and/or the alignment of the nematic phases. Sub-stances of this type are described, for example, in DE-A 22 09 127, 22 40 864, 23 21 632, 23 38 281, 24 50 088, 26 37 430 and 28 53 728.

The individual components of the preferred embodiments a)-z) of the LC media according to the invention are either known or methods for the preparation thereof can readily be derived from the prior art by the person skilled in the relevant art, since they are based on standard methods described in the literature. Corresponding compounds of the formula CY are described, for example, in EP-A-0 364 538. Corresponding compounds of the formula ZK are described, for example, in DE-A-26 36 684 and DE-A-33 21 373.

The LC media which can be used in accordance with the invention are prepared in a manner conventional per se, for example by mixing one or more of the above-mentioned compounds with one or more polymerisable compounds as defined above, and optionally with further liquid-crystalline compounds and/or additives. In general, the desired amount of the components used in lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing. The invention furthermore relates to the process for the preparation of the LC media according to the invention.

It goes without saying to the person skilled in the art that the LC media according to the invention may also comprise compounds in which, for example, H, N, O, Cl, F have been replaced by the corresponding isotopes like deuterium etc.

The following examples explain the present invention without restricting it. However, they show the person skilled in the art preferred mixture concepts with compounds preferably to be employed and the respective concentrations thereof and combinations thereof with one another. In addition, the examples illustrate which properties and property combinations are accessible.

Preferred mixture components are shown in Tables A1 and A2 below. The compounds shown in Table A1 are especially suitable for use in LC mixtures with positive dielectric anisotropy. The compounds shown in Table A2 are especially suitable for use in LC mixtures with negative dielectric anisotropy.

In Table A1, m and n are independently of each other an integer from 1 to 12, preferably 1, 2, 3, 4, 5 or 6, k is 0, 1, 2, 3, 4, 5 or 6, and $(O)C_mH_{2m+1}$ means $C_mH_{2m+1}$ or $OC_mH_{2m+1}$.

TABLE A1

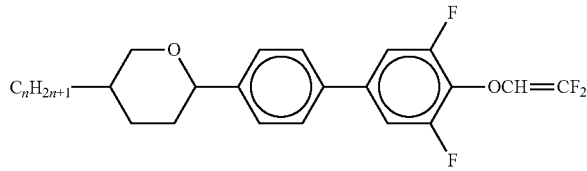

APU-n-OXF

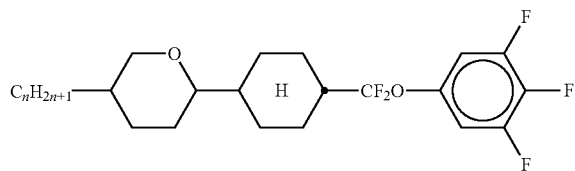

ACQU-n-F

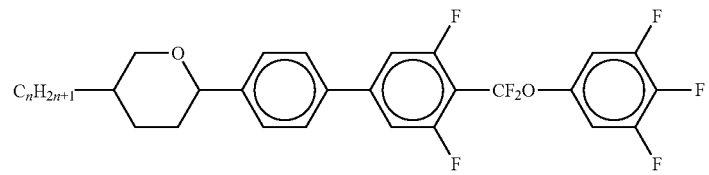

APUQU-n-F

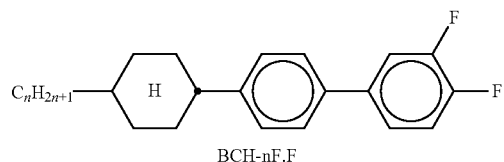

BCH-nF.F

TABLE A1-continued
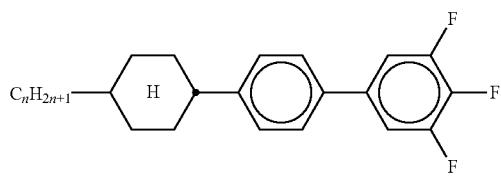
BCH-nF.F.F
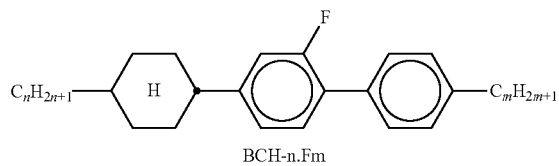
BCH-n.Fm
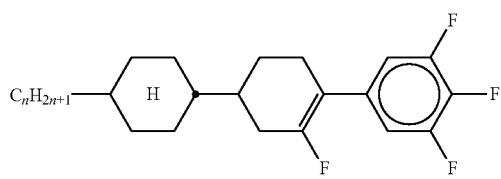
CFU-n-F
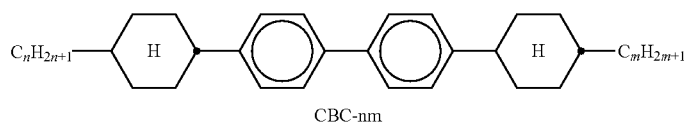
CBC-nm
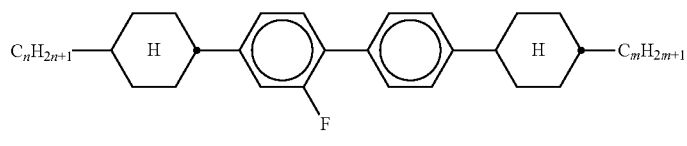
CBC-nmF
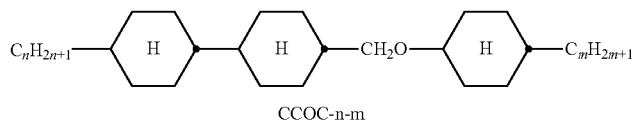
CCOC-n-m
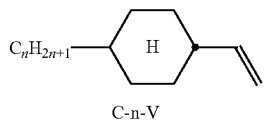
C-n-V
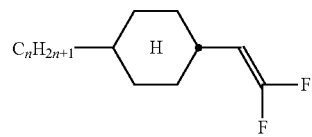
C-n-XF
C-n-m TABLE A1-continued
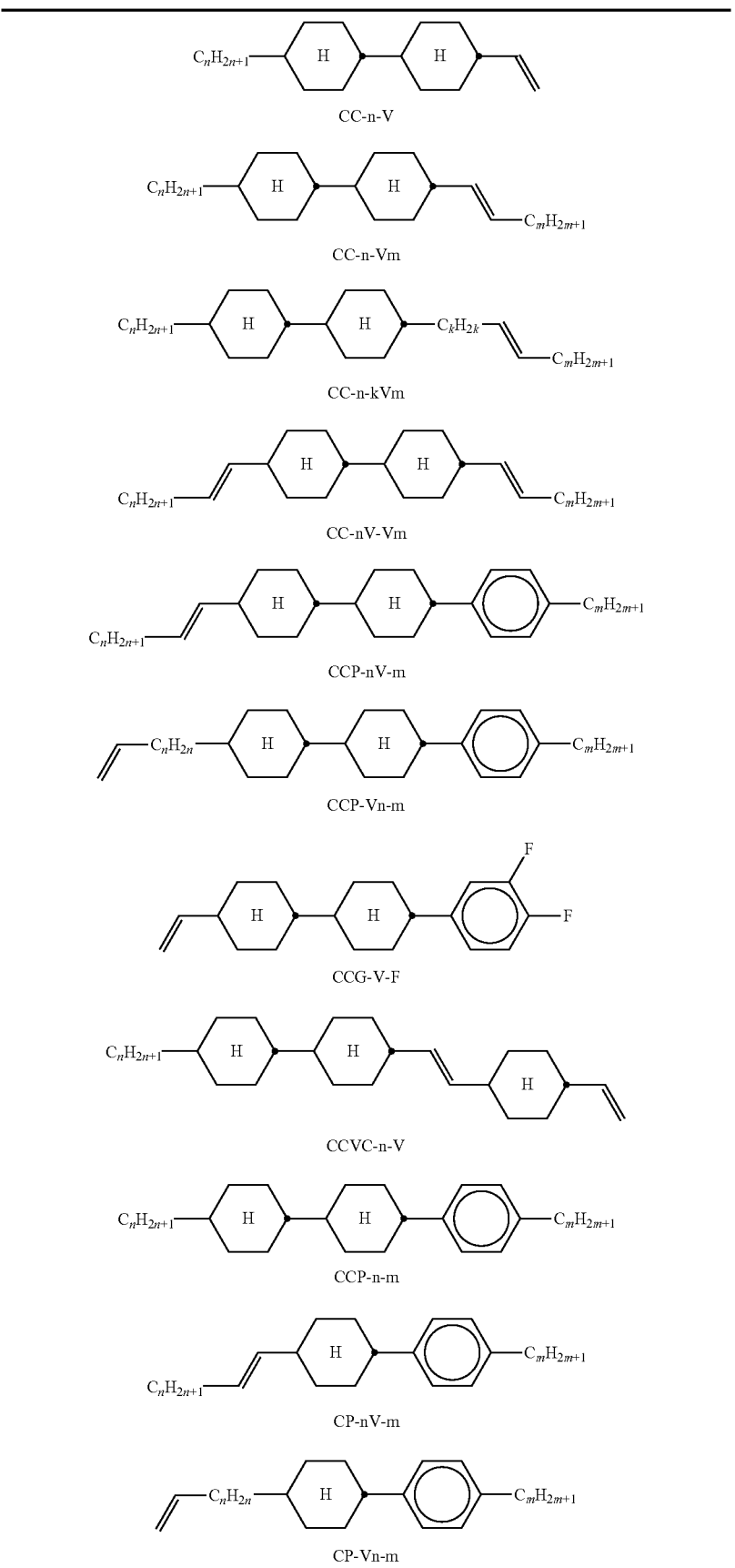

TABLE A1-continued
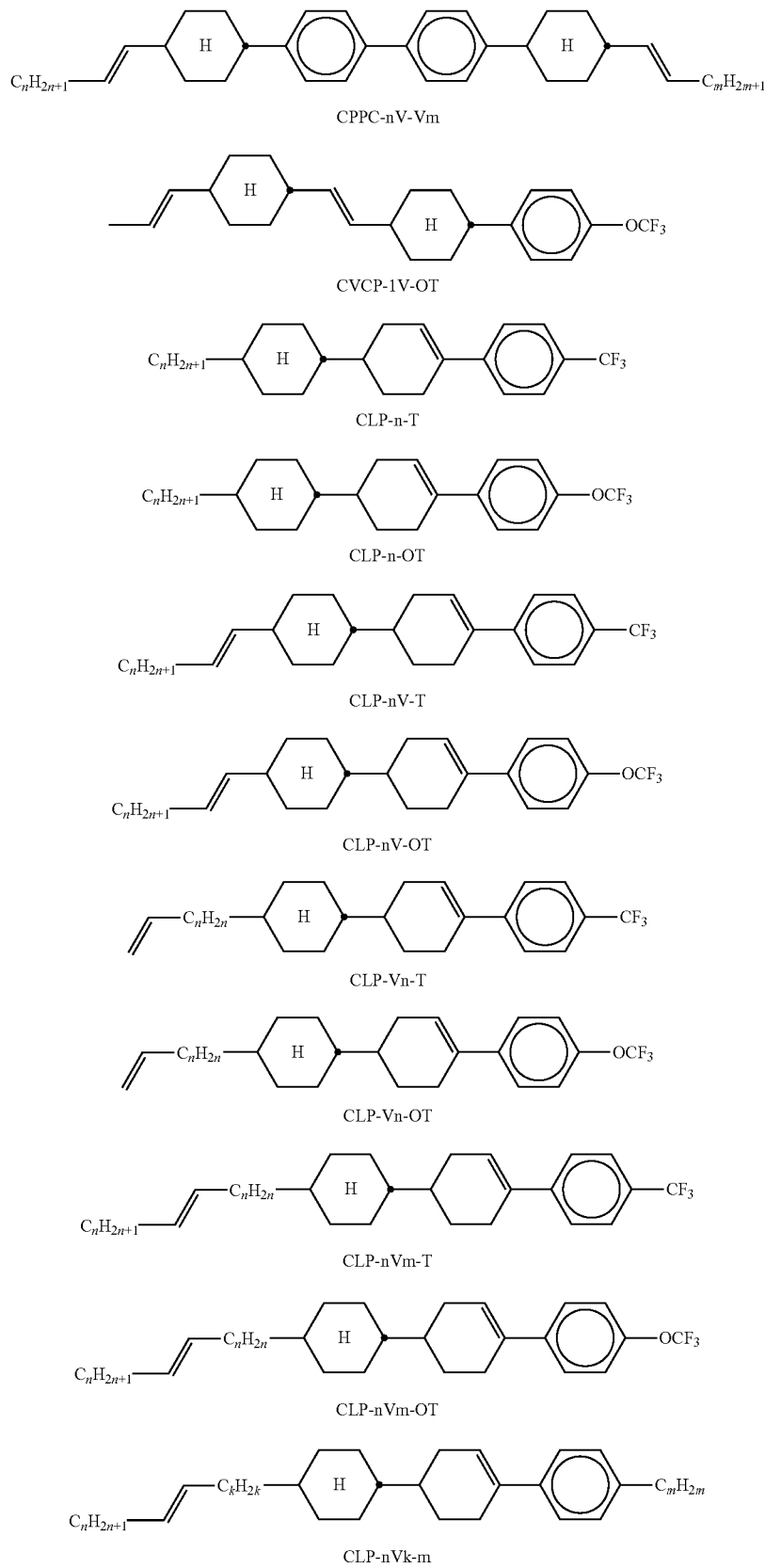

TABLE A1-continued
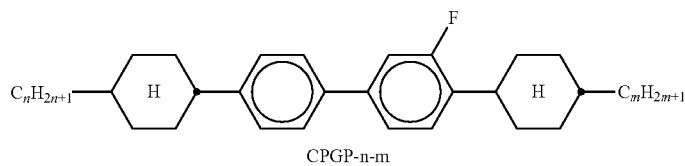
CPGP-n-m
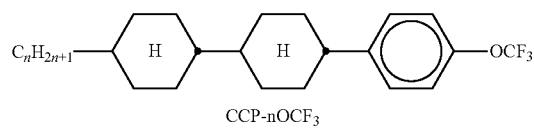
CCP-nOCF$_3$
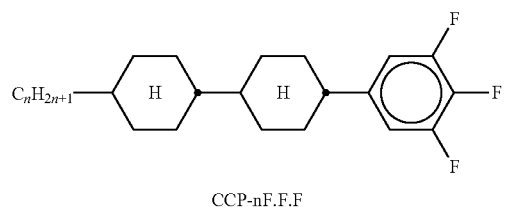
CCP-nF.F.F
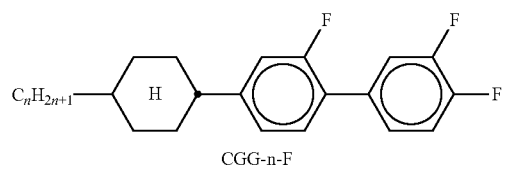
CGG-n-F
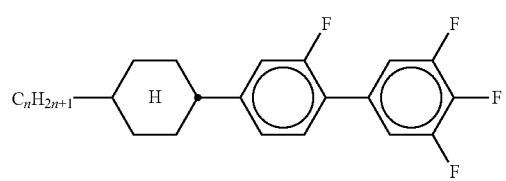
CGU-n-F
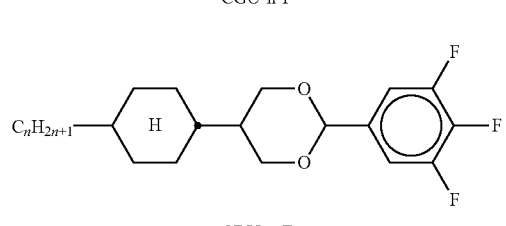
CDU-n-F
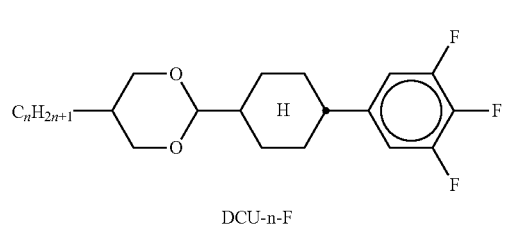
DCU-n-F
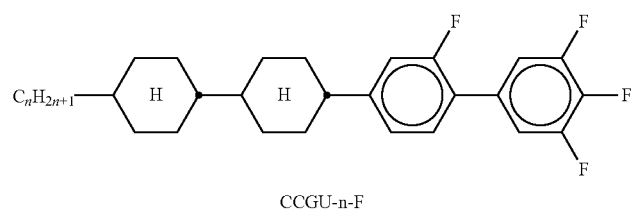
CCGU-n-F TABLE A1-continued
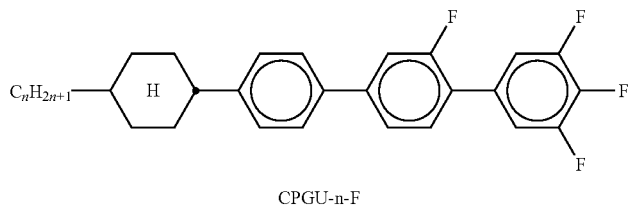
CPGU-n-F
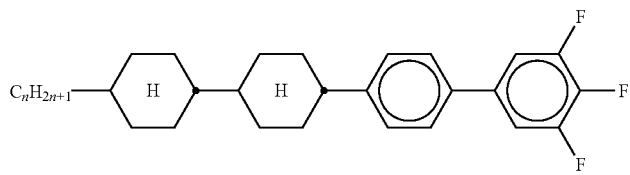
CCPU-n-F
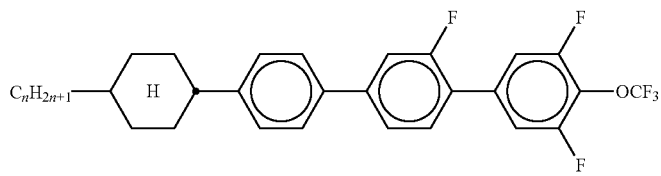
CPGU-n-OT
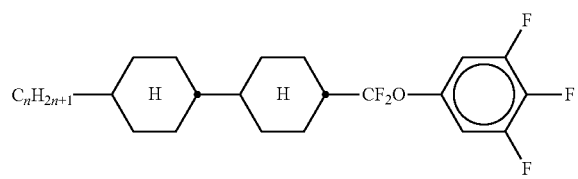
CCQU-n-F
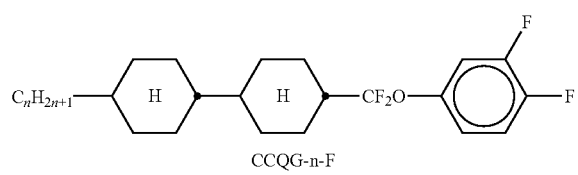
CCQG-n-F
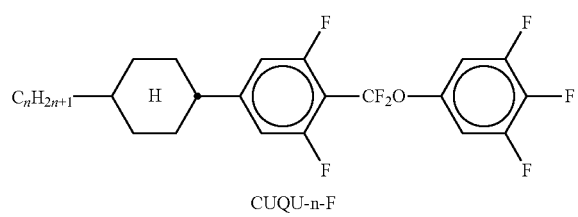
CUQU-n-F
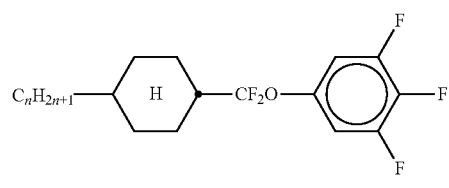
CQU-n-F TABLE A1-continued
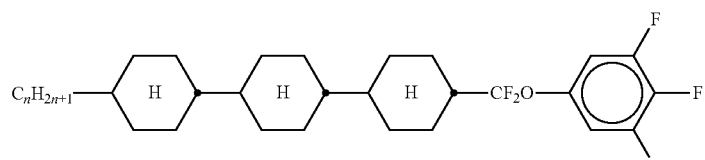
CCCQU-n-F
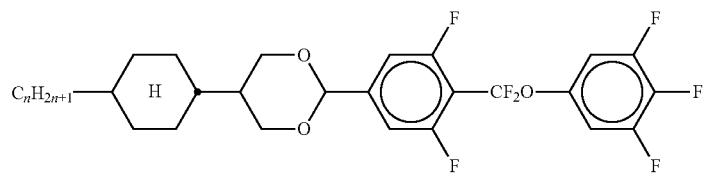
CDUQU-n-F
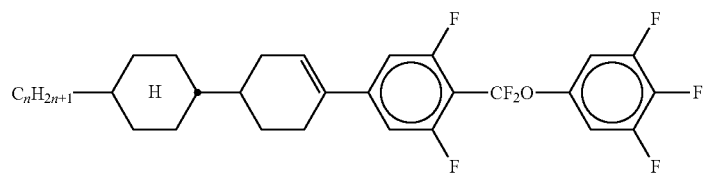
CLUQU-n-F
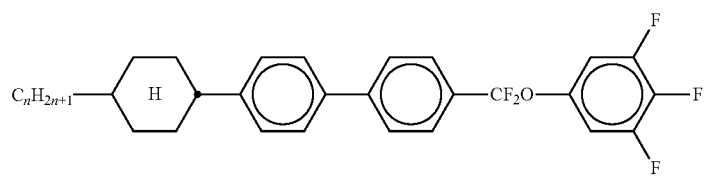
CPPQU-n-F
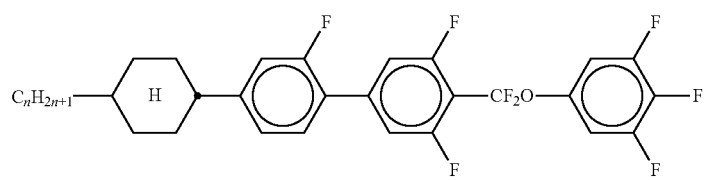
CQUQU-n-F
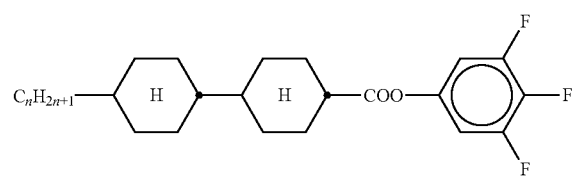
CCZU-n-F
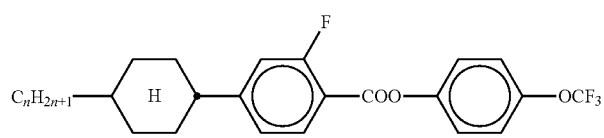
CGZP-n-OT TABLE A1-continued
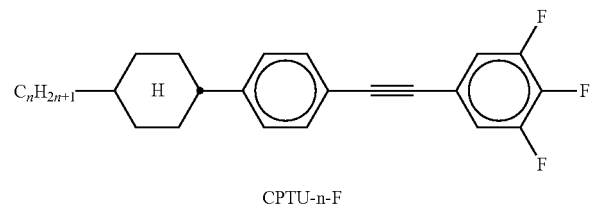
CPTU-n-F
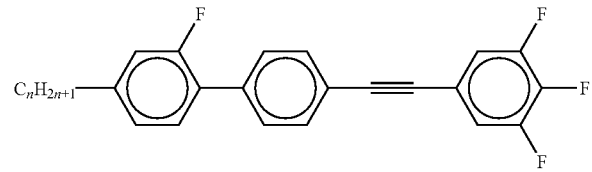
GPTU-n-F
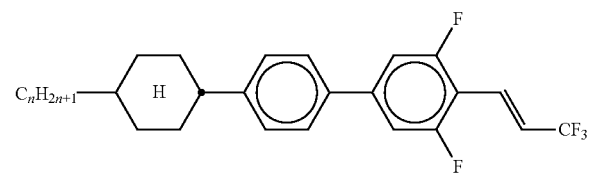
CPU-n-VT
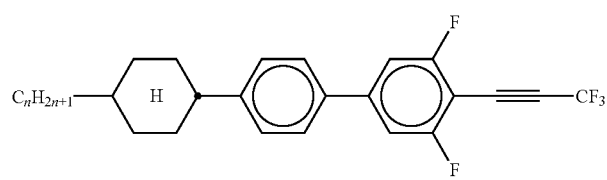
CPU-n-AT
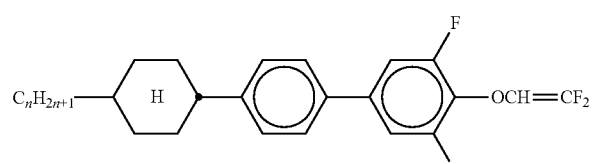
CPU-n-OXF
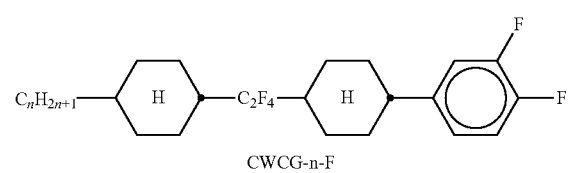
CWCG-n-F
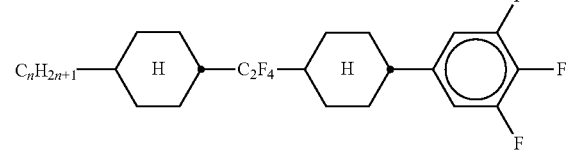
CWCU-n-F TABLE A1-continued
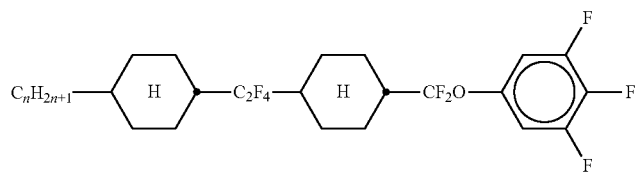
CWCQU-n-F
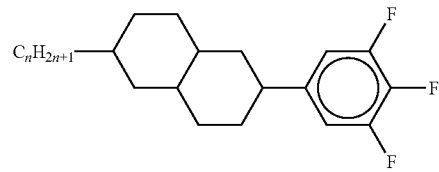
Dec-U-n-F
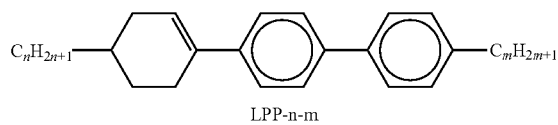
LPP-n-m
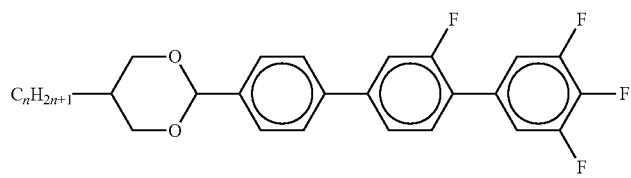
DPGU-n-F
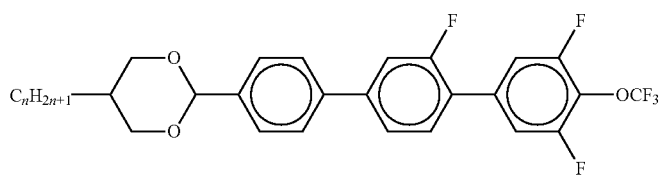
DPGU-n-OT
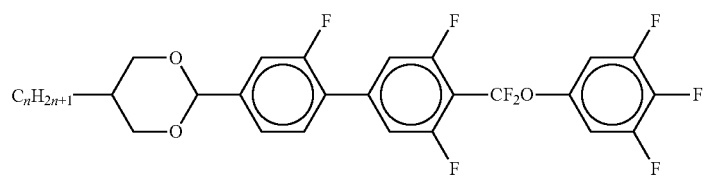
DGUQU-n-F
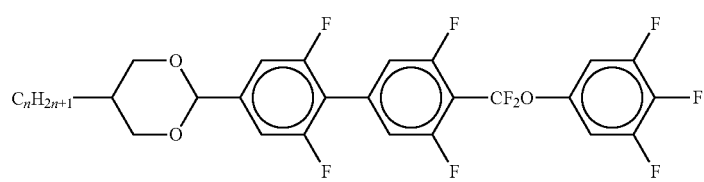
DUUQU-n-F
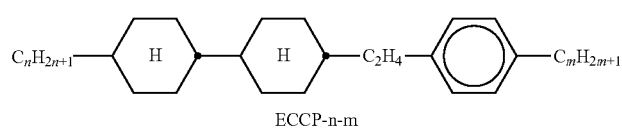
ECCP-n-m TABLE A1-continued
ECCP-nOCF₃
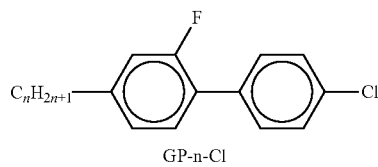
GP-n-Cl
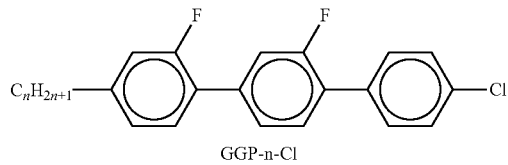
GGP-n-Cl
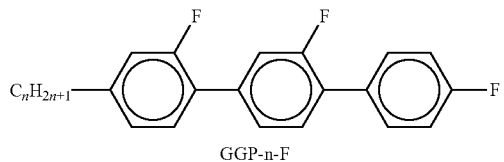
GGP-n-F
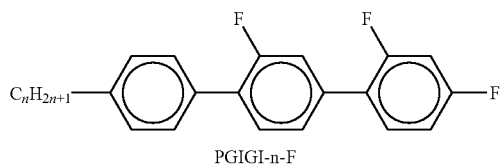
PGIGI-n-F
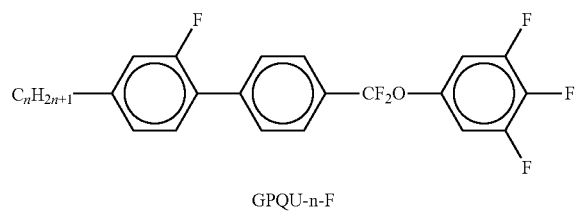
GPQU-n-F
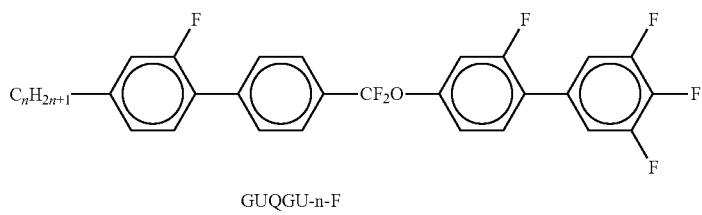
GUQGU-n-F
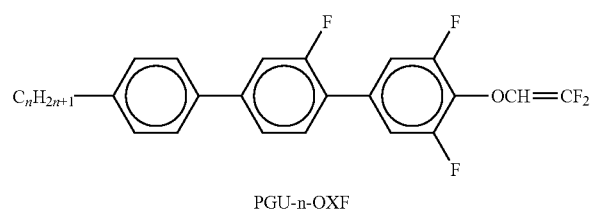
PGU-n-OXF
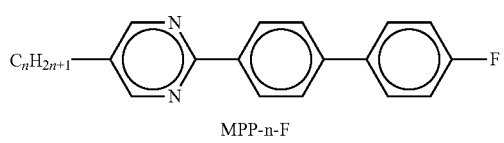
MPP-n-F TABLE A1-continued
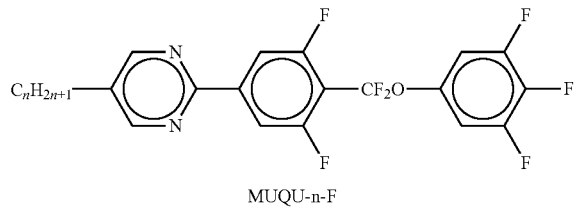
MUQU-n-F
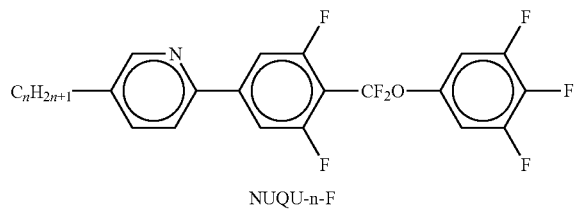
NUQU-n-F
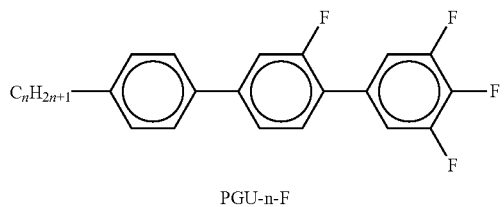
PGU-n-F
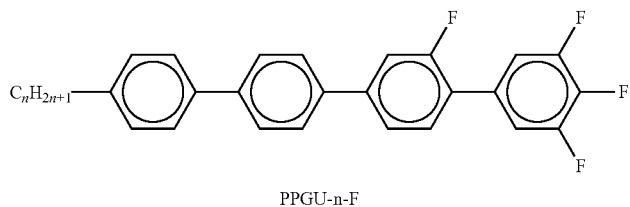
PPGU-n-F
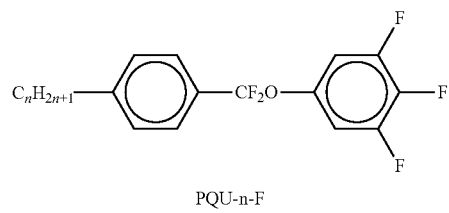
PQU-n-F
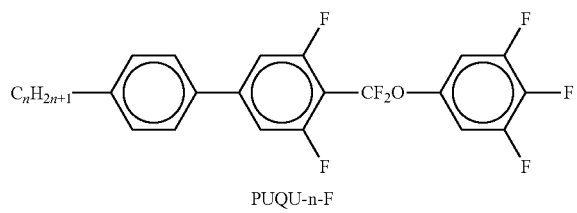
PUQU-n-F
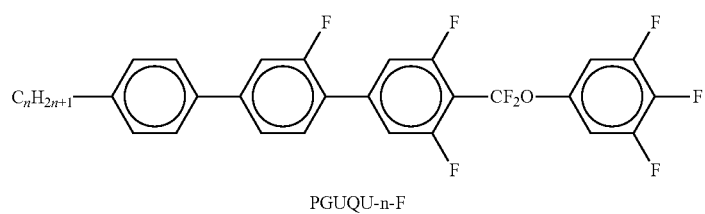
PGUQU-n-F TABLE A1-continued
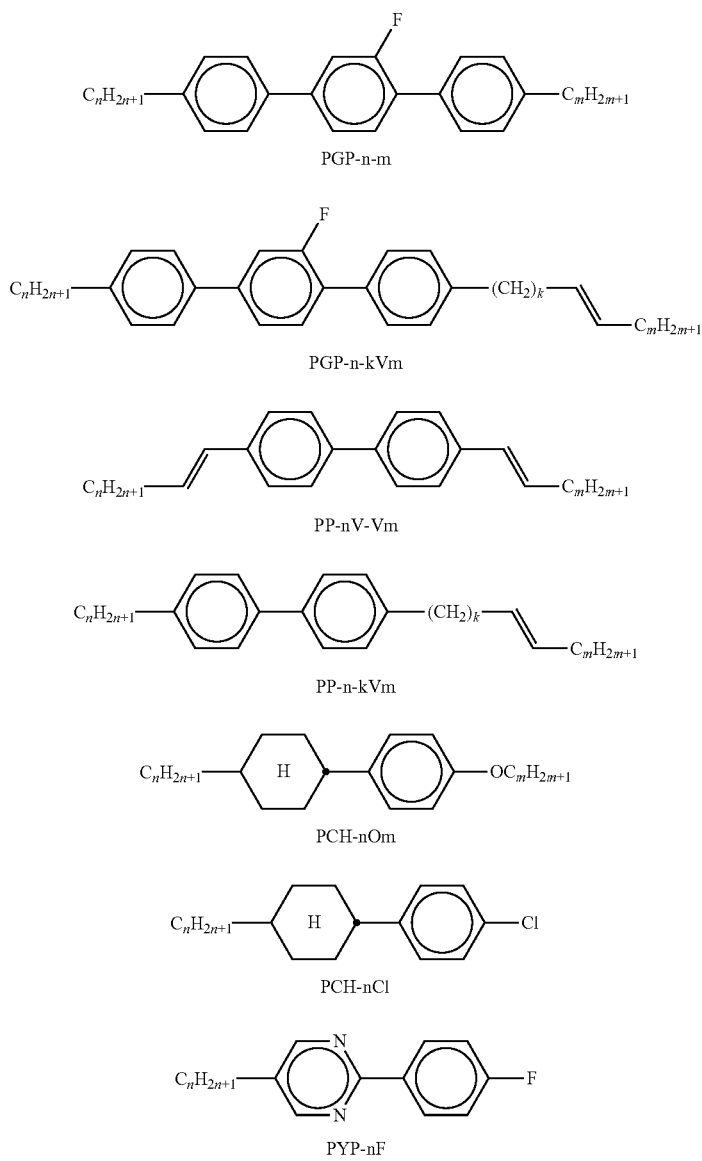
In Table A1, m and n are independently of each other an integer from 1 to 12, preferably 1, 2, 3, 4, 5 or 6, k is 0, 1, 2, 3, 4, 5 or 6, and $(O)C_mH_{2m+1}$ means $C_mH_{2m+1}$ or $OC_mH_{2m+1}$.
TABLE A2
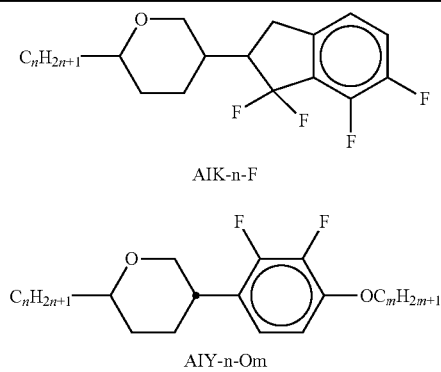

TABLE A2-continued
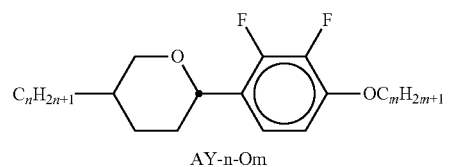
AY-n-Om
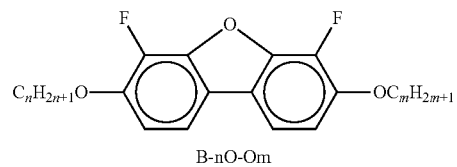
B-nO-Om
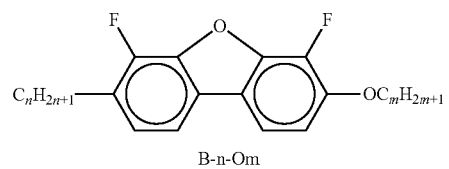
B-n-Om
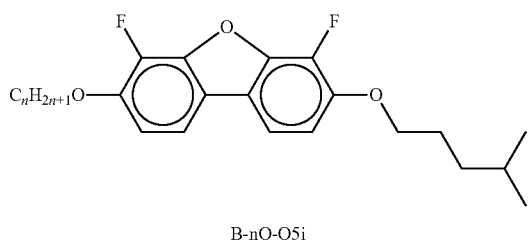
B-nO-O5i
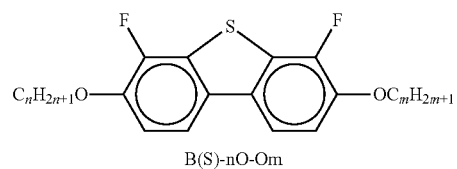
B(S)-nO-Om
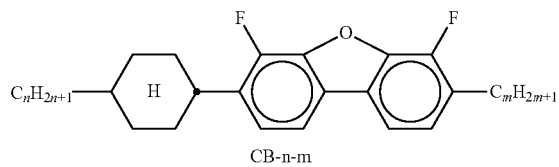
CB-n-m
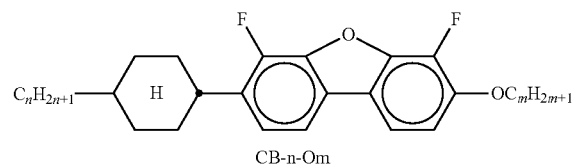
CB-n-Om
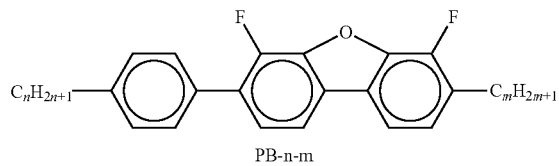
PB-n-m TABLE A2-continued
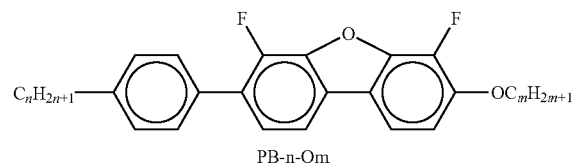
PB-n-Om
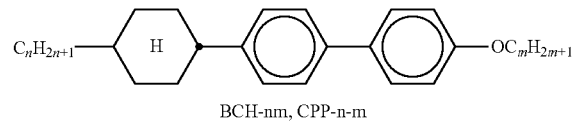
BCH-nm, CPP-n-m
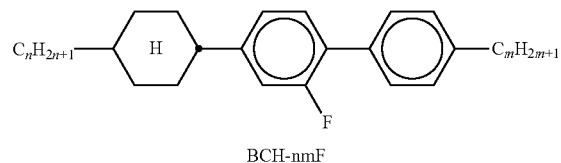
BCH-nmF
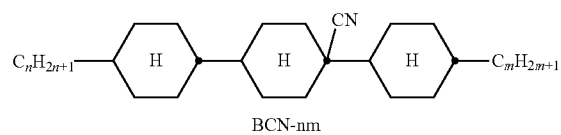
BCN-nm
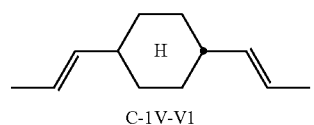
C-1V-V1
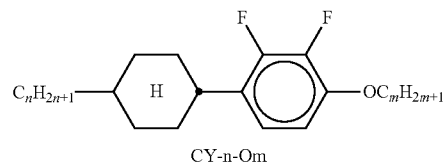
CY-n-Om
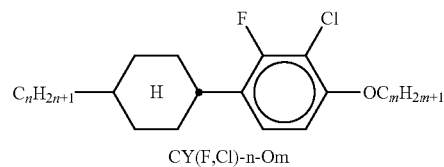
CY(F,Cl)-n-Om
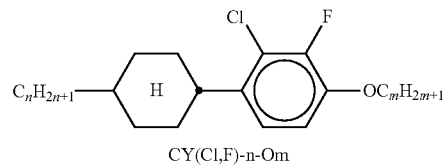
CY(Cl,F)-n-Om
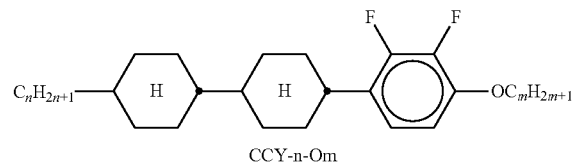
CCY-n-Om TABLE A2-continued
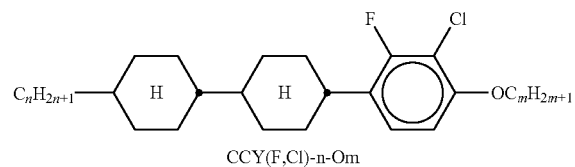
CCY(F,Cl)-n-Om
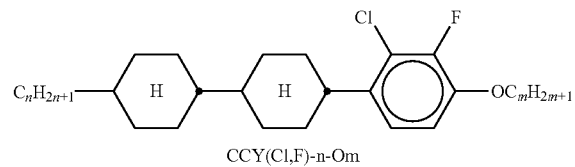
CCY(Cl,F)-n-Om
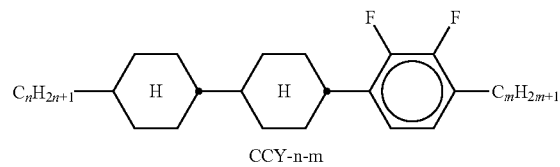
CCY-n-m
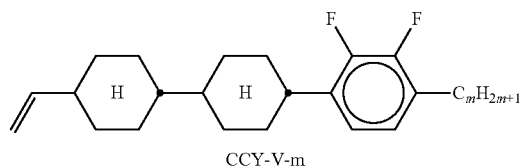
CCY-V-m
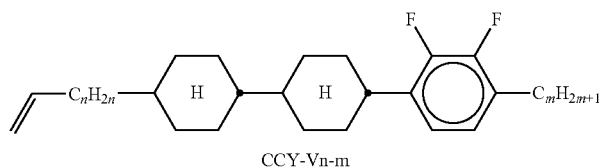
CCY-Vn-m
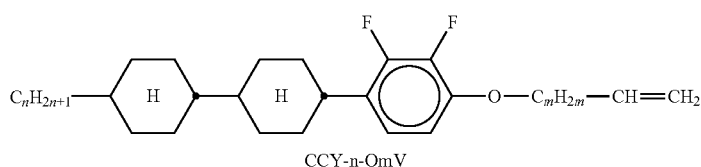
CCY-n-OmV
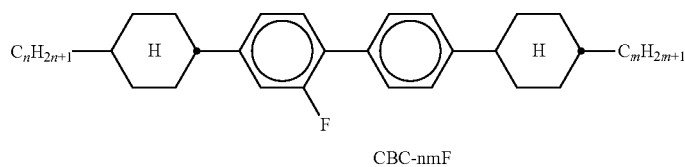
CBC-nmF
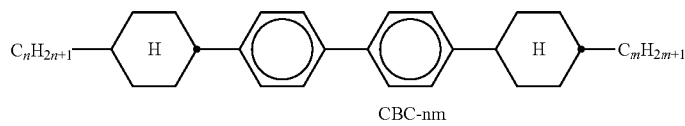
CBC-nm
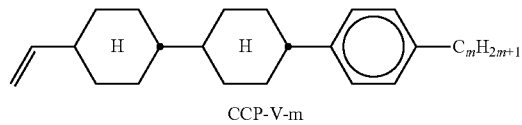
CCP-V-m TABLE A2-continued
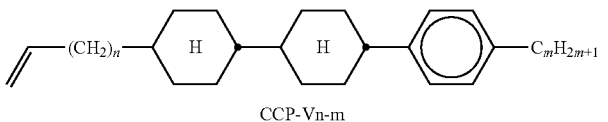
CCP-Vn-m
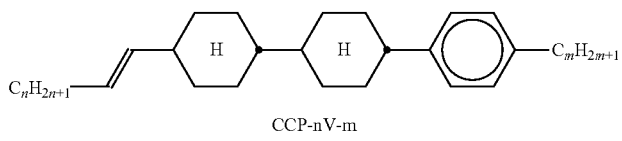
CCP-nV-m
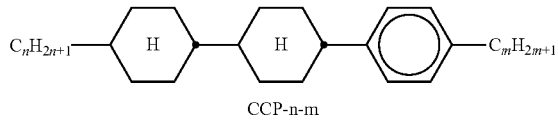
CCP-n-m
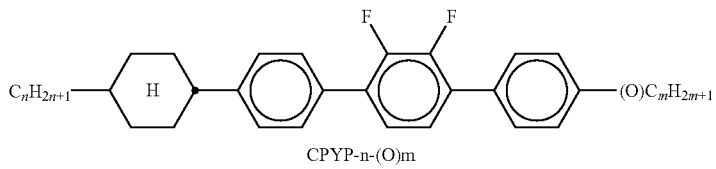
CPYP-n-(O)m
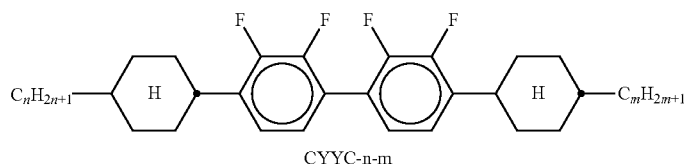
CYYC-n-m
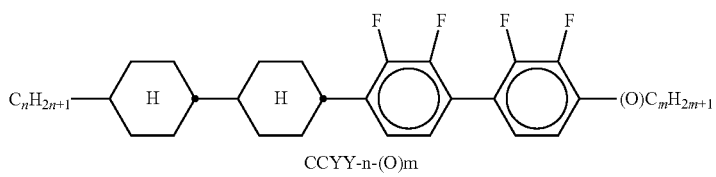
CCYY-n-(O)m
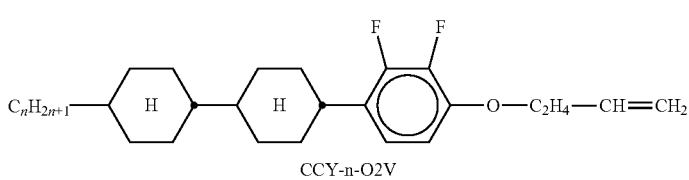
CCY-n-O2V
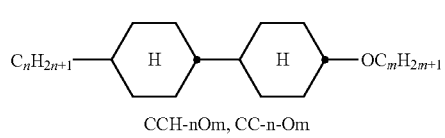
CCH-nOm, CC-n-Om
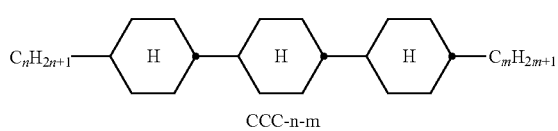
CCC-n-m
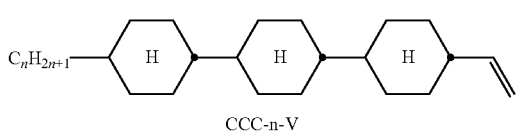
CCC-n-V TABLE A2-continued
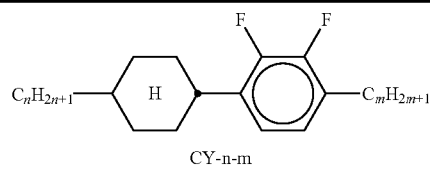
CY-n-m
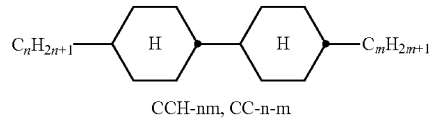
CCH-nm, CC-n-m
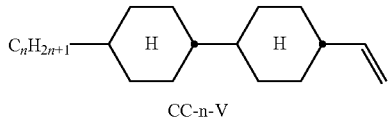
CC-n-V
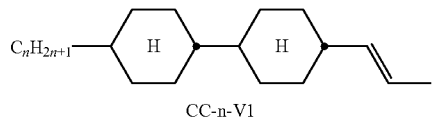
CC-n-V1
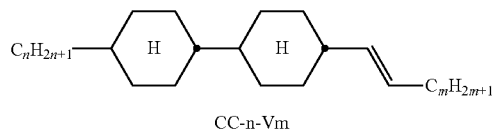
CC-n-Vm
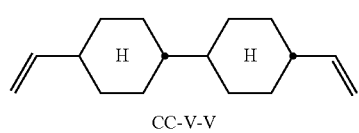
CC-V-V
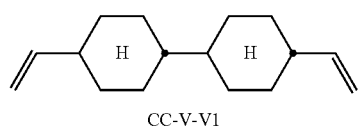
CC-V-V1
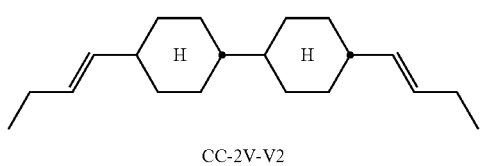
CC-2V-V2
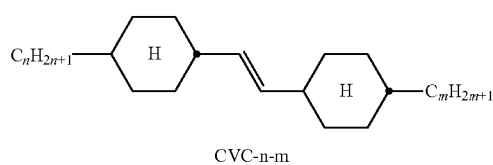
CVC-n-m
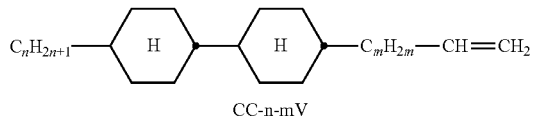
CC-n-mV
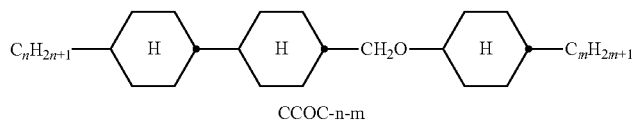
CCOC-n-m TABLE A2-continued
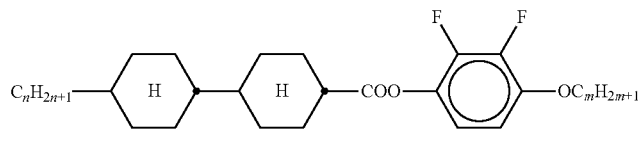
CP-nOmFF
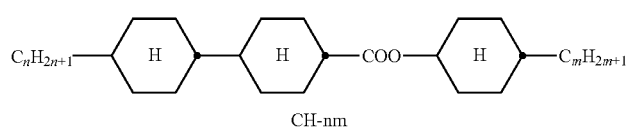
CH-nm
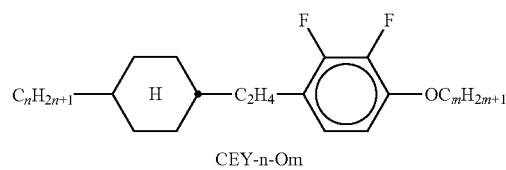
CEY-n-Om
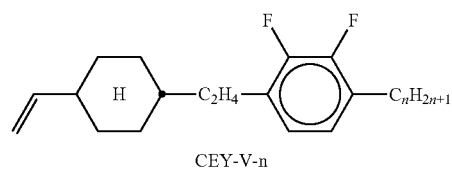
CEY-V-n
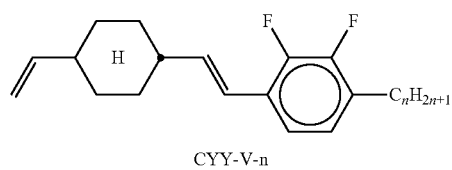
CYY-V-n
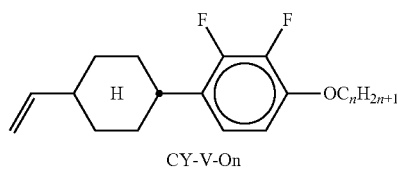
CY-V-On
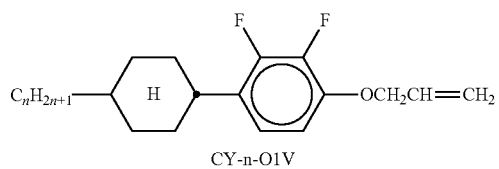
CY-n-O1V
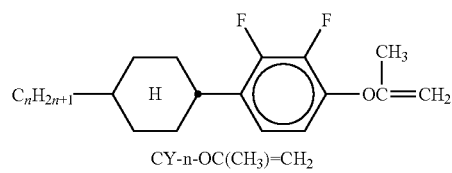
CY-n-OC(CH₃)=CH₂
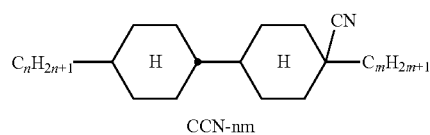
CCN-nm TABLE A2-continued
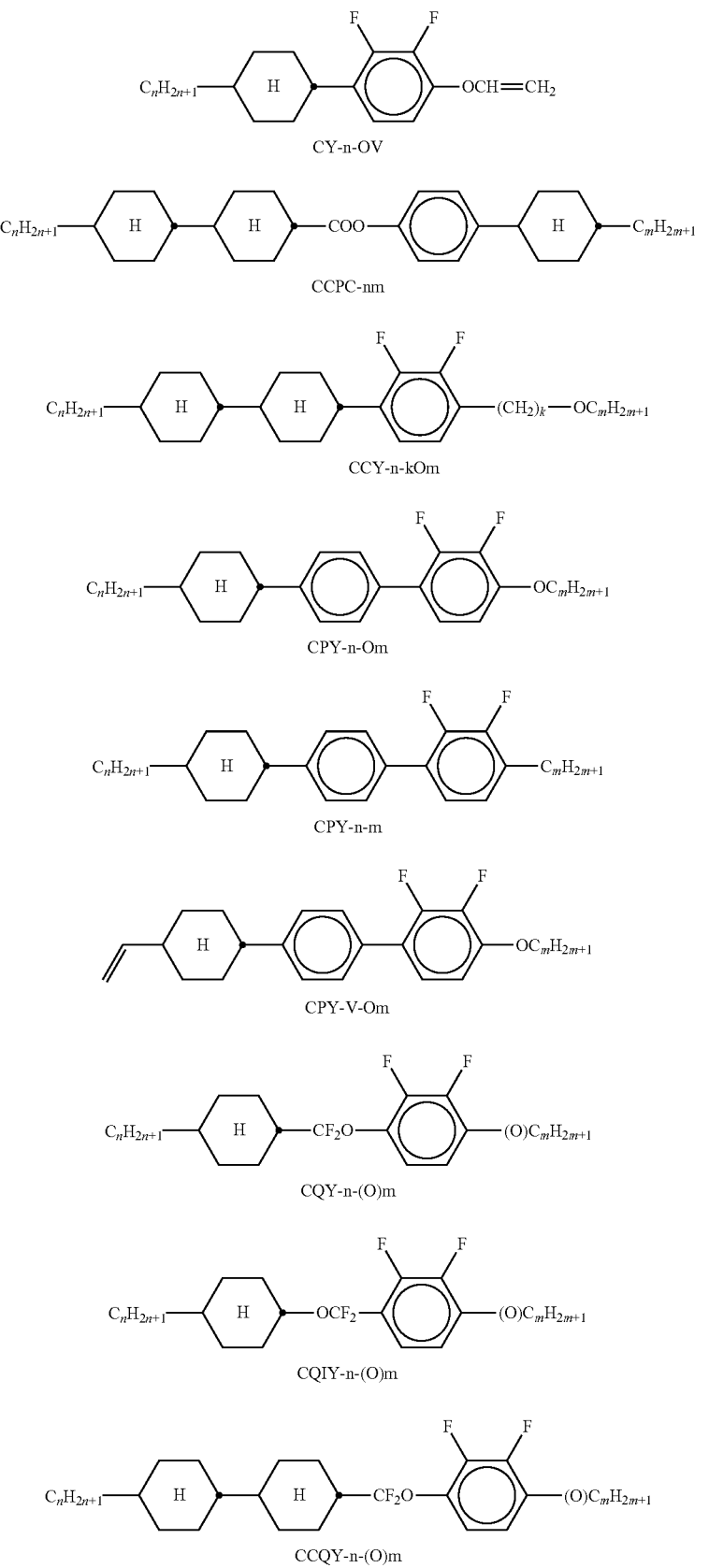

TABLE A2-continued
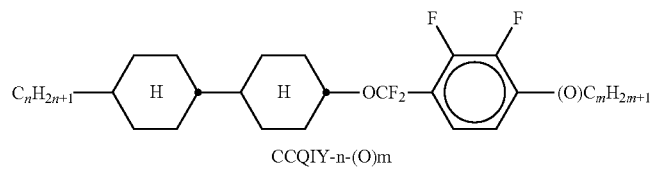
CCQIY-n-(O)m
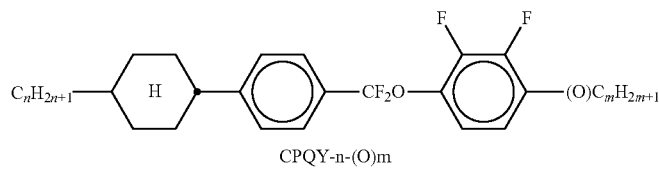
CPQY-n-(O)m
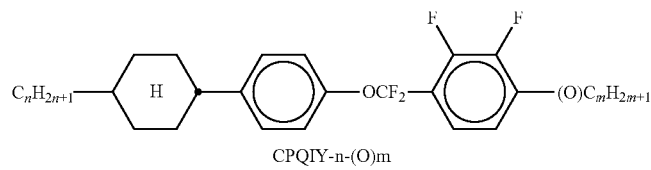
CPQIY-n-(O)m
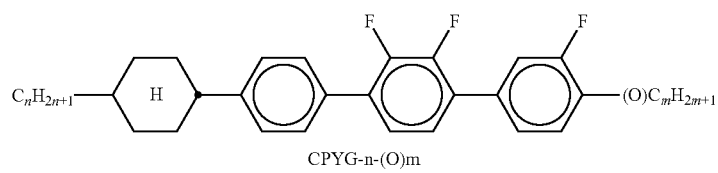
CPYG-n-(O)m
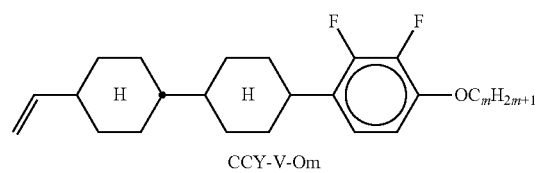
CCY-V-Om
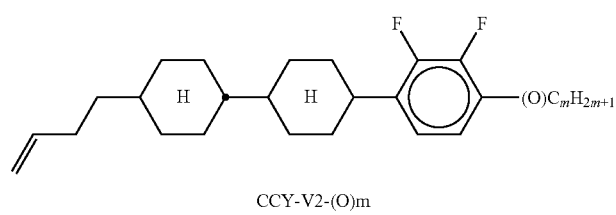
CCY-V2-(O)m
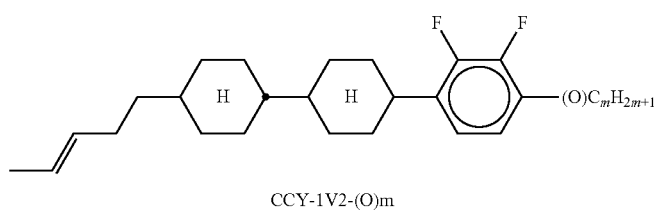
CCY-1V2-(O)m
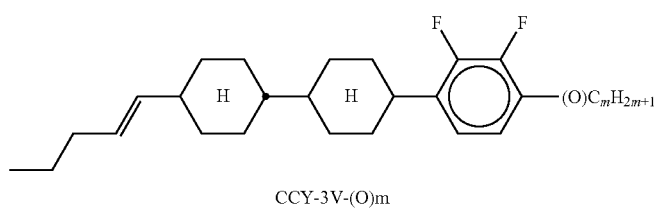
CCY-3V-(O)m TABLE A2-continued
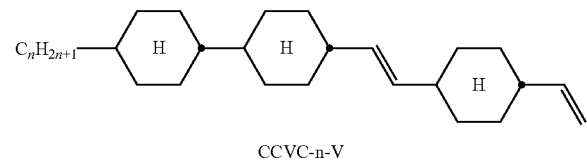
CCVC-n-V
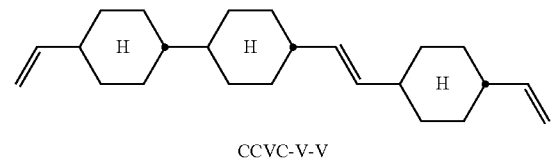
CCVC-V-V
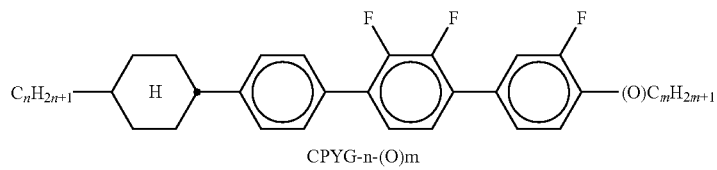
CPYG-n-(O)m
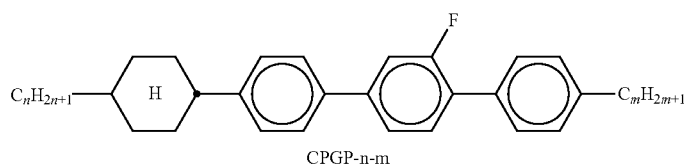
CPGP-n-m
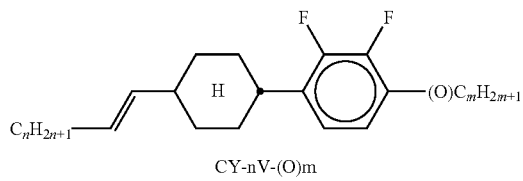
CY-nV-(O)m
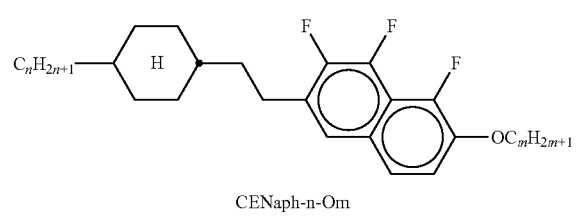
CENaph-n-Om
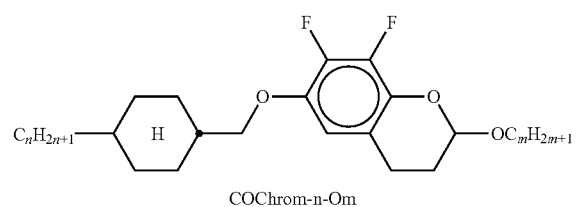
COChrom-n-Om
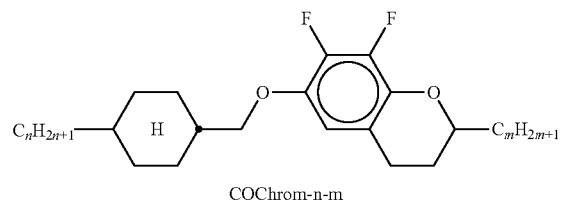
COChrom-n-m TABLE A2-continued
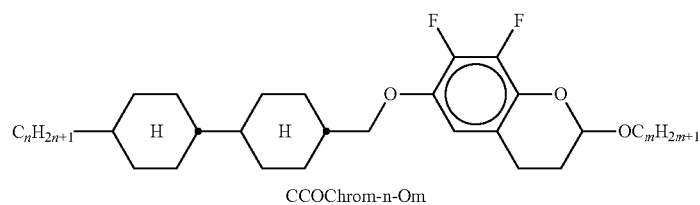
CCOChrom-n-Om
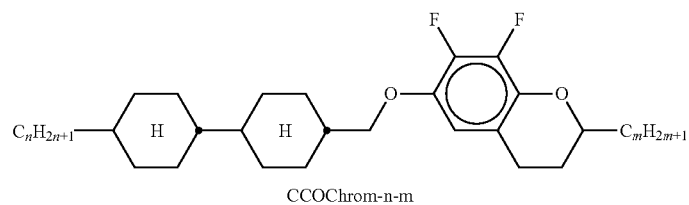
CCOChrom-n-m
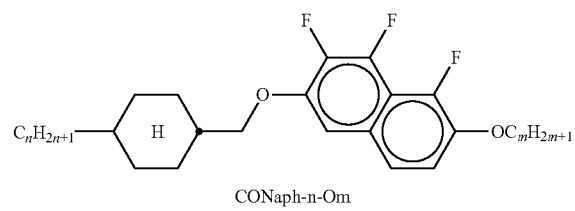
CONaph-n-Om
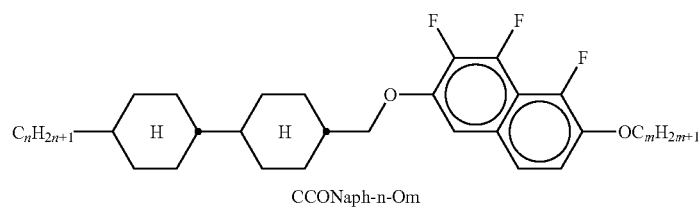
CCONaph-n-Om
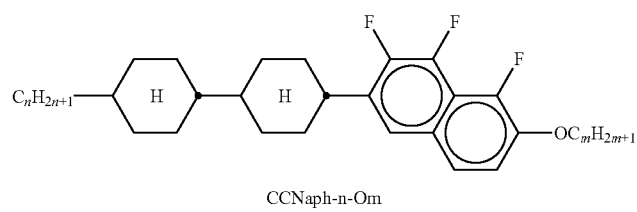
CCNaph-n-Om
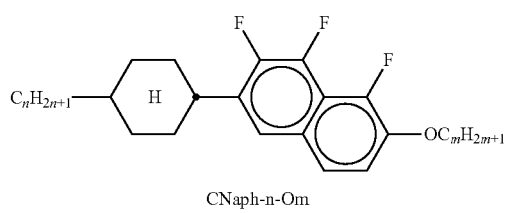
CNaph-n-Om
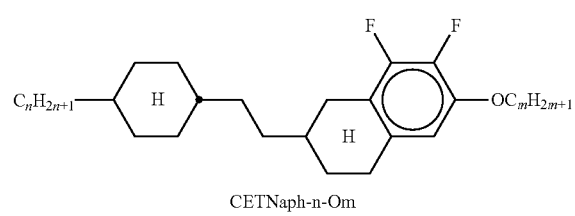
CETNaph-n-Om TABLE A2-continued
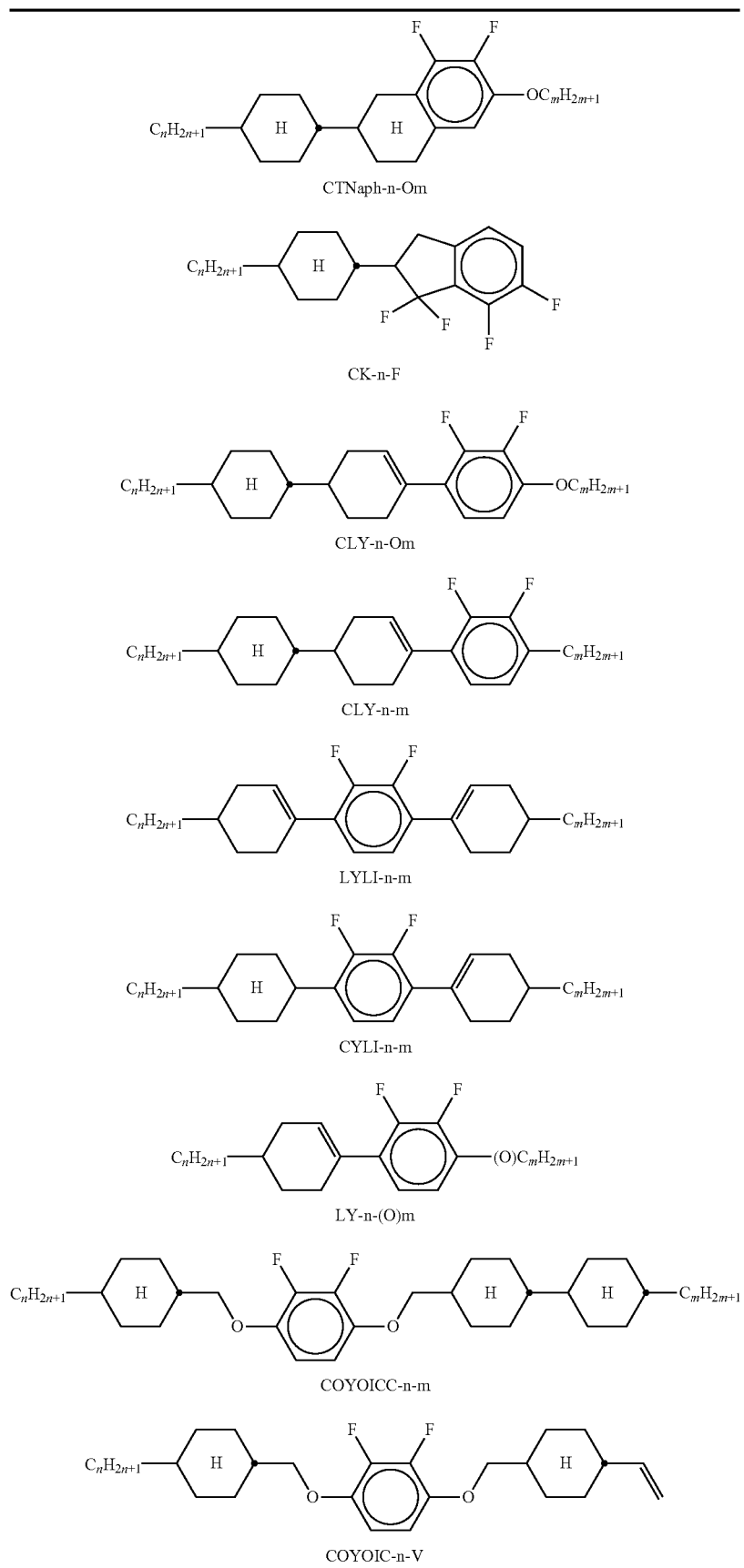

TABLE A2-continued
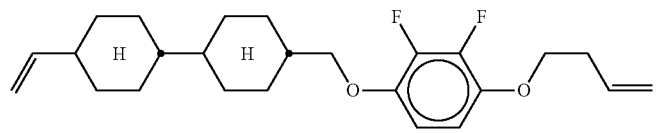
CCOY-V-O2V
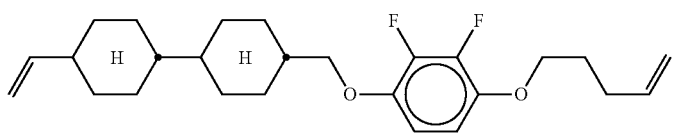
CCOY-V-O3V
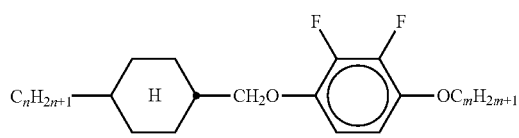
COY-n-Om
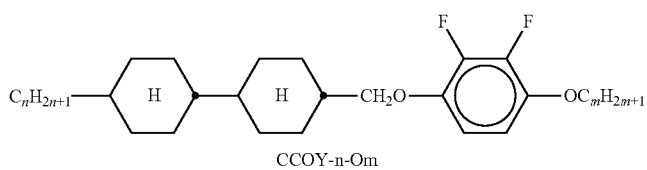
CCOY-n-Om
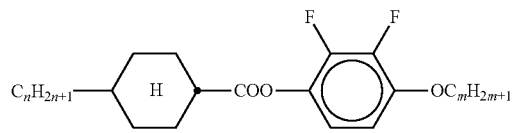
D-nOmFF
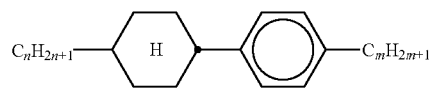
PCH-nm, CP-n-m
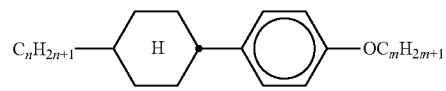
PCH-nOm, CP-n-Om
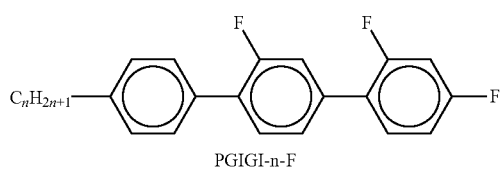
PGIGI-n-F
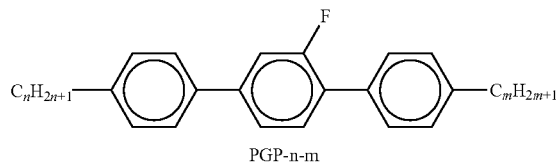
PGP-n-m TABLE A2-continued
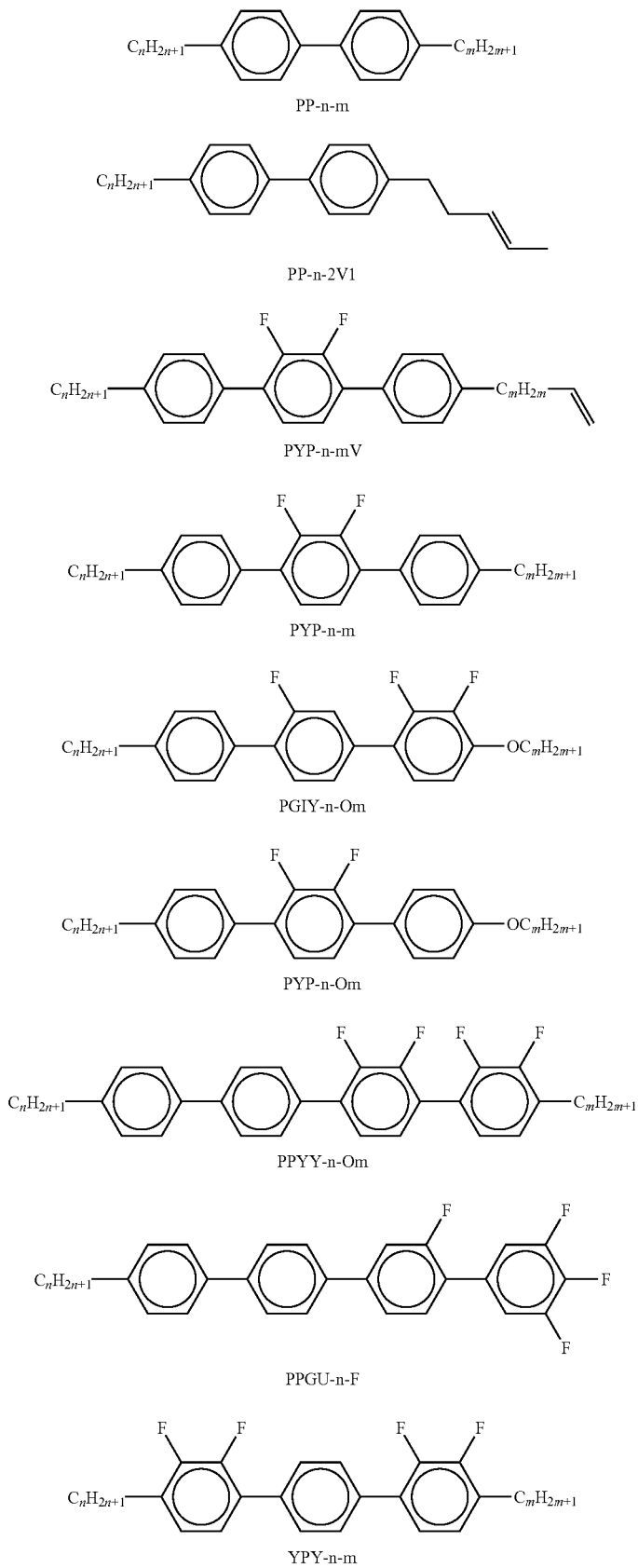

TABLE A2-continued
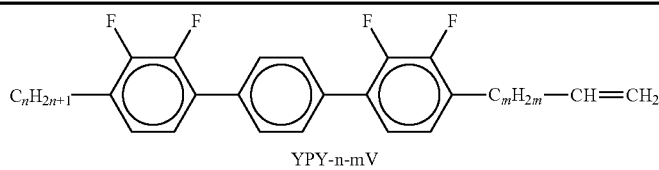
YPY-n-mV
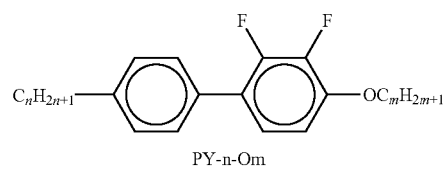
PY-n-Om
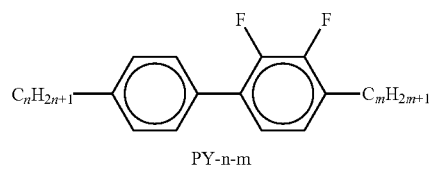
PY-n-m
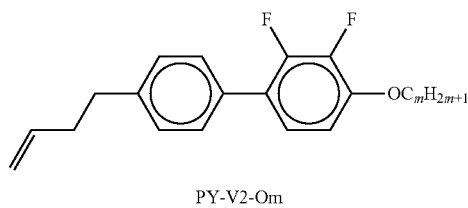
PY-V2-Om
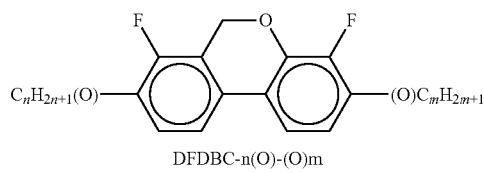
DFDBC-n(O)-(O)m
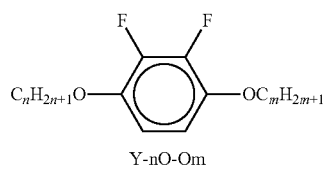
Y-nO-Om
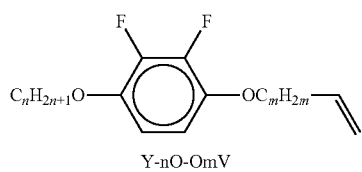
Y-nO-OmV
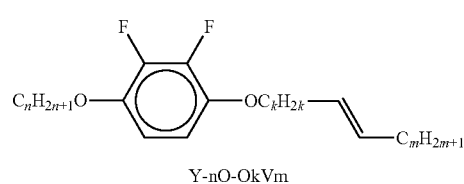
Y-nO-OkVm
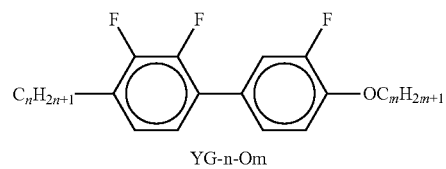
YG-n-Om TABLE A2-continued

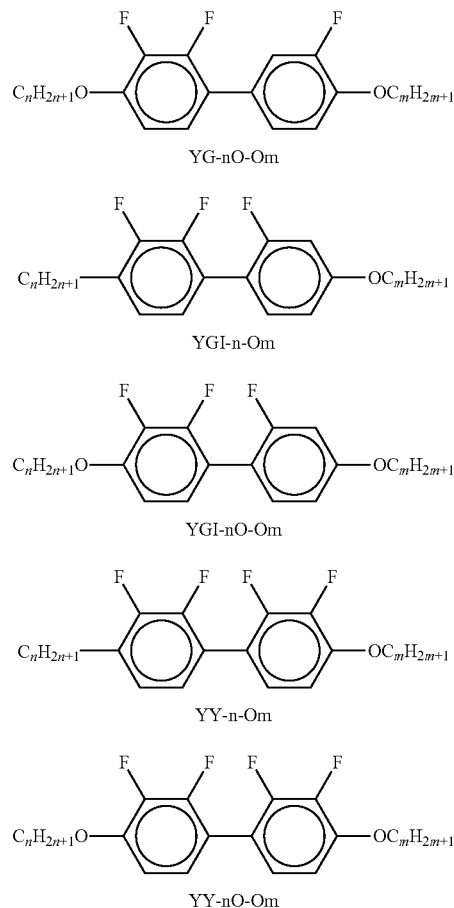

In Table A2, m and n are independently of each other an integer from 1 to 12, preferably 1, 2, 3, 4, 5 or 6, k is 0, 1, 2, 3, 4, 5 or 6, and (O)$C_mH_{2m+1}$ means $C_mH_{2m+1}$ or $OC_mH_{2m+1}$.

In a first preferred embodiment of the present invention, the LC media according to the invention, especially those with positive dielectric anisotropy, comprise one or more compounds selected from the group consisting of compounds from Table A1.

In a second preferred embodiment of the present invention, the LC media according to the invention, especially those with negative dielectric anisotropy, comprise one or more compounds selected from the group consisting of compounds from Table A2.

Table B shows possible chiral dopants which can be added to the LC media according to the invention.

TABLE B

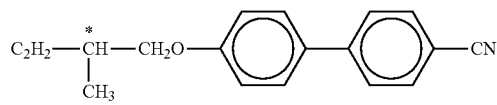

C 15

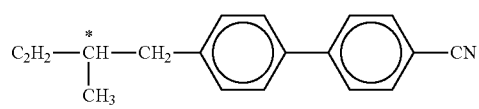

CB 15

TABLE B-continued
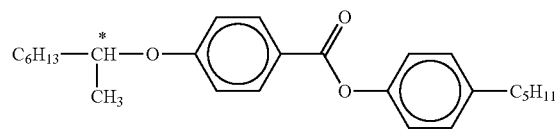
CM 21
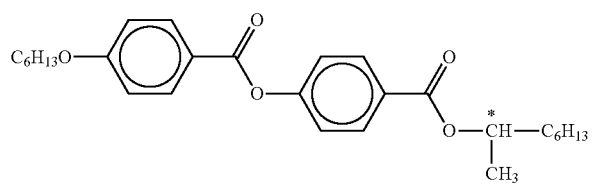
R/S-811
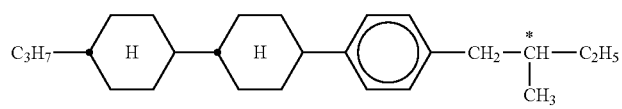
CM 44
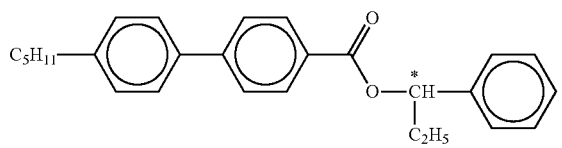
CM 45
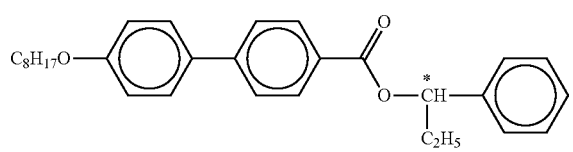
CM 47
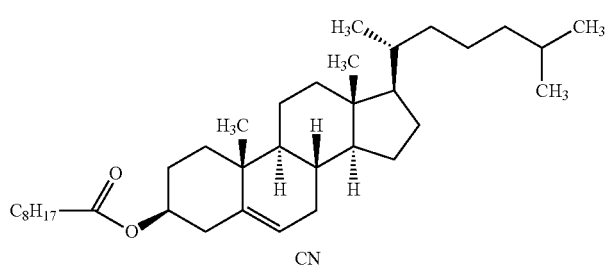
CN
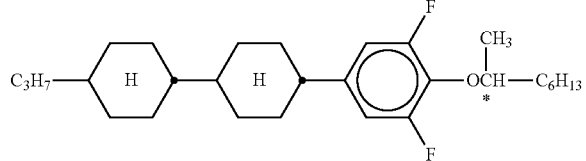
R/S-2011
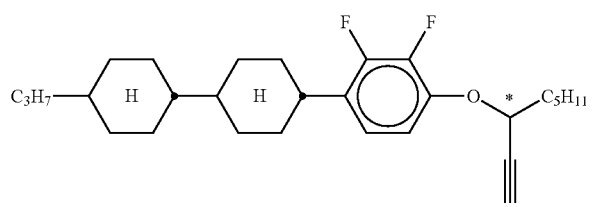
R/S-3011

TABLE B-continued

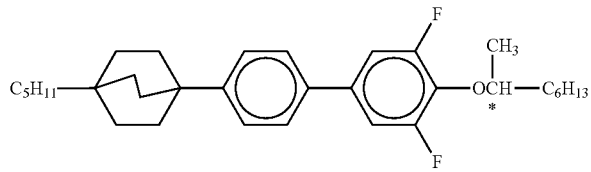

R/S-4011

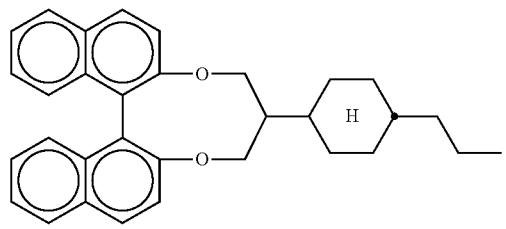

R/S-5011

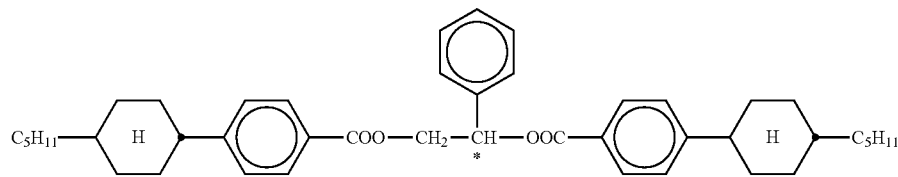

R/S-1011

The LC media preferably comprise 0 to 10% by weight, in particular 0.01 to 5% by weight, particularly preferably 0.1 to 3% by weight, of dopants. The LC media preferably comprise one or more dopants selected from the group consisting of compounds from Table B.

Table C shows possible stabilisers which can be added to the LC media according to the invention. Therein n denotes an integer from 1 to 12, preferably 1, 2, 3, 4, 5, 6, 7 or 8, and terminal methyl groups are not shown.

TABLE C

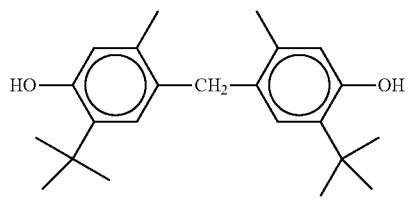

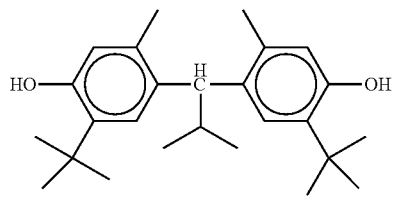

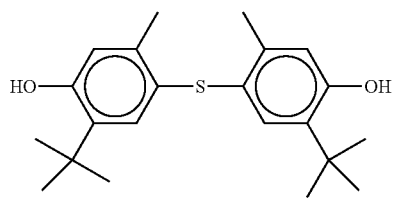

TABLE C-continued
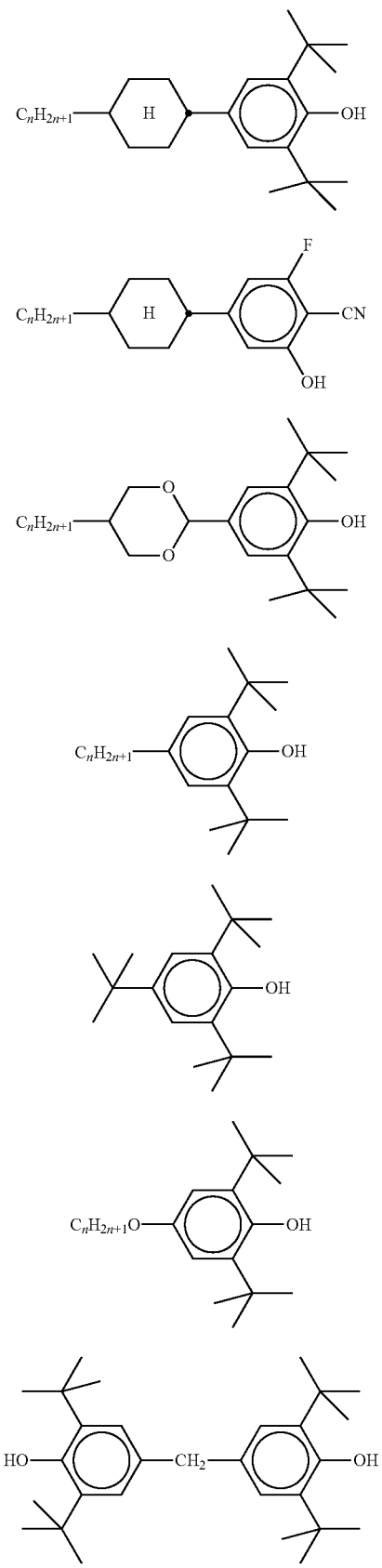

TABLE C-continued
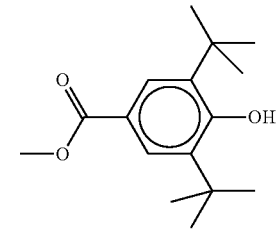
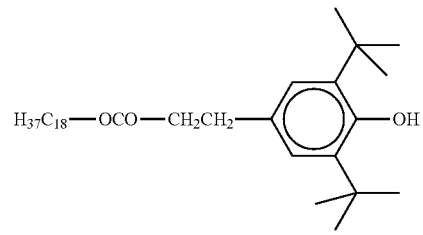
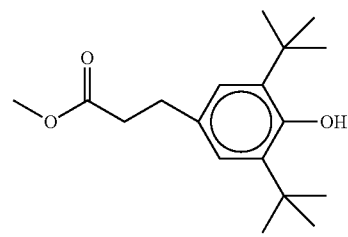
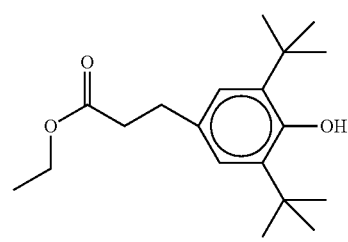
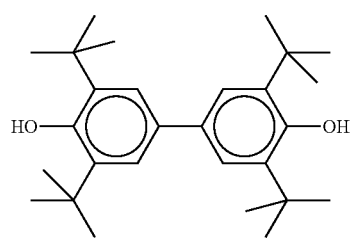

TABLE C-continued
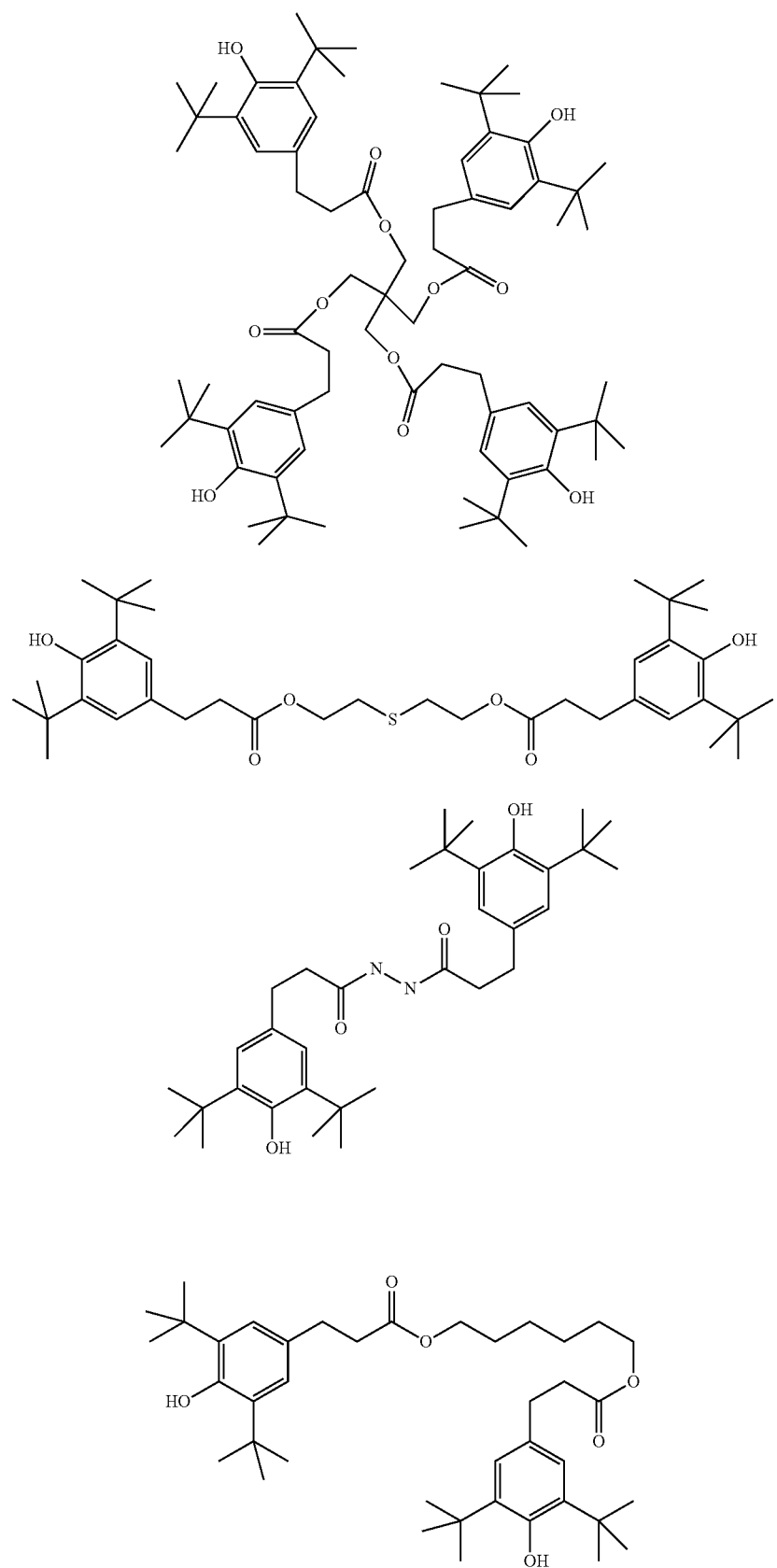

TABLE C-continued
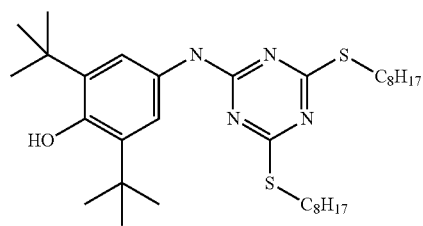
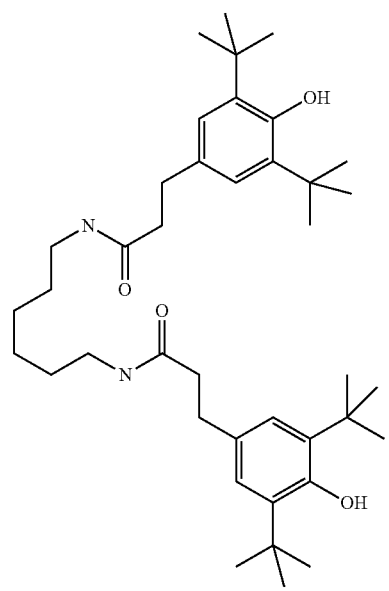 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]
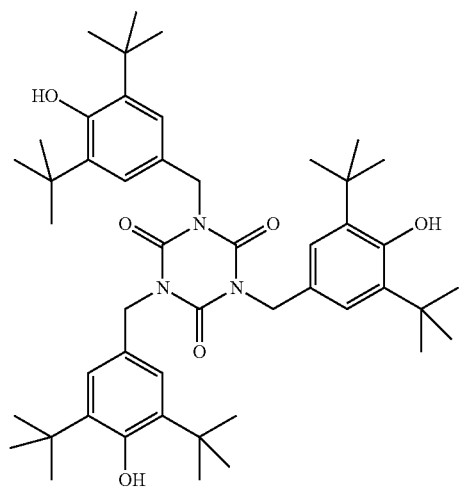 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]

TABLE C-continued
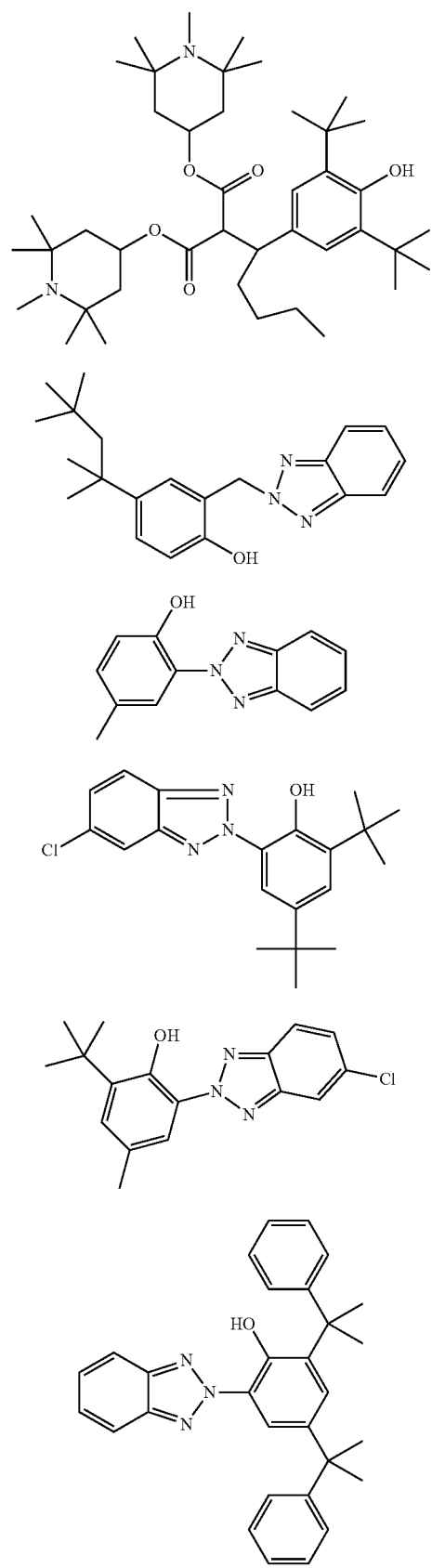

TABLE C-continued
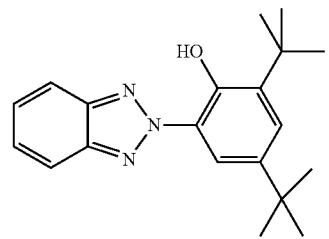 [SMILES: CC(C)(C)c1cc(-n2nc3ccccc3n2)c(O)c(C(C)(C)C)c1]
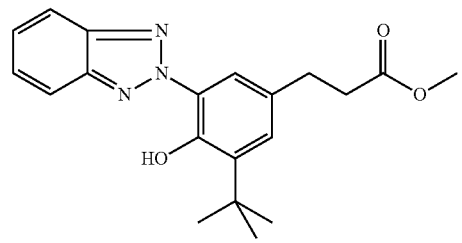 [SMILES: COC(=O)CCc1cc(-n2nc3ccccc3n2)c(O)c(C(C)(C)C)c1]
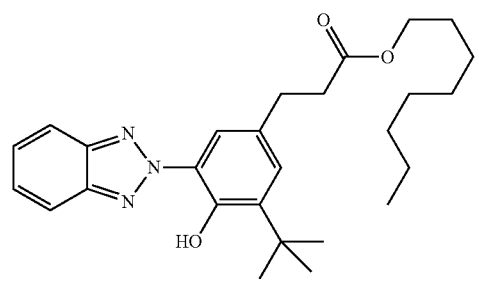 [SMILES: CCCCCCCCOC(=O)CCc1cc(-n2nc3ccccc3n2)c(O)c(C(C)(C)C)c1]
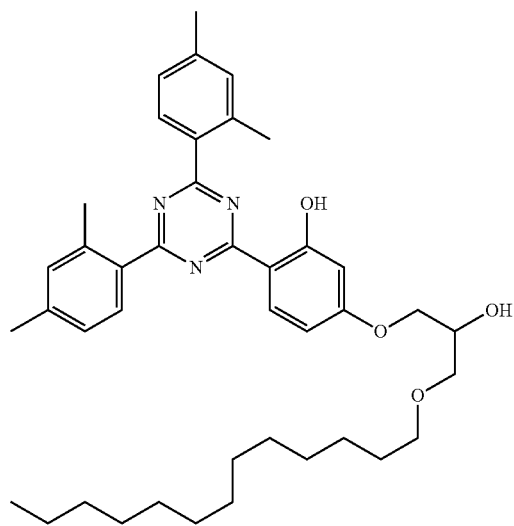 [SMILES: CCCCCCCCCCCCCOCC(O)COc1ccc(-c2nc(-c3ccc(C)cc3C)nc(-c3ccc(C)cc3C)n2)c(O)c1]

TABLE C-continued
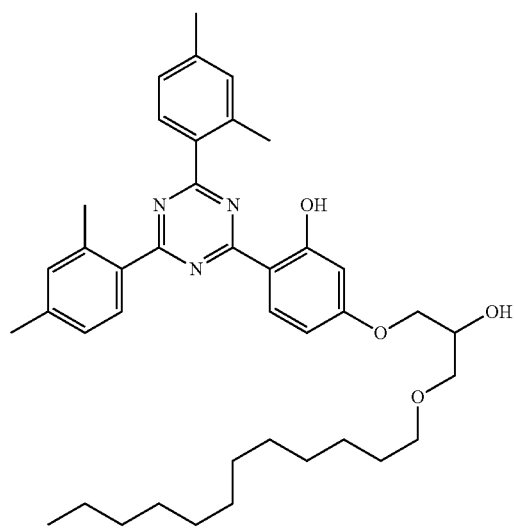 [SMILES: CCCCCCCCCCCCOCC(O)COc1ccc(-c2nc(-c3ccc(C)cc3C)nc(-c3ccc(C)cc3C)n2)c(O)c1]
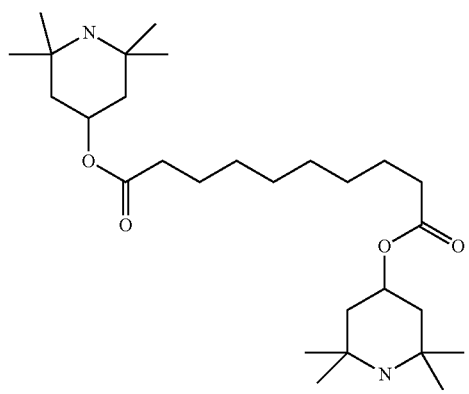
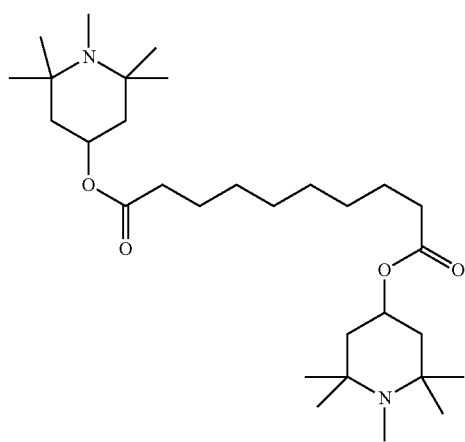

TABLE C-continued
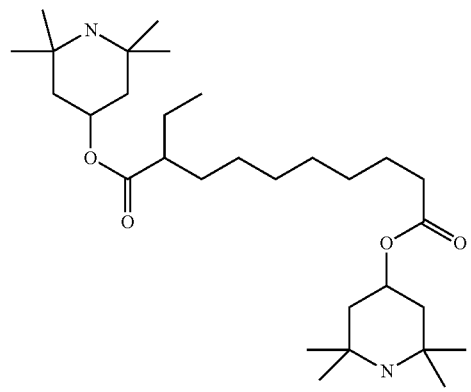
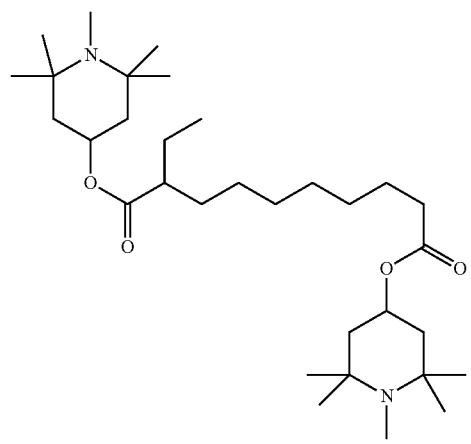
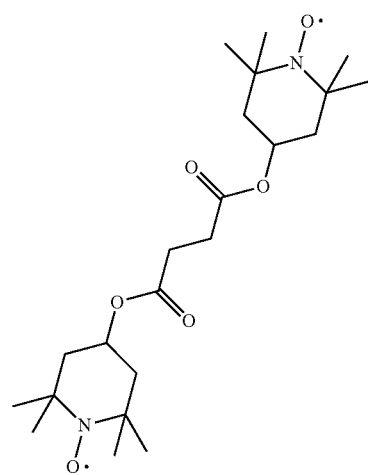

TABLE C-continued
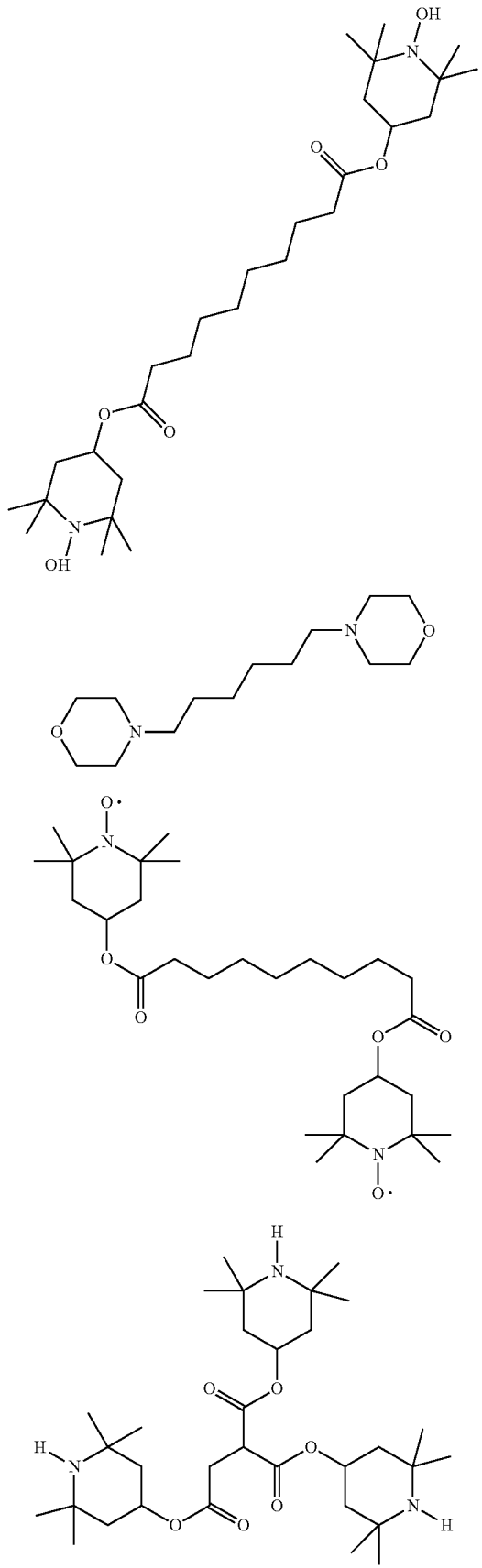

TABLE C-continued
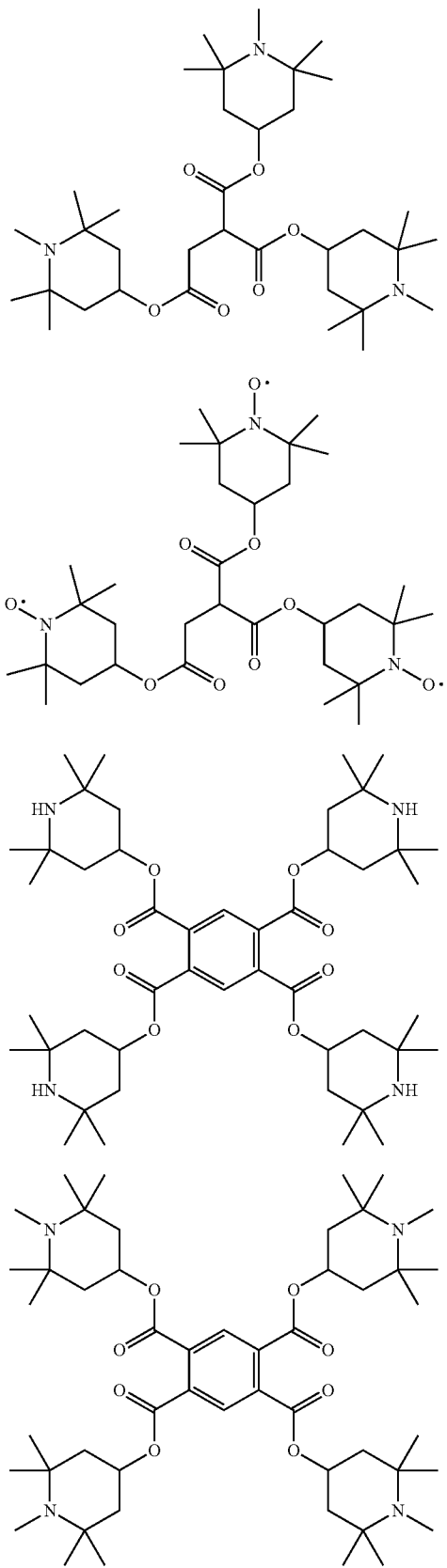

TABLE C-continued

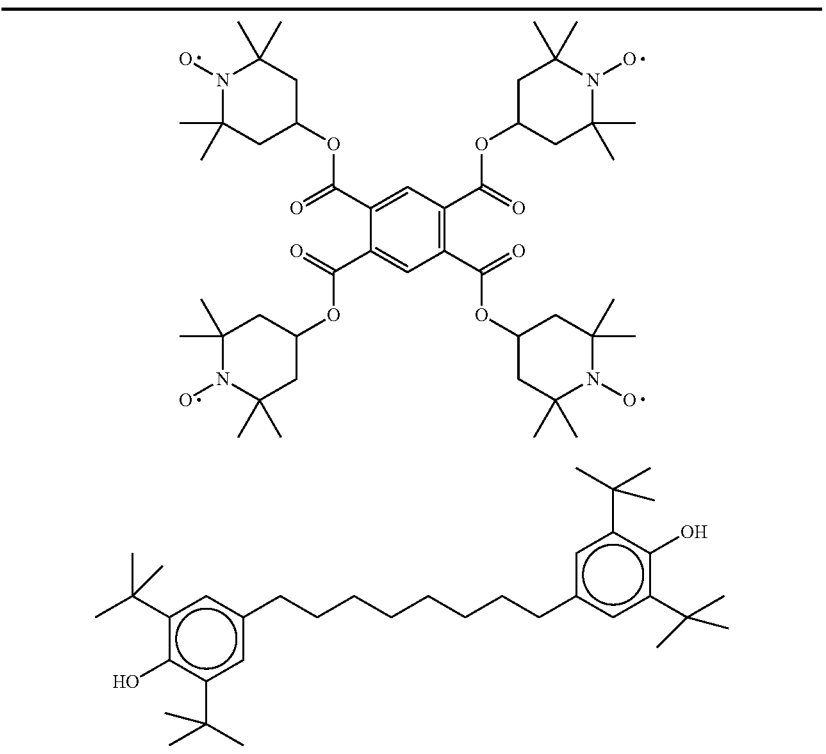

The LC media preferably comprise 0 to 10% by weight, in particular 1 ppm to 5% by weight, particularly preferably 1 ppm to 1% by weight, of stabilisers. The LC media preferably comprise one or more stabilisers selected from the group consisting of compounds from Table C.

Table D shows illustrative reactive mesogenic compounds which can be used in the LC media in accordance with the present invention.

TABLE D

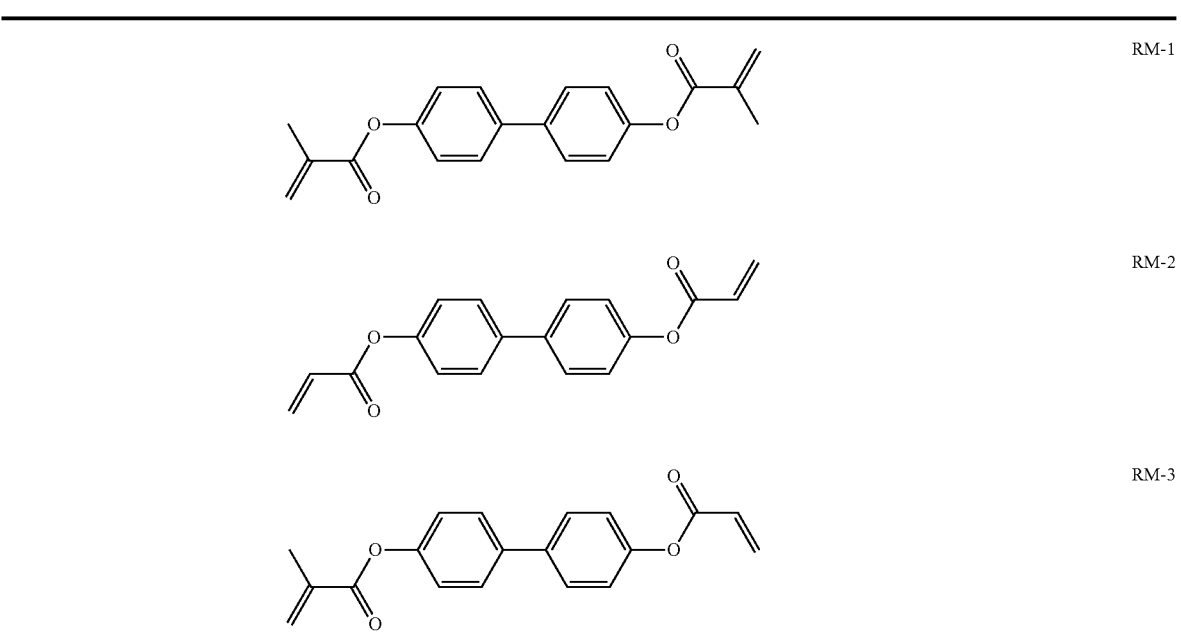

TABLE D-continued
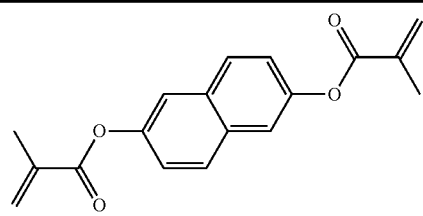 RM-4
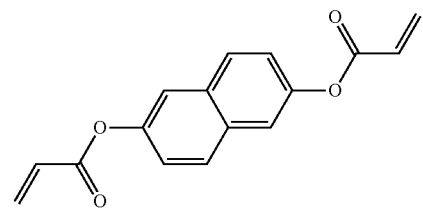 [SMILES: C=CC(=O)Oc1ccc2cc(OC(=O)C=C)ccc2c1] RM-5
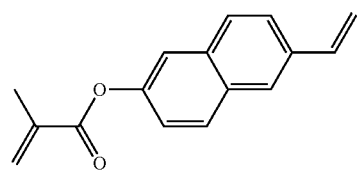 [SMILES: C=Cc1ccc2cc(OC(=O)C(=C)C)ccc2c1] RM-6
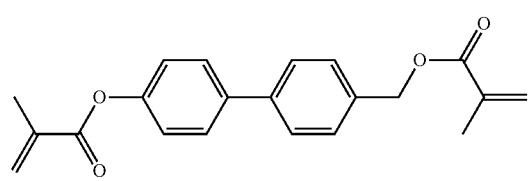 [SMILES: C=C(C)C(=O)OCc1ccc(-c2ccc(OC(=O)C(=C)C)cc2)cc1] RM-7
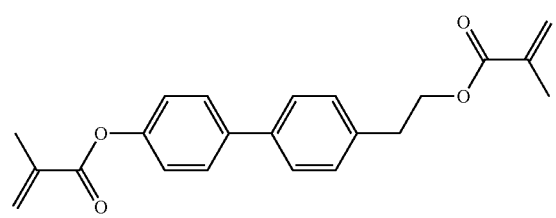 [SMILES: C=C(C)C(=O)OCCc1ccc(-c2ccc(OC(=O)C(=C)C)cc2)cc1] RM-8
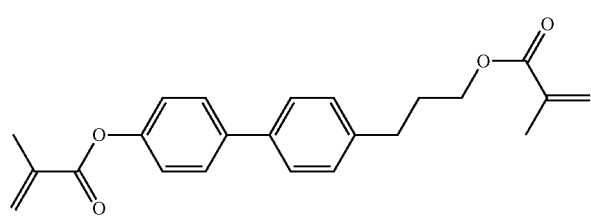 [SMILES: C=C(C)C(=O)OCCCc1ccc(-c2ccc(OC(=O)C(=C)C)cc2)cc1] RM-9
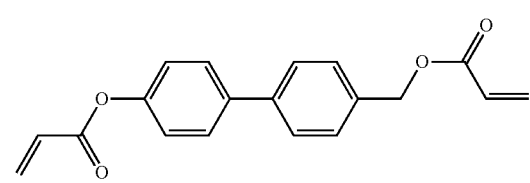 [SMILES: C=CC(=O)OCc1ccc(-c2ccc(OC(=O)C=C)cc2)cc1] RM-10
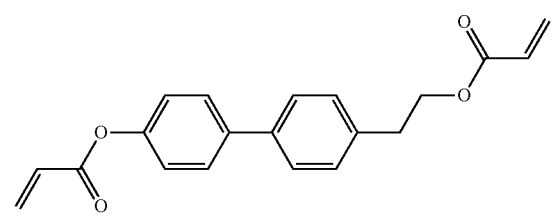 [SMILES: C=CC(=O)OCCc1ccc(-c2ccc(OC(=O)C=C)cc2)cc1] RM-11

TABLE D-continued
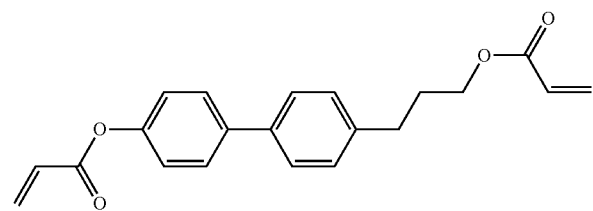 [SMILES: C=CC(=O)OCCCc1ccc(-c2ccc(OC(=O)C=C)cc2)cc1]
RM-12
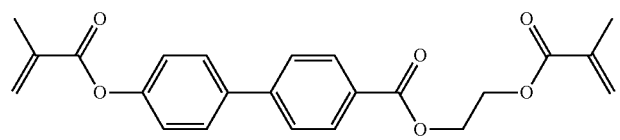
RM-13
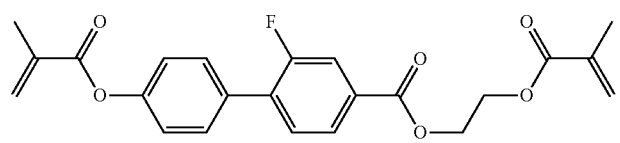 [SMILES: C=C(C)C(=O)OCCOC(=O)c1ccc(-c2ccc(OC(=O)C(=C)C)cc2)c(F)c1]
RM-14
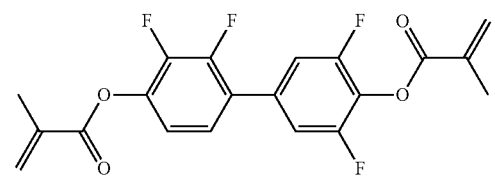
RM-15
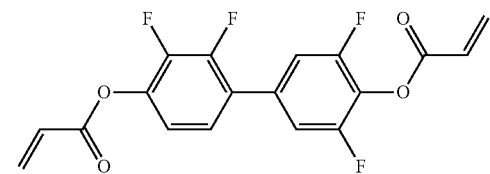 [SMILES: C=CC(=O)Oc1ccc(-c2cc(F)c(OC(=O)C=C)c(F)c2)c(F)c1F]
RM-16
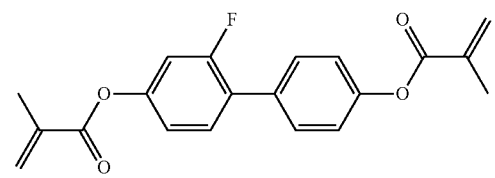
RM-17
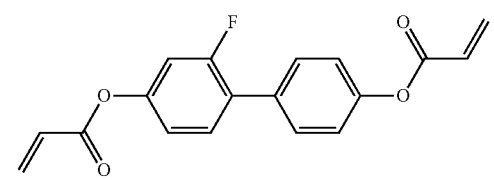
RM-18
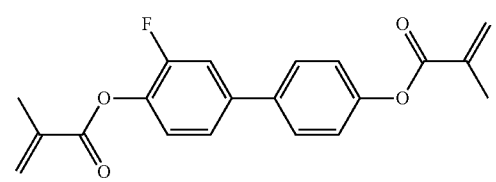
RM-19
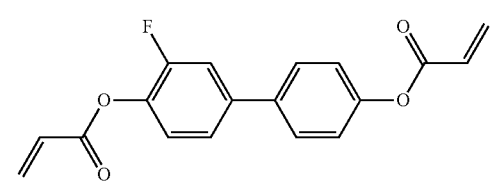 [SMILES: C=CC(=O)Oc1ccc(-c2ccc(OC(=O)C=C)c(F)c2)cc1]
RM-20

TABLE D-continued
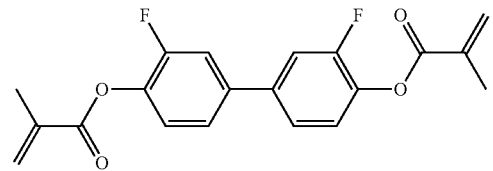
RM-21
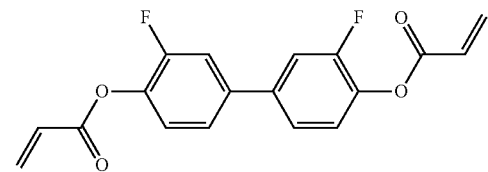
RM-22
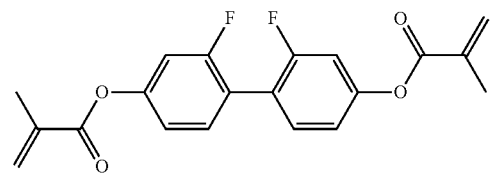 [SMILES: C=C(C)C(=O)Oc1ccc(-c2ccc(OC(=O)C(=C)C)cc2F)c(F)c1]
RM-23
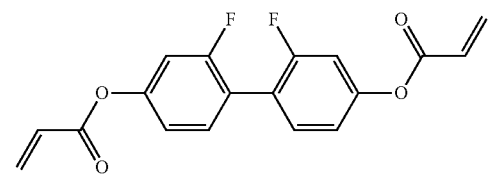 [SMILES: C=CC(=O)Oc1ccc(-c2ccc(OC(=O)C=C)cc2F)c(F)c1]
RM-24
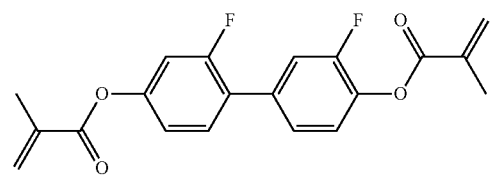
RM-25
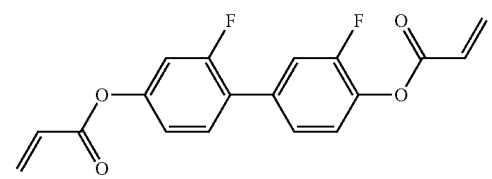
RM-26
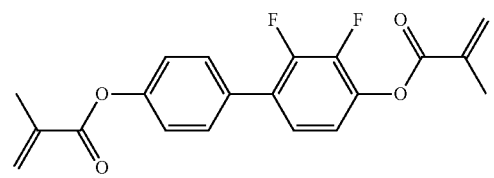
RM-27
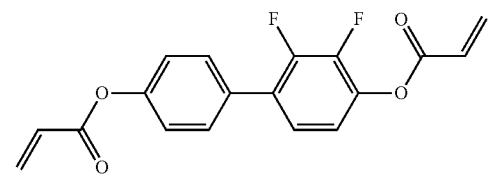 [SMILES: C=CC(=O)Oc1ccc(-c2ccc(OC(=O)C=C)c(F)c2F)cc1]
RM-28
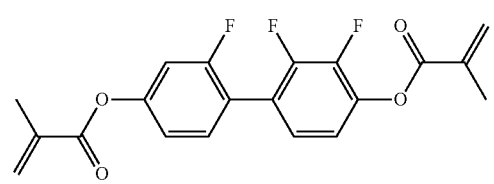 [SMILES: C=C(C)C(=O)Oc1ccc(-c2ccc(OC(=O)C(=C)C)c(F)c2F)c(F)c1]
RM-29

TABLE D-continued
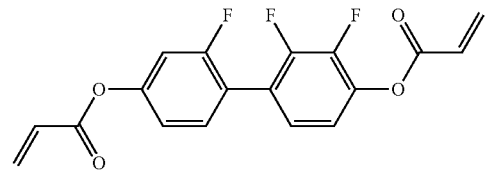 [SMILES: C=CC(=O)Oc1ccc(-c2ccc(OC(=O)C=C)c(F)c2F)c(F)c1] RM-30
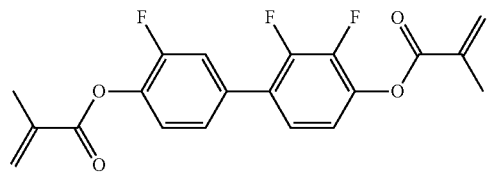 RM-31
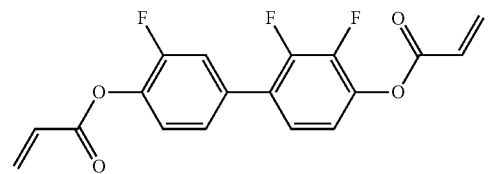 [SMILES: C=CC(=O)Oc1ccc(-c2ccc(OC(=O)C=C)c(F)c2F)cc1F] RM-32
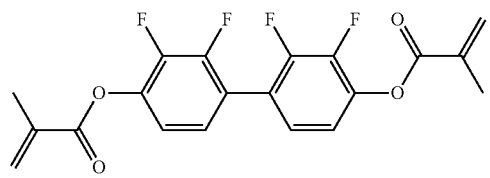 [SMILES: C=C(C)C(=O)Oc1ccc(-c2ccc(OC(=O)C(=C)C)c(F)c2F)c(F)c1F] RM-33
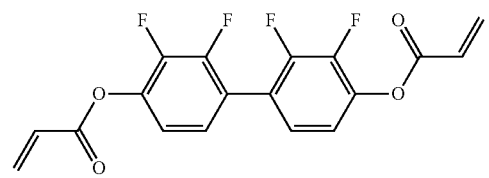 [SMILES: C=CC(=O)Oc1ccc(-c2ccc(OC(=O)C=C)c(F)c2F)c(F)c1F] RM-34
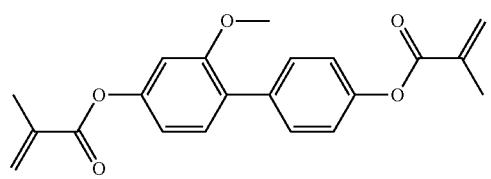 RM-35
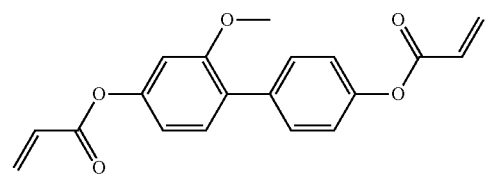 RM-36
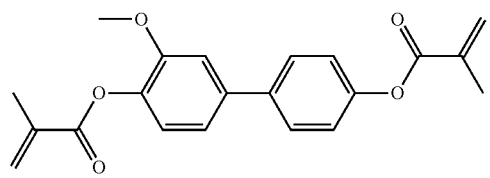 [SMILES: C=C(C)C(=O)Oc1ccc(-c2ccc(OC(=O)C(=C)C)c(OC)c2)cc1] RM-37
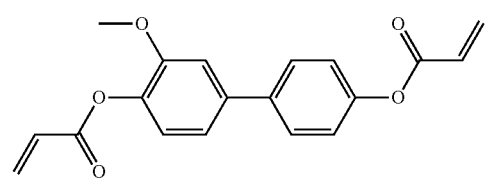 [SMILES: C=CC(=O)Oc1ccc(-c2ccc(OC(=O)C=C)c(OC)c2)cc1] RM-38

TABLE D-continued
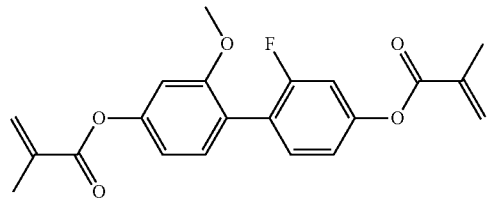 [SMILES: C=C(C)C(=O)Oc1ccc(-c2ccc(OC(=O)C(=C)C)cc2OC)c(F)c1] RM-39
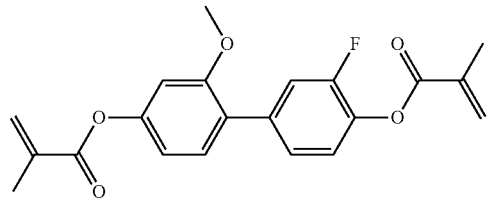 [SMILES: C=C(C)C(=O)Oc1ccc(-c2ccc(OC(=O)C(=C)C)c(F)c2)c(OC)c1] RM-40
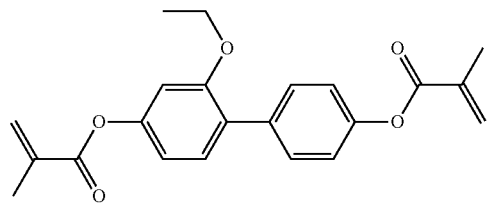 [SMILES: C=C(C)C(=O)Oc1ccc(-c2ccc(OC(=O)C(=C)C)cc2OCC)cc1] RM-41
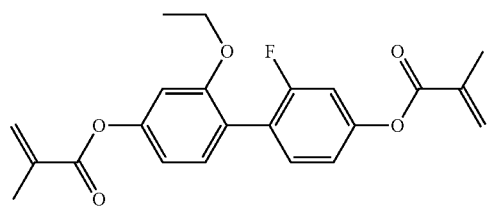 RM-42
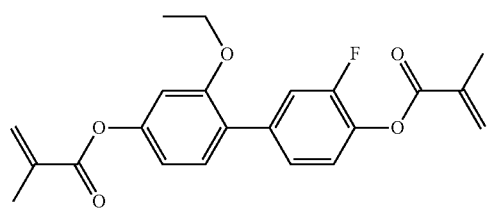 [SMILES: C=C(C)C(=O)Oc1ccc(-c2ccc(OC(=O)C(=C)C)c(F)c2)c(OCC)c1] RM-43
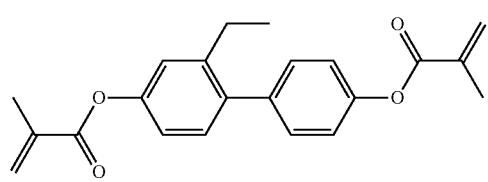 [SMILES: C=C(C)C(=O)Oc1ccc(-c2ccc(OC(=O)C(=C)C)cc2CC)cc1] RM-44
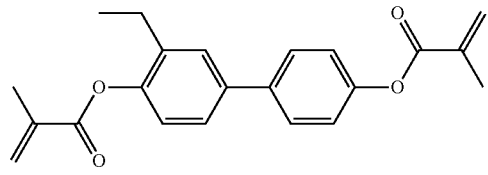 RM-45
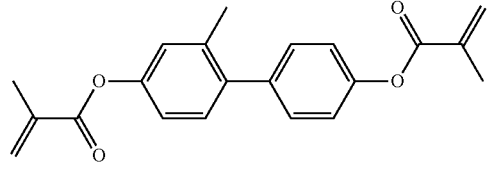 [SMILES: C=C(C)C(=O)Oc1ccc(-c2ccc(OC(=O)C(=C)C)cc2C)cc1] RM-46

TABLE D-continued
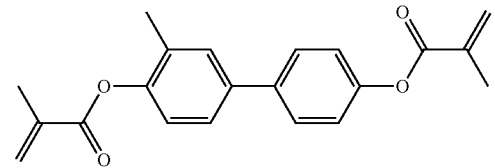
RM-47
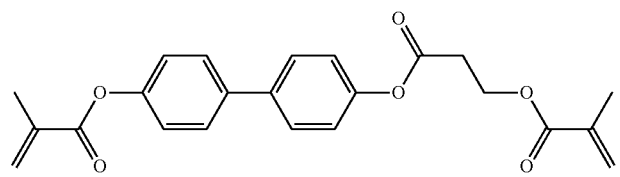 [SMILES: C=C(C)C(=O)OCCC(=O)Oc1ccc(-c2ccc(OC(=O)C(=C)C)cc2)cc1]
RM-48
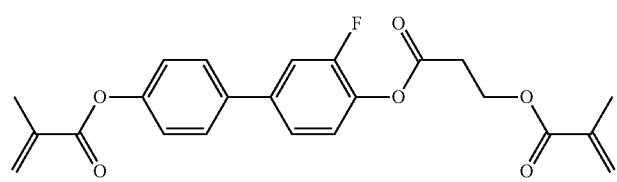 [SMILES: C=C(C)C(=O)OCCC(=O)Oc1ccc(-c2ccc(OC(=O)C(=C)C)cc2)cc1F]
RM-49
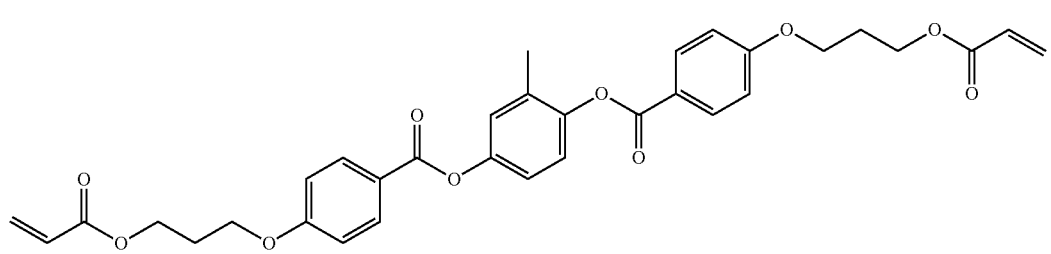 [SMILES: C=CC(=O)OCCCOc1ccc(C(=O)Oc2ccc(OC(=O)c3ccc(OCCCOC(=O)C=C)cc3)c(C)c2)cc1]
RM-50
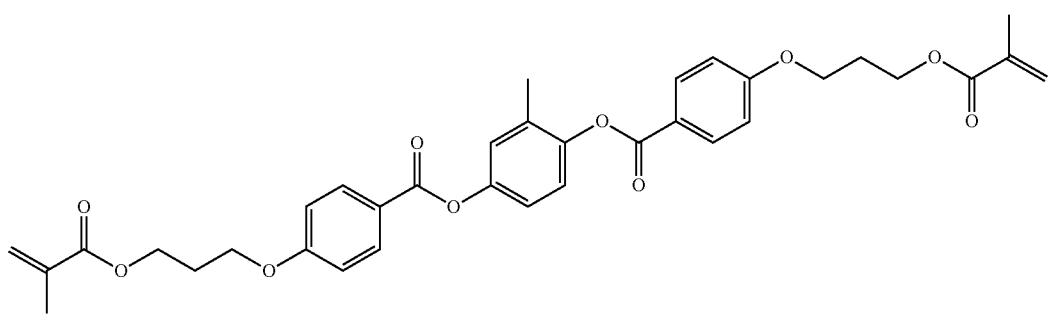 [SMILES: C=C(C)C(=O)OCCCOc1ccc(C(=O)Oc2ccc(OC(=O)c3ccc(OCCCOC(=O)C(=C)C)cc3)c(C)c2)cc1]
RM-51
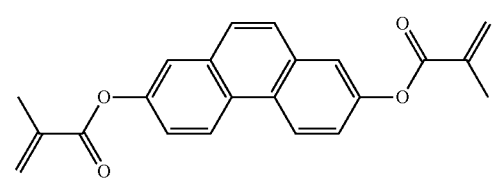 [SMILES: C=C(C)C(=O)Oc1ccc2c(ccc3cc(OC(=O)C(=C)C)ccc32)c1]
RM-52
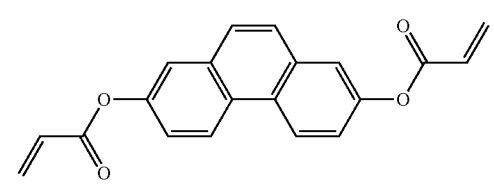 [SMILES: C=CC(=O)Oc1ccc2c(ccc3cc(OC(=O)C=C)ccc32)c1]
RM-53

TABLE D-continued
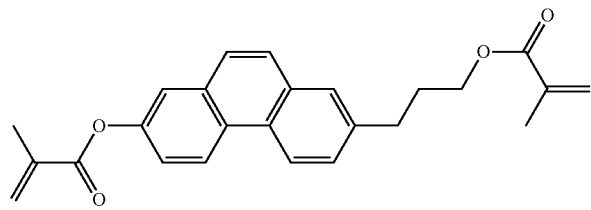 [SMILES: C=C(C)C(=O)OCCCc1ccc2c(ccc3cc(OC(=O)C(=C)C)ccc32)c1]
RM-54
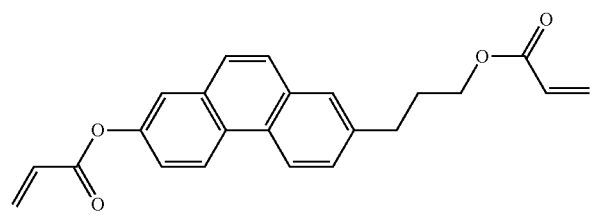 [SMILES: C=CC(=O)OCCCc1ccc2c(ccc3cc(OC(=O)C=C)ccc32)c1]
RM-55
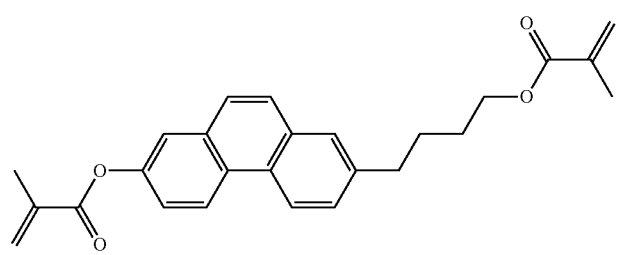 [SMILES: C=C(C)C(=O)OCCCCc1ccc2c(ccc3cc(OC(=O)C(=C)C)ccc32)c1]
RM-56
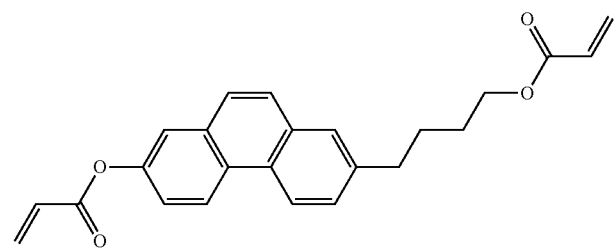 [SMILES: C=CC(=O)OCCCCc1ccc2c(ccc3cc(OC(=O)C=C)ccc32)c1]
RM-57
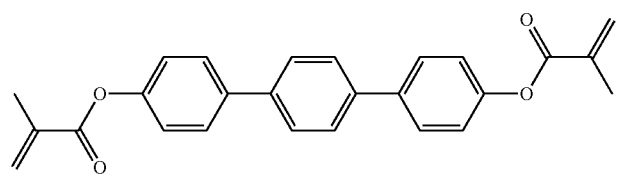 [SMILES: C=C(C)C(=O)Oc1ccc(-c2ccc(-c3ccc(OC(=O)C(=C)C)cc3)cc2)cc1]
RM-58
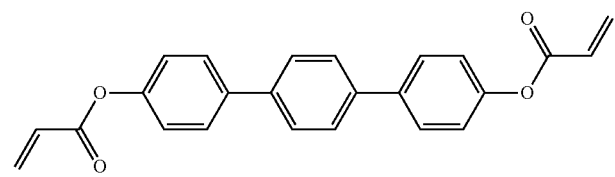 [SMILES: C=CC(=O)Oc1ccc(-c2ccc(-c3ccc(OC(=O)C=C)cc3)cc2)cc1]
RM-59
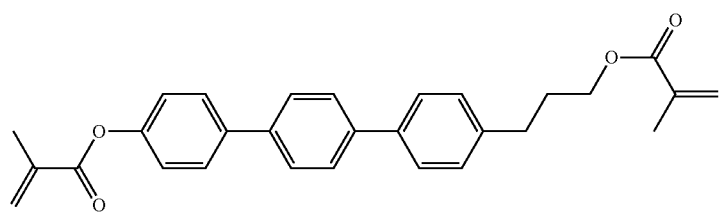 [SMILES: C=C(C)C(=O)OCCCc1ccc(-c2ccc(-c3ccc(OC(=O)C(=C)C)cc3)cc2)cc1]
RM-60

TABLE D-continued
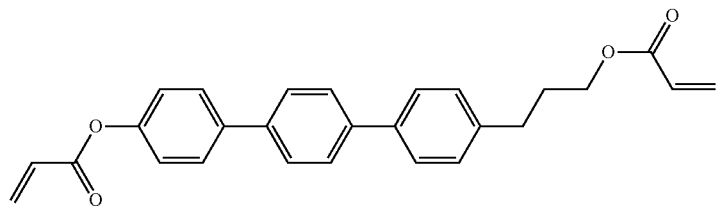 [SMILES: C=CC(=O)OCCCc1ccc(-c2ccc(-c3ccc(OC(=O)C=C)cc3)cc2)cc1]
RM-61
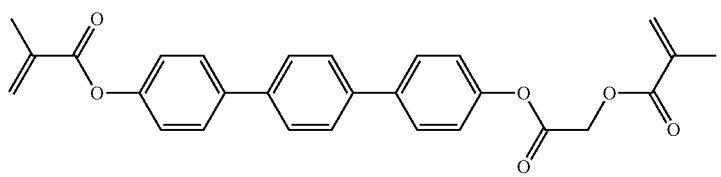 [SMILES: C=C(C)C(=O)OCC(=O)Oc1ccc(-c2ccc(-c3ccc(OC(=O)C(=C)C)cc3)cc2)cc1]
RM-62
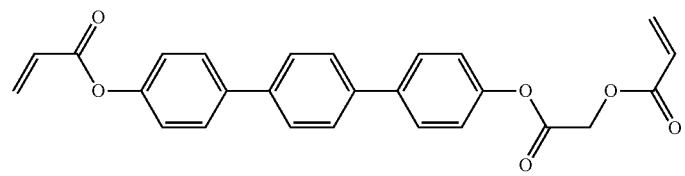 [SMILES: C=CC(=O)OCC(=O)Oc1ccc(-c2ccc(-c3ccc(OC(=O)C=C)cc3)cc2)cc1]
RM-63
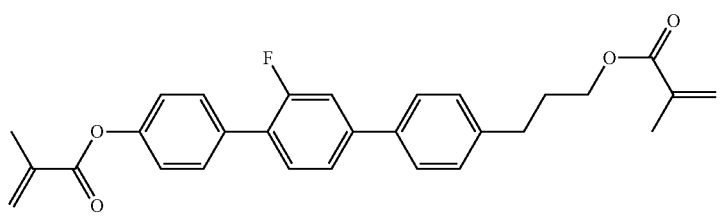 [SMILES: C=C(C)C(=O)OCCCc1ccc(-c2ccc(-c3ccc(OC(=O)C(=C)C)cc3)c(F)c2)cc1]
RM-64
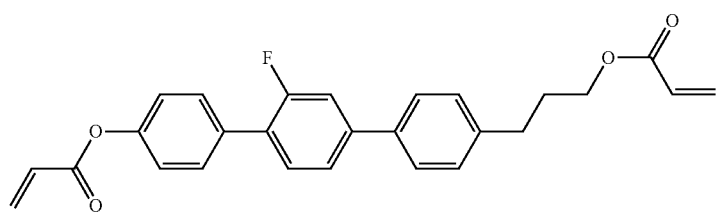 [SMILES: C=CC(=O)OCCCc1ccc(-c2ccc(-c3ccc(OC(=O)C=C)cc3)c(F)c2)cc1]
RM-65
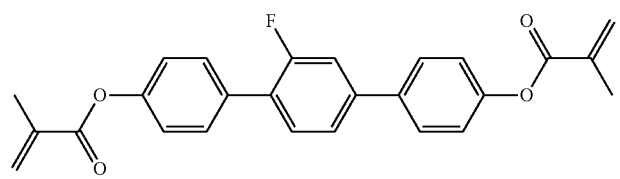 [SMILES: C=C(C)C(=O)Oc1ccc(-c2ccc(-c3ccc(OC(=O)C(=C)C)cc3)c(F)c2)cc1]
RM-66
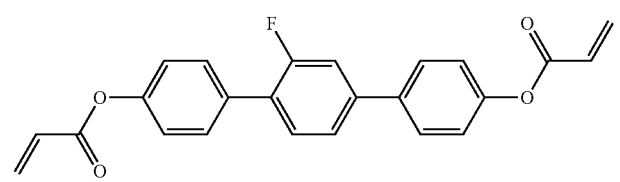
RM-67
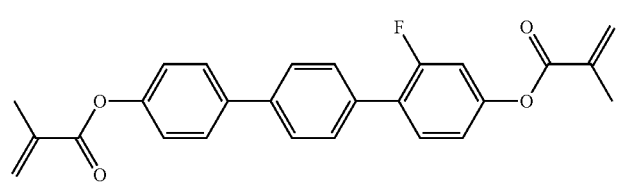
RM-68

TABLE D-continued
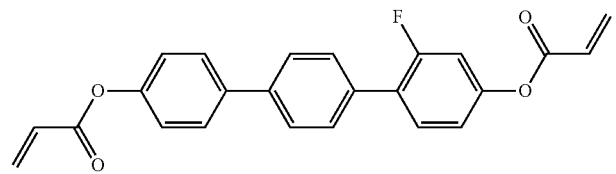 RM-69
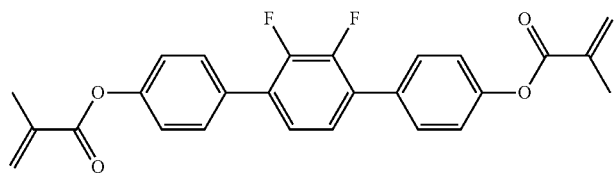 RM-70
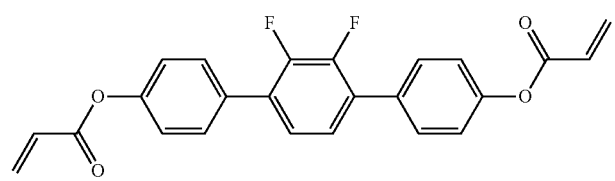 RM-71
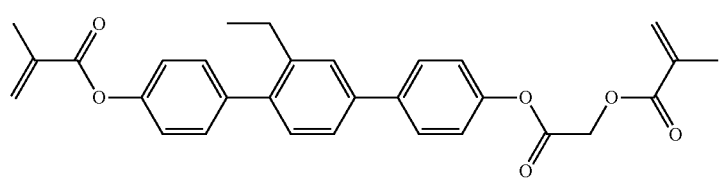 RM-72
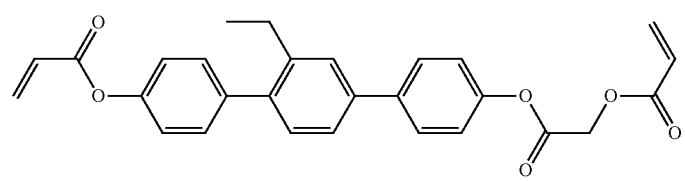 [SMILES: C=CC(=O)OCC(=O)Oc1ccc(-c2ccc(-c3ccc(OC(=O)C=C)cc3)c(CC)c2)cc1] RM-73
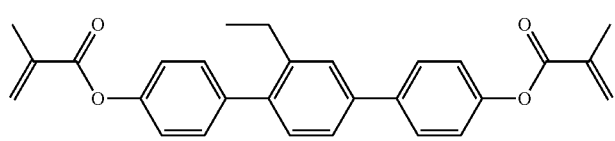 [SMILES: C=C(C)C(=O)Oc1ccc(-c2ccc(-c3ccc(OC(=O)C(=C)C)cc3)c(CC)c2)cc1] RM-74
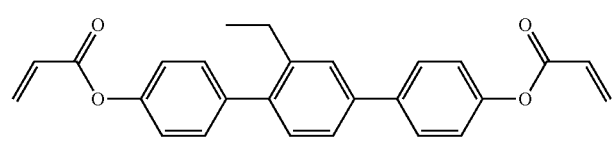 [SMILES: C=CC(=O)Oc1ccc(-c2ccc(-c3ccc(OC(=O)C=C)cc3)c(CC)c2)cc1] RM-75
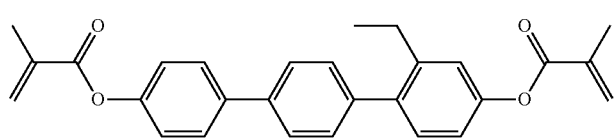 RM-76
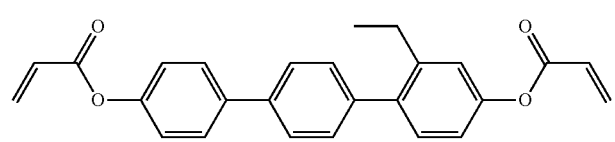 [SMILES: C=CC(=O)Oc1ccc(-c2ccc(-c3ccc(OC(=O)C=C)cc3CC)cc2)cc1] RM-77

TABLE D-continued
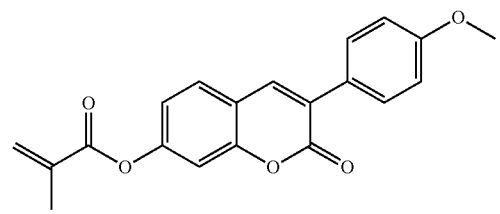 [SMILES: C=C(C)C(=O)Oc1ccc2cc(-c3ccc(OC)cc3)c(=O)oc2c1] RM-78
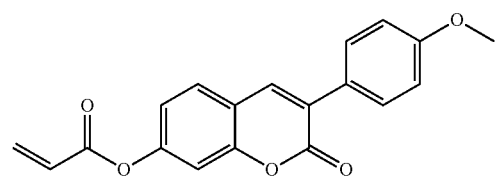 [SMILES: C=CC(=O)Oc1ccc2cc(-c3ccc(OC)cc3)c(=O)oc2c1] RM-79
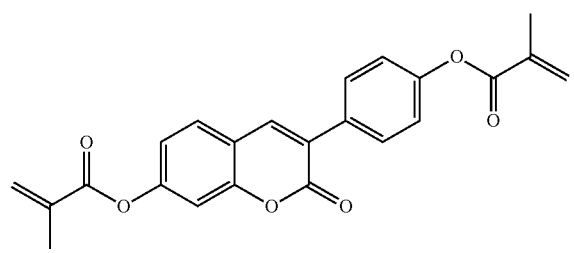 [SMILES: C=C(C)C(=O)Oc1ccc(-c2cc3ccc(OC(=O)C(=C)C)cc3oc2=O)cc1] RM-80
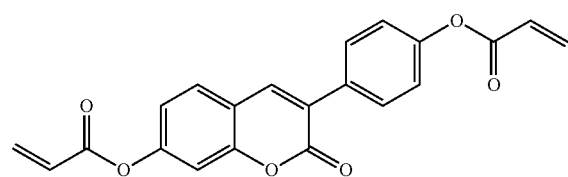 [SMILES: C=CC(=O)Oc1ccc(-c2cc3ccc(OC(=O)C=C)cc3oc2=O)cc1] RM-81
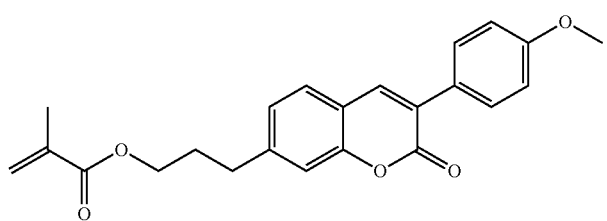 [SMILES: C=C(C)C(=O)OCCCc1ccc2cc(-c3ccc(OC)cc3)c(=O)oc2c1] RM-82
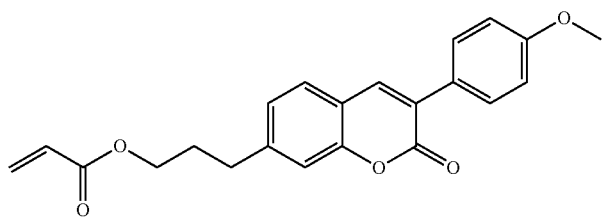 [SMILES: C=CC(=O)OCCCc1ccc2cc(-c3ccc(OC)cc3)c(=O)oc2c1] RM-83
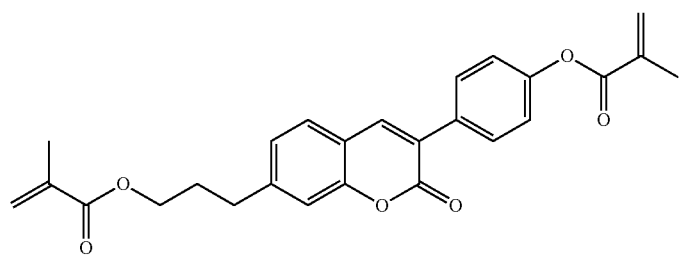 [SMILES: C=C(C)C(=O)OCCCc1ccc2cc(-c3ccc(OC(=O)C(=C)C)cc3)c(=O)oc2c1] RM-84

TABLE D-continued
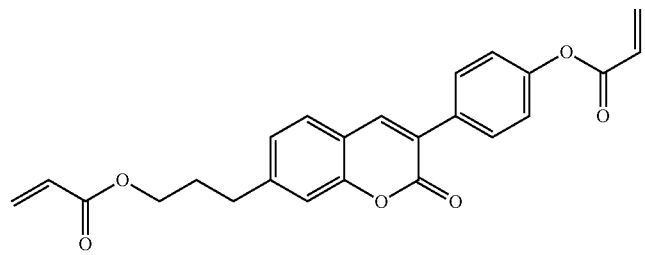 [SMILES: C=CC(=O)OCCCc1ccc2cc(-c3ccc(OC(=O)C=C)cc3)c(=O)oc2c1] RM-85
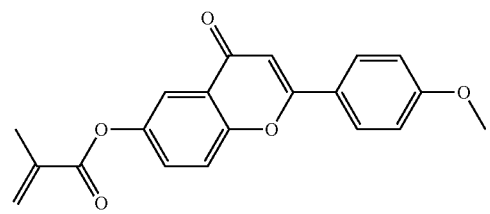 [SMILES: C=C(C)C(=O)Oc1ccc2oc(-c3ccc(OC)cc3)cc(=O)c2c1] RM-86
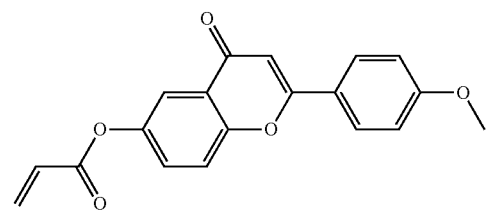 [SMILES: C=CC(=O)Oc1ccc2oc(-c3ccc(OC)cc3)cc(=O)c2c1] RM-87
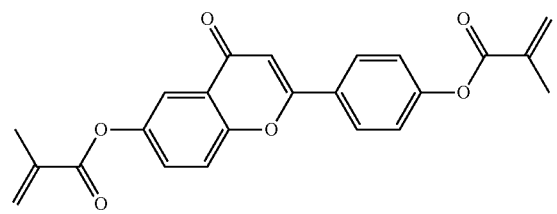 [SMILES: C=C(C)C(=O)Oc1ccc(-c2cc(=O)c3cc(OC(=O)C(=C)C)ccc3o2)cc1] RM-88
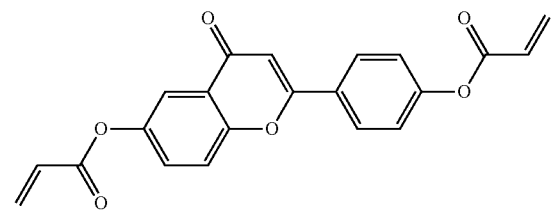 [SMILES: C=CC(=O)Oc1ccc(-c2cc(=O)c3cc(OC(=O)C=C)ccc3o2)cc1] RM-89
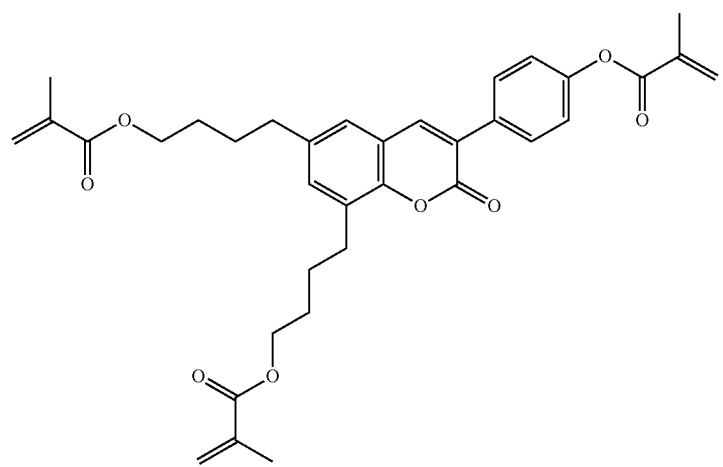 [SMILES: C=C(C)C(=O)OCCCCc1cc(CCCCOC(=O)C(=C)C)c2oc(=O)c(-c3ccc(OC(=O)C(=C)C)cc3)cc2c1] RM-90

TABLE D-continued
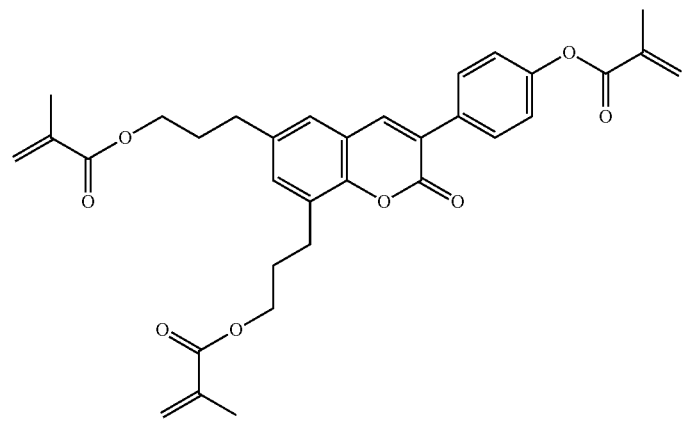 [SMILES: C=C(C)C(=O)OCCCc1cc(CCCOC(=O)C(=C)C)c2oc(=O)c(-c3ccc(OC(=O)C(=C)C)cc3)cc2c1]
RM-91
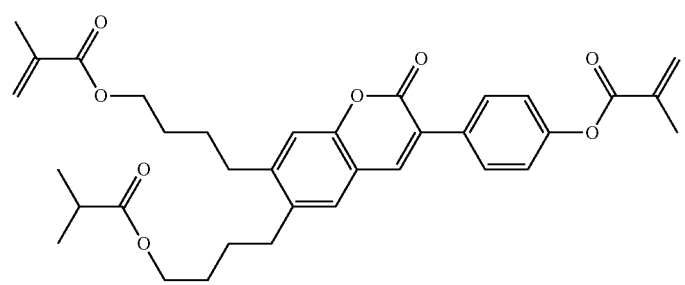 [SMILES: C=C(C)C(=O)OCCCCc1cc2oc(=O)c(-c3ccc(OC(=O)C(=C)C)cc3)cc2cc1CCCCOC(=O)C(C)C]
RM-92
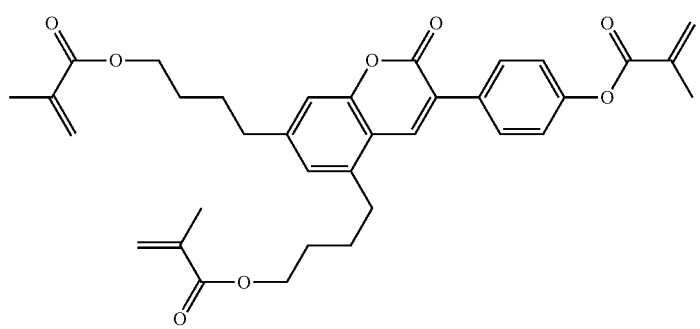 [SMILES: C=C(C)C(=O)OCCCCc1cc(CCCCOC(=O)C(=C)C)c2cc(-c3ccc(OC(=O)C(=C)C)cc3)c(=O)oc2c1]
RM-93
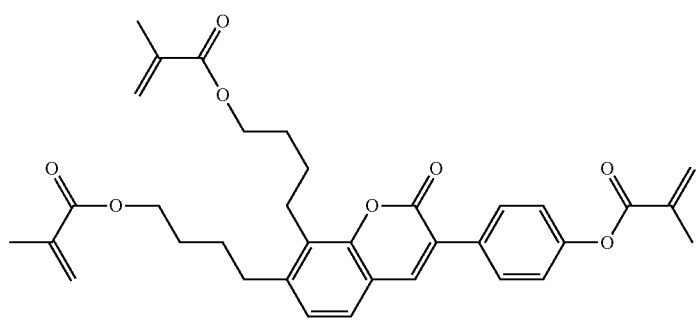 [SMILES: C=C(C)C(=O)OCCCCc1ccc2cc(-c3ccc(OC(=O)C(=C)C)cc3)c(=O)oc2c1CCCCOC(=O)C(=C)C]
RM-94
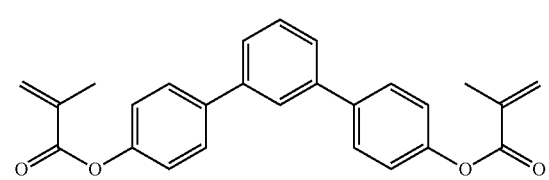 [SMILES: C=C(C)C(=O)Oc1ccc(-c2cccc(-c3ccc(OC(=O)C(=C)C)cc3)c2)cc1]
RM-95

TABLE D-continued
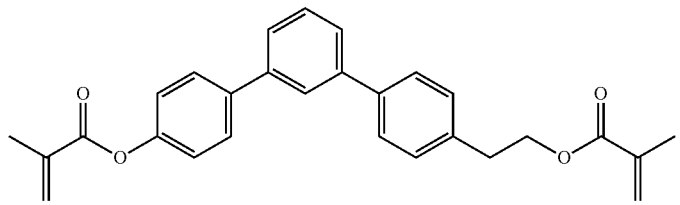 [SMILES: C=C(C)C(=O)OCCc1ccc(-c2cccc(-c3ccc(OC(=O)C(=C)C)cc3)c2)cc1]
RM-96
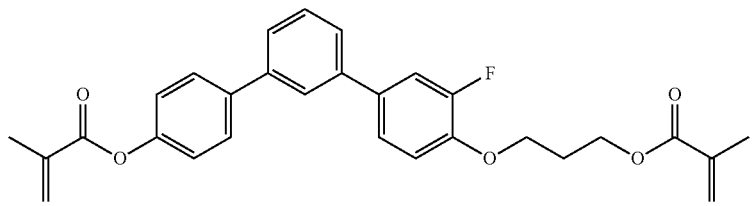 [SMILES: C=C(C)C(=O)OCCCOc1ccc(-c2cccc(-c3ccc(OC(=O)C(=C)C)cc3)c2)cc1F]
RM-97
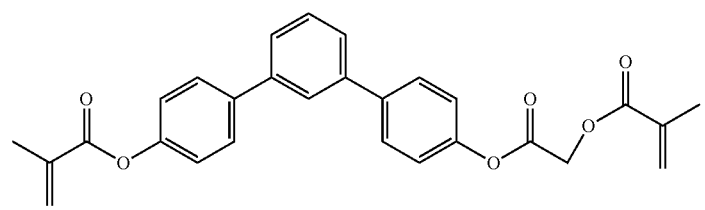 [SMILES: C=C(C)C(=O)OCC(=O)Oc1ccc(-c2cccc(-c3ccc(OC(=O)C(=C)C)cc3)c2)cc1]
RM-98
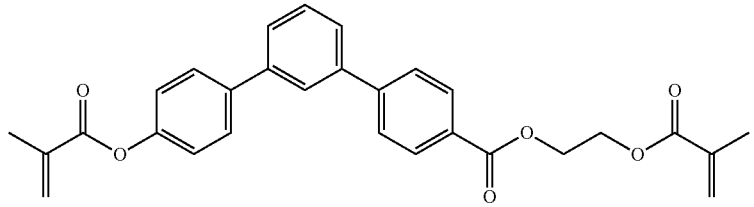 [SMILES: C=C(C)C(=O)OCCOC(=O)c1ccc(-c2cccc(-c3ccc(OC(=O)C(=C)C)cc3)c2)cc1]
RM-99
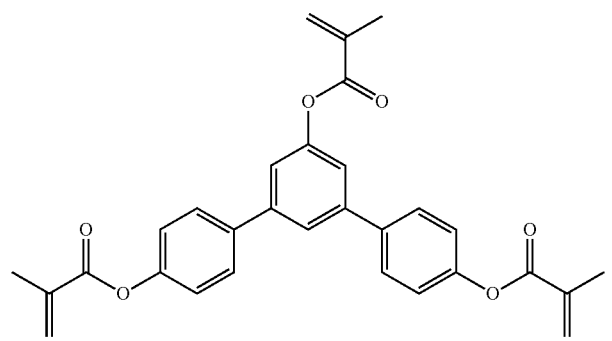 [SMILES: C=C(C)C(=O)Oc1ccc(-c2cc(OC(=O)C(=C)C)cc(-c3ccc(OC(=O)C(=C)C)cc3)c2)cc1]
RM-100
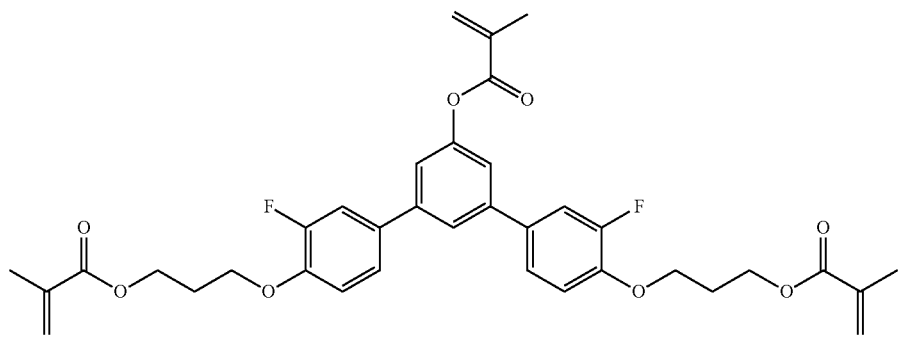 [SMILES: C=C(C)C(=O)OCCCOc1ccc(-c2cc(OC(=O)C(=C)C)cc(-c3ccc(OCCCOC(=O)C(=C)C)c(F)c3)c2)cc1F]
RM-101

TABLE D-continued
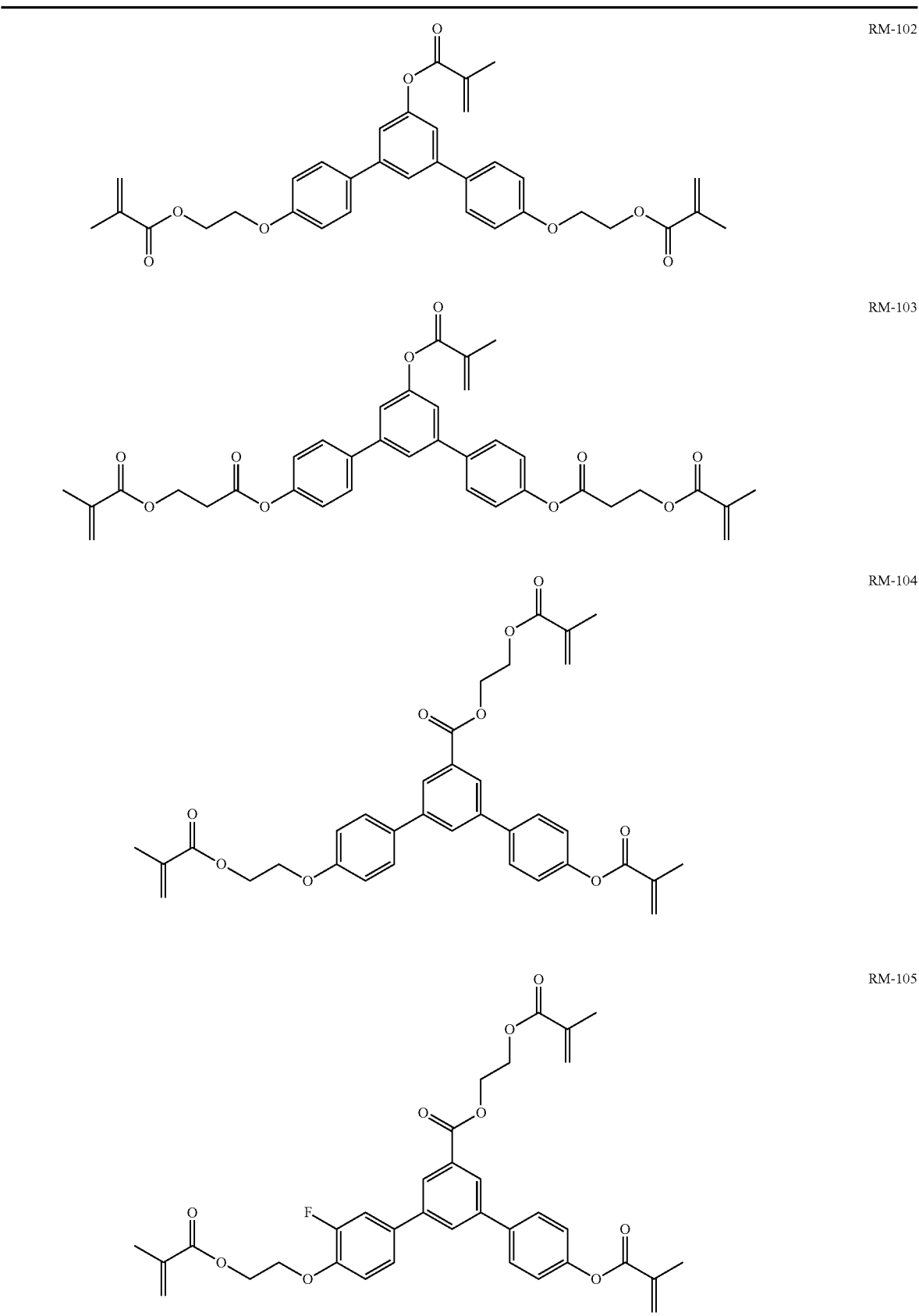

TABLE D-continued
RM-106
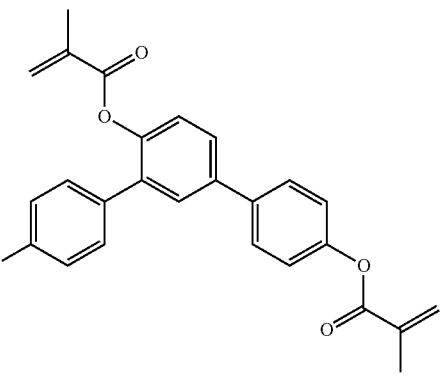
RM-107
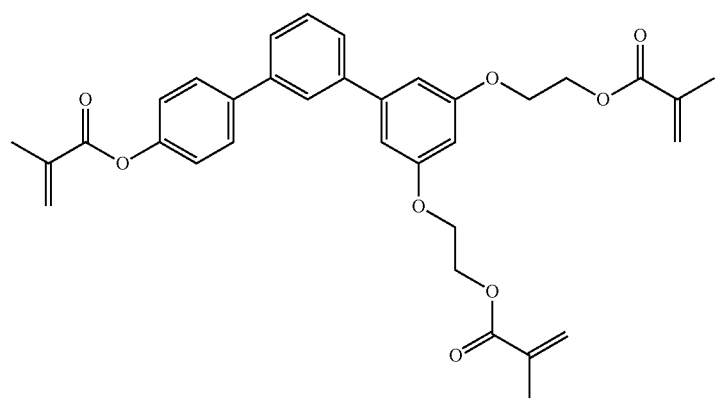 [SMILES: C=C(C)C(=O)OCCOc1cc(OCCOC(=O)C(=C)C)cc(-c2cccc(-c3ccc(OC(=O)C(=C)C)cc3)c2)c1]
RM-108
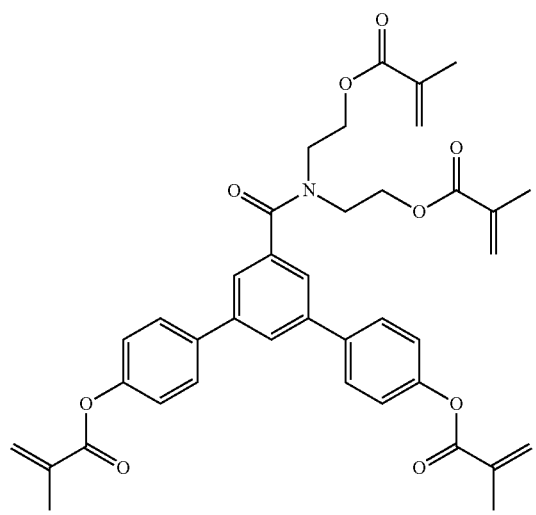 [SMILES: C=C(C)C(=O)OCCN(CCOC(=O)C(=C)C)C(=O)c1cc(-c2ccc(OC(=O)C(=C)C)cc2)cc(-c2ccc(OC(=O)C(=C)C)cc2)c1]
RM-109
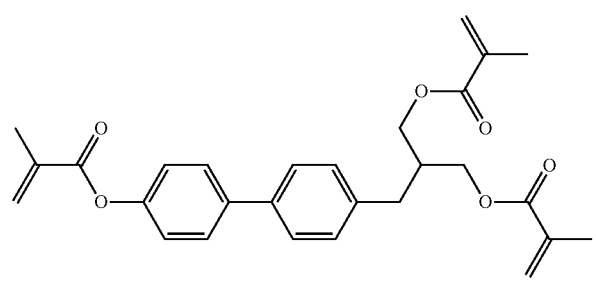 [SMILES: C=C(C)C(=O)OCC(COC(=O)C(=C)C)Cc1ccc(-c2ccc(OC(=O)C(=C)C)cc2)cc1]

TABLE D-continued
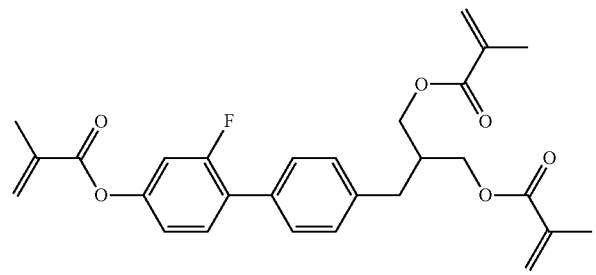 [SMILES: C=C(C)C(=O)OCC(COC(=O)C(=C)C)Cc1ccc(-c2ccc(OC(=O)C(=C)C)cc2F)cc1]
RM-110
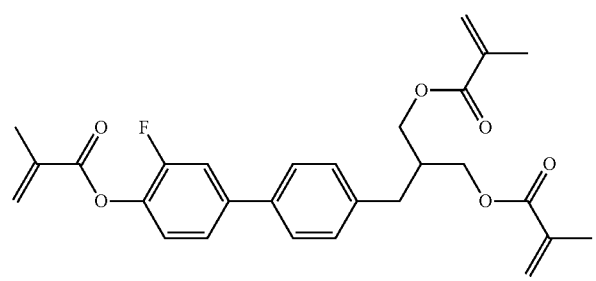 [SMILES: C=C(C)C(=O)OCC(COC(=O)C(=C)C)Cc1ccc(-c2ccc(OC(=O)C(=C)C)c(F)c2)cc1]
RM-111
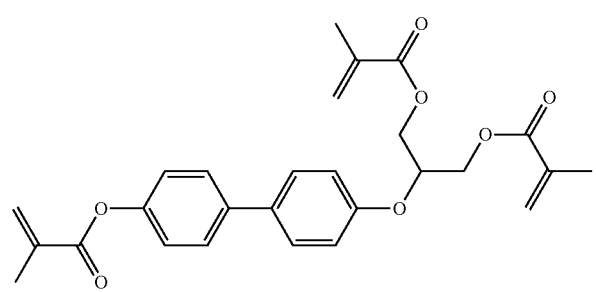 [SMILES: C=C(C)C(=O)OCC(COC(=O)C(=C)C)Oc1ccc(-c2ccc(OC(=O)C(=C)C)cc2)cc1]
RM-112
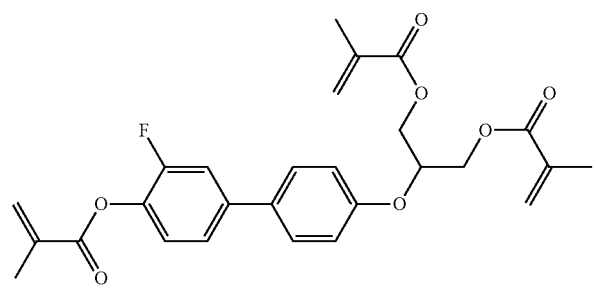 [SMILES: C=C(C)C(=O)OCC(COC(=O)C(=C)C)Oc1ccc(-c2ccc(OC(=O)C(=C)C)c(F)c2)cc1]
RM-113
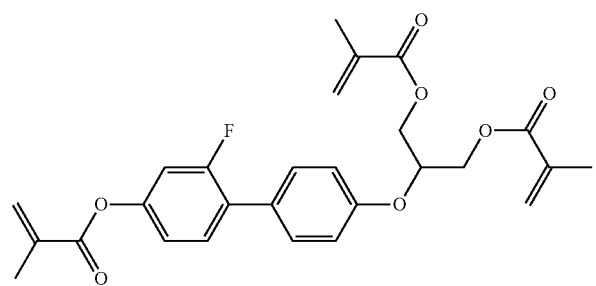 [SMILES: C=C(C)C(=O)OCC(COC(=O)C(=C)C)Oc1ccc(-c2ccc(OC(=O)C(=C)C)cc2F)cc1]
RM-114

TABLE D-continued
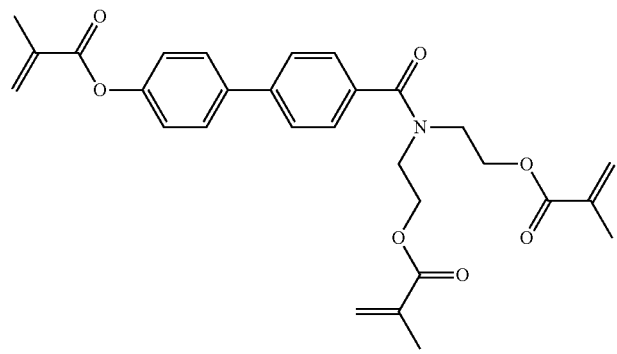 [SMILES: C=C(C)C(=O)OCCN(CCOC(=O)C(=C)C)C(=O)c1ccc(-c2ccc(OC(=O)C(=C)C)cc2)cc1]
RM-115
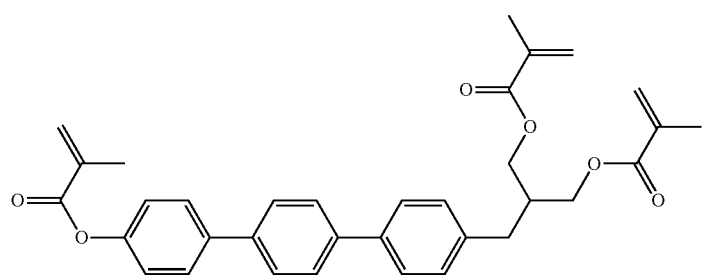 [SMILES: C=C(C)C(=O)OCC(COC(=O)C(=C)C)Cc1ccc(-c2ccc(-c3ccc(OC(=O)C(=C)C)cc3)cc2)cc1]
RM-116
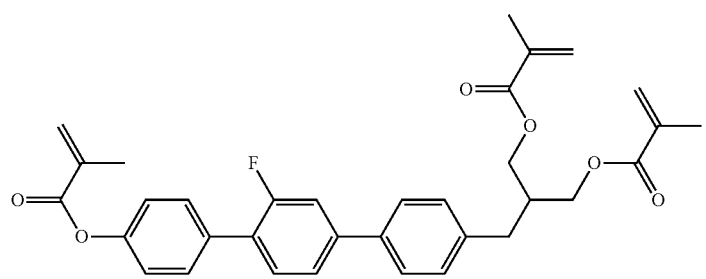 [SMILES: C=C(C)C(=O)OCC(COC(=O)C(=C)C)Cc1ccc(-c2ccc(-c3ccc(OC(=O)C(=C)C)cc3)c(F)c2)cc1]
RM-117
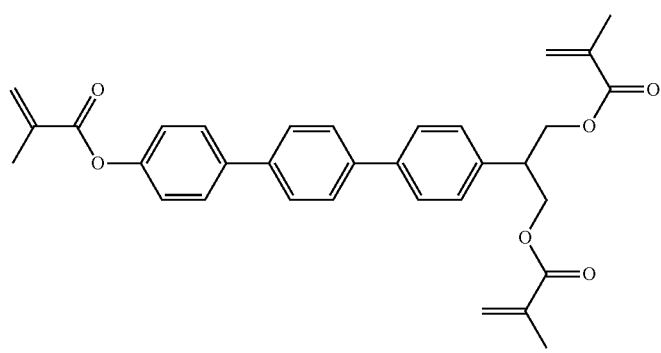 [SMILES: C=C(C)C(=O)OCC(COC(=O)C(=C)C)c1ccc(-c2ccc(-c3ccc(OC(=O)C(=C)C)cc3)cc2)cc1]
RM-118
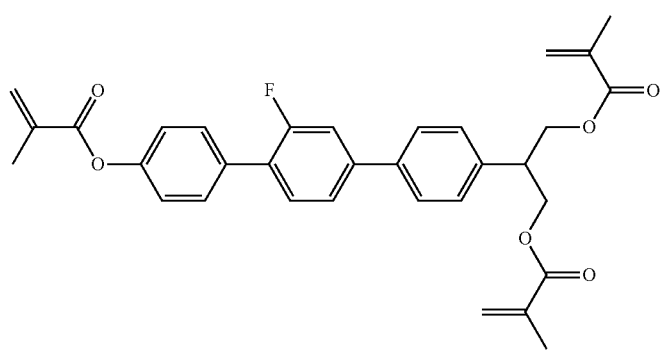 [SMILES: C=C(C)C(=O)OCC(COC(=O)C(=C)C)c1ccc(-c2ccc(-c3ccc(OC(=O)C(=C)C)cc3)c(F)c2)cc1]
RM-119

TABLE D-continued
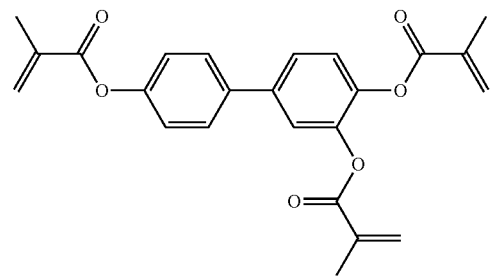 [SMILES: C=C(C)C(=O)Oc1ccc(-c2ccc(OC(=O)C(=C)C)c(OC(=O)C(=C)C)c2)cc1]
RM-120
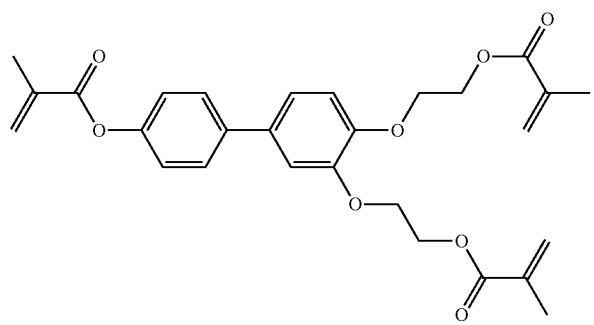 [SMILES: C=C(C)C(=O)OCCOc1ccc(-c2ccc(OC(=O)C(=C)C)cc2)cc1OCCOC(=O)C(=C)C]
RM-121
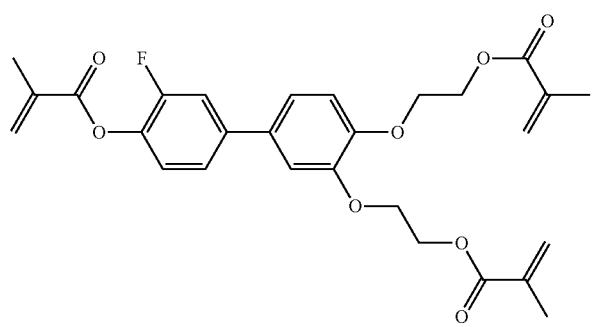 [SMILES: C=C(C)C(=O)OCCOc1ccc(-c2ccc(OC(=O)C(=C)C)c(F)c2)cc1OCCOC(=O)C(=C)C]
RM-122
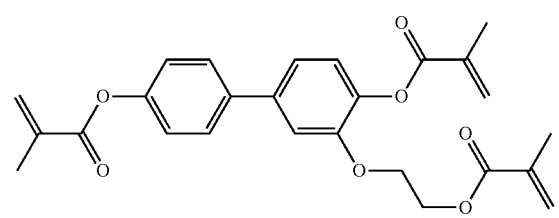 [SMILES: C=C(C)C(=O)OCCOc1cc(-c2ccc(OC(=O)C(=C)C)cc2)ccc1OC(=O)C(=C)C]
RM-123
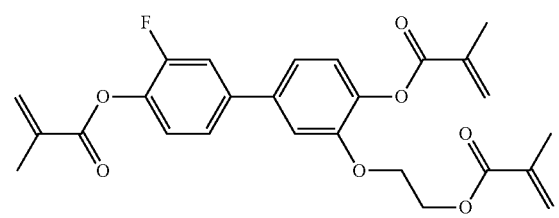 [SMILES: C=C(C)C(=O)OCCOc1cc(-c2ccc(OC(=O)C(=C)C)c(F)c2)ccc1OC(=O)C(=C)C]
RM-124

TABLE D-continued
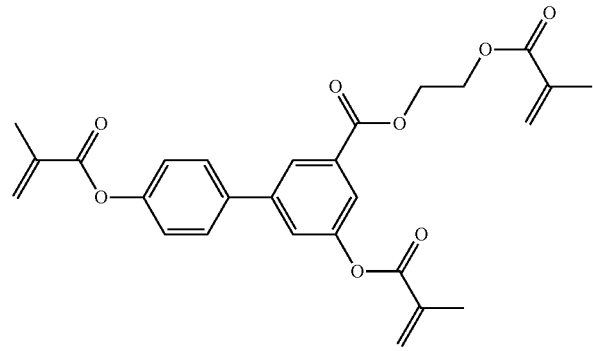 [SMILES: C=C(C)C(=O)OCCOC(=O)c1cc(OC(=O)C(=C)C)cc(-c2ccc(OC(=O)C(=C)C)cc2)c1]
RM-125
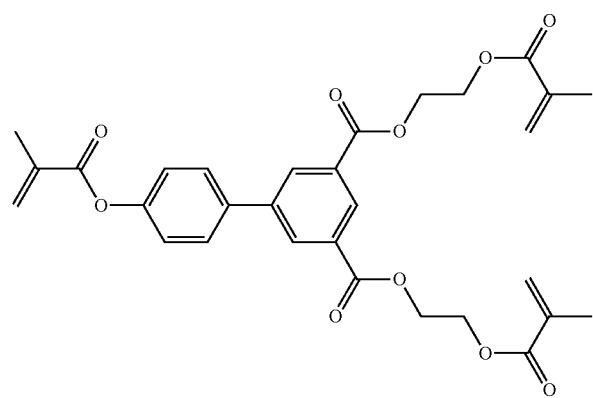 [SMILES: C=C(C)C(=O)OCCOC(=O)c1cc(C(=O)OCCOC(=O)C(=C)C)cc(-c2ccc(OC(=O)C(=C)C)cc2)c1]
RM-126
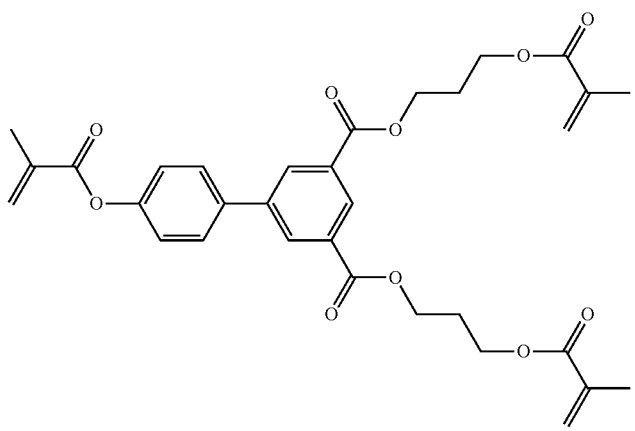 [SMILES: C=C(C)C(=O)OCCCOC(=O)c1cc(C(=O)OCCCOC(=O)C(=C)C)cc(-c2ccc(OC(=O)C(=C)C)cc2)c1]
RM-127
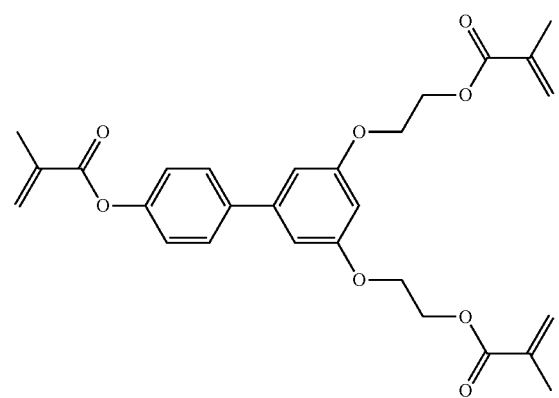 [SMILES: C=C(C)C(=O)OCCOc1cc(OCCOC(=O)C(=C)C)cc(-c2ccc(OC(=O)C(=C)C)cc2)c1]
RM-128

TABLE D-continued
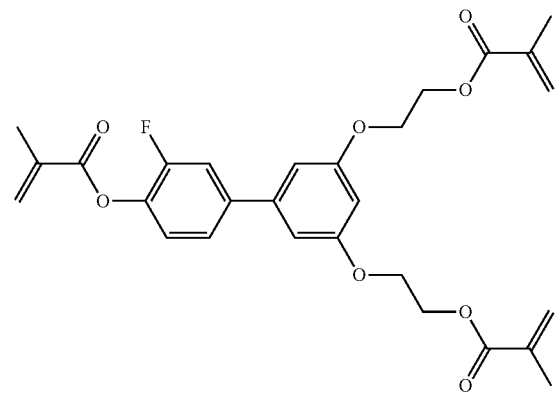 [SMILES: C=C(C)C(=O)OCCOc1cc(OCCOC(=O)C(=C)C)cc(-c2ccc(OC(=O)C(=C)C)c(F)c2)c1]
RM-129
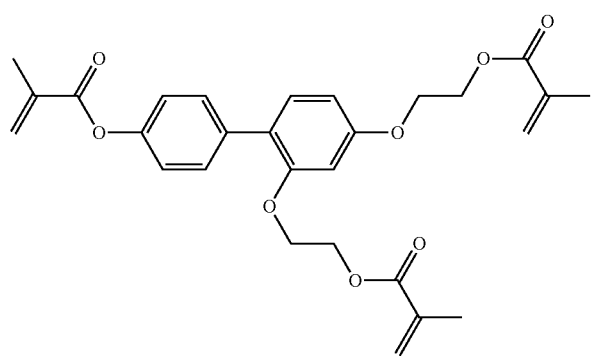 [SMILES: C=C(C)C(=O)OCCOc1ccc(-c2ccc(OC(=O)C(=C)C)cc2)c(OCCOC(=O)C(=C)C)c1]
RM-130
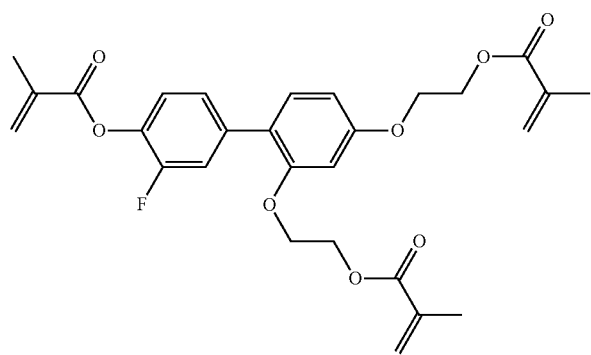 [SMILES: C=C(C)C(=O)OCCOc1ccc(-c2ccc(OC(=O)C(=C)C)c(F)c2)c(OCCOC(=O)C(=C)C)c1]
RM-131
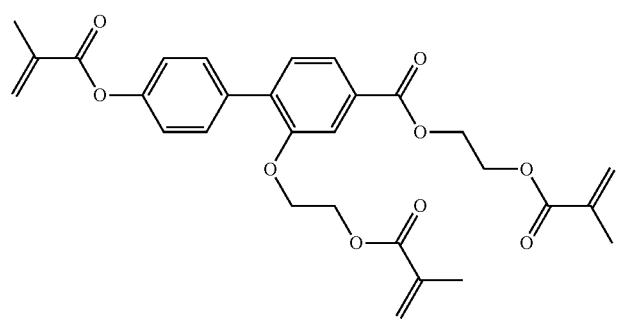 [SMILES: C=C(C)C(=O)OCCOC(=O)c1ccc(-c2ccc(OC(=O)C(=C)C)cc2)c(OCCOC(=O)C(=C)C)c1]
RM-132

TABLE D-continued
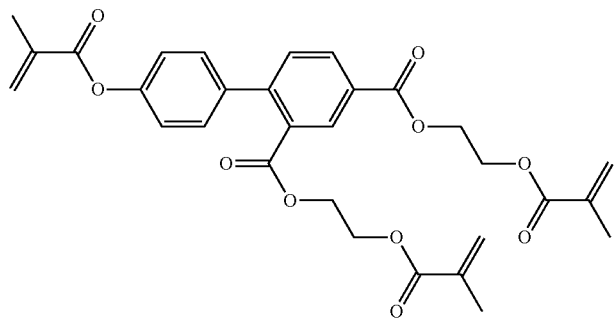 [SMILES: C=C(C)C(=O)OCCOC(=O)c1ccc(-c2ccc(OC(=O)C(=C)C)cc2)c(C(=O)OCCOC(=O)C(=C)C)c1]
RM-133
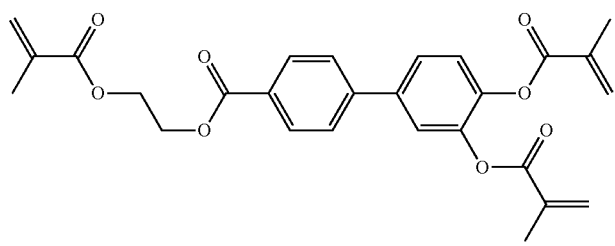 [SMILES: C=C(C)C(=O)OCCOC(=O)c1ccc(-c2ccc(OC(=O)C(=C)C)c(OC(=O)C(=C)C)c2)cc1]
RM-134
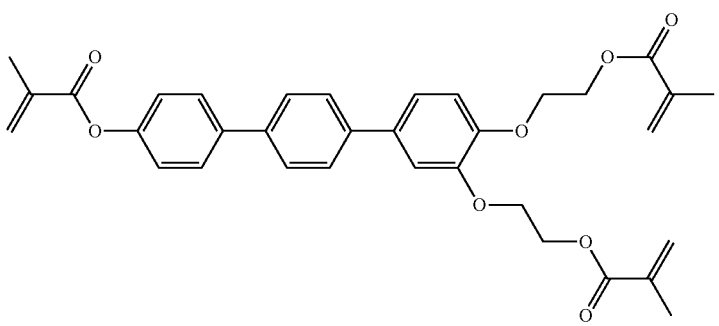 [SMILES: C=C(C)C(=O)OCCOc1ccc(-c2ccc(-c3ccc(OC(=O)C(=C)C)cc3)cc2)cc1OCCOC(=O)C(=C)C]
RM-135
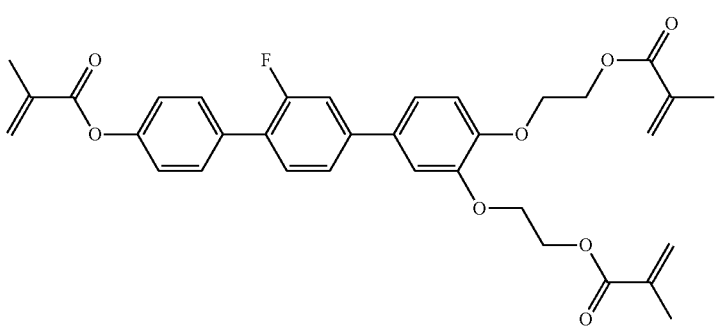 [SMILES: C=C(C)C(=O)OCCOc1ccc(-c2ccc(-c3ccc(OC(=O)C(=C)C)cc3)c(F)c2)cc1OCCOC(=O)C(=C)C]
RM-136
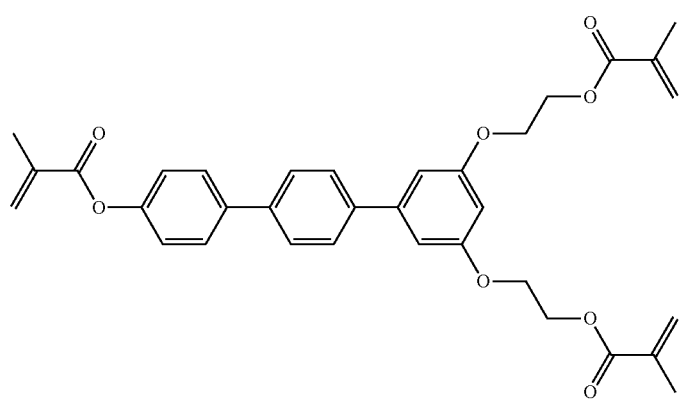 [SMILES: C=C(C)C(=O)OCCOc1cc(OCCOC(=O)C(=C)C)cc(-c2ccc(-c3ccc(OC(=O)C(=C)C)cc3)cc2)c1]
RM-137

TABLE D-continued
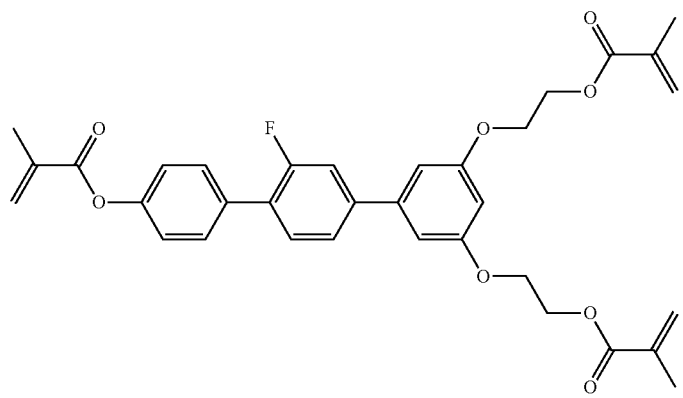 [SMILES: C=C(C)C(=O)OCCOc1cc(OCCOC(=O)C(=C)C)cc(-c2ccc(-c3ccc(OC(=O)C(=C)C)cc3)c(F)c2)c1] RM-138
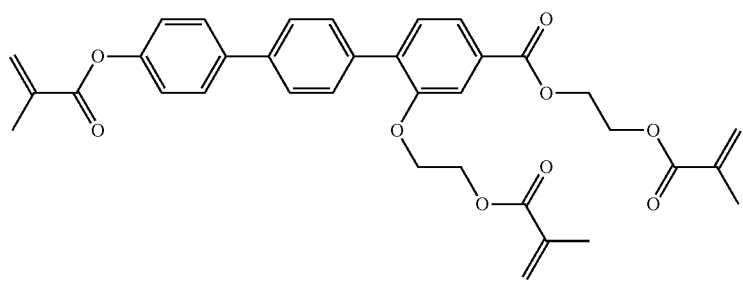 [SMILES: C=C(C)C(=O)OCCOC(=O)c1ccc(-c2ccc(-c3ccc(OC(=O)C(=C)C)cc3)cc2)c(OCCOC(=O)C(=C)C)c1] RM-139
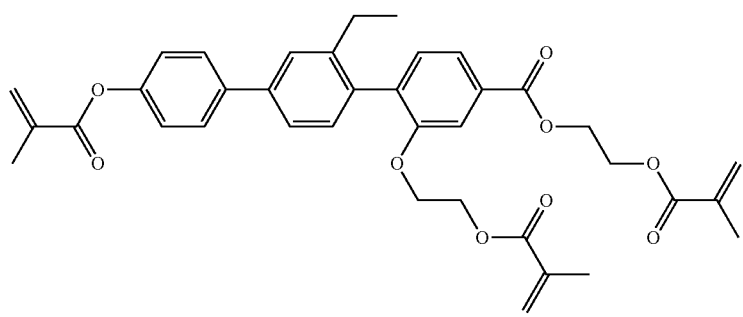 [SMILES: C=C(C)C(=O)OCCOC(=O)c1ccc(-c2ccc(-c3ccc(OC(=O)C(=C)C)cc3)cc2CC)c(OCCOC(=O)C(=C)C)c1] RM-140
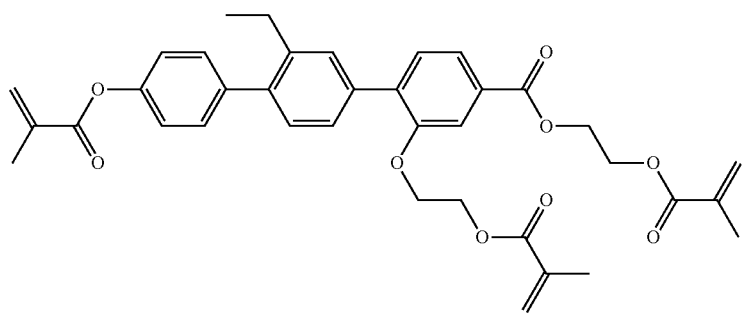 [SMILES: C=C(C)C(=O)OCCOC(=O)c1ccc(-c2ccc(-c3ccc(OC(=O)C(=C)C)cc3)c(CC)c2)c(OCCOC(=O)C(=C)C)c1] RM-141
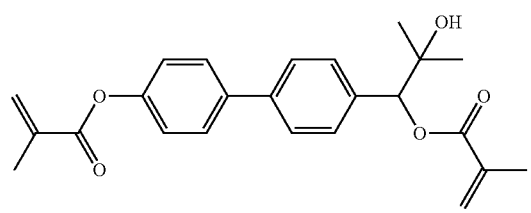 [SMILES: C=C(C)C(=O)Oc1ccc(-c2ccc(C(OC(=O)C(=C)C)C(C)(C)O)cc2)cc1] RM-142

TABLE D-continued
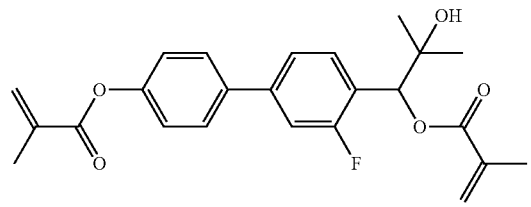 [SMILES: C=C(C)C(=O)Oc1ccc(-c2ccc(C(OC(=O)C(=C)C)C(C)(C)O)c(F)c2)cc1] RM-143
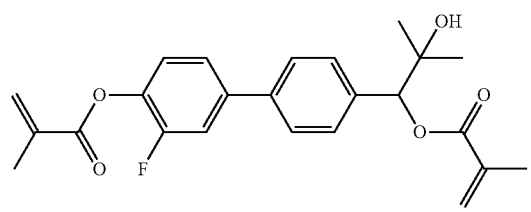 [SMILES: C=C(C)C(=O)Oc1ccc(-c2ccc(C(OC(=O)C(=C)C)C(C)(C)O)cc2)cc1F] RM-144
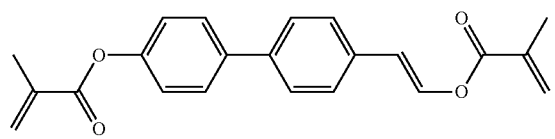 [SMILES: C=C(C)C(=O)O/C=C/c1ccc(-c2ccc(OC(=O)C(=C)C)cc2)cc1] RM-145
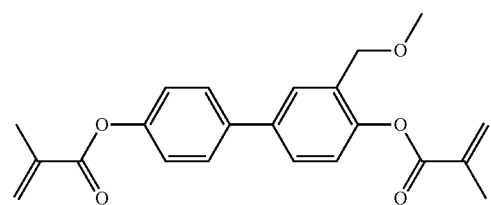 [SMILES: C=C(C)C(=O)Oc1ccc(-c2ccc(OC(=O)C(=C)C)c(COC)c2)cc1] RM-146
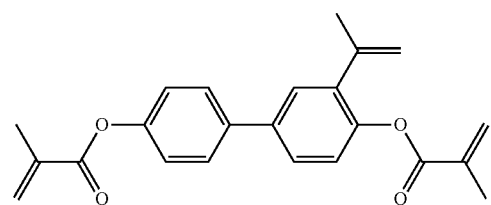 [SMILES: C=C(C)C(=O)Oc1ccc(-c2ccc(OC(=O)C(=C)C)c(C(=C)C)c2)cc1] RM-147
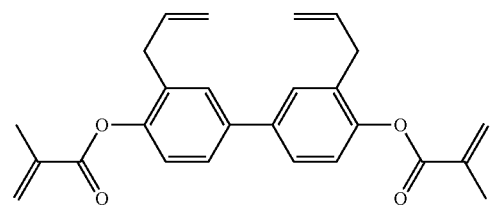 [SMILES: C=CCc1cc(-c2ccc(OC(=O)C(=C)C)c(CC=C)c2)ccc1OC(=O)C(=C)C] RM-148
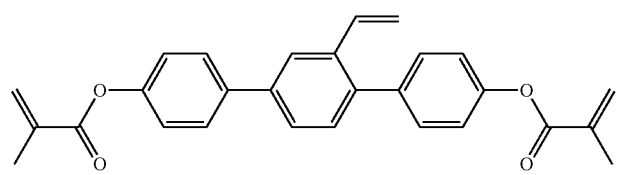 [SMILES: C=Cc1cc(-c2ccc(OC(=O)C(=C)C)cc2)ccc1-c1ccc(OC(=O)C(=C)C)cc1] RM-149
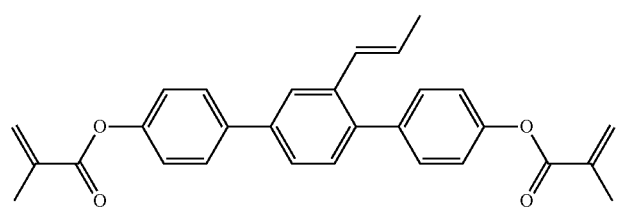 [SMILES: C=C(C)C(=O)Oc1ccc(-c2ccc(-c3ccc(OC(=O)C(=C)C)cc3)c(/C=C/C)c2)cc1] RM-150

TABLE D-continued

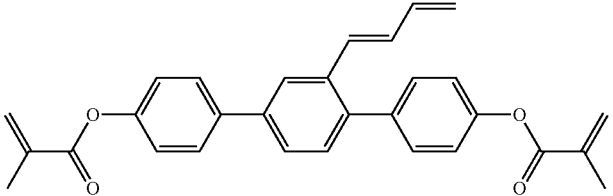 [SMILES: C=C/C=C/c1cc(-c2ccc(OC(=O)C(=C)C)cc2)ccc1-c1ccc(OC(=O)C(=C)C)cc1]

RM-151

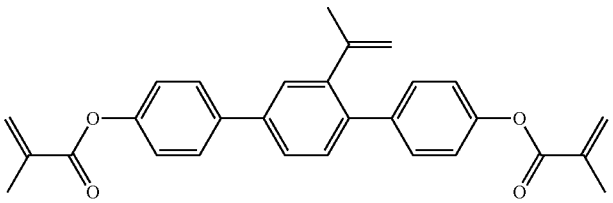 [SMILES: C=C(C)C(=O)Oc1ccc(-c2ccc(-c3ccc(OC(=O)C(=C)C)cc3)c(C(=C)C)c2)cc1]

RM-152

In a preferred embodiment, the mixtures according to the invention comprise one or more polymerisable compounds, preferably selected from the polymerisable compounds of the formulae RM-1 to RM-144. Of these, compounds RM-1, RM-4, RM-8, RM-17, RM-19, RM-35, RM-37, RM-39, RM-40, RM-41, RM-48, RM-52, RM-54, RM-57, RM-64, RM-74, RM-76, RM-88, RM-102, RM-103, RM-109, RM-117, RM-120, RM-121, RM-122 and RM-145 to RM-152 are particularly preferred.

In another preferred embodiment, the mixtures according to the invention comprise one or more polymerisable compounds selected from the formulae RM-145 to RM-152, very preferably from the formulae RM-147 to RM-152.

Table E shows self-alignment additives for vertical alignment which can be used in LC media for SA-VA and SA-FFS displays according to the present invention together with the polymerizable compounds of formula I:

TABLE E

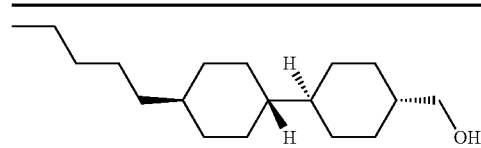

SA-1

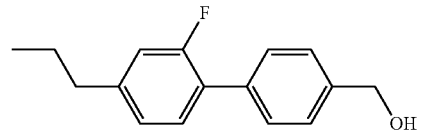 [SMILES: CCCc1ccc(-c2ccc(CO)cc2)c(F)c1]

SA-2

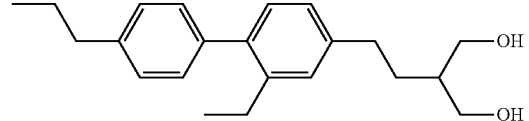 [SMILES: CCCc1ccc(-c2ccc(CCC(CO)CO)cc2CC)cc1]

SA-3

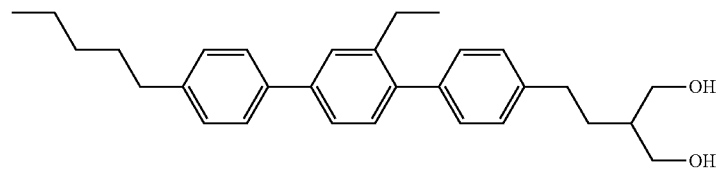 [SMILES: CCCCCc1ccc(-c2ccc(-c3ccc(CCC(CO)CO)cc3)c(CC)c2)cc1]

SA-4

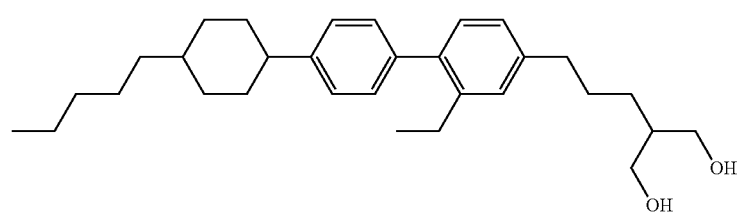 [SMILES: CCCCCC1CCC(c2ccc(-c3ccc(CCCC(CO)CO)cc3CC)cc2)CC1]

SA-5

TABLE E-continued
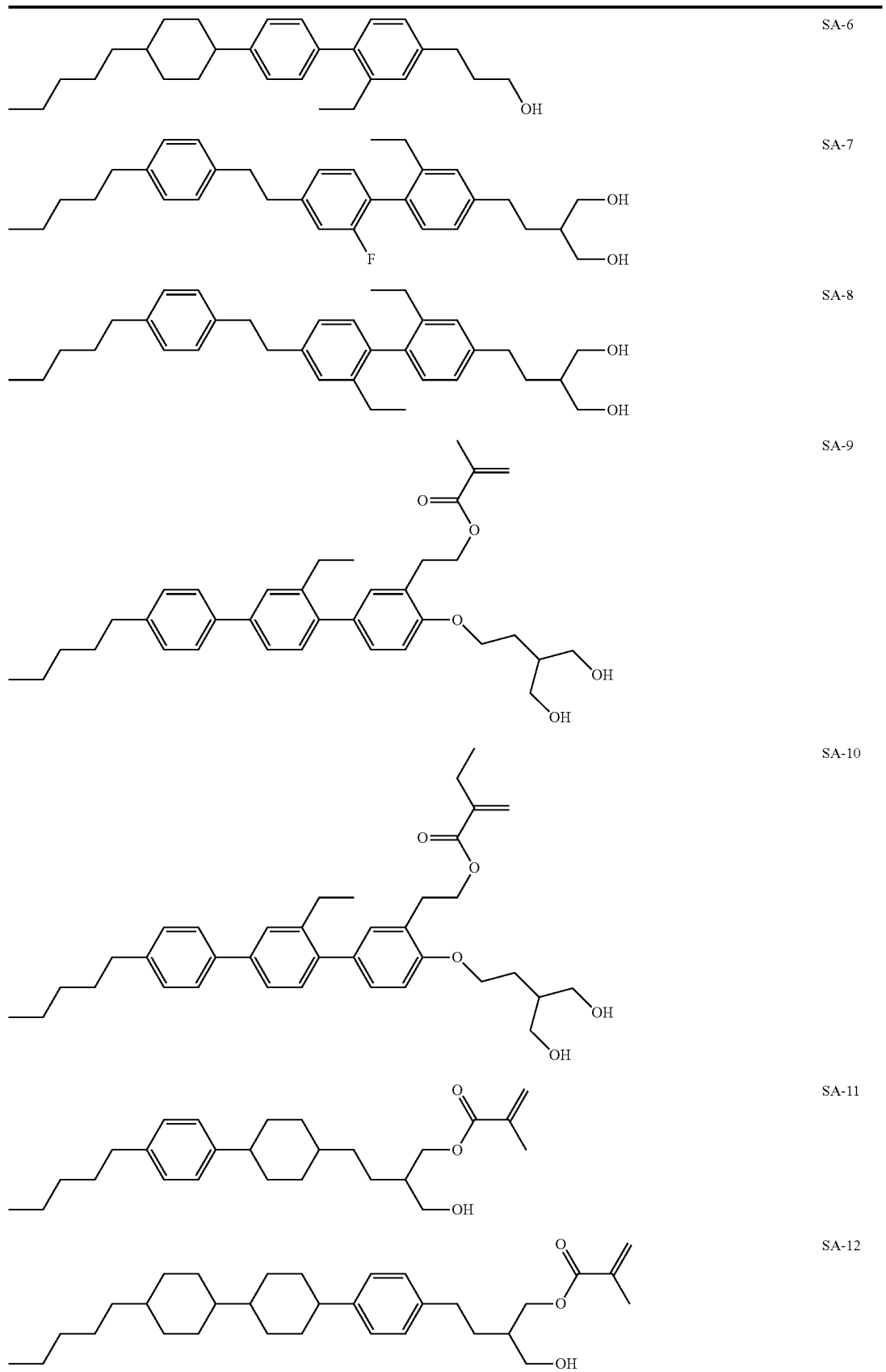
SA-6
SA-7
SA-8
SA-9
SA-10
SA-11
SA-12

TABLE E-continued
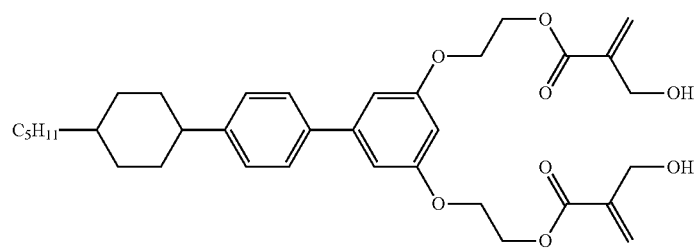
SA-13
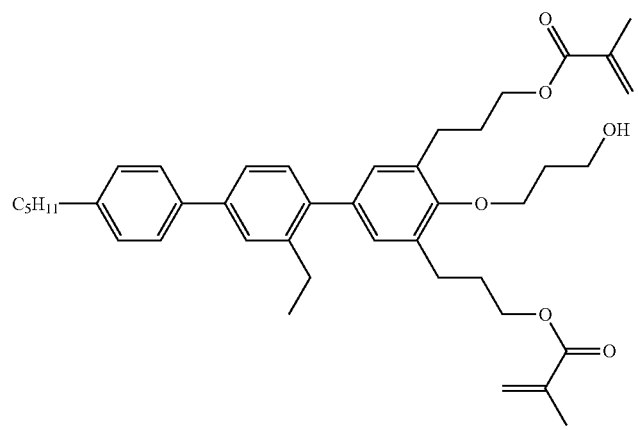
SA-14
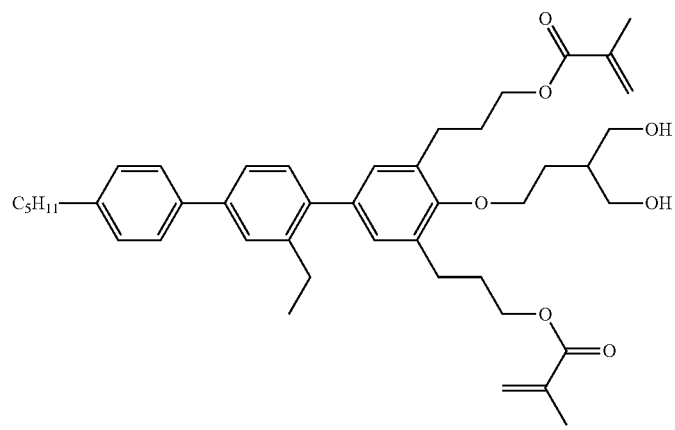
SA-15
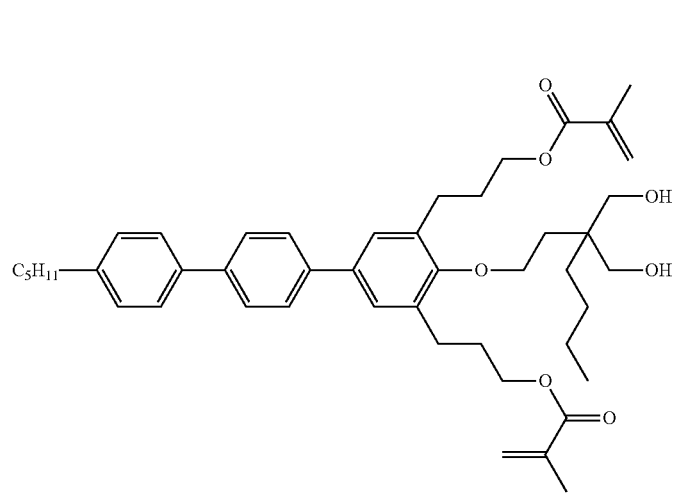
SA-16

TABLE E-continued
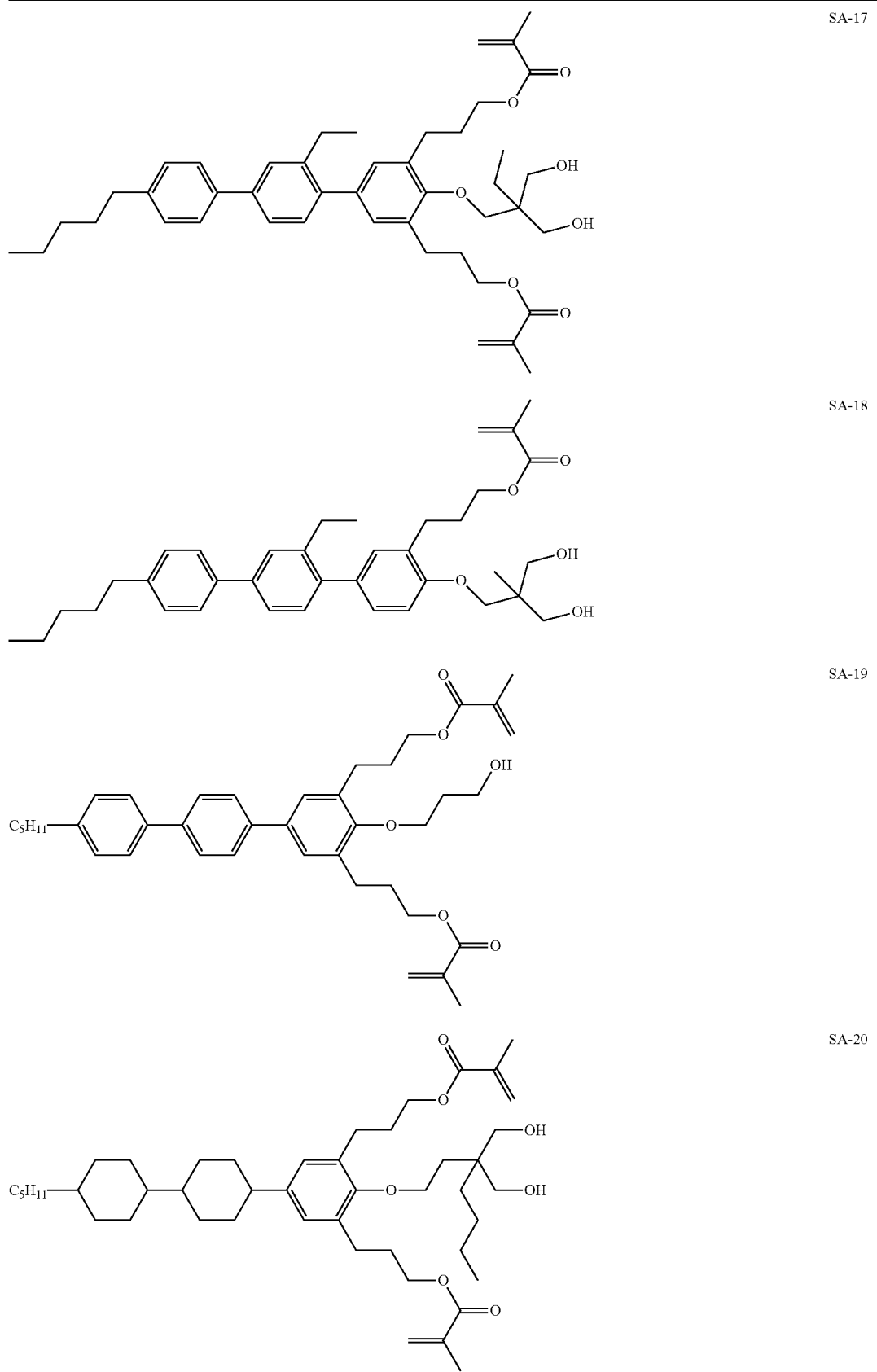
SA-17
SA-18
SA-19
SA-20

TABLE E-continued
SA-21
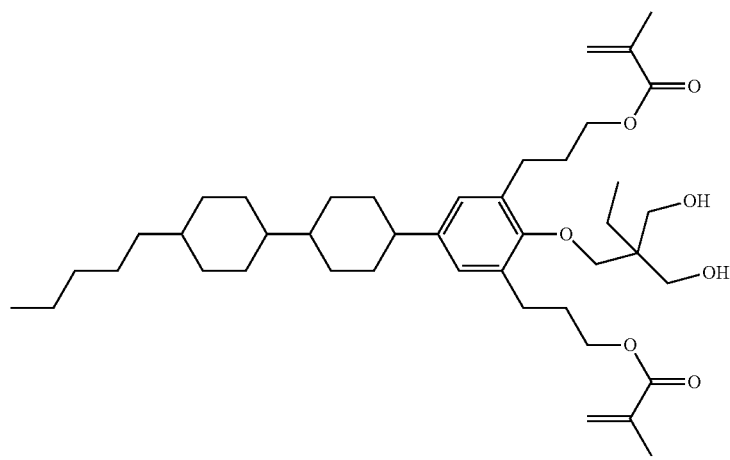 [SMILES: C=C(C)C(=O)OCCCc1cc(C2CCC(C3CCC(CCCCC)CC3)CC2)cc(CCCOC(=O)C(=C)C)c1OCC(CC)(CO)CO]
SA-22
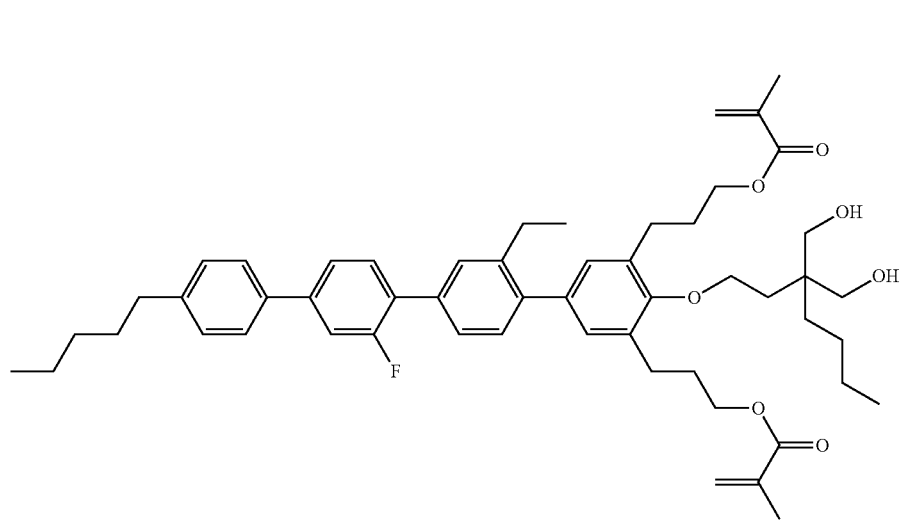 [SMILES: C=C(C)C(=O)OCCCc1cc(-c2ccc(-c3ccc(-c4ccc(CCCCC)cc4)cc3F)cc2CC)cc(CCCOC(=O)C(=C)C)c1OCCC(CO)(CO)CCCC]
SA-23
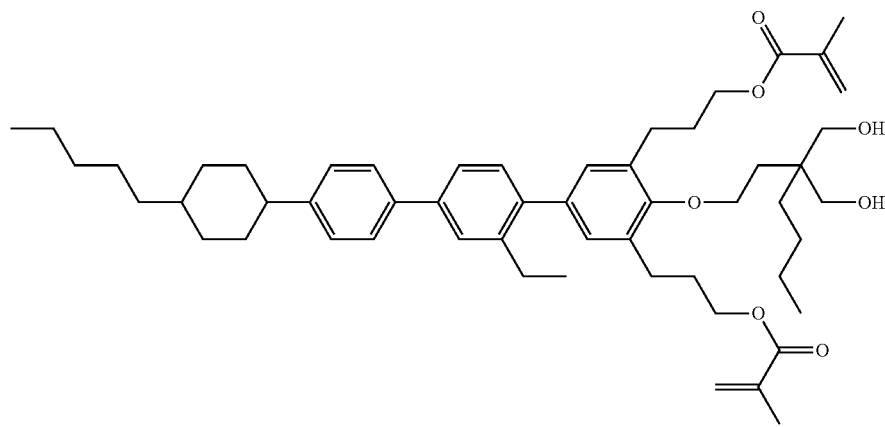 [SMILES: C=C(C)C(=O)OCCCc1cc(-c2ccc(-c3ccc(C4CCC(CCCCC)CC4)cc3)cc2CC)cc(CCCOC(=O)C(=C)C)c1OCCC(CO)(CO)CCCC]

TABLE E-continued
SA-24
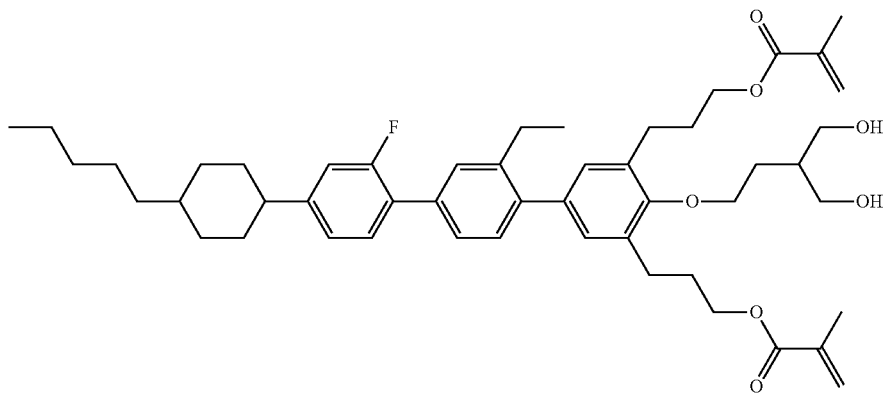 [SMILES: C=C(C)C(=O)OCCCc1cc(-c2ccc(-c3ccc(C4CCC(CCCCC)CC4)cc3F)cc2CC)cc(CCCOC(=O)C(=C)C)c1OCCC(CO)CO]
SA-25
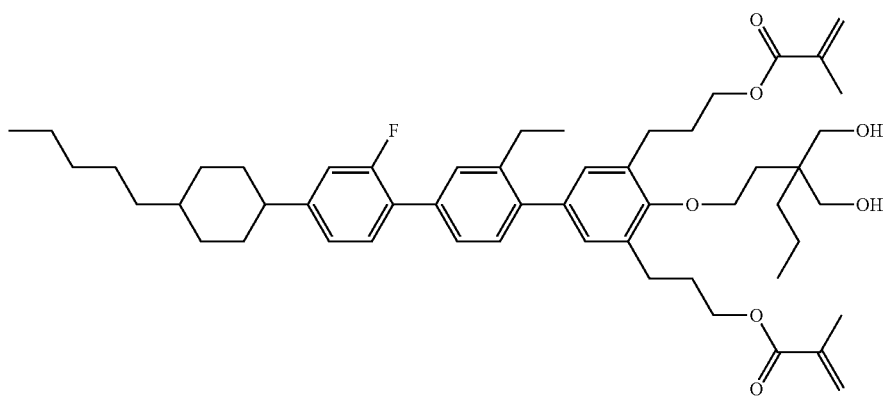 [SMILES: C=C(C)C(=O)OCCCc1cc(-c2ccc(-c3ccc(C4CCC(CCCCC)CC4)cc3F)cc2CC)cc(CCCOC(=O)C(=C)C)c1OCCC(CO)(CO)CCC]
SA-26
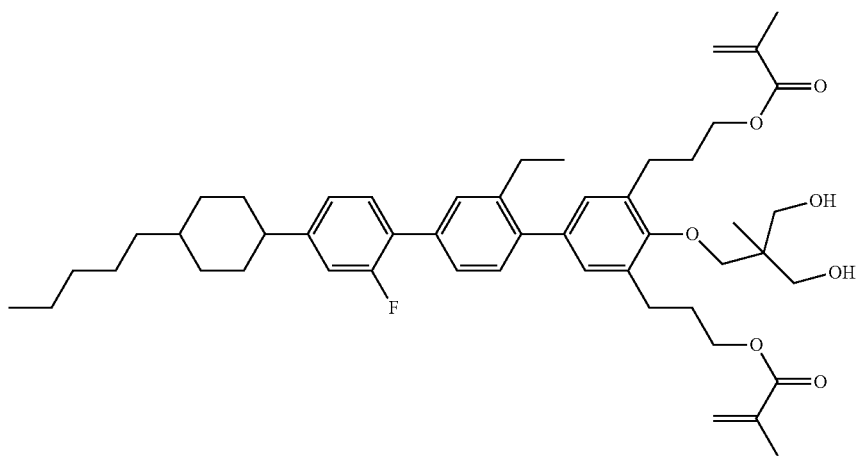 [SMILES: C=C(C)C(=O)OCCCc1cc(-c2ccc(-c3ccc(C4CCC(CCCCC)CC4)cc3F)cc2CC)cc(CCCOC(=O)C(=C)C)c1OCC(C)(CO)CO]

TABLE E-continued
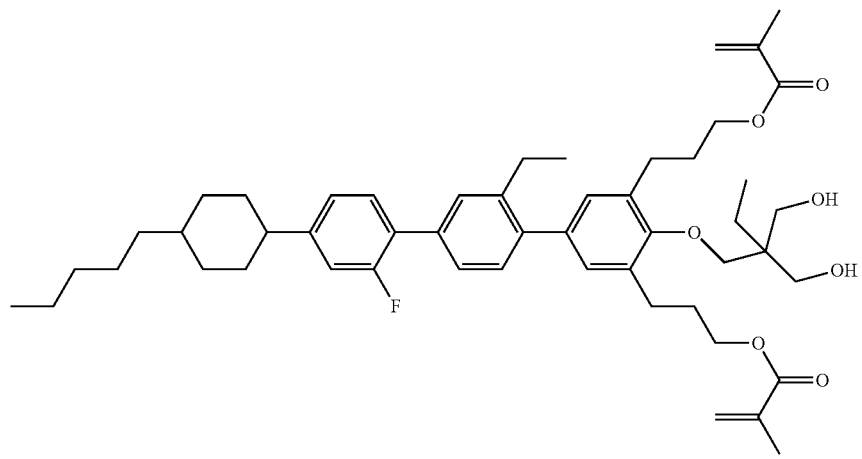 [SMILES: C=C(C)C(=O)OCCCc1cc(-c2ccc(-c3ccc(C4CCC(CCCCC)CC4)cc3F)cc2CC)cc(CCCOC(=O)C(=C)C)c1OCC(CC)(CO)CO]
SA-27
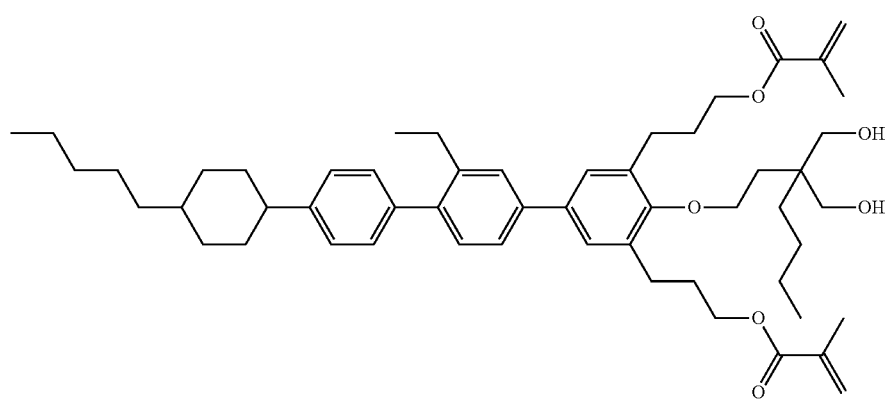 [SMILES: C=C(C)C(=O)OCCCc1cc(-c2ccc(-c3ccc(C4CCC(CCCCC)CC4)cc3)c(CC)c2)cc(CCCOC(=O)C(=C)C)c1OCCC(CO)(CO)CCCC]
SA-28
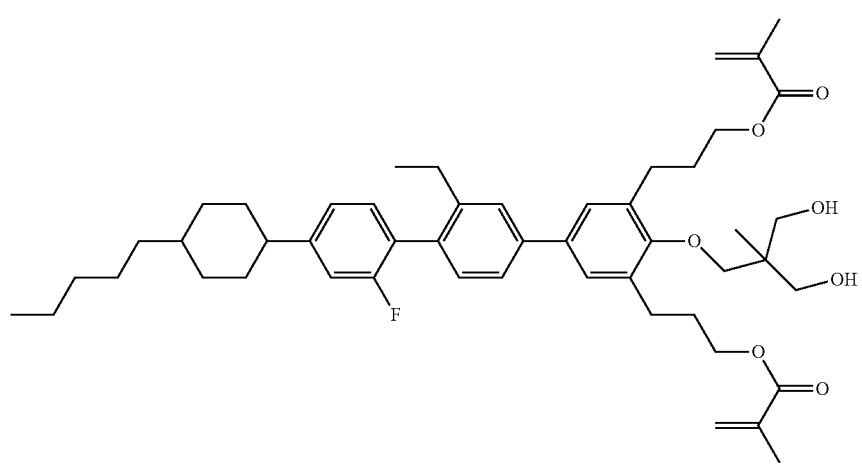 [SMILES: C=C(C)C(=O)OCCCc1cc(-c2ccc(-c3ccc(C4CCC(CCCCC)CC4)cc3F)c(CC)c2)cc(CCCOC(=O)C(=C)C)c1OCC(C)(CO)CO]
SA-29

TABLE E-continued
SA-30
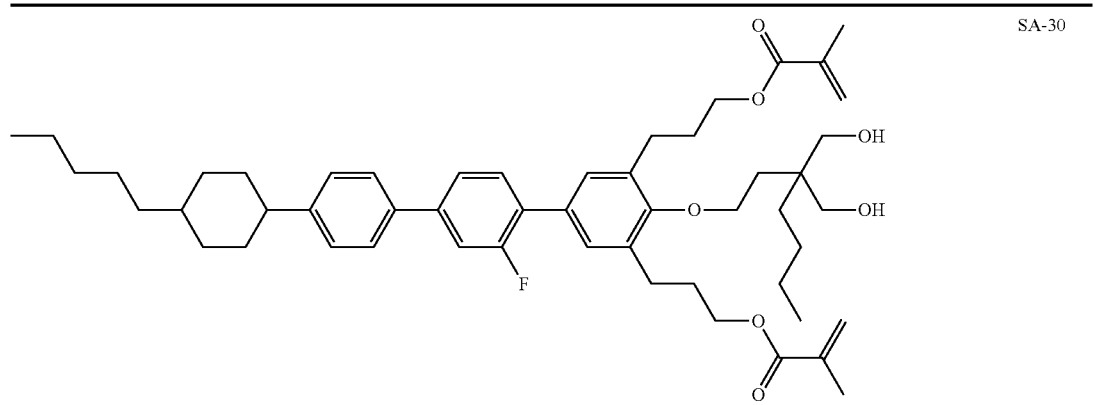
SA-31
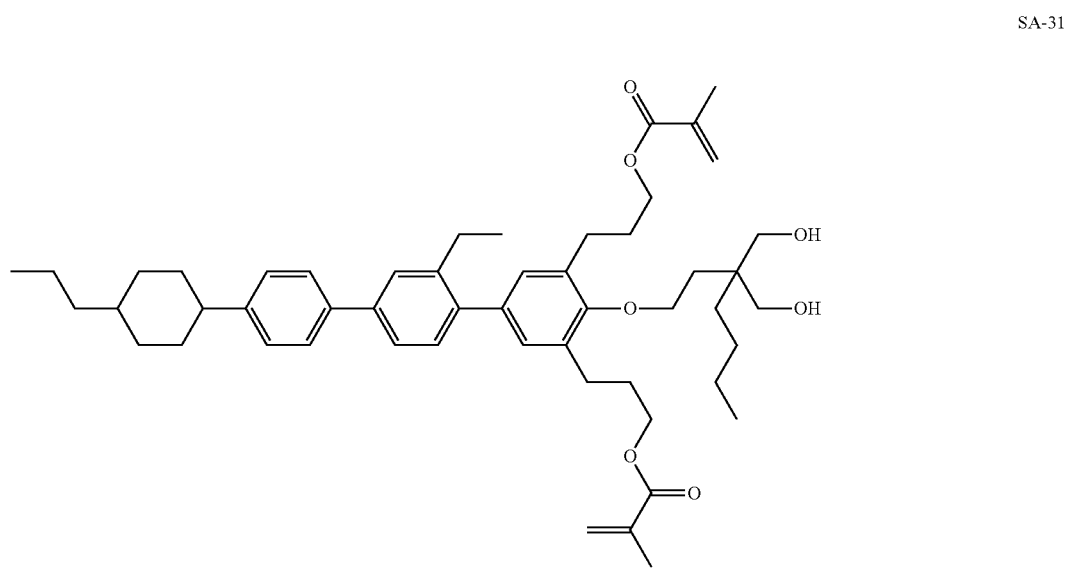
SA-32
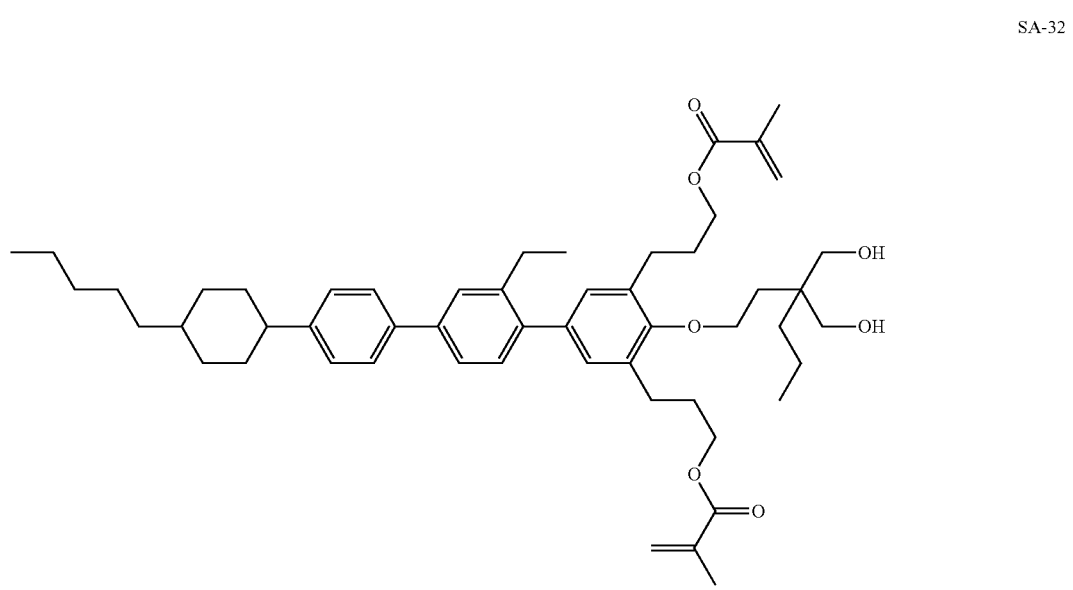

TABLE E-continued
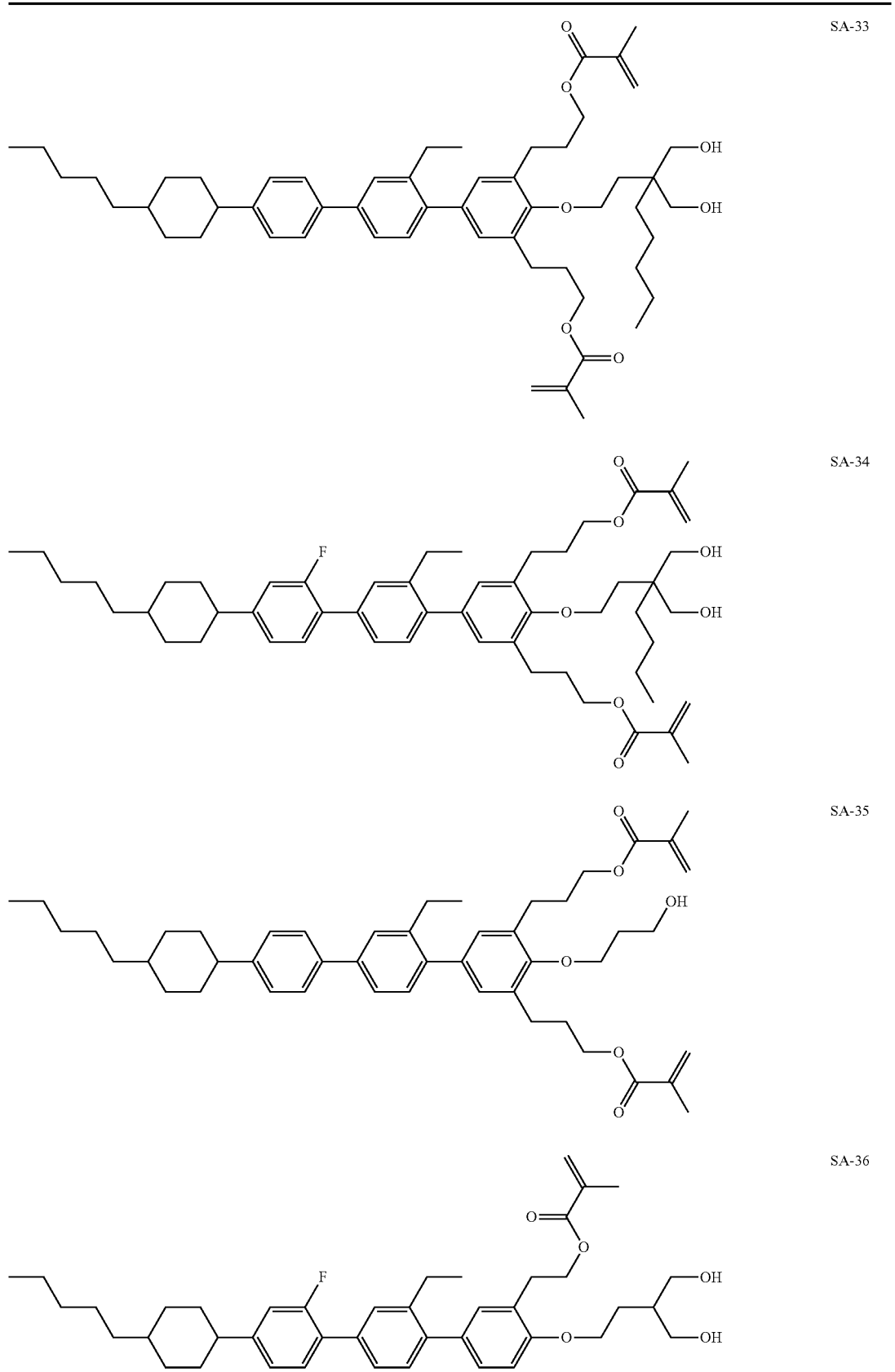

TABLE E-continued
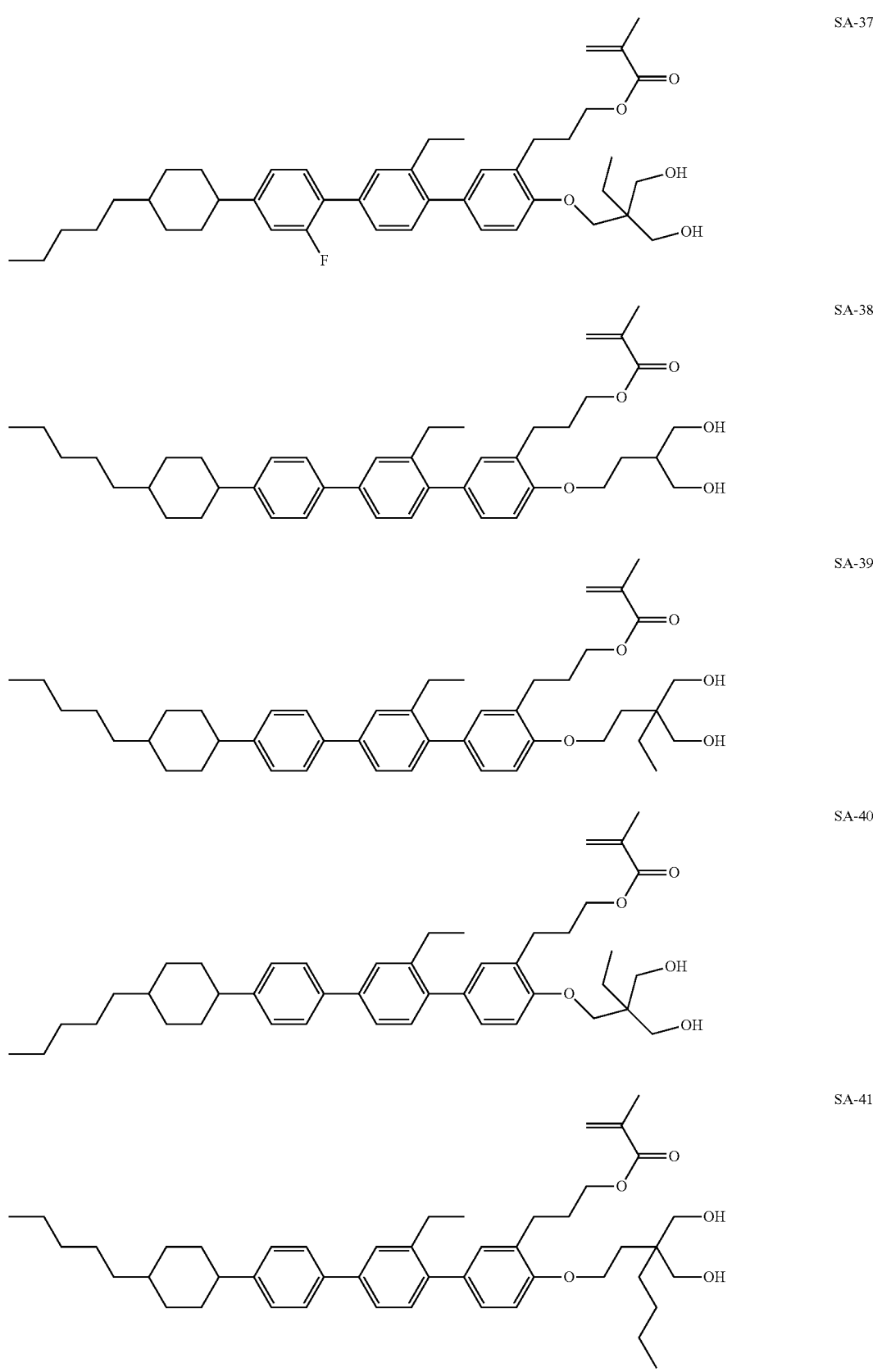

TABLE E-continued
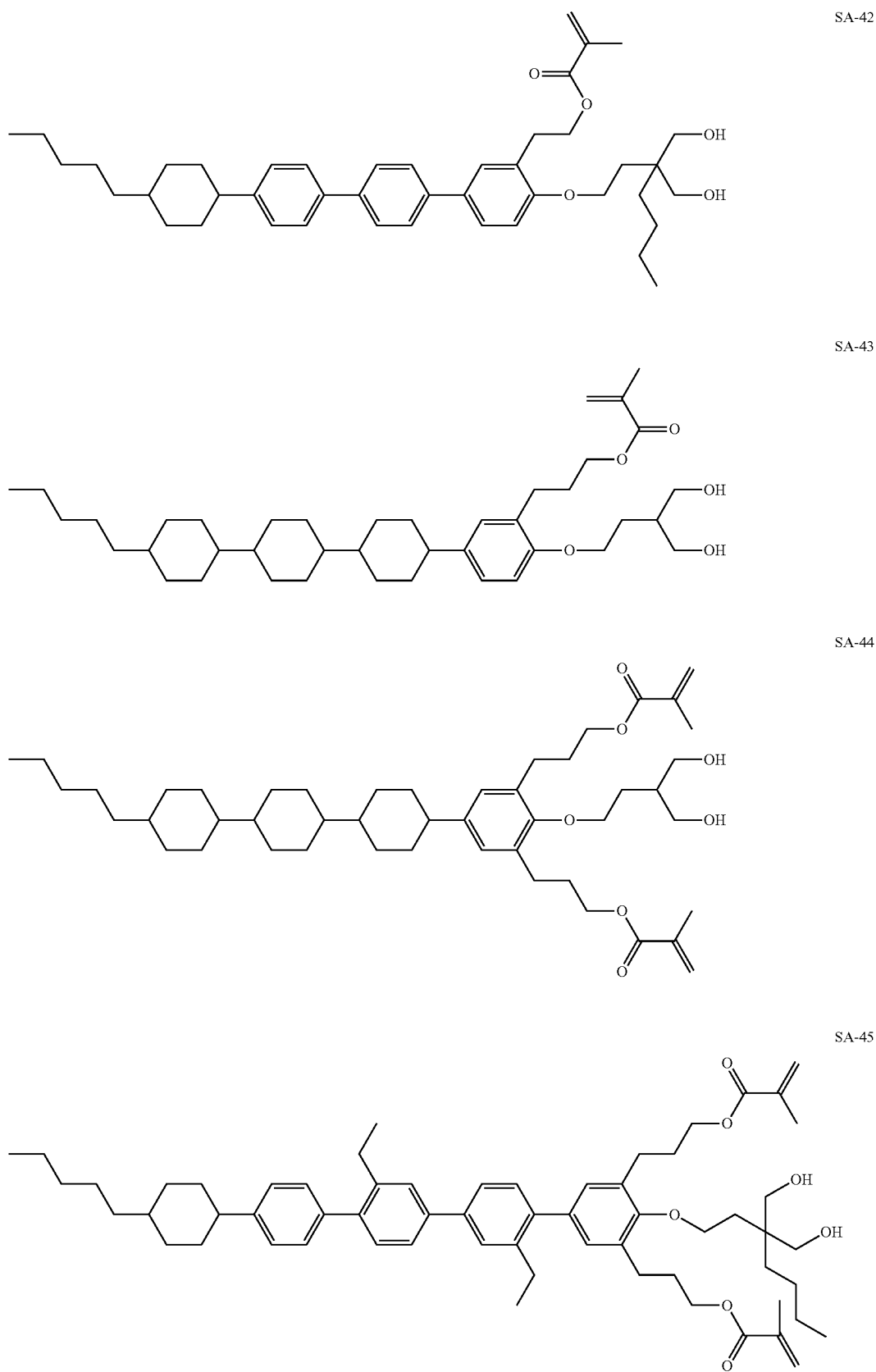

TABLE E-continued

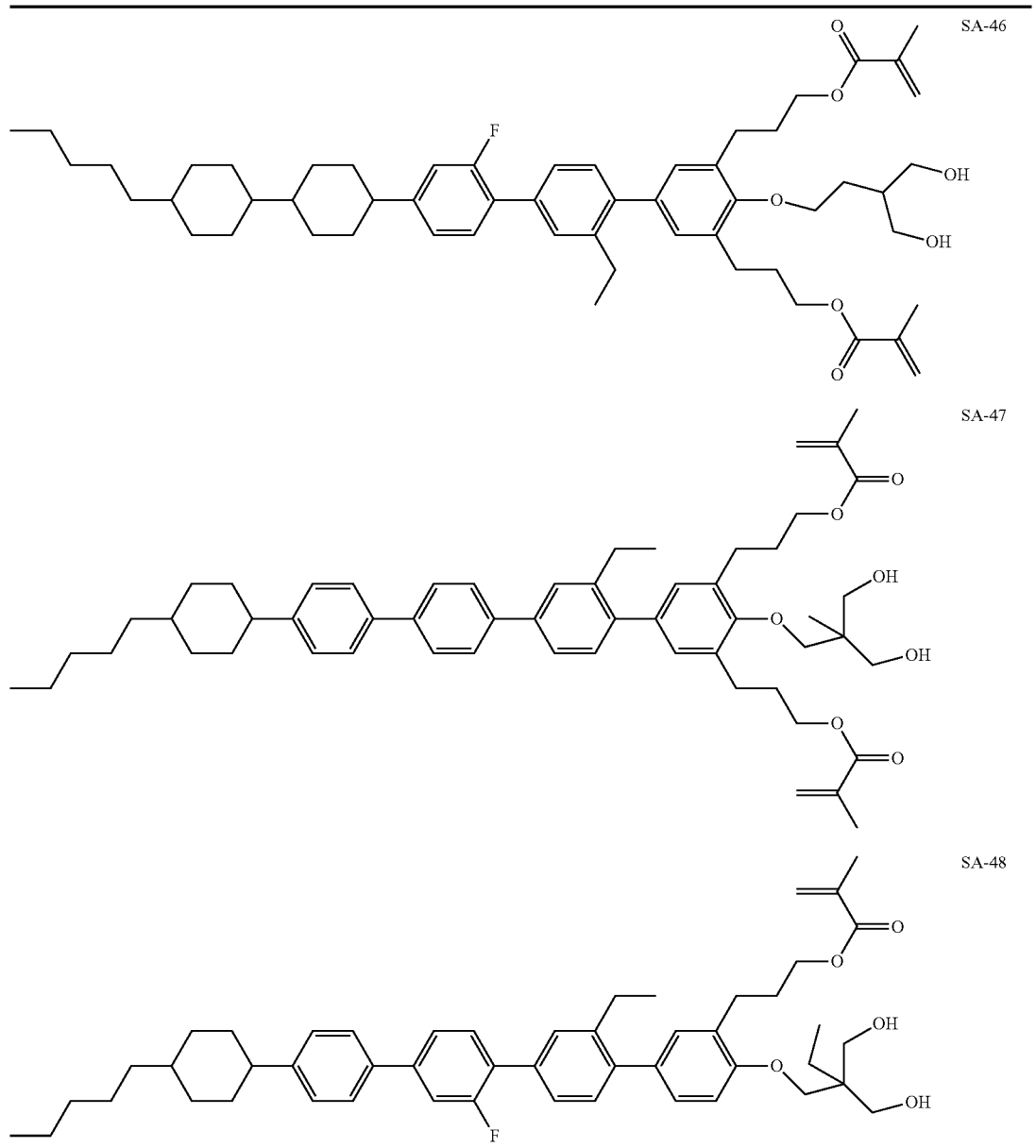

In a preferred embodiment, the LC media, SA-VA and SA-FFS displays according to the present invention comprise one or more SA additives selected from formulae SA-1 to SA-48, preferably from formulae SA-14 to SA-48, very preferably from formulae SA-20 to SA-34 and SA-44, in combination with one or more RMs of formula I.

EXAMPLES

The following examples explain the present invention without restricting it. However, they show the person skilled in the art preferred mixture concepts with compounds preferably to be employed and the respective concentrations thereof and combinations thereof with one another. In addition, the examples illustrate which properties and property combinations are accessible.

In addition, the following abbreviations and symbols are used:

$V_0$ threshold voltage, capacitive [V] at 20° C.,
$n_e$ extraordinary refractive index at 20° C. and 589 nm,
$n_o$ ordinary refractive index at 20° C. and 589 nm,
$\Delta n$ optical anisotropy at 20° C. and 589 nm,
$\varepsilon_\perp$ dielectric permittivity perpendicular to the director at 20° C. and 1 kHz,
$\varepsilon_\parallel$ dielectric permittivity parallel to the director at 20° C. and 1 kHz,
$\Delta\varepsilon$ dielectric anisotropy at 20° C. and 1 kHz,
cl.p., T(N,I) clearing point [° C.],
$\gamma_1$ rotational viscosity at 20° C. [mPa·s],
$K_1$ elastic constant, "splay" deformation at 20° C. [pN],
$K_2$ elastic constant, "twist" deformation at 20° C. [pN],
$K_3$ elastic constant, "bend" deformation at 20° C. [pN].

Unless explicitly noted otherwise, all concentrations in the present application are quoted in percent by weight and relate to the corresponding mixture as a whole, comprising all solid or liquid-crystalline components, without solvents.

Unless explicitly noted otherwise, all temperature values indicated in the present application, such as, for example, for the melting point T(C,N), the transition from the smectic (S) to the nematic (N) phase T(S,N) and the clearing point T(N,I), are quoted in degrees Celsius (° C.). M.p. denotes melting point, cl.p.=clearing point. Furthermore, C=crystalline state, N=nematic phase, S=smectic phase and I=isotropic phase. The data between these symbols represent the transition temperatures.

All physical properties are and have been determined in accordance with "Merck Liquid Crystals, Physical Properties of Liquid Crystals", Status Nov. 1997, Merck KGaA, Germany, and apply for a temperature of 20° C., and Δn is determined at 589 nm and Δε at 1 kHz, unless explicitly indicated otherwise in each case.

The term "threshold voltage" for the present invention relates to the capacitive threshold ($V_0$), also known as the Freedericks threshold, unless explicitly indicated otherwise. In the examples, the optical threshold may also, as generally usual, be quoted for 10% relative contrast ($V_{10}$).

Unless stated otherwise, the process of polymerising the polymerisable compounds in the PSA displays as described above and below is carried out at a temperature where the LC medium exhibits a liquid crystal phase, preferably a nematic phase, and most preferably is carried out at room temperature.

Unless stated otherwise, methods of preparing test cells and measuring their electrooptical and other properties are carried out by the methods as described hereinafter or in analogy thereto.

The display used for measurement of the capacitive threshold voltage consists of two plane-parallel glass outer plates at a separation of 25 μm, each of which has on the inside an electrode layer and an unrubbed polyimide alignment layer on top, which effect a homeotropic edge alignment of the liquid-crystal molecules.

The PSVA display or PSVA test cell used for measurement of the tilt angles consists of two plane-parallel glass outer plates at a separation of 4 μm unless stated otherwise, each of which has on the inside an electrode layer and a polyimide alignment layer on top, where the two polyimide layers are rubbed antiparallel to one another and effect a homeotropic edge alignment of the liquid-crystal molecules. The SAVA display or test cell has the same structure but wherein one or both polyimide layers are omitted.

The polymerisable compounds are polymerised in the display or test cell by irradiation with UV light of defined intensity for a prespecified time, with a voltage simultaneously being applied to the display (usually 10 V to 30 V alternating current, 1 kHz). In the examples, unless indicated otherwise, a metal halide lamp and an intensity of 100 mW/cm² is used for polymerisation. The intensity is measured using a standard meter (Hoenle UV-meter high end with UV sensor).

The tilt angle is determined using the Mueller Matrix Polarimeter "AxoScan" from Axometrics. A low value (i.e. a large deviation from the 90° angle) corresponds to a large tilt here.

Unless stated otherwise, the term "tilt angle" means the angle between the LC director and the substrate, and "LC director" means in a layer of LC molecules with uniform orientation the preferred orientation direction of the optical main axis of the LC molecules, which corresponds, in case of calamitic, uniaxially positive birefringent LC molecules, to their molecular long axis.

Example 1

Compound 1 ([9-methylene-7-(2-methylprop-2-enoyloxy)fluoren-2-yl] 2-methylprop-2-enoate) is prepared as follows

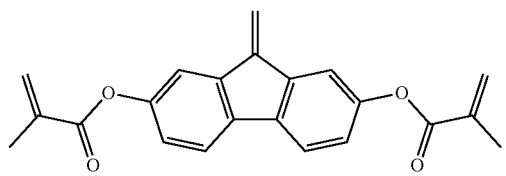

(1)

Synthesis of 2,7-di(tetrahydropyran-2-yloxy)fluoren-9-one (1.1)

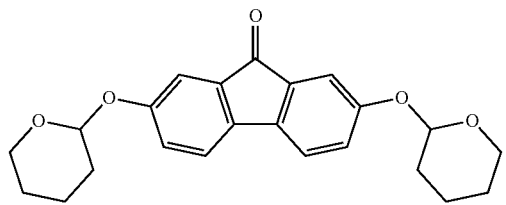

(1.1)

100.0 g (471.3 mmol) 2,7-dihydroxyfluoren-9-one are dissolved at RT in 1 L dichloromethane, 25.00 g (99.00 mmol) Toluene-4-sulfonatepyridinium salt are added and 170.0 ML (1.879 mol) 3,4-Dihydro-2H-pyran are added dropwise. The reaction mixture was stirred for 16 h at RT and under cooling treated with 500 mL saturated $Na_2CO_3$ solution. The organic layer is separated, the water layer is extracted with dichloromethane and the combined organic layers are washed with saturated $Na_2CO_3$ solution, dried with $Na_2SO_4$, filtered and evaporated under vacuum. The remaining water is removed by azeotrope distillation with toluene. The crude product is filtered with dichloromethane (DCM) and MTB (95:5) over silica gel. The product fractions are combined and evaporated under vacuum. The solid product is dissolved in acetonitrile (ACN) and EE (4:1) at 70° C. and crystalized at RT overnight to give the product as orange colored crystals.

¹H NMR (500 MHz, Chloroform-d) δ 7.37-7.29 (m, 4H), 7.11 (dd, J=8.1, 2.4 Hz, 2H), 5.44 (t, J=3.4 Hz, 2H), 4.07-3.82 (m, 2H), 3.65 (dtd, J=11.5, 4.2, 1.3 Hz, 2H), 2.08-1.95 (m, 2H), 1.95-1.79 (m, 4H), 1.78-1.59 (m, 6H).

Synthesis of 9-methyl-2,7-di(tetrahydropyran-2-yloxy)fluoren-9-ol (1.2)

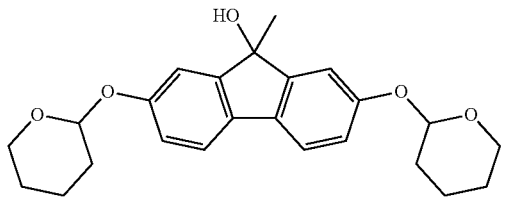

(1.2)

135.00 g (354.9 mmol) of ketone (1.1) is dissolved at RT in 1 L THF, cooled to −10° C. and 380.0 mL (532.0 mmol) methylmagnesium bromide (1.4 M in THF/Toluene 1:3) is being added dropwise during which the colour changes from orange to colourless. The reaction mixture is quenched carefully at 0° C. with saturated NH$_4$Cl solution (release of methane gas) and the layers are separated. The water layer is extracted with acetic acid ethyl ester (EE) and the organic layers are combined, washed with brine, dried over Na$_2$SO$_4$, filtered and evaporated under vacuum. The crude product is crystallized from acetonitrile at 5° C. to give the product as a beige solid.

Synthesis of 9-methylfluorene-2,7,9-triol (1.3)

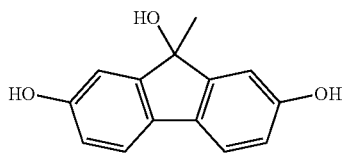

(1.3)

117.8 g (293.3 mmol) of fluorenol (1.2) is dissolved at RT in 1200 mL THF and 400.0 mL (2 M, 800.0 mmol) HCl is added dropwise and stirred for 3 h at RT. The reaction mixture is neutralized carefully with 400.0 (800.0 mmol) mL NaOH solution and the layers are separated. The water layer was extracted with EE, the organic layers combined, washed brine, dried over Na$_2$SO$_4$, filtered and evaporated under vacuum. Remaining water is removed by azeotrope distillation with toluene. The crude product is stirred at 40° C. in a mixture of dichloromethane (DCM) and MTB (8:1) to give after filtration the product as a beige solid.

$^1$H NMR (500 MHz, DMSO-d$_6$) δ 9.31 (s, 2H), 7.34 (d, J=8.1 Hz, 2H), 6.86 (d, J=2.3 Hz, 2H), 6.66 (dd, J=8.1, 2.3 Hz, 2H), 5.37 (s, 1H), 1.45 (s, 3H).

Synthesis of 9-methylenefluorene-2,7-diol (1.4)

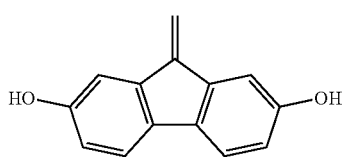

(1.4)

56.00 g (245.4 mmol) of the triol (1.3) is dissolved at RT in 1.0 L THF, cooled to 5° C. and 650.0 mL (25% HCl solution, 5.0 mol) is added that the temp is max. 20-25° C. The mixture is stirred at RT for 16 h and cooled to 5° C. 462.0 mL, (32%, 5.0 mol) NaOH solution is being added carefully at max. 15° C. and diluted with 0.5 L water. The Layers are separated, the water layer is extracted with EE and the combined organic layers are washed with brine, dried over Na$_2$SO$_4$, filtered and evaporated under vacuum. The crude product is filtered with DCM/MeOH (9:1) over silica gel and the product fractions are combined and evaporated under vacuum. The green-yellow solid is dissolved in 400.0 mL MTB at reflux and crystallized over 48 h at −25° C. to give the product as yellow crystals.

$^1$H NMR (500 MHz, DMSO-d$_6$) δ 9.37 (s, 2H), 7.41 (d, J=8.1 Hz, 2H), 7.14 (d, J=2.2 Hz, 2H), 6.74 (dd, J=8.1, 2.2 Hz, 2H), 6.04 (s, 2H).

Synthesis of [9-methylene-7-(2-methylprop-2-enoyloxy)fluoren-2-yl] 2-methylprop-2-enoate (1)

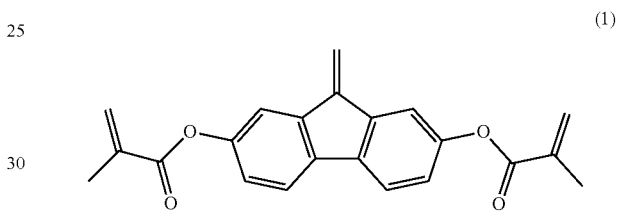

(1)

22.00 g (104.7 mmol) of the diol (1.4), 26.60 ml (313.9 mmol) methacrylic acid and 2.60 g (314 mmol) 4-(dimethylamino)-pyridine are dissolved in DCM and cooled to 3° C. To the mixture is added at 3-6° C. 60.20 g (313.9 mmol) N-(3-dimethylaminopropyl)-N'ethylcarbodiimide-hydrochloride and the reaction mixture is stirred at RT for 2 h. The reaction mixture is poured carefully on a 0° C. cooled mixture of 1.0 L HCl (1N) and 400.0 mL brine. The layers are separated. The water layer is extracted with DCM and the organic layers are combined, washed with brine, dried over Na$_2$SO$_4$, and filtered over silica gel. The combined product fractions are diluted with heptane and evaporated under vacuum till first crystals appeared and was the crystallized at 5° C. to give the product as slightly yellow crystals.

Melting point: 124° C.

$^1$H NMR (500 MHz, Chloroform-d) δ 7.68 (d, J=8.2 Hz, 2H), 7.50 (d, J=2.1 Hz, 2H), 7.15 (dd, J=8.2, 2.1 Hz, 2H), 6.50-6.31 (m, 2H), 6.09 (s, 2H), 5.81 (p, J=1.5 Hz, 2H), 2.12 (t, J=1.2 Hz, 6H).

Mixture Examples

H1: Nematic Host Mixture (Δε<0)

| | | | |
|---|---|---|---|
| CPP-3-2 | 6.50% | Clearing point [° C.]: | 74.7 |
| CC-3-V1 | 8.00% | Δn (589 nm, 20° C.): | 0.1039 |
| CC-2-3 | 17.00% | Δε (1 kHz, 20° C.): | −3.0 |
| CC-3-4 | 6.50% | ε$_\parallel$ (1 kHz, 20° C.): | 3.4 |
| CCY-3-O1 | 3.50% | K$_3$/K$_1$ | 1.07 |
| CCY-3-O2 | 12.50% | γ$_1$ (20° C.) [mPa · s]: | 106 |
| CPY-2-O2 | 5.50% | V$_0$ (20° C.) [V]: | 2.10 |
| CPY-3-O2 | 10.00% | | |
| CY-3-O2 | 15.50% | | |

-continued

| | |
|---|---|
| PCH-3O1 | 4.50% |
| PP-1-2V1 | 5.00% |
| PY-3-O2 | 5.50% |

A polymerisable mixture is prepared by adding to nematic LC host mixture H1 1.0% of the reactive mesogen 1 and 0.6% of the SA-additive SA-23.

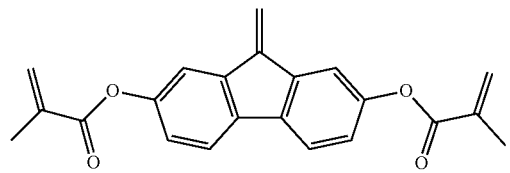

1

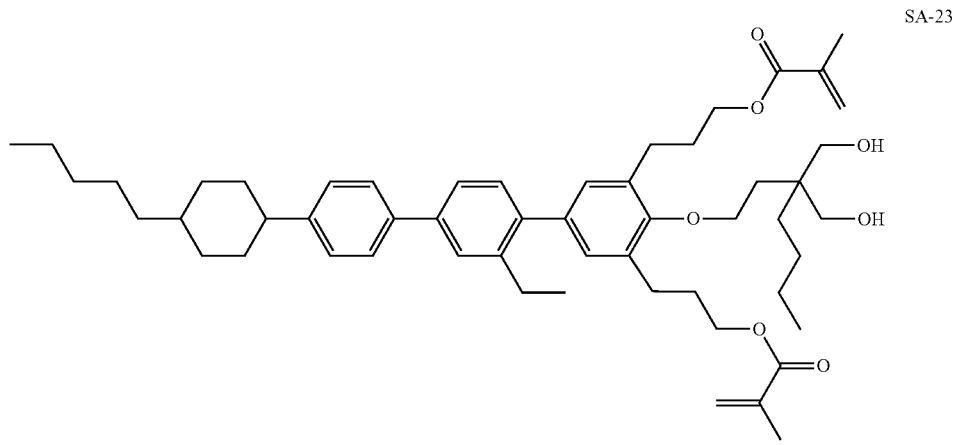

SA-23

H2: Nematic Host Mixture (Δε<0)

| | | | |
|---|---|---|---|
| CCH-501 | 9.00% | cl.p. | 70.0° C. |
| CCH-35 | 14.00% | Δn | 0.0825 |
| PCH-53 | 8.00% | Δε | −3.5 |
| CY-3-O4 | 14.00% | $\varepsilon_\|$ | 3.5 |
| CY-5-O4 | 13.00% | $K_3/K_1$ | 1.00 |
| CCY-2-1 | 9.00% | $\gamma_1$ | 141 mPa · s |
| CCY-3-1 | 9.00% | $V_0$ | 2.10 V |
| CCY-3-O2 | 8.00% | | |
| CCY-5-O2 | 8.00% | | |
| CPY-2-O2 | 8.00% | | |

A polymerisable mixture is prepared by adding to nematic LC host mixture H2 0.3% of the reactive mesogen 1.

H3: Nematic Host Mixture (Δε<0)

| | | | |
|---|---|---|---|
| CPP-3-2 | 6.0% | Clearing point [° C.]: | 74.8 |
| CC-3-V1 | 6.0% | Δn (589 nm, 20° C.): | 0.107 |
| CC-3-4 | 9.0% | Δε (1 kHz, 20° C.): | −3.3 |
| CC-3-5 | 7.0% | $\varepsilon_\|$ (1 kHz, 20° C.): | 3.6 |
| CCP-3-1 | 8.0% | $\varepsilon_\perp$ (1 kHz, 20° C.): | 6.9 |
| CCP-3-3 | 3.0% | $K_1$ (20° C.) [pN]: | 14.2 |
| CCY-3-1 | 2.0% | $K_3$ (20° C.) [pN]: | 16.5 |
| CCY-3-O2 | 10.5% | $\gamma_1$ (20° C.) [mPa · s]: | 118 |
| CCY-4-O2 | 5.0% | $V_0$ (20° C.) [V]: | |
| CPY-3-O2 | 3.5% | | |
| CY-3-O2 | 14% | | |
| CP-3-O1 | 5.5% | | |
| PY-1-O4 | 6.5% | | |
| PY-3-O2 | 14% | | |

A polymerisable mixture is prepared by adding to nematic LC host mixture H3 0.5% of reactive mesogen 1.

H4: Nematic Host Mixture (Δε<0)

| | | | |
|---|---|---|---|
| CY-3-O2 | 15.5% | Clearing point [° C.]: | 75.1 |
| CCY-3-O3 | 8.00% | Δn (589 nm, 20° C.): | 0.098 |
| CCY-4-O2 | 10.0% | Δε (1 kHz, 20° C.): | −3.0 |

-continued

| | | | |
|---|---|---|---|
| CPY-2-O2 | 5.50% | $\varepsilon_\|$ (1 kHz, 20° C.): | 3.4 |
| CPY-3-O2 | 11.5% | $\varepsilon_\perp$ (1 kHz, 20° C.): | 6.4 |
| CC-3-4 | 9.25% | $K_1$ (20° C.) [pN]: | 13.1 |
| CC-2-3 | 24.5% | $K_3$ (20° C.) [pN]: | 13.3 |
| PYP-2-3 | 8.75% | $\gamma_1$ (20° C.) [mPa · s]: | 113 |
| CP-3-O1 | 7.00% | $V_0$ (20° C.) [V]: | 2.22 |

A polymerisable mixture is prepared by adding to nematic LC host mixture H4 1.0% of reactive mesogen 1, 0.3% of the reactive mesogen RM-147 and 0.6% of SA-additive SA-23.

H5: Nematic Host Mixture (Δε<0)

| | | | |
|---|---|---|---|
| CY-3-O4 | 14.0% | Clearing point [° C.]: | 80.0 |
| CCY-3-O2 | 9.00% | Δn (589 nm, 20° C.): | 0.090 |
| CCY-3-O3 | 9.00% | Δε (1 kHz, 20° C.): | −3.3 |
| CPY-2-O2 | 10.0% | $\varepsilon_\|$ (1 kHz, 20° C.): | 3.4 |
| CPY-3-O2 | 10.0% | $\varepsilon_\perp$ (1 kHz, 20° C.): | 6.7 |
| CCY-3-1 | 8.00% | $K_1$ (20° C.) [pN]: | 15.1 |
| CC-3-4 | 9.00% | $K_3$ (20° C.) [pN]: | 14.6 |
| CC-3-5 | 6.00% | $\gamma_1$ (20° C.) [mPa · s]: | 140 |
| CP-5-3 | 10.0% | $V_0$ (20° C.) [V]: | 2.23 |
| CC-3-O1 | 6.00% | | |
| CC-3-O3 | 9.00% | | |

A polymerisable mixture is prepared by adding to nematic LC host mixture H5 0.3% of the reactive mesogen 1.

H6: Nematic Host Mixture (Δε<0)

| | | | |
|---|---|---|---|
| CC-3-V1 | 9.00% | Clearing point [° C.]: | 74.7 |
| CC-2-3 | 18.0% | Δn (589 nm, 20° C.): | 0.098 |
| CC-3-4 | 3.00% | Δε (1 kHz, 20° C.): | −3.4 |
| CC-3-5 | 7.00% | $\varepsilon_\parallel$ (1 kHz, 20° C.): | 3.5 |
| CCP-3-1 | 5.50% | $\varepsilon_\perp$ (1 kHz, 20° C.): | 6.9 |
| CCY-3-O2 | 11.5% | $K_1$ (20° C.) [pN]: | 14.9 |
| CPY-2-O2 | 8.00% | $K_3$ (20° C.) [pN]: | 15.9 |
| CPY-3-O2 | 11.0% | $\gamma_1$ (20° C.) [mPa·s]: | 108 |
| CY-3-O2 | 15.5% | $V_0$ (20° C.) [V]: | 2.28 |
| PY-3-O2 | 11.5% | | |

A polymerisable mixture is prepared by adding to nematic LC host mixture H6 0.5% of the reactive mesogen 1 and 100 ppm of stabiliser S1-1.

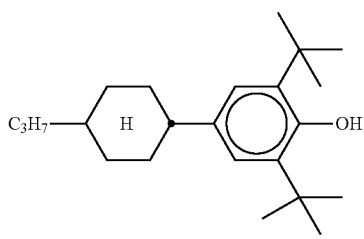

S1-1

H7: Nematic Host Mixture (Δε<0)

| | | | |
|---|---|---|---|
| CC-3-V | 37.5% | Clearing point [° C.]: | 74.8 |
| CC-3-V1 | 2.00% | Δn (589 nm, 20° C.): | 0.099 |
| CCY-4-O2 | 14.5% | Δε (1 kHz, 20° C.): | −2.9 |
| CPY-2-O2 | 10.5% | $\varepsilon_\parallel$ (1 kHz, 20° C.): | 3.7 |
| CPY-3-O2 | 9.50% | $\varepsilon_\perp$ (1 kHz, 20° C.): | 6.6 |
| CY-3-O2 | 15.0% | $K_1$ (20° C.) [pN]: | 12.2 |
| CY-3-O4 | 4.50% | $K_3$ (20° C.) [pN]: | 13.4 |
| PYP-2-4 | 5.50% | $\gamma_1$ (20° C.) [mPa·s]: | 92 |
| PPGU-3-F | 1.00% | $V_0$ (20° C.) [V]: | 2.28 |

A polymerisable mixture is prepared by adding to nematic LC host mixture H7 0.5% of the reactive mesogen 1 and 0.6% of SA-additive SA-23.

H8: Nematic Host Mixture (Δε<0)

| | | | |
|---|---|---|---|
| CC-2-3 | 20.0% | Clearing point [° C.]: | 74.8 |
| CC-3-O1 | 6.00% | Δn (589 nm, 20° C.): | 0.105 |
| CC-3-4 | 6.00% | Δε (1 kHz, 20° C.): | −3.2 |
| CCP-3-1 | 3.00% | $\varepsilon_\parallel$ (1 kHz, 20° C.): | 3.5 |
| CCY-3-O2 | 11.0% | $\varepsilon_\perp$ (1 kHz, 20° C.): | 6.8 |
| CPY-2-O2 | 12.0% | $K_1$ (20° C.) [pN]: | 12.7 |
| CPY-3-O2 | 11.0% | $K_3$ (20° C.) [pN]: | 13.6 |
| CY-3-O2 | 14.0% | $\gamma_1$ (20° C.) [mPa·s]: | 120 |
| CY-3-O4 | 4.00% | $V_0$ (20° C.) [V]: | 2.16 |
| CP-3-O1 | 4.00% | | |
| PYP-2-3 | 9.00% | | |

A polymerisable mixture is prepared by adding to nematic LC host mixture H8 1.0% of reactive mesogen 1, 0.6% of SA-additive SA-23, and 50 ppm of stabiliser S2-1

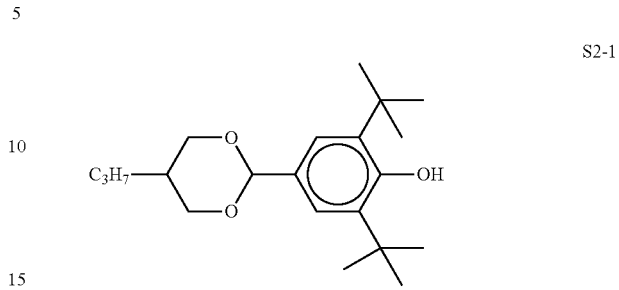

S2-1

H9: Nematic Host Mixture (Δε<0)

| | | | |
|---|---|---|---|
| CC-4-V | 17.0% | Clearing point [° C.]: | 106.1 |
| CCP-V-1 | 15.0% | Δn (589 nm, 20° C.): | 0.120 |
| CCEPC-3-3 | 2.50% | Δε (1 kHz, 20° C.): | −3.6 |
| CCY-3-O2 | 4.00% | $\varepsilon_\parallel$ (1 kHz, 20° C.): | 3.5 |
| CCY-3-O3 | 5.00% | $\varepsilon_\perp$ (1 kHz, 20° C.): | 7.0 |
| CCY-4-O2 | 5.00% | $K_1$ (20° C.) [pN]: | 16.8 |
| CLY-3-O2 | 3.50% | $K_3$ (20° C.) [pN]: | 17.3 |
| CLY-3-O3 | 2.00% | $\gamma_1$ (20° C.) [mPa·s]: | 207 |
| CPY-2-O2 | 8.00% | $V_0$ (20° C.) [V]: | 2.33 |
| CPY-3-O2 | 10.0% | | |
| CY-3-O4 | 17.0% | | |
| PYP-2-3 | 11.0% | | |

A polymerisable mixture is prepared by adding to nematic LC host mixture H9 0.3% of reactive mesogen 1.

H10: Nematic Host Mixture (Δε<0)

| | | | |
|---|---|---|---|
| CY-3-O2 | 15.0% | Clearing point [° C.]: | 75.5 |
| CCY-4-O2 | 9.50% | Δn (589 nm, 20° C.): | 0.108 |
| CCY-5-O2 | 5.00% | Δε (1 kHz, 20° C.): | −3.0 |
| CPY-2-O2 | 9.00% | $\varepsilon_\parallel$ (1 kHz, 20° C.): | 3.5 |
| CPY-3-O2 | 9.00% | $\varepsilon_\perp$ (1 kHz, 20° C.): | 6.5 |
| CC-3-4 | 9.00% | $K_1$ (20° C.) [pN]: | 12.9 |
| CC-2-3 | 22.0% | $K_3$ (20° C.) [pN]: | 13.0 |
| PYP-2-3 | 7.00% | $\gamma_1$ (20° C.) [mPa·s]: | 115 |
| PYP-2-4 | 7.50% | $V_0$ (20° C.) [V]: | 2.20 |
| CP-3-O1 | 7.00% | | |

A polymerisable mixture is prepared by adding to nematic LC host mixture H10 1.0% of the reactive mesogen 1, 0.3% of the reactive mesogen RM-145 and 0.6% of SA-additive SA-23.

H11: Nematic Host Mixture (Δε<0)

| | | | |
|---|---|---|---|
| CY-3-O2 | 15.0% | Clearing point [° C.]: | 74.7 |
| CY-5-O2 | 6.50% | Δn (589 nm, 20° C.): | 0.108 |
| CCY-3-O2 | 11.0% | Δε (1 kHz, 20° C.): | −3.0 |
| CPY-2-O2 | 5.50% | $\varepsilon_\parallel$ (1 kHz, 20° C.): | 3.6 |
| CPY-3-O2 | 10.5% | $\varepsilon_\perp$ (1 kHz, 20° C.): | 6.6 |
| CC-3-V | 28.5% | $K_1$ (20° C.) [pN]: | 12.9 |
| CC-3-V1 | 10.0% | $K_3$ (20° C.) [pN]: | 15.7 |
| PYP-2-3 | 12.5% | $\gamma_1$ (20° C.) [mPa·s]: | 97 |
| PPGU-3-F | 0.50% | $V_0$ (20° C.) [V]: | 2.42 |

A polymerisable mixture is prepared by adding to nematic LC host mixture H11 0.4% of reactive mesogen 1 and 100 ppm of stabiliser S3-1

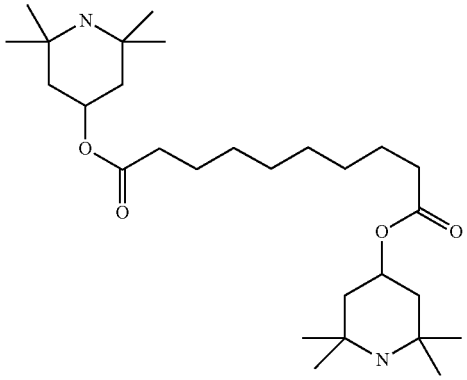

S3-1

H12: Nematic Host Mixture (Δε<0)

| CC-3-5 | 9.50% | Clearing point [° C.]: | 79.1 |
|---|---|---|---|
| CC-5-O1 | 5.00% | Δn (589 nm, 20° C.): | 0.091 |
| CCY-2-1 | 9.50% | Δε (1 kHz, 20° C.): | −3.6 |
| CCY-3-1 | 10.5% | ε$_\parallel$ (1 kHz, 20° C.): | 3.5 |
| CCY-3-O2 | 10.5% | ε$_\perp$ (1 kHz, 20° C.): | 7.1 |
| CCY-5-O2 | 9.50% | $K_1$ (20° C.) [pN]: | 14.6 |
| CPY-2-O2 | 12.0% | $K_3$ (20° C.) [pN]: | 14.5 |
| CY-3-O4 | 9.00% | $\gamma_1$ (20° C.) [mPa · s]: | 178 |
| CY-5-O4 | 11.0% | $V_0$ (20° C.) [V]: | 2.12 |
| CP-5-3 | 13.5% | | |

A polymerisable mixture is prepared by adding to nematic LC host mixture H12 1.0% of reactive mesogen 1, 0.3% of the reactive mesogen RM-146 and 0.6% of SA-additive SA-23.

H13: Nematic Host Mixture (Δε<0)

| CPP-3-2 | 4.00% | Clearing point [° C.]: | 74.8 |
|---|---|---|---|
| CC-3-V1 | 8.00% | Δn (589 nm, 20° C.): | 0.106 |
| CC-2-3 | 13.0% | Δε (1 kHz, 20° C.): | −3.5 |
| CC-3-4 | 7.00% | ε$_\parallel$ (1 kHz, 20° C.): | 3.6 |
| CC-3-5 | 7.00% | ε$_\perp$ (1 kHz, 20° C.): | 7.1 |
| CCY-3-O2 | 13.0% | $K_1$ (20° C.) [pN]: | 14.8 |
| CPY-2-O2 | 7.00% | $K_3$ (20° C.) [pN]: | 15.8 |
| CPY-3-O2 | 12.0% | $\gamma_1$ (20° C.) [mPa · s]: | 115 |
| CY-3-O2 | 12.0% | $V_0$ (20° C.) [V]: | 2.23 |
| CP-3-O1 | 2.00% | | |
| PY-3-O2 | 15.0% | | |

A polymerisable mixture is prepared by adding to nematic LC host mixture H13 0.3% of reactive mesogen 1 and 0.6% of SA-additive SA-23.

H14: Nematic Host Mixture (Δε<0)

| CY-3-O4 | 22.0% | Clearing point [° C.]: | 86.9 |
|---|---|---|---|
| CY-5-O4 | 12.0% | Δn (589 nm, 20° C.): | 0.111 |
| CCY-3-O2 | 6.00% | Δε (1 kHz, 20° C.): | −4.9 |
| CCY-3-O3 | 6.00% | ε$_\parallel$ (1 kHz, 20° C.): | 3.8 |
| CCY-4-O2 | 6.00% | ε$_\perp$ (1 kHz, 20° C.): | 8.7 |
| CPY-2-O2 | 10.0% | $K_1$ (20° C.) [pN]: | 14.9 |
| CPY-3-O2 | 10.0% | $K_3$ (20° C.) [pN]: | 15.9 |
| PYP-2-3 | 7.00% | $\gamma_1$ (20° C.) [mPa · s]: | 222 |
| CC-3-V1 | 7.00% | $V_0$ (20° C.) [V]: | 1.91 |
| CC-5-V | 10.0% | | |
| CCEPC-3-3 | 2.00% | | |
| CCEPC-3-5 | 2.00% | | |

A polymerisable mixture is prepared by adding to nematic LC host mixture H14 0.5% of reactive mesogen 1.

H15: Nematic Host Mixture (Δε<0)

| CY-3-O4 | 12.0% | Clearing point [° C.]: | 86.0 |
|---|---|---|---|
| CY-5-O2 | 10.0% | Δn (589 nm, 20° C.): | 0.110 |
| CY-5-O4 | 8.00% | Δε (1 kHz, 20° C.): | −5.0 |
| CCY-3-O2 | 8.00% | ε$_\parallel$ (1 kHz, 20° C.): | 3.8 |
| CCY-4-O2 | 7.00% | ε$_\perp$ (1 kHz, 20° C.): | 8.8 |
| CCY-5-O2 | 6.00% | $K_1$ (20° C.) [pN]: | 14.7 |
| CCY-2-1 | 8.00% | $K_3$ (20° C.) [pN]: | 16.0 |
| CCY-3-1 | 7.00% | $\gamma_1$ (20° C.) [mPa · s]: | 250 |
| CPY-3-O2 | 9.00% | $V_0$ (20° C.) [V]: | 1.90 |
| CPY-3-O2 | 9.00% | | |
| CPP-3-2 | 6.00% | | |
| CP-5-3 | 10.0% | | |

A polymerisable mixture is prepared by adding to nematic LC host mixture H15 1.0% of reactive mesogen 1 and 0.6% of SA-additive SA-23.

H16: Nematic Host Mixture (Δε<0)

| CC-3-V1 | 10.25% | Clearing point [° C.]: | 74.7 |
|---|---|---|---|
| CC-2-3 | 18.5% | Δn (589 nm, 20° C.): | 0.103 |
| CC-3-5 | 6.75% | Δε (1 kHz, 20° C.): | −3.1 |
| CCP-3-1 | 6.00% | ε$_\parallel$ (1 kHz, 2000): | 3.4 |
| CCY-3-1 | 2.50% | ε$_\perp$ (1 kHz, 20° C.): | 6.4 |
| CCY-3-O2 | 12.0% | $K_1$ (20° C.) [pN]: | 15.4 |
| CPY-2-O2 | 6.00% | $K_3$ (20° C.) [pN]: | 16.8 |
| CPY-3-O2 | 9.75% | $\gamma_1$ (20° C.) [mPa · s]: | 104 |
| CY-3-O2 | 11.5% | $V_0$ (20° C.) [V]: | 2.46 |
| PP-1-2V1 | 3.75% | | |
| PY-3-O2 | 13.0% | | |

A polymerisable mixture is prepared by adding to nematic LC host mixture H16 0.4% of reactive mesogen 1 and 100 ppm of stabiliser S3-2.

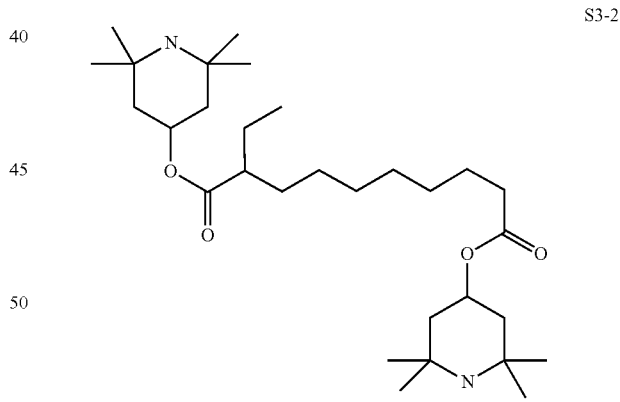

S3-2

H17: Nematic Host Mixture (Δε<0)

| CC-3-V | 27.5% | Clearing point [° C.]: | 74.7 |
|---|---|---|---|
| CC-3-V1 | 10.0% | Δn (589 nm, 20° C.): | 0.104 |
| CC-3-5 | 8.00% | Δε (1 kHz, 20° C.): | −3.0 |
| CCY-3-O2 | 9.25% | ε$_\parallel$ (1 kHz, 20° C.): | 3.4 |
| CLY-3-O2 | 10.0% | ε$_\perp$ (1 kHz, 20° C.): | 6.4 |
| CPY-3-O2 | 11.75% | $K_1$ (20° C.) [pN]: | 15.3 |
| PY-3-O2 | 14.0% | $K_3$ (20° C.) [pN]: | 16.2 |
| PY-4-O2 | 9.00% | $\gamma_1$ (20° C.) [mPa · s]: | 88 |
| PYP-2-4 | 0.50% | $V_0$ (20° C.) [V]: | 2.44 |

A polymerisable mixture is prepared by adding to nematic LC host mixture H17 0.5% of reactive mesogen 1 and 0.6% of SA-additive SA-23.

H18: Nematic Host Mixture (Δε<0)

| | | | |
|---|---|---|---|
| CPP-3-2 | 6.50% | Clearing point [° C.]: | 74.7 |
| CC-3-V1 | 8.00% | Δn (589 nm, 20° C.): | 0.104 |
| CC-2-3 | 17.0% | Δε (1 kHz, 20° C.): | −3.0 |
| CC-3-4 | 6.50% | ε∥ (1 kHz, 20° C.): | 3.4 |
| CCY-3-O1 | 3.50% | ε⊥ (1 kHz, 20° C.): | 6.3 |
| CCY-3-O2 | 12.5% | $K_1$ (20° C.) [pN]: | 14.8 |
| CPY-2-O2 | 5.50% | $K_3$ (20° C.) [pN]: | 15.8 |
| CPY-3-O2 | 10.0% | $\gamma_1$ (20° C.) [mPa · s]: | 106 |
| CY-3-O2 | 15.5% | | |
| CP-3-O1 | 4.50% | | |
| PP-1-2V1 | 5.00% | | |
| PY-3-O2 | 5.50% | | |

A polymerisable mixture is prepared by adding to nematic LC host mixture H18 0.5% of reactive mesogen 1.

H19: Nematic Host Mixture (Δε<0)

| | | | |
|---|---|---|---|
| CPP-3-2 | 10.5% | Clearing point [° C.]: | 74.5 |
| CC-3-4 | 9.0% | Δn (589 nm, 20° C.): | 0.104 |
| CC-3-5 | 9.0% | Δε (1 kHz, 20° C.): | −3.4 |
| CCP-3-1 | 8.0% | ε∥ (1 kHz, 20° C.): | 3.7 |
| CCY-3-O2 | 9.5% | ε⊥ (1 kHz, 20° C.): | 7 |
| CCY-4-O2 | 5.5% | $K_1$ (20° C.) [pN]: | 14 |
| CPY-3-O2 | 5.5% | $K_3$ (20° C.) [pN]: | 15.7 |
| CY-3-O2 | 15% | $\gamma_1$ (20° C.) [mPa · s]: | 128 |
| CY-5-O2 | 5.0% | | |
| CP-3-O1 | 7.0% | | |
| PY-3-O2 | 16% | | |

A polymerisable mixture is prepared by adding to nematic LC host mixture H19 0.3% of reactive mesogen 1 and 50 ppm of stabiliser S1-1.

H20: Nematic Host Mixture (Δε>0)

| | | | |
|---|---|---|---|
| CC-4-V | 10.0% | Clearing point [° C.]: | 77.0 |
| CC-5-V | 13.5% | Δn (589 nm, 20° C.): | 0.113 |
| PGU-3-F | 6.50% | Δε (1 kHz, 20° C.): | 19.2 |
| ACQU-2-F | 10.0% | ε∥ (1 kHz, 20° C.): | 23.8 |
| ACQU-3-F | 12.0% | ε⊥ (1 kHz, 20° C.): | 4.6 |
| PUQU-3-F | 11.0% | $K_1$ (20° C.) [pN]: | 11.5 |
| CCP-V-1 | 12.0% | $K_3$ (20° C.) [pN]: | 11.1 |
| APUQU-2-F | 6.00% | $\gamma_1$ (20° C.) [mPa · s]: | 122 |
| APUQU-3-F | 7.00% | $V_0$ (20° C.) [V]: | 0.81 |
| PGUQU-3-F | 8.00% | | |
| CPGU-3-OT | 4.00% | | |

A polymerisable mixture is prepared by adding to nematic LC host mixture H20 1.0% of reactive mesogen 1 and 50 ppm of stabiliser S3-3.

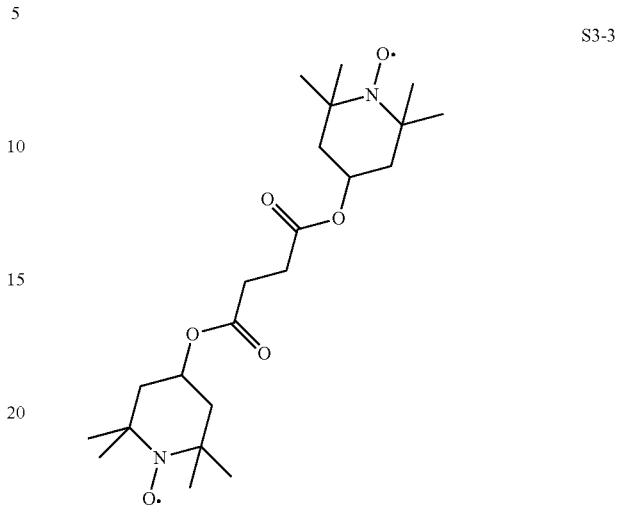

S3-3

H21: Nematic Host Mixture (Δε>0)

| | | | |
|---|---|---|---|
| PGU-2-F | 3.50% | Clearing point [° C.]: | 77.0 |
| PGU-3-F | 7.00% | Δn (589 nm, 20° C.): | 0.105 |
| CC-3-V1 | 15.0% | Δε (1 kHz, 20° C.): | 7.2 |
| CC-4-V | 18.0% | ε∥ (1 kHz, 20° C.): | 10.3 |
| CC-5-V | 20.0% | ε⊥ (1 kHz, 20° C.): | 3.1 |
| CCP-V-1 | 6.00% | $K_1$ (20° C.) [pN]: | 15.3 |
| APUQU-3-F | 15.0% | $K_3$ (20° C.) [pN]: | 13.5 |
| PUQU-3-F | 5.50% | $\gamma_1$ (20° C.) [mPa · s]: | 63 |
| PGP-2-4 | 3.00% | $V_0$ (20° C.) [V]: | 1.53 |
| CPP-3-2 | 7.00% | | |

A polymerisable mixture is prepared by adding to nematic LC host mixture H21 0.3% of reactive mesogen 1 and 100 ppm of stabiliser S1-1.

H22: Nematic Host Mixture (Δε>0)

| | | | |
|---|---|---|---|
| APUQU-2-F | 6.00% | Clearing point [° C.]: | 74.0 |
| APUQU-3-F | 12.0% | Δn (589 nm, 20° C.): | 0.120 |
| PUQU-3-F | 18.0% | Δε (1 kHz, 20° C.): | 17.4 |
| CPGU-3-OT | 9.00% | ε∥ (1 kHz, 20° C.): | 22.0 |
| CCGU-3-F | 3.00% | ε⊥ (1 kHz, 20° C.): | 4.5 |
| CPU-3-F | 14.0% | $K_1$ (20° C.) [pN]: | 10.1 |
| CCQU-3-F | 10.0% | $K_3$ (20° C.) [pN]: | 10.8 |
| CC-3-V | 25.0% | $\gamma_1$ (20° C.) [mPa · s]: | 111 |
| PGP-2-2V | 3.00% | $V_0$ (20° C.) [V]: | 0.80 |

A polymerisable mixture is prepared by adding to nematic LC host mixture H22 0.3% of reactive mesogen 1.

H23: Nematic Host Mixture (Δε>0)

| | | | |
|---|---|---|---|
| PUQU-3-F | 15.0% | Clearing point [° C.]: | 74.3 |
| APUQU-2-F | 5.00% | Δn (589 nm, 20° C.): | 0.120 |
| APUQU-3-F | 12.0% | Δε (1 kHz, 20° C.): | 14.9 |
| CCQU-3-F | 11.0% | ε∥ (1 kHz, 20° C.): | 19.1 |
| CCQU-5-F | 1.50% | ε⊥ (1 kHz, 20° C.): | 4.3 |
| CPGU-3-OT | 5.00% | $K_1$ (20° C.) [pN]: | 11.2 |
| CPP-3-OT | 4.50% | $K_3$ (20° C.) [pN]: | 10.8 |
| CGU-3-F | 10.0% | $\gamma_1$ (20° C.) [mPa · s]: | 98 |
| PGP-2-3 | 1.50% | $V_0$ (20° C.) [V]: | 0.91 |
| PGP-2-2V | 8.00% | | |
| CC-3-V | 26.5% | | |

A polymerisable mixture is prepared by adding to nematic LC host mixture H23 1.0% of reactive mesogen 1.

H24: Nematic Host Mixture (Δε>0)

| | | | |
|---|---|---|---|
| CCQU-3-F | 9.00% | Clearing point [° C.]: | 94.5 |
| CCQU-5-F | 9.00% | Δn (589 nm, 20° C.): | 0.121 |
| PUQU-3-F | 16.0% | Δε (1 kHz, 20° C.): | 20.4 |
| APUQU-2-F | 8.00% | ε∥ (1 kHz, 20° C.): | 24.7 |
| APUQU-3-F | 9.00% | ε⊥ (1 kHz, 20° C.): | 4.3 |
| PGUQU-3-F | 8.00% | K₁ (20° C.) [pN]: | 12.1 |
| CPGU-3-OT | 7.00% | K₃ (20° C.) [pN]: | 13.9 |
| CC-4-V | 18.0% | γ₁ (20° C.) [mPa · s]: | 163 |
| CC-5-V | 5.00% | V₀ (20° C.) [V]: | 0.81 |
| CCP-V-1 | 6.00% | | |
| CCEPC-3-3 | 3.00% | | |
| PPGU-3-F | 2.00% | | |

A polymerisable mixture is prepared by adding to nematic LC host mixture H24 0.4% of reactive mesogen 1, 0.6% of SA-additive SA-23, and 50 ppm of stabiliser S1-1.

H25: Nematic Host Mixture (Δε>0)

| | | | |
|---|---|---|---|
| CC-3-V | 28.50% | Clearing point [° C.]: | 85.6 |
| CCP-V-1 | 3.00% | Δn (589 nm, 20° C.): | 0.121 |
| CCEPC-3-3 | 2.00% | Δε (1 kHz, 20° C.): | 19.5 |
| PGU-2-F | 4.00% | ε∥ (1 kHz, 20° C.): | 23.8 |
| CCQU-3-F | 8.00% | ε⊥ (1 kHz, 20° C.): | 4.3 |
| CCQU-5-F | 6.00% | K₁ (20° C.) [pN]: | 11.6 |
| CCGU-3-F | 3.00% | K₃ (20° C.) [pN]: | 12.7 |
| PUQU-2-F | 2.00% | γ₁ (20° C.) [mPa · s]: | 126 |
| PUQU-3-F | 10.0% | V₀ (20° C.) [V]: | 0.81 |
| APUQU-2-F | 6.00% | | |
| APUQU-3-F | 9.00% | | |
| PGUQU-3-F | 5.00% | | |
| PGUQU-4-F | 5.00% | | |
| PGUQU-5-F | 4.00% | | |
| CPGU-3-OT | 4.00% | | |
| PPGU-3-F | 0.50% | | |

A polymerisable mixture is prepared by adding to nematic LC host mixture H25 1.0% of reactive mesogen 1, 0.3% of the reactive mesogen RM-152 and 0.6% of SA-additive SA-23.

H26: Nematic Host Mixture (Δε<0)

| | | | |
|---|---|---|---|
| CC-3-V1 | 9.00% | Clearing point [° C.]: | 74.6 |
| CC-3-O1 | 3.50% | Δn (589 nm, 20° C.): | 0.0984 |
| CC-3-4 | 8.00% | Δε (1 kHz, 20° C.): | -3.6 |
| CC-3-5 | 8.00% | ε∥ (1 kHz, 20° C.): | 3.6 |
| CCP-3-1 | 6.00% | ε⊥ (1 kHz, 20° C.): | 7.1 |
| CCY-3-O1 | 6.50% | K₁ (20° C.) [pN]: | 14.1 |
| CCY-3-O2 | 12.5% | K₃ (20° C.) [pN]: | 17 |
| CPY-3-O2 | 10.0% | γ₁ (20° C.) [mPa · s]: | 119 |
| CY-3-O2 | 15.5% | V₀ (20° C.) [V]: | 2.31 |
| CP-3-O1 | 8.5% | | |
| PY-3-O2 | 12.5% | | |

A polymerisable mixture is prepared by adding to nematic LC host Mixture H26 1.0% of reactive mesogen 1, 0.6% of SA-additive SA-23, and 50 ppm of stabiliser S2-1.

H27: Nematic Host Mixture (Δε<0)

| | | | |
|---|---|---|---|
| CC-3-5 | 9.50% | Clearing point [° C.]: | 79.1 |
| CC-5-O1 | 5.00% | Δn (589 nm, 20° C.): | 0.0911 |
| CCY-2-1 | 9.50% | Δε (1 kHz, 20° C.): | -3.6 |
| CCY-3-1 | 10.5% | ε∥ (1 kHz, 20° C.): | 3.5 |
| CCY-3-O2 | 10.5% | ε⊥ (1 kHz, 20° C.): | 7.1 |
| CCY-5-O2 | 9.50% | K₁ (20° C.) [pN]: | 14.6 |
| CPY-2-O2 | 12.0% | K₃ (20° C.) [pN]: | 14.5 |
| CY-3-O4 | 9.00% | γ₁ (20° C.) [mPa · s]: | 178 |
| CY-5-O4 | 11.0% | V₀ (20° C.) [V]: | 2.12 |
| CP-5-3 | 13.5% | | |

A polymerisable mixture is prepared by adding to nematic LC host Mixture H27 0.6% of reactive mesogen 1.

H28: Nematic Host Mixture (Δε<0)

| | | | |
|---|---|---|---|
| CC-3-V | 37.5% | Clearing point [° C.]: | 74.8 |
| CC-3-V1 | 2.00% | Δn (589 nm, 20° C.): | 0.0987 |
| CCY-4-O2 | 14.5% | Δε (1 kHz, 20° C.): | -2.9 |
| CPY-2-O2 | 10.5% | ε∥ (1 kHz, 20° C.): | 3.7 |
| CPY-3-O2 | 9.5% | ε⊥ (1 kHz, 20° C.): | 6.6 |
| CY-3-O2 | 15.0% | K₁ (20° C.) [pN]: | 12.2 |
| CY-3-O4 | 4.50% | K₃ (20° C.) [pN]: | 13.4 |
| PYP-2-4 | 5.50% | γ₁ (20° C.) [mPa · s]: | 92 |
| PPGU-3-F | 1.00% | V₀ (20° C.) [V]: | 2.28 |

A polymerisable mixture is prepared by adding to nematic LC host Mixture H28 0.4% of reactive mesogen 1 and 100 ppm of stabiliser S2-1.

H29: Nematic Host Mixture (Δε<0)

| | | | |
|---|---|---|---|
| CC-3-V | 37.5% | Clearing point [° C.]: | 75.4 |
| CC-5-O1 | 2.00% | Δn (589 nm, 20° C.): | 0.1034 |
| CCY-3-O2 | 12.0% | Δε (1 kHz, 20° C.): | -3.3 |
| CCY-3-O3 | 6.50% | ε∥ (1 kHz, 20° C.): | 3.6 |
| CPY-2-O2 | 12.0% | ε⊥ (1 kHz, 20° C.): | 6.9 |
| CPY-3-O2 | 10.0% | K₁ (20° C.) [pN]: | 13.4 |
| CY-3-O2 | 2.00% | K₃ (20° C.) [pN]: | 15 |
| PY-3-O2 | 16.0% | γ₁ (20° C.) [mPa · s]: | 95 |
| CP-3-O1 | 2.00% | V₀ (20° C.) [V]: | 2.24 |

A polymerisable mixture is prepared by adding to nematic LC host Mixture H29 1.0% of reactive mesogen 1, 0.3% of the reactive mesogen RM-149 and 0.6% of SA-additive SA-23.

H30: Nematic Host Mixture (Δε<0)

| | | | |
|---|---|---|---|
| CC-3-V | 22.5% | Clearing point [° C.]: | 74.8 |
| CC-3-V1 | 9.75% | Δn (589 nm, 20° C.): | 0.1027 |
| CC-1-3 | 0.75% | Δε (1 kHz, 20° C.): | -3.2 |
| CC-3-4 | 5.5% | ε∥ (1 kHz, 20° C.): | 3.5 |
| CC-3-5 | 4.00% | ε⊥ (1 kHz, 20° C.): | 6.8 |
| CCY-3-O1 | 10% | K₁ (20° C.) [pN]: | 14.4 |
| CCY-3-O2 | 12% | K₃ (20° C.) [pN]: | 15.2 |
| CPY-2-O2 | 10% | γ₁ (20° C.) [mPa · s]: | |
| CPY-3-O2 | 2.0% | V₀ (20° C.) [V]: | 2.29 |
| CY-3-O2 | 0.5% | | |
| PP-1-2V1 | 0.25% | | |
| PY-1-O4 | 4.25% | | |
| PY-3-O2 | 17% | | |
| PYP-2-3 | 1.5% | | |

A polymerisable mixture is prepared by adding to nematic LC host Mixture H30 0.5% of reactive mesogen 1.

H31: Nematic Host Mixture (Δε<0)

| | | | |
|---|---|---|---|
| CPP-3-2 | 4.0% | Clearing point [° C.]: | 74.6 |
| CC-3-V | 10% | Δn (589 nm, 20° C.): | 0.099 |
| CC-3-V1 | 8.5% | Δε (1 kHz, 20° C.): | -3.4 |
| CC-3-4 | 4.5% | ε∥ (1 kHz, 20° C.): | 3.6 |
| CC-3-5 | 8.0% | ε⊥ (1 kHz, 20° C.): | 7 |
| CCP-3-1 | 4.25% | K₁ (20° C.) [pN]: | 14.2 |
| CCY-3-O1 | 6.5% | K₃ (20° C.) [pN]: | 15.9 |
| CCY-3-O2 | 12.75% | γ₁ (20° C.) [mPa · s]: | 108 |
| CCY-4-O2 | 6.0% | V₀ (20° C.) [V]: | 2.28 |
| CY-3-O2 | 15.5% | | |

-continued

| | |
|---|---|
| CP-3-O1 | 2.0% |
| PY-3-O2 | 16% |
| PYP-2-3 | 2.0% |

A polymerisable mixture is prepared by adding to nematic LC host Mixture H31 0.5% of reactive mesogen 1 and 0.6% of SA-additive SA-23.

H32: Nematic Host Mixture ($\Delta\varepsilon<0$)

| | | | |
|---|---|---|---|
| CC-3-V | 15% | Clearing point [° C.]: | 74.4 |
| CC-3-V1 | 9.0% | $\Delta n$ (589 nm, 20° C.): | 0.1086 |
| CC-2-3 | 8.0% | $\Delta\varepsilon$ (1 kHz, 20° C.): | −3.2 |
| CC-3-4 | 7.5% | $\varepsilon_{\parallel}$ (1 kHz, 20° C.): | 3.5 |
| CCY-3-O2 | 10% | $\varepsilon_{\perp}$ (1 kHz, 20° C.): | 6.7 |
| CCY-5-O2 | 8.0% | $K_1$ (20° C.) [pN]: | 14.3 |
| CPY-2-O2 | 3.0% | $K_3$ (20° C.) [pN]: | 15.7 |
| CPY-3-O2 | 8.5% | $\gamma_1$ (20° C.) [mPa · s]: | 102 |
| CY-3-O2 | 7.0% | $V_0$ (20° C.) [V]: | 2.33 |
| PY-3-O2 | 16% | | |
| PYP-2-3 | 8.0% | | |

A polymerisable mixture is prepared by adding to nematic LC host Mixture H32 0.5% of reactive mesogen 1, 0.6% of SA-additive SA-23, and 50 ppm of stabiliser S3-3.

H33: Nematic Host Mixture ($\Delta\varepsilon<0$)

| | | | |
|---|---|---|---|
| CPP-3-2 | 6.0% | Clearing point [° C.]: | 75.2 |
| CC-3-O1 | 4.0% | $\Delta n$ (589 nm, 20° C.): | 0.1095 |
| CC-3-4 | 9.0% | $\Delta\varepsilon$ (1 kHz, 20° C.): | −3.1 |
| CC-3-5 | 9.0% | $\varepsilon_{\parallel}$ (1 kHz, 20° C.): | 3.6 |
| CCP-3-1 | 8.0% | $\varepsilon_{\perp}$ (1 kHz, 20° C.): | 6.7 |
| CCP-3-3 | 1.0% | $K_1$ (20° C.) [pN]: | 13.8 |
| CCY-3-O2 | 12% | $K_3$ (20° C.) [pN]: | 16.5 |
| CLY-3-O2 | 1.0% | $\gamma_1$ (20° C.) [mPa · s]: | 119 |
| CPY-3-O2 | 11% | $V_0$ (20° C.) [V]: | 2.41 |
| CY-3-O2 | 9.5% | | |
| CP-3-O1 | 11.5% | | |
| PY-3-O2 | 18% | | |

A polymerisable mixture is prepared by adding to nematic LC host Mixture H33 0.5% of reactive mesogen 1 and 0.6% of SA-additive SA-23.

H34: Nematic Host Mixture ($\Delta\varepsilon<0$)

| | | | |
|---|---|---|---|
| CPP-3-2 | 3.0% | Clearing point [° C.]: | 75.2 |
| CC-3-V1 | 9.0% | $\Delta n$ (589 nm, 20° C.): | 0.1098 |
| CC-3-O1 | 2.5% | $\Delta\varepsilon$ (1 kHz, 20° C.): | −3.1 |
| CC-3-4 | 9.0% | $\varepsilon_{\parallel}$ (1 kHz, 20° C.): | 3.6 |
| CC-3-5 | 9.0% | $\varepsilon_{\perp}$ (1 kHz, 20° C.): | 6.7 |
| CCP-3-1 | 7.5% | $K_1$ (20° C.) [pN]: | 14.6 |
| CCP-V2-1 | 5.0% | $K_3$ (20° C.) [pN]: | 16.6 |
| CCY-3-O2 | 4.0% | $\gamma_1$ (20° C.) [mPa · s]: | 114 |
| CPY-2-O2 | 5.5% | $V_0$ (20° C.) [V]: | 2.43 |
| CPY-3-O2 | 10.5% | | |
| CY-3-O2 | 15% | | |
| CP-3-O1 | 1.5% | | |
| PY-3-O2 | 18% | | |
| PPGU-3-F | 0.5% | | |

A polymerisable mixture is prepared by adding to nematic LC host Mixture H34 0.5% of reactive mesogen 1.

H35: Nematic Host Mixture ($\Delta\varepsilon<0$)

| | | | |
|---|---|---|---|
| CPP-3-2 | 8.5% | Clearing point [° C.]: | 74.7 |
| CC-3-V1 | 9.0% | $\Delta n$ (589 nm, 20° C.): | 0.1097 |
| CC-3-O1 | 2.0% | $\Delta\varepsilon$ (1 kHz, 20° C.): | −3.1 |
| CC-3-4 | 9.0% | $\varepsilon_{\parallel}$ (1 kHz, 20° C.): | 3.5 |
| CC-3-5 | 9.0% | $\varepsilon_{\perp}$ (1 kHz, 20° C.): | 6.6 |
| CCP-3-1 | 2.5% | $K_1$ (20° C.) [pN]: | 14.2 |
| CCP-V2-1 | 5.0% | $K_3$ (20° C.) [pN]: | 16.6 |
| CCY-3-O2 | 7.5% | $\gamma_1$ (20° C.) [mPa · s]: | 112 |
| CLY-3-O2 | 1.0% | $V_0$ (20° C.) [V]: | 2.44 |
| CPY-3-O2 | 10.5% | | |
| CY-3-O2 | 15% | | |
| CP-3-O1 | 3.0% | | |
| PY-3-O2 | 18% | | |

A polymerisable mixture is prepared by adding to nematic LC host Mixture H35 1.0% of reactive mesogen 1, 0.3% of the reactive mesogen RM-150 and 0.6% of SA-additive SA-23.

H36: Nematic Host Mixture ($\Delta\varepsilon<0$)

| | | | |
|---|---|---|---|
| B-2O-O5 | 4.0% | Clearing point [° C.]: | 75 |
| CPP-3-2 | 2.0% | $\Delta n$ (589 nm, 20° C.): | 0.1094 |
| CC-3-O1 | 5.0% | $\Delta\varepsilon$ (1 kHz, 20° C.): | −3.1 |
| CC-3-4 | 9.0% | $\varepsilon_{\parallel}$ (1 kHz, 20° C.): | 3.6 |
| CC-3-5 | 9.0% | $\varepsilon_{\perp}$ (1 kHz, 20° C.): | 6.7 |
| CCP-3-1 | 8.0% | $K_1$ (20° C.) [pN]: | 13.9 |
| CCP-3-3 | 5.0% | $K_3$ (20° C.) [pN]: | 16.4 |
| CCY-3-O2 | 11.5% | $\gamma_1$ (20° C.) [mPa · s]: | 117 |
| CLY-3-O2 | 1.0% | $V_0$ (20° C.) [V]: | 2.42 |
| CPY-3-O2 | 10.5% | | |
| CY-3-O2 | 2.0% | | |
| CP-3-O1 | 15% | | |
| PY-3-O2 | 18% | | |

A polymerisable mixture is prepared by adding to nematic LC host Mixture H36 0.6% of reactive mesogen 1 and 100 ppm of stabiliser S2-1.

H37: Nematic Host Mixture ($\Delta\varepsilon<0$)

| | | | |
|---|---|---|---|
| CPP-3-2 | 7.5% | Clearing point [° C.]: | 74.8 |
| CC-3-V1 | 9.0% | $\Delta n$ (589 nm, 20° C.): | 0.1098 |
| CC-3-O1 | 1.5% | $\Delta\varepsilon$ (1 kHz, 20° C.): | −3.1 |
| CC-3-4 | 9.0% | $\varepsilon_{\parallel}$ (1 kHz, 20° C.): | 3.5 |
| CC-3-5 | 9.0% | $\varepsilon_{\perp}$ (1 kHz, 20° C.): | 6.6 |
| CCP-3-1 | 4.0% | $K_1$ (20° C.) [pN]: | 14.4 |
| CCP-V2-1 | 5.0% | $K_3$ (20° C.) [pN]: | 16.6 |
| CCY-3-O2 | 7.0% | $\gamma_1$ (20° C.) [mPa · s]: | 112 |
| CPY-2-O2 | 2.0% | $V_0$ (20° C.) [V]: | 2.44 |
| CPY-3-O2 | 10% | | |
| CY-3-O2 | 15% | | |
| CP-3-O1 | 3.0% | | |
| PY-3-O2 | 18% | | |

A polymerisable mixture is prepared by adding to nematic LC host Mixture H37 0.5% of reactive mesogen 1 and 100 ppm of stabiliser S3-2.

H38: Nematic Host Mixture ($\Delta\varepsilon<0$)

| | | | |
|---|---|---|---|
| CY-3-O2 | 10% | Clearing point [° C.]: | 100 |
| CY-3-O4 | 20% | $\Delta n$ (589 nm, 20° C.): | 0.0865 |
| CY-5-O4 | 20% | $\Delta\varepsilon$ (1 kHz, 20° C.): | −5.4 |
| CCY-3-O2 | 6.0% | $\varepsilon_{\parallel}$ (1 kHz, 20° C.): | 3.9 |
| CCY-3-O3 | 6.0% | $\varepsilon_{\perp}$ (1 kHz, 20° C.): | 9.3 |
| CCY-4-O2 | 6.0% | $K_1$ (20° C.) [pN]: | 15.6 |
| CCY-5-O2 | 6.0% | $K_3$ (20° C.) [pN]: | 16.6 |
| CCZC-3-3 | 3.0% | $\gamma_1$ (20° C.) [mPa · s]: | 347 |
| CCZC-3-5 | 3.5% | $V_0$ (20° C.) [V]: | 1.84 |
| CCZC-4-3 | 3.5% | | |
| CCZC-4-5 | 3.5% | | |
| CCEPC-3-3 | 4.0% | | |
| CCEPC-3-4 | 4.5% | | |
| CCEPC-3-5 | 4.0% | | |

A polymerisable mixture is prepared by adding to nematic LC host Mixture H38 0.5% of reactive mesogen 1, 0.6% of SA-additive SA-23, and 50 ppm of stabiliser S3-1.

H39: Nematic Host Mixture ($\Delta\varepsilon<0$)

| | | | |
|---|---|---|---|
| Y-4O-O4 | 12.5% | Clearing point [° C.]: | 105 |
| CY-3-O4 | 5.0% | $\Delta n$ (589 nm, 20° C.): | 0.0868 |
| CY-5-O4 | 18% | $\Delta\varepsilon$ (1 kHz, 20° C.): | −5.4 |
| CCY-3-O1 | 4.0% | $\varepsilon_{\parallel}$ (1 kHz, 20° C.): | 4.2 |
| CCY-3-O2 | 6.0% | $\varepsilon_{\perp}$ (1 kHz, 20° C.): | 9.6 |
| CCY-3-O3 | 6.0% | $K_1$ (20° C.) [pN]: | 16.7 |
| CCY-4-O2 | 6.0% | $K_3$ (20° C.) [pN]: | 16.5 |
| CCY-5-O2 | 6.0% | $\gamma_1$ (20° C.) [mPa · s]: | |
| CPY-3-O2 | 4.5% | $V_0$ (20° C.) [V]: | 1.85 |
| CCZC-3-3 | 4.0% | | |
| CCZC-3-5 | 4.0% | | |
| CCZC-4-3 | 4.0% | | |
| CCZC-4-5 | 4.0% | | |
| CCOC-3-3 | 2.0% | | |
| CCOC-4-3 | 2.0% | | |
| CCEPC-3-3 | 4.0% | | |
| CCEPC-3-4 | 4.0% | | |
| CCEPC-3-5 | 4.0% | | |

A polymerisable mixture is prepared by adding to nematic LC host Mixture H39 0.6% of reactive mesogen 1 and 0.6% of SA-additive SA-23.

H40: Nematic Host Mixture ($\Delta\varepsilon<0$)

| | | | |
|---|---|---|---|
| Y-4O-O4 | 3.0% | Clearing point [° C.]: | 108 |
| CY-3-O4 | 8.0% | $\Delta n$ (589 nm, 20° C.): | 0.1096 |
| CCY-3-O1 | 4.0% | $\Delta\varepsilon$ (1 kHz, 20° C.): | −2.4 |
| CCY-3-O2 | 6.0% | $\varepsilon_{\parallel}$ (1 kHz, 20° C.): | 3.2 |
| CCY-3-O3 | 6.0% | $\varepsilon_{\perp}$ (1 kHz, 20° C.): | 5.6 |
| CPY-2-O2 | 8.0% | $K_1$ (20° C.) [pN]: | 16.3 |
| CPY-3-O2 | 8.0% | $K_3$ (20° C.) [pN]: | 18.9 |
| CP-3-O1 | 5.5% | $\gamma_1$ (20° C.) [mPa · s]: | |
| CC-4-V | 15% | $V_0$ (20° C.) [V]: | 2.99 |
| CC-3-V1 | 5.5% | | |
| CCP-V-1 | 13% | | |
| CCP-V2-1 | 13% | | |
| CPTP-3-O1 | 5.0% | | |

A polymerisable mixture is prepared by adding to nematic LC host Mixture H40 1.0% of reactive mesogen 1.

H41: Nematic Host Mixture ($\Delta\varepsilon<0$)

| | | | |
|---|---|---|---|
| CY-3-O4 | 16% | Clearing point [° C.]: | 109 |
| CCY-3-O1 | 4.0% | $\Delta n$ (589 nm, 20° C.): | 0.0854 |
| CCY-3-O2 | 6.0% | $\Delta\varepsilon$ (1 kHz, 20° C.): | −2.3 |
| CCY-3-O3 | 6.0% | $\varepsilon_{\parallel}$ (1 kHz, 20° C.): | 3.1 |
| CCY-4-O2 | 6.0% | $\varepsilon_{\perp}$ (1 kHz, 20° C.): | 5.4 |
| CCY-5-O2 | 5.0% | $K_1$ (20° C.) [pN]: | 16.3 |
| CC-3-O1 | 6.0% | $K_3$ (20° C.) [pN]: | 19.4 |
| CC-4-V | 15% | $\gamma_1$ (20° C.) [mPa · s]: | |
| CC-3-V1 | 6.0% | $V_0$ (20° C.) [V]: | 3.08 |
| CCP-V-1 | 13% | | |
| CCP-V2-1 | 13% | | |
| CCEPC-3-3 | 4.0% | | |

A polymerisable mixture is prepared by adding to nematic LC host Mixture H41 0.8% of reactive mesogen 1 and 0.6% of SA-additive SA-23.

H42: Nematic Host Mixture ($\Delta\varepsilon<0$)

| | | | |
|---|---|---|---|
| Y-4O-O4 | 10% | Clearing point [° C.]: | 107 |
| CY-3-O2 | 7.0% | $\Delta n$ (589 nm, 20° C.): | 0.1104 |
| CY-3-O4 | 15% | $\Delta\varepsilon$ (1 kHz, 20° C.): | −6 |
| CCY-3-O1 | 4.0% | $\varepsilon_{\parallel}$ (1 kHz, 20° C.): | 4.3 |
| CCY-3-O2 | 6.0% | $\varepsilon_{\perp}$ (1 kHz, 20° C.): | 10.3 |
| CCY-3-O3 | 6.0% | $K_1$ (20° C.) [pN]: | 15.7 |
| CCY-4-O2 | 6.0% | $K_3$ (20° C.) [pN]: | 19.1 |
| CCY-5-O2 | 6.0% | $\gamma_1$ (20° C.) [mPa · s]: | |
| CPY-2-O2 | 9.0% | $V_0$ (20° C.) [V]: | 1.88 |
| CPY-3-O2 | 9.0% | | |
| CCP-V-1 | 8.5% | | |
| CCEPC-3-3 | 4.0% | | |
| CCEPC-3-4 | 4.0% | | |
| CCEPC-3-5 | 3.5% | | |
| CGPC-3-3 | 2.0% | | |

A polymerisable mixture is prepared by adding to nematic LC host Mixture H42 0.5% of reactive mesogen 1 and 50 ppm of stabiliser S3-1.

H43: Nematic Host Mixture ($\Delta\varepsilon<0$)

| | | | |
|---|---|---|---|
| Y-4O-O4 | 10% | Clearing point [° C.]: | 108 |
| CY-3-O2 | 4.0% | $\Delta n$ (589 nm, 20° C.): | 0.1403 |
| CY-3-O4 | 15% | $\Delta\varepsilon$ (1 kHz, 20° C.): | −6.4 |
| CCY-3-O1 | 4.0% | $\varepsilon_{\parallel}$ (1 kHz, 20° C.): | 4.3 |
| CCY-3-O2 | 6.0% | $\varepsilon_{\perp}$ (1 kHz, 20° C.): | 10.7 |
| CCY-3-O3 | 6.0% | $K_1$ (20° C.) [pN]: | 16.8 |
| CCY-4-O2 | 6.0% | $K_3$ (20° C.) [pN]: | 20.5 |
| CLY-3-O2 | 5.0% | $\gamma_1$ (20° C.) [mPa · s]: | |
| CPY-2-O2 | 5.0% | $V_0$ (20° C.) [V]: | 1.89 |
| CPY-3-O2 | 5.0% | | |
| PTY-3-O2 | 10% | | |
| PTY-5-O2 | 10% | | |
| CCP-V-1 | 7.0% | | |
| CCP-V2-1 | 7.0% | | |

A polymerisable mixture is prepared by adding to nematic LC host Mixture H43 1.0% of reactive mesogen 1, 0.6% of SA-additive SA-23, and 100 ppm of stabiliser S1-1.

H44: Nematic Host Mixture ($\Delta\varepsilon<0$)

| | | | |
|---|---|---|---|
| Y-4O-O4 | 10% | Clearing point [° C.]: | 109 |
| CCY-3-O1 | 5.0% | $\Delta n$ (589 nm, 20° C.): | 0.1405 |
| PTY-3-O2 | 3.0% | $\Delta\varepsilon$ (1 kHz, 20° C.): | −2 |
| PTY-3-O2 | 10% | $\varepsilon_{\parallel}$ (1 kHz, 20° C.): | 3.4 |
| PTY-5-O2 | 10% | $\varepsilon_{\perp}$ (1 kHz, 20° C.): | 5.4 |
| CP-3-O1 | 4.0% | $K_1$ (20° C.) [pN]: | 16.5 |
| CC-4-V | 15% | $K_3$ (20° C.) [pN]: | 19.9 |
| CC-3-V1 | 8.0% | $\gamma_1$ (20° C.) [mPa · s]: | |
| CCP-V-1 | 13% | $V_0$ (20° C.) [V]: | 3.34 |
| CCP-V2-1 | 13% | | |
| CPTP-3-1 | 4.5% | | |
| CPTP-3-2 | 4.5% | | |

A polymerisable mixture is prepared by adding to nematic LC host Mixture H44 0.6% of reactive mesogen 1.

H45: Nematic Host Mixture ($\Delta\varepsilon<0$)

| | | | |
|---|---|---|---|
| CY-3-O4 | 13% | Clearing point [° C.]: | 107 |
| CCY-3-O1 | 4.0% | $\Delta n$ (589 nm, 20° C.): | 0.082 |
| CCY-3-O2 | 5.0% | $\Delta\varepsilon$ (1 kHz, 20° C.): | −2 |
| CCY-3-O3 | 5.0% | $\varepsilon_{\parallel}$ (1 kHz, 20° C.): | 3 |
| CCY-4-O2 | 5.0% | $\varepsilon_{\perp}$ (1 kHz, 20° C.): | 5 |
| CCY-5-O2 | 5.0% | $K_1$ (20° C.) [pN]: | 16.3 |
| CC-3-O1 | 13% | $K_3$ (20° C.) [pN]: | 19.2 |
| CC-4-V | 12% | $\gamma_1$ (20° C.) [mPa · s]: | |
| CC-3-V1 | 6.0% | $V_0$ (20° C.) [V]: | 3.29 |
| CCP-V-1 | 13% | | |
| CCP-V2-1 | 13% | | |
| CCZC-3-3 | 3.0% | | |
| CCEPC-3-3 | 3.0% | | |

A polymerisable mixture is prepared by adding to nematic LC host Mixture H45 1.0% of reactive mesogen 1 and 0.6% of SA-additive SA-23.

H46: Nematic Host Mixture ($\Delta\varepsilon<0$)

| | | | |
|---|---|---|---|
| Y-4O-O4 | 5.0% | Clearing point [° C.]: | 107 |
| CY-3-O4 | 15% | $\Delta n$ (589 nm, 20° C.): | 0.0821 |
| CY-5-O4 | 14.5% | $\Delta\varepsilon$ (1 kHz, 20° C.): | −4.5 |
| CCY-3-O1 | 5.0% | $\varepsilon_{\parallel}$ (1 kHz, 20° C.): | 3.7 |
| CCY-3-O2 | 6.0% | $\varepsilon_{\perp}$ (1 kHz, 20° C.): | 8.2 |
| CCY-3-O3 | 6.0% | $K_1$ (20° C.) [pN]: | 16 |
| CCY-4-O2 | 6.0% | $K_3$ (20° C.) [pN]: | 17 |
| CCY-5-O2 | 6.0% | $\gamma_1$ (20° C.) [mPa · s]: | 109 |
| CC-4-V | 8.5% | $V_0$ (20° C.) [V]: | 2.04 |
| CCZC-3-3 | 3.0% | | |
| CCZC-3-5 | 3.0% | | |
| CCZC-4-3 | 3.0% | | |
| CCZC-4-5 | 3.0% | | |
| CCOC-3-3 | 4.0% | | |
| CCEPC-3-3 | 4.0% | | |
| CCEPC-3-4 | 4.0% | | |
| CCEPC-3-5 | 4.0% | | |

A polymerisable mixture is prepared by adding to nematic LC host Mixture H46 0.6% of reactive mesogen 1 and 0.6% of SA-additive SA-23.

H47: Nematic Host Mixture ($\Delta\varepsilon<0$)

| | | | |
|---|---|---|---|
| B-2O-O5 | 4.0% | Clearing point [° C.]: | 75 |
| CPP-3-2 | 4.5% | $\Delta n$ (589 nm, 20° C.): | 0.1095 |
| CC-3-V1 | 9.0% | $\Delta\varepsilon$ (1 kHz, 20° C.): | −3.1 |
| CC-3-O1 | 3.0% | $\varepsilon_{\parallel}$ (1 kHz, 20° C.): | 3.6 |
| CC-3-4 | 9.0% | $\varepsilon_{\perp}$ (1 kHz, 20° C.): | 6.7 |
| CC-3-5 | 9.0% | $K_1$ (20° C.) [pN]: | 14.5 |
| CCP-3-1 | 8.0% | $K_3$ (20° C.) [pN]: | 16.7 |
| CCP-V2-1 | 5.0% | $\gamma_1$ (20° C.) [mPa · s]: | 109 |
| CCY-3-O2 | 6.0% | $V_0$ (20° C.) [V]: | 2.43 |
| CPY-3-O2 | 10.5% | | |
| CY-3-O2 | 9.5% | | |
| CP-3-O1 | 4.5% | | |
| PY-3-O2 | 18% | | |

A polymerisable mixture is prepared by adding to nematic LC host Mixture H47 1.0% of reactive mesogen 1 and 0.6% of SA-additive SA-23.

H48: Nematic Host Mixture ($\Delta\varepsilon<0$)

| | | | |
|---|---|---|---|
| B-2O-O5 | 4.0% | Clearing point [° C.]: | 75.2 |
| CPP-3-2 | 12% | $\Delta n$ (589 nm, 20° C.): | 0.1101 |
| CC-3-V1 | 9.0% | $\Delta\varepsilon$ (1 kHz, 20° C.): | −3.1 |
| CC-3-5 | 5.5% | $\varepsilon_{\parallel}$ (1 kHz, 20° C.): | 3.6 |
| CCP-3-1 | 5.5% | $\varepsilon_{\perp}$ (1 kHz, 20° C.): | 6.7 |
| CCP-V2-1 | 5.0% | $K_1$ (20° C.) [pN]: | 13 |
| CCY-3-O2 | 4.0% | $K_3$ (20° C.) [pN]: | 16.3 |
| CLY-3-O2 | 1.0% | $\gamma_1$ (20° C.) [mPa · s]: | 121 |
| CPY-2-O2 | 2.5% | $V_0$ (20° C.) [V]: | 2.39 |
| CPY-3-O2 | 10.5% | | |
| CY-3-O2 | 15% | | |
| CY-3-O4 | 11% | | |
| CP-3-O1 | 15% | | |

A polymerisable mixture is prepared by adding to nematic LC host Mixture H48 1.0% of reactive mesogen 1 and 0.6% of SA-additive SA-23.

Use Example A

Polymerisable Mixtures

Polymerisable mixtures are prepared by adding to nematic LC host Mixture H1 one or more of reactive mesogen 1 according to the invention, reference reactive mesogen RM-1 according to prior art, and SA additive SA-23.

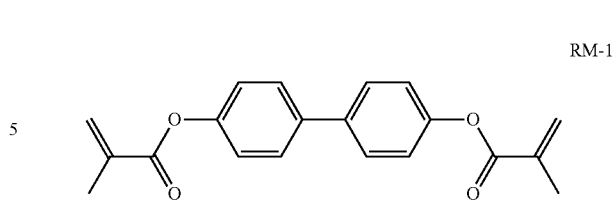

RM-1

Further polymerisable mixtures are prepared by adding to nematic LC host mixture H1 one or more of reactive mesogen 1 according to the invention, reactive mesogen RM-149, and SA additive SA-23.

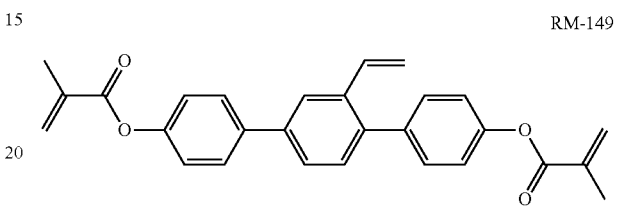

RM-149

The polymerisable mixture compositions are shown in Table 1.

TABLE 1

| Polymerisable mixture compositions | | | | |
|---|---|---|---|---|
| Mixture | PC11 | P11 | P12 | P13 |
| LC Host | H1 | H1 | H1 | N1 |
| 1$^{st}$ RM | RM-1 | 1 | 1 | 1 |
| wt. % 1$^{st}$ RM | 0.3% | 1.0% | 1.0% | 1.0% |
| 2$^{nd}$ RM | — | — | RM-1 | RM-1 |
| wt. % 2$^{nd}$ RM | — | — | 0.3% | 0.5% |
| 3rd RM | — | — | — | RM-149 |
| wt. % 3rd RM | — | — | — | 0.3% |
| wt. % SA-23 | 0.6% | 0.6% | 0.6% | 0.6% |

Test Cells

The individual polymerisable mixtures from Table 1 are filled into SA-VA test cells with different cell thickness (3.3 µm and 6 µm, respectively), and the polymerisable compounds are photopolymerised by UV exposure under application of a voltage of 0 V.

The test cells used are SA-VA resinBM cells without PI. Afterwards the test cells are irradiated by UV light in two steps:

UV1: UV irradiation at 100 mW/cm$^2$ (measured with Hönle 365 nm Sensor). Lamp type: Hönle MH lamp UV-A Cube 2000. Cut-off filter 320 nm. Applied voltage 0 V. Temperature 40° C. Irradiation time 2 min.

UV2: Type fluorescent UV lamp, room temperature, 120 min.

The total reflectivity averaged over wavelengths between 400 nm and 700 nm after UV exposure is measured for each polymerised mixture with a spectral photometer CM-700d (Konica Minolta). The results are shown in Table 2.

TABLE 2

| | Reflectivity | | | |
|---|---|---|---|---|
| Mixture | PC11 | P11 | P12 | P13 |
| Reflectivity after UV (3.3 µm cell) | 12.2 | n.a. | 11.5 | 11.3 |

TABLE 2-continued

| | Reflectivity | | | |
|---|---|---|---|---|
| Mixture | PC11 | P11 | P12 | P13 |
| Reflectivity after UV (6 μm cell) | 11.1 | 10.4 | n.a. | n.a. |

It can be seen that the polymerisable mixtures P11-P13 according to the present invention, which contain the reactive mesogen 1 of formula I, show a reduced reflectivity after UV processing compared to the polymerisable mixture PC1 which contains reactive mesogen RM-1 according to prior art.

The polymerisable mixtures P11-P13 are therefore especially suitable for use in polymer stabilised SA-VA-displays.

Use Example B

Polymerisable Mixtures

Polymerisable mixtures are prepared by adding to nematic LC host Mixture H2 the reactive mesogen 1 according to the invention or the reactive mesogen RM-1 according to prior art. The compositions of the individual polymerisable mixtures are shown in Table 3.

TABLE 3

| Polymerisable mixture composition | | |
|---|---|---|
| Mixture | PC21 | P21 |
| LC Host | H2 | H2 |
| RM | C1 | 1 |
| wt. % RM | 0.3% | 0.3% |

Test Cells

The individual polymerisable mixtures from Table 3 are filled into test cells, the RM was photopolymerised by UV exposure under application of a voltage, leading to generation of a tilt angle.

Tilt Angle

The UV photopolymerization is carried out by illumination under a metal halide lamp (UC cube 2000) using a 320 nm long pass filter and a light intensity of 100 mW/cm². The test cells are given at least 12 hours to relax before the final tilt angle is measured and calculated with an Axometrics AxoScan®.

Residual RM

The residual content of unpolymerised RM (in % by weight) in the mixture is determined after UV photopolymerisation. The smaller the residual RM content after a given time interval, the faster the polymerization. For this purpose the polymerisable mixtures are filled in test cells and polymerised as described above. After photopolymerisation the test cells are opened, and the mixture is dissolved and rinsed out of the test cell with 2 ml ethyl methyl ketone and analyzed by High Performance Liquid Chromatography (HPLC).

The results are shown in Table 6.

TABLE 6

| Tilt Angle, Residual RM | | |
|---|---|---|
| Mixture | PC21 | P21 |
| Tilt (°) after 1 min UVA exposure | 88.2 | 88.7 |
| residual RM (%) after 7 min UVA exposure | 0.17 | 0.08 |

From Table 6 it can be seen that the tilt angle generated in the polymerisable mixture P21 according to the invention with reactive mesogen 1 is comparable to the mixture PC21 with reactive mesogen RM-1 of prior art. It can also be seen that polymerisation in the polymerisable mixture P21 according to the invention with reactive mesogen 1 is faster, with less amount of residual monomer, compared to mixture PC21 with reactive mesogen RM-1 of prior art.

Polymerisable mixture P21 is therefore especially suitable for use in PS-VA-displays.

The invention claimed is:
1. A compound of formula I

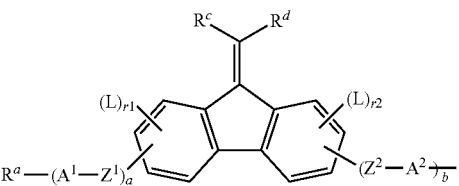

wherein the individual radicals, independently of each other and on each occurrence identically or differently, have the following meanings
$A^1$, $A^2$ an alicyclic, heterocyclic, aromatic or heteroaromatic group with 4 to 30 ring atoms, which may also contain fused rings, and is optionally substituted by one or more groups L, R or P-Sp-,
$Z^1$, $Z^2$ —O—, —S—, —CO—, —CO—O—, —O—CO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CH$_2$)$_{n1}$—, —CF$_2$CH$_2$—, —CH$_2$CF$_2$—, —(CF$_2$)$_{n1}$—, —CH=CH—, —CF=CF—, —CH=CF—, —CF=CH—, —C≡C—, —CH=CH—CO—O—, —O—CO—CH=CH—, —CH$_2$—CH$_2$—CO—O—, —O—CO—CH$_2$—CH$_2$—, —CR$^0$R$^{00}$—, or a single bond,
$R^0$, $R^{00}$ H or alkyl having 1 to 12 C atoms,
$R^a$, $R^b$ P-Sp-, R or H, wherein at least one of $R^a$ and $R^b$ denotes P-Sp-,
$R^c$, $R^d$ H, $C_{1-12}$-straight-chain or $C_{3-12}$-branched alkyl or $C_{2-12}$-straight-chain or $C_{3-12}$-branched alkenyl, wherein one or more H atoms are each optionally replaced by F or Cl,
R H, F, Cl, —CN, or $C_{1-25}$-straight chain, $C_{3-25}$-branched or $C_{3-25}$-cyclic alkyl, wherein one or more non-adjacent CH$_2$-groups are optionally replaced by —O—, —S—, —CO—, —CO—O—, —O—CO—, —O—CO—O—, —N(R$^0$)—, —Si(R$^0$R$^{00}$)—, —CH=CH— or —C≡C— in such a manner that O- and/or S-atoms are not directly connected with each other, and wherein one or more H atoms are each optionally replaced by F or Cl,
P a polymerizable group,
Sp a spacer group that is optionally substituted by one or more groups P, or a single bond, L F, Cl, —CN, P, P-Sp-, or $C_{1-25}$-straight chain, $C_{3-25}$-branched or $C_{3-25}$-cyclic alkyl, wherein one or more non-adjacent $CH_2$-groups are optionally replaced by —O—, —S—, —CO—, —CO—O—, —O—CO—, —O—CO—O—, —N(R$^o$)—, —Si(R$^o$R$^{oo}$)—, —CH=CH— or —C≡C— in such a manner that O- and/or S-atoms are not directly connected with each other, and wherein one or more H atoms are each optionally replaced by P, P-Sp-, F or Cl, a, b 0, 1 or 2, r1, r2 0, 1, 2 or 3, n1 1, 2, 3 or 4.

2. The compound according to claim 1, wherein $(A^1-Z^1)_a$ and $(Z^2-A^2)_b$ are benzene, biphenylene, p-terphenylene (1,4-diphenylbenzene), m-terphenylene (1,3-diphenylbenzene), naphthylene, 2-phenyl-naphthylene, phenanthrene, anthracene, dibenzofuran or dibenzothiophene, all of which are optionally substituted by one or more groups L or P-Sp-.

3. The compound according to claim 1, of formula IA

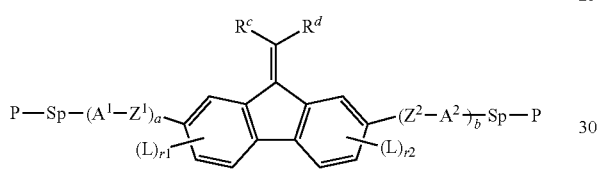

IA wherein P, Sp, R$^c$, R$^d$, A$^1$, A$^2$, Z$^1$, Z$^2$, L, a, b, r1 and r2 have the meanings given in claim 1.

4. The compound according to claim 1, of the following subformulae

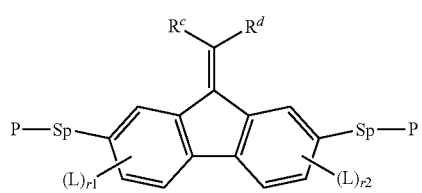

I1

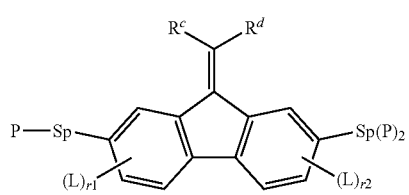

I2

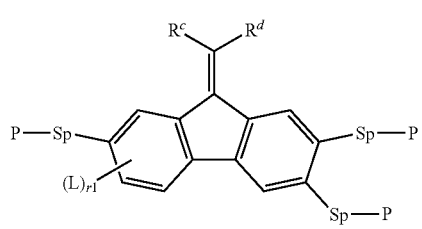

I3

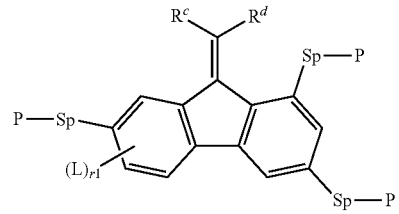

I4

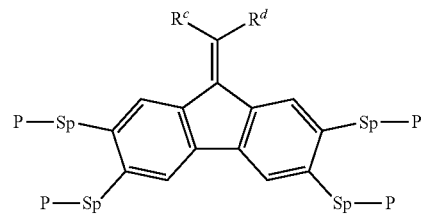

I5

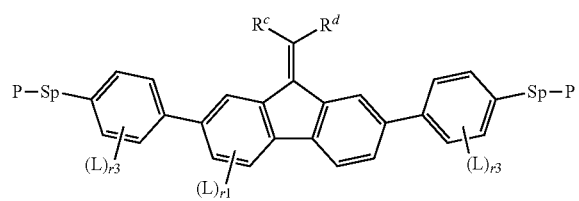

I6

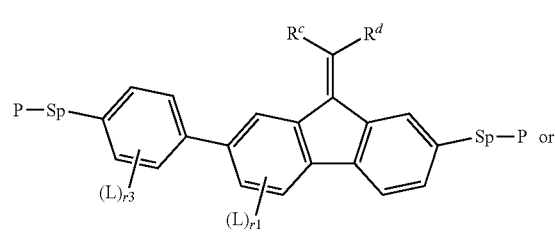

I7

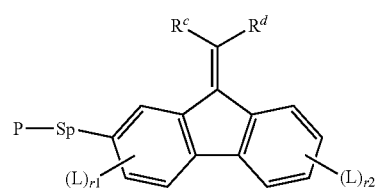

I8 wherein P, Sp, R$^c$, R$^d$, L, r1 and r2 have the meanings given in claim 1, and r3 and r4 are independently of each other 0, 1, 2, 3 or 4.

5. The compound according to claim 1, wherein R$_c$ and R$^d$ are H, $CH_3$, $C_2H_5$, $C_3H_7$, —CH=$CH_2$ or —$CH_2$—CH=$CH_2$.

6. The compound according to claim 1, wherein all groups Sp are a single bond, or one of the groups Sp is a single bond and the other groups Sp are different from a single bond.

7. The compound according to claim 1, wherein Sp, when being different from a single bond, is —$(CH_2)_{p1}$—, —$(CH_2)_{p2}$—CH=CH—$(CH_2)_{p3}$—, —$(CH_2)_{p1}$—O—, —$(CH_2)_{p1}$—CO—O—, —$(CH_2)_{p1}$—O—CO—, wherein p1 is 2, 3, 4, 5 or 6, p2 and p3 are independently of each other 0, 1, 2 or 3, and the O-atom or the CO-group, respectively, is connected to the benzene ring.

8. The compound according to claim 1, wherein one of r1 and r2 is 0, 1 or 2 and the other is 1 or 2, and L is F, Cl, CN, alkyl, alkoxy, alkylcarbonyl, alkoxycarbonyl, alkylcarbonyloxy or alkoxycarbonyloxy each having 1 to 6 C atoms, in which one or more H atoms may optionally be replaced by F or Cl.

9. The compound according to claim 1, wherein P is vinyloxy, acrylate, methacrylate, fluoroacrylate, chloroacrylate, oxetane and or epoxide.
10. The compound according to claim 1, of the following subformulae:
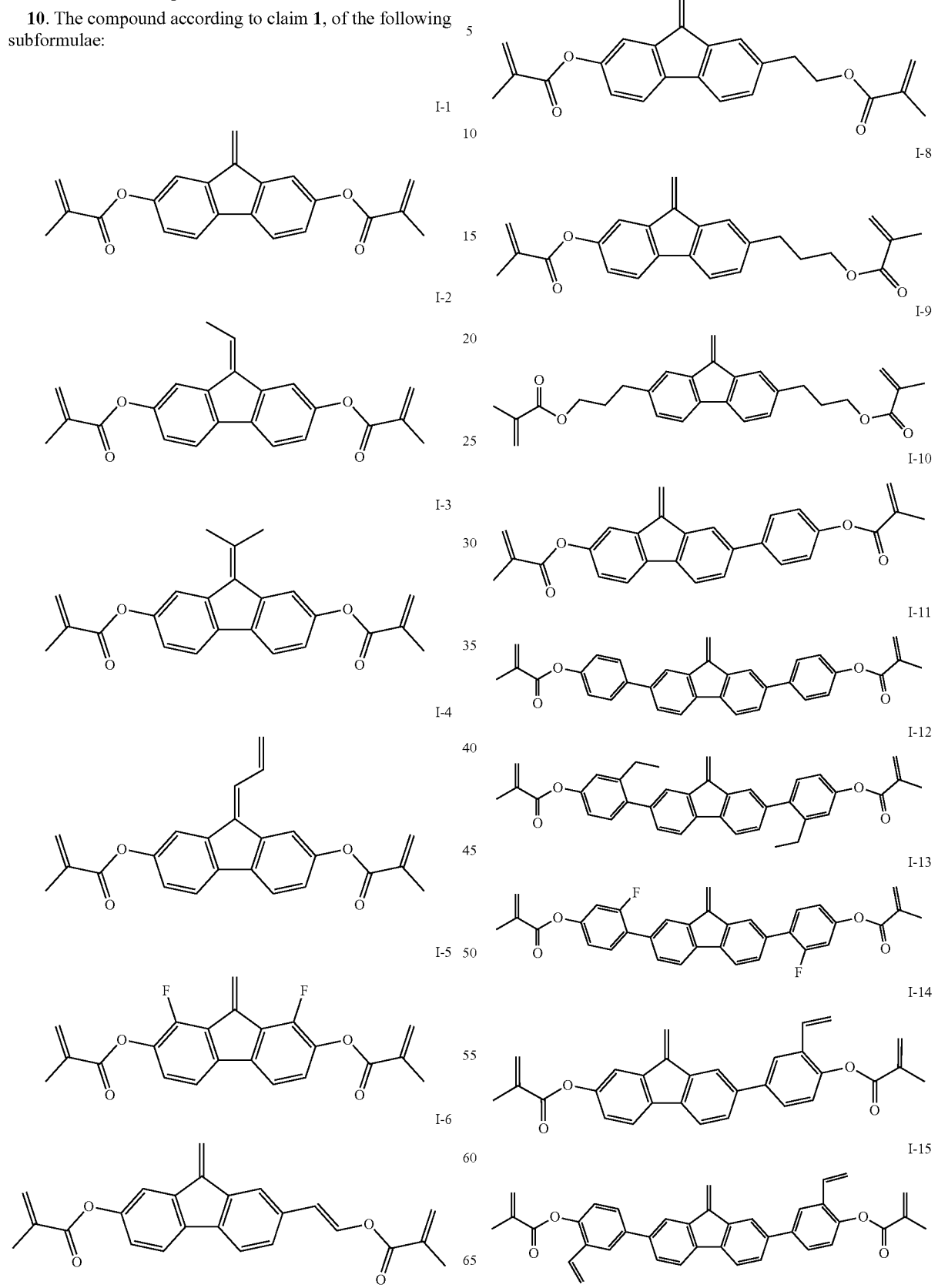

-continued

I-16
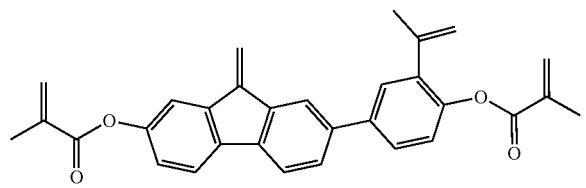

I-17
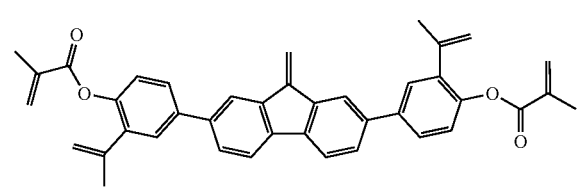

I-18
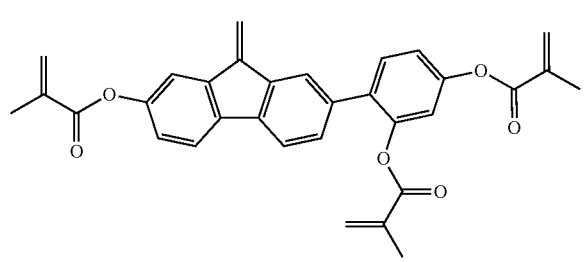

I-19
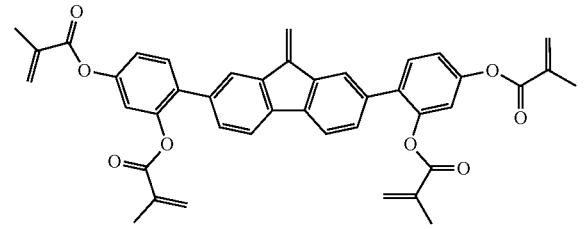

I-20
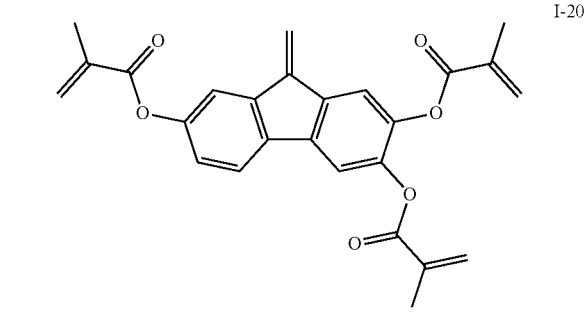

I-21
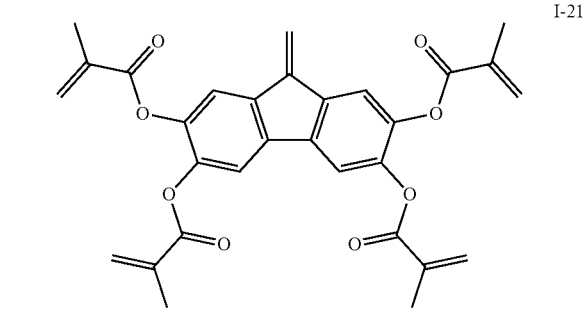

-continued

I-22
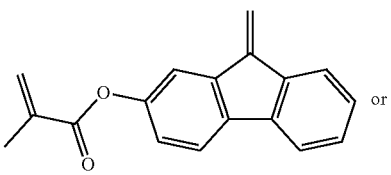

or

I-23
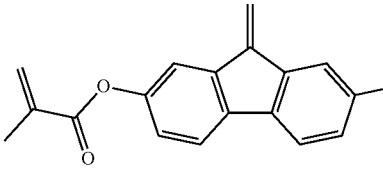

11. A liquid crystal (LC) medium comprising one or more compounds formula I as defined in claim 1.

12. The LC medium according to claim 11, wherein the compounds of formula I are polymerized.

13. A process of preparing an LC medium of claim 11, comprising mixing one or more mesogenic or liquid-crystalline compounds with one or more compounds of formula I and optionally with further liquid-crystalline compounds and/or additives, and optionally polymerizing compounds of formula I.

14. An LC display comprising one or more compounds of formula I as defined in claim 1.

15. The LC display of claim 14, which is a PSA or polymer stabilized SA display.

16. The LC display of claim 15, which is a PS-VA, PS-OCB, PS-IPS, PS-FFS, PS-UB-FFS, PS-poli-VA, PS-TN, polymer stabilized SA-VA or polymer stabilized SA-HB-FFS display.

17. The LC display of claim 15, comprising two substrates, at least one which is transparent to light, an electrode provided on each substrate or two electrodes provided on only one of the substrates, and located between the substrates a layer of an LC medium comprising one or more compounds of formula I, wherein the polymerizable compounds are polymerized between the substrates of the display.

18. A process for the production of an LC display according to claim 17, comprising providing an LC medium comprising one or more compounds of formula I between the substrates of the display, and polymerizing the compounds.

19. A compound of formula IN

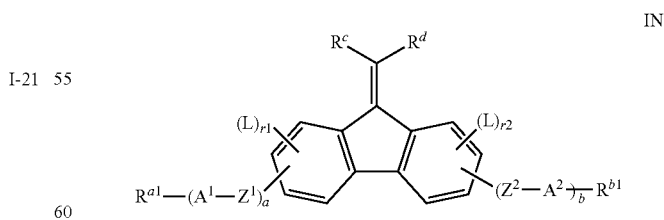

one of $R^{a1}$ and $R^{b1}$ is Pg-Sp- and the other is R or Pg-Sp-,
Pg is OH or a protected or masked OH group, and
$A^1$, $A^2$ an alicyclic, heterocyclic, aromatic or heteroaromatic group with 4 to 30 ring atoms, which may also contain fused rings, and is optionally substituted by one or more groups L, R or P-Sp-, $Z^1$, $Z^2$ —O—, —S—, —CO—, —CO—O—, —O—CO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CH$_2$)$_{n1}$—, —CF$_2$CH$_2$—, —CH$_2$CF$_2$—, —(CF$_2$)$_{n1}$—, —CH=CH—, —CF=CF—, —CH=CF—, —CF=CH—, —C≡C—, —CH=CH—CO—O—, —O—CO—CH=CH—, —CH$_2$—CH$_2$—CO—O—, —O—CO—CH$_2$—CH$_2$—, —CR$^0$R$^{00}$—, or a single bond, $R^0$, $R^{00}$ H or alkyl having 1 to 12 C atoms, $R^c$, $R^d$ H, C$_{1-12}$-straight-chain or C$_{3-12}$-branched alkyl or C$_{2-12}$-straight-chain or C$_{3-12}$-branched alkenyl, wherein one or more H atoms are each optionally replaced by F or Cl, R H, F, Cl, —CN, or C$_{1-25}$-straight chain, C$_{3-25}$-branched or C$_{3-25}$-cyclic alkyl, wherein one or more non-adjacent CH$_2$-groups are optionally replaced by —O—, —S—, —CO—, —CO—O—, —O—CO—, —O—CO—O—, —N(R$^0$)—, —Si(R$^0$R$^{00}$)—, —CH=CH— or —C≡C— in such a manner that O- and/or S-atoms are not directly connected with each other, and wherein one or more H atoms are each optionally replaced by F or Cl, P a polymerizable group, Sp a spacer group that is optionally substituted by one or more groups P, or a single bond, L F, Cl, —CN, P, P-Sp-, or C$_{1-25}$-straight chain, C$_{3-25}$-branched or C$_{3-25}$-cyclic alkyl, wherein one or more non-adjacent CH$_2$-groups are optionally replaced by —O—, —S—, —CO—, —CO—O—, —O—CO—, —O—CO—O—, —N(R$^0$)—, —Si(R$^0$R$^{00}$)—, —CH=CH— or —C≡C— in such a manner that O- and/or S-atoms are not directly connected with each other, and wherein one or more H atoms are each optionally replaced by P, P-Sp-, F or Cl, a, b 0, 1 or 2, r1, r2 0, 1, 2 or 3.

20. A process for preparing a compound of formula I

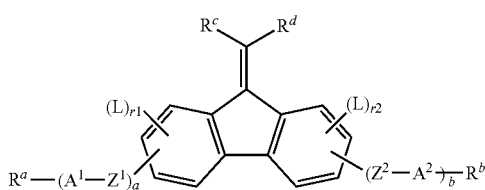

I wherein the individual radicals, independently of each other and on each occurrence identically or differently, have the following meanings $A^1$, $A^2$ an alicyclic, heterocyclic, aromatic or heteroaromatic group with 4 to 30 ring atoms, which may also contain fused rings, and is optionally substituted by one or more groups L, R or P-Sp-, $Z^1$, $Z^2$ —O—, —S—, —CO—, —CO—O—, —O—CO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CH$_2$)$_{n1}$—, —CF$_2$CH$_2$—, —CH$_2$CF$_2$—, —(CF$_2$)$_{n1}$—, —CH=CH—, —CF=CF—, —CH=CF—, —CF=CH—, —C≡C—, —CH=CH—CO—O—, —O—CO—CH=CH—, —CH$_2$—CH$_2$—CO—O—, —O—CO—CH$_2$—CH$_2$—, —CR$^0$R$^{00}$—, or a single bond, $R^0$, $R^{00}$ H or alkyl having 1 to 12 C atoms, $R^a$, $R^b$P-Sp-, R or H, wherein at least one of $R^a$ and $R^b$ denotes P-Sp-, $R^c$, $R^d$ H, C$_{1-12}$-straight-chain or C$_{3-12}$-branched alkyl or C$_{2-12}$-straight-chain or C$_{3-12}$-branched alkenyl, wherein one or more H atoms are each optionally replaced by F or Cl, R H, F, Cl, —CN, or C$_{1-25}$-straight chain, C$_{3-25}$-branched or C$_{3-25}$-cyclic alkyl, wherein one or more non-adjacent CH$_2$-groups are optionally replaced by —O—, —S—, —CO—, —CO—O—, —O—CO—, —O—CO—O—, —N(R$^0$)—, —Si(R$^0$R$^{00}$)—, —CH=CH— or —C≡C— in such a manner that O- and/or S-atoms are not directly connected with each other, and wherein one or more H atoms are each optionally replaced by F or Cl, P a polymerizable group, Sp a spacer group that is optionally substituted by one or more groups P, or a single bond, L F, Cl, —CN, P, P-Sp-, or C$_{1-25}$-straight chain, C$_{3-25}$-branched or C$_{3-25}$-cyclic alkyl, wherein one or more non-adjacent CH$_2$-groups are optionally replaced by —O—, —S—, —CO—, —CO—O—, —O—CO—, —O—CO—O—, —N(R$^0$)—, —Si(R$^0$R$^{00}$)—, —CH=CH— or —C≡C— in such a manner that O- and/or S-atoms are not directly connected with each other, and wherein one or more H atoms are each optionally replaced by P, P-Sp-, F or Cl, a, b 0, 1 or 2, r1, r2 0, 1, 2 or 3, n1 1, 2, 3 or 4, by esterification of a compound of claim 19, wherein Pg denotes OH, using corresponding acids, acid derivatives, or halogenated compounds containing a group P, in the presence of a dehydrating reagent.

21. A process for preparing an LC medium according to claim 12, comprising mixing one or more mesogenic or liquid-crystalline compounds with one or more compounds of formula I, and optionally with further liquid-crystalline compounds and/or additives, and polymerizing the compounds of formula I.

22. An LC display comprising an LC medium as defined in claim 11.

23. An LC display comprising an LC medium as defined in claim 12.

* * * * *